US010968259B2

(12) United States Patent
Moellering et al.

(10) Patent No.: US 10,968,259 B2
(45) Date of Patent: Apr. 6, 2021

(54) HIGH PRODUCTIVITY ALGAL MUTANTS HAVING REDUCED PHOTOSYNTHETIC ANTENNA

(71) Applicant: Synthetic Genomics, Inc., La Jolla, CA (US)

(72) Inventors: Eric R. Moellering, San Diego, CA (US); Nicholas Bauman, San Diego, CA (US); Randor R. Radakovits, Poway, CA (US); Roberto Spreafico, San Diego, CA (US); Fedor Kuzminov, San Diego, CA (US); Imad Ajjawi, San Diego, CA (US); Saheed Imam, San Diego, CA (US); Andrew Schultz, San Diego, CA (US); Kathleen Kwok, San Diego, CA (US); Moena Aqui, San Diego, CA (US); Jennifer Nominati, San Diego, CA (US); John Verruto, San Diego, CA (US); Shaun Bailey, San Diego, CA (US)

(73) Assignee: Synthetic Genomics, Inc., La Jolla, CA (US)

(*) Notice: Subject to any disclaimer, the term of this patent is extended or adjusted under 35 U.S.C. 154(b) by 224 days.

(21) Appl. No.: 15/859,094

(22) Filed: Dec. 29, 2017

(65) Prior Publication Data
US 2018/0186842 A1  Jul. 5, 2018

Related U.S. Application Data

(60) Provisional application No. 62/441,002, filed on Dec. 30, 2016.

(51) Int. Cl.
C07K 14/405 (2006.01)
C12N 1/36 (2006.01)
(Continued)

(52) U.S. Cl.
CPC .......... *C07K 14/405* (2013.01); *A01H 1/06* (2013.01); *C12N 1/12* (2013.01); *C12N 1/36* (2013.01);
(Continued)

(58) Field of Classification Search
CPC .................. C07K 14/405; C12N 1/12
See application file for complete search history.

(56) References Cited

U.S. PATENT DOCUMENTS

| 9,982,272 B2 * | 5/2018 | Bailey ............... C12N 15/825 |
| 2006/0185030 A1 | 8/2006 | Sheen et al. |
| 2016/0304896 A1 | 10/2016 | DiPetrillo et al. |

FOREIGN PATENT DOCUMENTS

WO  WO 2014/089533 A2  6/2014

OTHER PUBLICATIONS

International Search Report dated May 23, 2018, regarding PCT/US2017/069073.
(Continued)

*Primary Examiner* — Russell Kallis
(74) *Attorney, Agent, or Firm* — DLA Piper LLP (US)

(57) ABSTRACT

Disclosed herein are mutant photosynthetic microorgnaisms having an attenuated SGI1 gene. The mutants have reduced chlorophyll and increased productivity with respect to wild type cells. Also disclosed are methods of using such mutants for producing biomass or bioproducts, and methods of screening for such mutants.

40 Claims, 23 Drawing Sheets
Specification includes a Sequence Listing.

(51) Int. Cl.
- *C12N 1/12* (2006.01)
- *C12N 15/82* (2006.01)
- *C12P 21/00* (2006.01)
- *C12N 15/01* (2006.01)
- *C12P 7/64* (2006.01)
- *A01H 1/06* (2006.01)
- *C12R 1/89* (2006.01)

(52) U.S. Cl.
CPC ......... *C12N 15/01* (2013.01); *C12N 15/8269* (2013.01); *C12P 7/649* (2013.01); *C12P 7/6445* (2013.01); *C12P 7/6454* (2013.01); *C12P 21/00* (2013.01); *C12R 1/89* (2013.01); *Y02E 50/10* (2013.01)

(56) References Cited

OTHER PUBLICATIONS

Stephenson et al.: "*Improving photosynthesis for algal biofuels: toward a green revolution.*"; Trends in biotechnology 20.12 (2011): 615-623.

European Search Report dated May 29, 2020, regarding PCT/US2017/069073.

Henning Kirst et al.: "*The chloroplast signal recognition particle (CpSRP) pathway as a tool to minimize chlorophyll antenna size and maximize photosynthetic productivity*"; Biotechnology Advances., vol. 32, No. 1, Feb. 28, 2014, pp. 66-72.

De Mooij Tim et al.: :*Modeling the competition between antenna size mutant and wild type microalgae in outdoor mass culture*, Journal of Biotechnology, Elsevier, Amsterdam, NL, vol. 240, Oct. 13, 2016, pp. 1-13.

\* cited by examiner

```
Parachlorella     PAGLKVLVVDDDLMCLKVVSAMLKRCSYQVATCSSGSEALHLLRE-R[5]SDQFDLVLSDVYMPDMDGFKLLEHIGLELE  81
Coccomyxa         PAGLKVLVVDDDFPLCLKVVEHMLRRCNYQVTTCPNGKAALEKLRD-R         SVHFDLVLSDVYMPDMDGFKLLEHIGLELD  76
Ostreococcus      PAGLGVLVVDDDLLCLRVVEKMLKACKYKYKVTACSTAKTALELLRTrK       -EEFDIVLSDVHMPDMDGFKLLEIIQFELA  76
Chlamydomonas     PAGLRLLVVDDDPLCLKVVEQMLRKCSYEVTVCSNATTALNILRD-K         NTEYDLVLSDVYMPDMDGFRLLELVGLEMD  76
Chromochloris     --------------------------------------------            --------MDGFKLLETVGLELD         15
Volvox            PAGLRLLVVDDDPLCLKVVEQMLRKCSYDVTTCTNATMALNLLRD-K         STEYDLVLSDVYMPDMDGFKLLEVVGLEMD  76
Tetraselmis       PAGLRVLVADNDPASLQQVEKMLKKCSYQVTLCSSGKNSLEILRKrR         -EEFDLVLADANLPDIDGFKLLHVCHTELS  76
Oocystis          PAGLKVLVVDDDPLCLKVIDQMLRRCNYAATTCQSSLEALELLRSsK         ENHFDLVLSDVYMPUMDGFKLLEIIGLEMG  77
Micromonas        FIGLRVLVVDDDFLCLKIVEKMLKRCQYEVTTFSRGAEALKTLRErK         -DDFDIVLSDVHMPDMDGFKLLEHIALELD  76

Parachlorella  82 LPVIMMSSNGDTNVVLRGVTHGAVDFLIKPVRIEELRNVWQHVVRK--  126
Coccomyxa      77 LPVIMMSSNGETNVVLRGVTHGAVDFLIKPVREELRNVWQHVVRK--  123
Ostreococcus   77 LPVLMMSANSDSSVVLRGIIHGAVDYLLKPVRIEELRNIWQHVVRK--  122
Chlamydomonas  77 LPVIMMSSNGDTSNVLRGVTHGACDYLIKPVRLEELRNLWQHVVRRr  123
Chromochloris  16 LPVIMMSSNGEHTTVMRGVTHGACDFLIKPVRIEELRNIWQHVIRR-   61
Volvox         77 LPVIMMSSNGDTSNVLRGVTHGACDYLIKPVRLEELRNLWQHVVRRr  123
Tetraselmis    77 LPVVLMSGTSDTQLVMRGVMDGARDFLIKPLRVEELKVLWQHLVR--  121
Oocystis       78 LPVIMMSSNGETGVFRGVTHGAVDFLIKPVRIEELRNLWQHVVRK-   123
Micromonas     77 LPVMMSANCATDVVLRGIIHGAVDYLLKPVRIEELRNIWQHVVRRk   123
```

FIGURE 4

| | | | |
|---|---|---|---|
| Parachlorella | 1 : | KKPRVVWSVEMHQQFVNAVNSLGIDKAVPKRILDLMNVEG | LTRENVASHLQKYRLYLKRV-- 60 |
| Coccomyxa | 1 : | KKARVVWSVEMHQQFVQAVNQLGIDKAVPKRILDLMNVDG | LTRENVASHLQ----------- 51 |
| Ostreococcus | 1 : | KKPRVVWSAELHAQFVTAVNQLGIDKAVPKRILDLMGVQG | LTRENVASHLQKYRLYLKRLq 61 |
| Chlamydomonas | 1 : | KKARVVWSVEMHQQFVNAVNQLGIDKAVPKKILEIMGVDG[7]TSGRDVCGTV--YRLYLKRV-- 65 |
| Chromochloris | 1 : | KKPRVVWSVEMHQQFVQAVNQLGIDKAVPKRILDLMNVDG | LTRENVASHLQKYRLYLKRVq 61 |
| Volvox | 1 : | KKARVVWSVEMHQQFVNAVNQLGIDKAVPKKILEIMNVDG | LTRENVASHLQKYRIYLKRV-- 60 |
| Tetraselmis | 1 : | KKQRMNWSDEMHQQFVNAVNQLGIDKAVPKKILDLMSVEG | LTRENVASHLQKYRIYLKRM-- 60 |
| Oocystis | 1 : | KKPRVVWSVEMHQQFVNAVNQLGIDKAVPKRILDLMNVDG | LTRENVASHLQKYRLYLKRV-- 60 |
| Micromonas | 1 : | KKPRVVWSAELHQQFVTAVNQLGIDKAVPKRILDLMGVQG | LTRENVASHLQKYRLYLKRLq 61 |

FIGURE 5

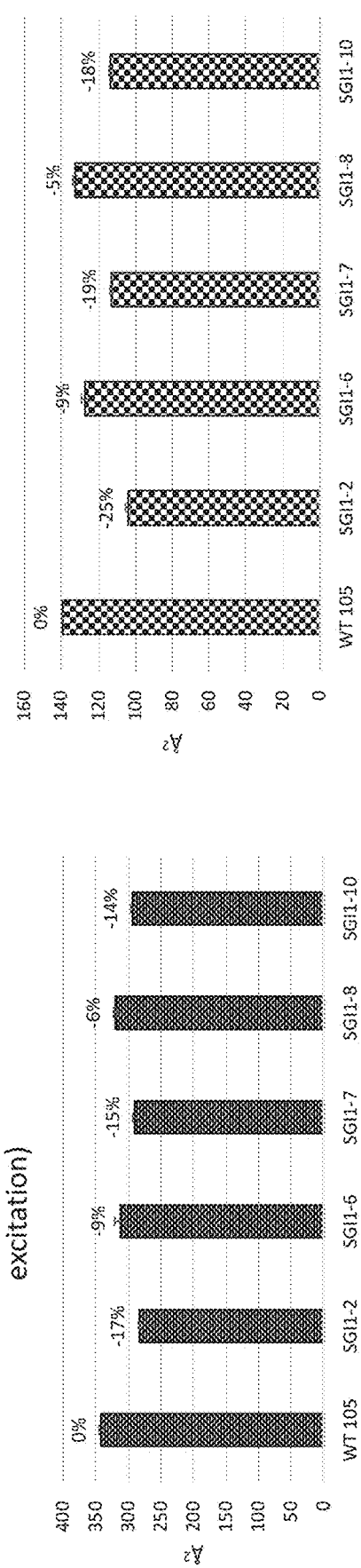
FIGURE 17A
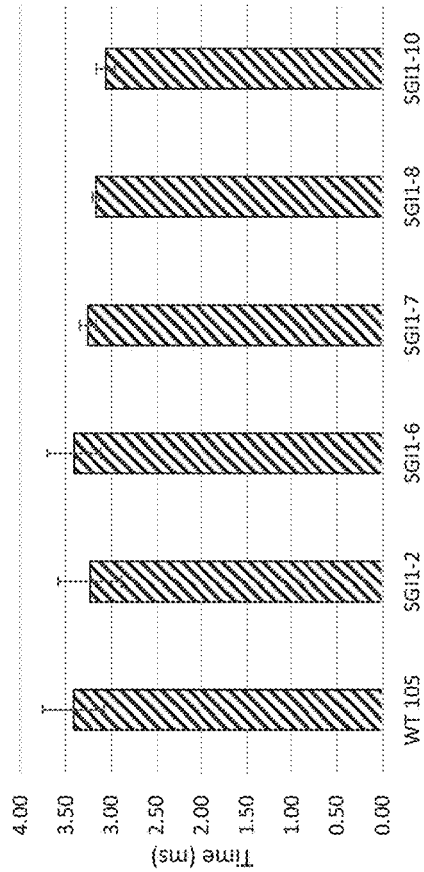
FIGURE 17B
FIGURE 17C
FIGURE 17D

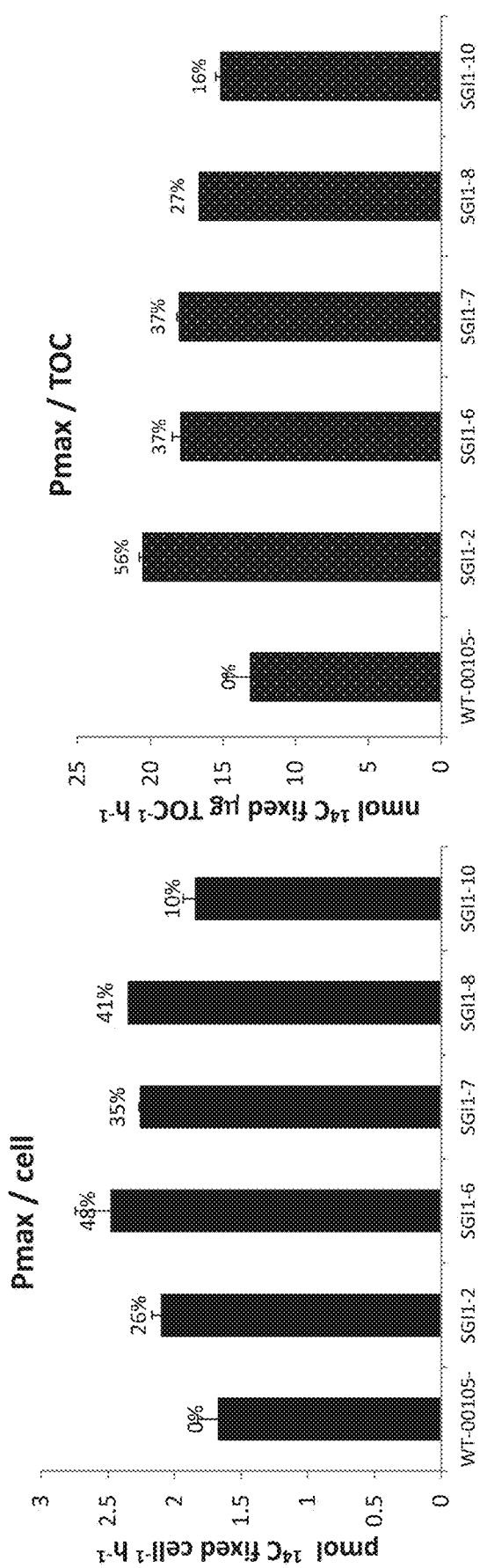
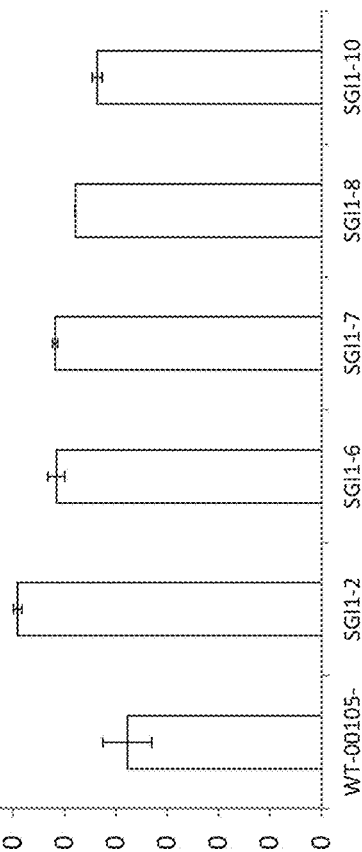
FIGURE 18A
FIGURE 18B
FIGURE 18C

HIGH PRODUCTIVITY ALGAL MUTANTS HAVING REDUCED PHOTOSYNTHETIC ANTENNA

CROSS REFERENCE TO RELATED APPLICATIONS

This application claims benefit of priority under 35 U.S.C. 119(e) to U.S. Ser. No. 62/441,002, filed Dec. 30, 2016, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGI2080_1WO_Sequence_Listing.txt, was created on Dec. 28, 2017, and is 265 kb. The file can be assessed using Microsoft Word on a computer that uses Windows OS.

FIELD OF THE INVENTION

The present invention relates to mutants of photosynthetic organisms having reduced chlorophyll and increased biomass and lipid productivity. The present invention also relates to methods of generating, selecting for, and screening for such mutants.

BACKGROUND

Engineering photosynthetic organisms to increase photosynthetic efficiency for higher productivity is a long-standing goal of plant and algal biologists. US 2014/0220638 and US 2016/030489, both of which are incorporated herein by reference, describe mutant screens to obtain algal mutants referred to as "LIHLA" mutants having reduced chlorophyll that are impaired in their ability to low light acclimate, that is, they retain the low chlorophyll state of high light adapted cells even in low light. US 2014/0220638 describes algal mutants having mutations in the Light Acclimation Regulator LAR1, LAR2, and LAR3 genes, and US 2016/0304896 discloses algal mutants having mutations in the chloroplastic SRP54 gene.

SUMMARY

Provided herein are mutant photosynthetic organisms that have an attenuated gene encoding a Significant Growth Improvement 1 (SGI1) polypeptide. The mutant photosynthetic organisms have higher productivity than control photosynthetic organisms that are substantially identical to the mutant photosynthetic microorganisms except that they do not have an attenuated SGI1 gene. Higher productivity can be measured as the rate of biomass accumulation or the rate of production of a bioproduct, such as, for example, lipid, protein, one or carbohydrates (e.g., one or more sugars or alcohols), pigments, antioxidants, terpenoids, vitamins, or polymers. The SGI1 mutants disclosed herein can exhibit increased productivity under photoautotrophic conditions.

As described herein, an SGI1 polypeptide is a polypeptide that has a Response Regulator receiver domain (RR domain) and a myb-like DNA-binding (myb) domain, where the RR domain is N-terminal to the myb domain, and the two domains are separated by a sequence of amino acids, referred to herein as a linker, that does not belong to either domain. The RR domain and myb domain in various embodiments can be in the N-terminal half of the protein.

An attenuated SGI1 gene is an SGI1 gene whose function or expression is disrupted such that the gene product (the SGI1 polypeptide) is reduced in amount or activity with respect to its abundance or activity in a wild type organism, that is, the function of the SGI1 polypeptide is diminished due to mutation of the SGI1 gene, or due to genetic manipulations outside the SGI1 gene itself that affect the expression of the SGI1 gene.

A mutant photosynthetic organism as provided herein that has an attenuated SGI1 gene exhibits higher productivity with respect to a control photosynthetic organism and has reduced chlorophyll with respect to the control photosynthetic organism. In some examples, a mutant photosynthetic organism having an attenuated SGI1 gene has a reduced amount of chlorophyll b, and in some examples, a mutant photosynthetic organism having an attenuated SGI1 gene has an increased chlorophyll a:chlorophyll b ratio. A mutant photosynthetic organism as provided herein that has an attenuated SGI1 gene can have decreased photosynthetic antenna size, for example reduced photosystem II (PSII) and/or reduced photosystem I (PSI) antenna size.

The high productivity SGI1 mutants can produce more biomass than a control photosynthetic organism, for example, more biomass per day than control or wild type photosynthetic organism from which the mutant photosynthetic organisms were derived. Biomass productivity can be ash free dry weight (AFDW), dry weight, wet weight, or total organic carbon (TOC) productivity. Alternatively or in addition, an SGI1 mutant can produce more of a bioproduct, such as but not limited to lipid, protein, carbohydrate, one or more polyketides, a terpenoid, a pigment, an antioxidant, a vitamin, one or more nucleotides, one or more nucleic acids, one or more amino acids, one or more carbohydrates, an alcohol, a hormone, a cytokine, a peptide, or a polymer than is produced by a control organism cultured under substantially the same conditions over the same period of time.

In some embodiments, a mutant photosynthetic organism as provided herein produces at least 10%, at least 15%, at least 20%, at least 25%, at least 30%, at least 35%, at least 40%, at least 45%, at least 50%, at least 60%, at least 70%, at least 80%, at least 90%, or at least 100% more biomass than a control photosynthetic organism cultured or cultivated under the substantially the same conditions, which for algae can be batch, semi-continuous, or continuous culture conditions and may be nutrient replete culture conditions or may be nitrogen deplete conditions, and may be photoautotrophic conditions.

The high productivity SGI1 mutants can have a reduced functional absorption cross section of PSII ($\sigma_{PSII}$) or "reduced PSII antenna size". For example, the cross-sectional unit size of the PSII antenna can be reduced by at least about 10%, at least 20%, at least 30%, at least 25%, at least 30%, at least 35%, at least 40%, at least 45%, at least 50%, at least 60%, at least about 70%, or at least about 80% with respect to the PSII antenna size of the control microorganism. An STI1 mutant can additionally have a reduced functional absorption cross section of PSI ($\sigma_{PSI}$). For example, the cross-sectional unit size of the PSI antenna can be reduced by at least 10%, at least 20%, at least 30%, at least 25%, at least 30%, at least 35%, at least 40%, at least 45%, at least 50%, or at least 60% with respect to the PSI antenna size of a control photosynthetic organism.

In various embodiments, a mutant photosynthetic organism as provided herein has increased Fv/Fm with respect to a control photosynthetic organism. For example, the mutant photosynthetic organism may have Fv/Fm increased by at least 5%, at least 10%, at least 12%, at least 15%, at least 20%, at least 30%, at least 40% or at least 50% with respect to a control photosynthetic organism, for example, increased by between about 5% and about 50%, or between about 5% and 30%, with respect to a control photosynthetic organism.

Further, a mutant photosynthetic organism as provided herein can have an increased rate of electron transport on the acceptor side of photosystem II ($1/\tau'_{Qa}$) with respect to a control or wild type cell. A mutant as provided herein can have a $1/\tau'_{Qa}$ value that is increased by at least about 20%, 30%, 40%, 50%, 60%, 80%, or 100% with respect to a wild type or control organism.

In addition, the rate of carbon fixation (Pmax (C)) in an SGI1 mutant as provided herein can be elevated with respect to a control organism. For example, Pmax ($^{14}$C) can be increased by at least about 20%, 30%, 40%, 50%, 60%, 80%, or 100% with respect to a wild type or control organism.

In some embodiments, SGI1 mutants have decreased PSI and/or PSII antenna size and can further have a higher amount of a ribulose bisphosphate carboxylase activase (Rubisco activase or "RA") than a control or wild type organism, for example, at least 1.2, 1.4, 1.6, 1.8, 2, 2.2, or 2.5 fold the amount of RA as a control organism. In some embodiments, the mutants demonstrate reduced expression of 6, 8, 10, 12, or 14 LHCP genes and increased expression of an RA gene, such as an RA-α or RA-β gene. Disclosed herein are mutant photosynthetic organisms having reduced chlorophyll and reduced reduced PSII antenna size where the mutants have a higher amount of Rubisco activase than control photosynthetic organisms. The mutants can have an attenuated SGI1 gene, and can have higher productivity than control photosynthetic organisms.

An SGI1 gene encodes a polypeptide having a response receiver (RR) domain and a myb domain, where the myb domain is C-terminal to the RR domain. In some embodiments the gene encodes a polypeptide that has the domain architecture (beginning from the N-terminal end) RR-linker-myb, where the linker is an amino acid sequence that is not part of the RR domain or the myb domain. The linker can optionally include a nuclear localization sequence (NLS). An SGI1 polypeptide can be a polypeptide having an RR domain N-terminal to a myb domain and separated from the myb domain by a linker that does not belong to either domain, where the polypeptide has a score of at least 350 when scanned with a Hidden Markov Model (HMM) that recognizes the SGI1 domain architecture of algal SGI1 polypeptides, as set forth in Example 6. Examples of such SGI polypeptides are provided in Tables 3 and 4. In various examples, the gene that is attenuated in a mutant as provided herein can (in a wild type organism) encode an SGI1 polypeptide that has a myb domain having at least 55%, at least 60%, at least 65%, at least 70%, at least 75%, at least 80%, at least 85%, at least 90%, or at least 95% amino acid sequence identity to a myb domain such as SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, or SEQ ID NO:75, and/or that includes an RR domain having at least 50%, at least 55%, at least 60%, at least 65%, at least 70%, at least 75%, at least 80%, at least 85%, at least 90%, or at least 95% amino acid sequence identity to an RR domain such as SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, or SEQ ID NO:57. Alternatively or in addition, the gene that is attenuated in a mutant as provided herein can (in a wild type organism) encode a polypeptide that includes an amino acid sequence having at least 50%, at least 55%, at least 60%, at least 65%, at least 70%, at least 75%, at least 80%, at least 85%, at least 90%, or at least 95% amino acid sequence identity to an SGI1 polypeptide such as SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, or SEQ ID NO:39.

Provided herein in some embodiments are mutant algal microorganisms having an attenuated SGI1 gene, where the mutants have higher biomass productivity, or produce more of a bioproduct, than a control algal microorganisms. The algal mutants can have reduced chlorophyll and can have reduced PSII antenna size. In some examples, the SGI1 gene that is attenuated can encode an SGI1 polypeptide that has a myb domain having at least 55%, at least 60%, at least 65%, at least 70%, at least 75%, at least 80%, at least 85%, at least 90%, or at least 95% amino acid sequence identity to a myb domain such as SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, and/or includes an RR domain having at least 50%, at least 55%, at least 60%, at least 65%, at least 70%, at least 75%, at least 80%, at least 85%, at least 90%, or at least 95% amino acid sequence identity to an RR domain such as SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49. Alternatively or in addition, the gene that is attenuated in a mutant alga as provided herein can (in a wild type alga) encode a polypeptide that includes an amino acid sequence having at least 50%, at least 55%, at least 60%, at least 65%, at least 70%, at least 75%, at least 80%, at least 85%, at least 90%, or at least 95% amino acid sequence identity to an SGI1 polypeptide such as SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Further provided herein are algal mutants having an attenuated SGI1 gene that have a higher protein content per unit biomass than the progenitor algae from which they are derived. The high protein content algae can have, for example, at least 5%, at least 10%, at least 15%, or at least 20% more protein on a per biomass basis than a control or wild type alga. In some embodiments the algal SGI1 mutants having increased protein content demonstrate a higher growth rate and/or a higher biomass productivity that the control or wild type algal strains from which they are derived. Also included is a high protein algal biomass, in which the algal biomass comprises mutant algal cells having an attenuated SGI1 gene, where the mutant algal cells have a higher protein content than the control or wild type alga from which they are derived. Further provided is a lysate of algal SGI1 mutant cells. The lysate can optionally have a higher protein content that an algal lysate of wild type algal cells.

A mutant algal microorganisms having an attenuated SGI1 gene can produce more biomass or more of a bioproduct than is produced by a control organism cultured under the substantially the same conditions. The bioproduct can be, for example, biomass, lipid, protein, or a carbohydrate. In various embodiments, an SGI1 mutant can produce more of one or more lipids, one or more proteins, one or more polyketides, a terpenoid, a pigment, an antioxidant, a vitamin, one or more nucleotides, one or more nucleic acids, one or more amino acids, one or more carbohydrates, an alcohol, a hormone, a cytokine, a peptide, or a polymer than is produced by a control alga that does not have an attenuated SGI1 gene. In some embodiments, the mutant alga having an attenuated SGI1 gene produces at least 10%, at least 15%, at least 20%, at least 25%, at least 30%, at least 35%, at least 40%, at least 45%, at least 50%, at least 60%, at least 70%, at least 80%, at least 90% or at least 100% more of a bioproduct than a control alga cultured under the substantially the same conditions, which can be batch, semi-continuous, or continuous culture conditions and may be nutrient replete culture conditions or may be nitrogen deplete conditions, and may be photoautotrophic conditions. Biomass can be measured as, for example, ash free dry weight (AFDW) or total organic carbon (TOC).

Further, an algal mutant having an attenuated SGI1 gene and having higher productivity with respect to a control or wild type alga can have reduced chlorophyll with respect to a control or wild type alga. For example, total chlorophyll may be reduced by about 20% to about 80% with respect to wild type levels, for example, by about 30% to about 70% of wild type levels.

A mutant algal microorganism having an attenuated SGI1 gene as provided herein can have a reduced photosystem II (PSII) antenna size. For example, the cross-sectional unit size of the PSII antenna can be reduced by at least 10%, at least 20%, at least 30%, at least 25%, at least 30%, at least 35%, at least 40%, at least 45%, at least 50%, or at least 60% with respect to the PSII antenna size of the control microorganism.

An algal mutant as provided herein having an attenuated SGI1 gene and demonstrating higher productivity than a control microorganism can optionally additionally have a reduced photosystem I (PSI) antenna. For example, the cross-sectional unit size of the PSII antenna can be reduced by at least 10%, at least 20%, at least 30%, at least 25%, at least 30%, at least 35%, at least 40%, at least 45%, at least 50%, or at least 60% with respect to the PSII antenna size of the control microorganism.

Additionally, a mutant alga as provided herein having an attenuated SGI1 gene can have increased carbon absorption, indicative of the rate of photosynthesis, with respect to a control alga, e.g., increased Pmax (C) with respect to a control alga. Pmax (C) can be increased by about by at least 10%, at least 20%, at least 25%, at least 30%, at least 40%, at least 45%, or at least 50% with respect to the Pmax (C) of a control microorganism.

An algal mutant as provided herein having an attenuated SGI1 gene can further have reduced expression of LHC genes. For example, at least 6, at least 8, at least 10, or at least 12 LHC genes can be downregulated with respect to their expression level in a control cell. The reduction in expression of the LHC genes can be, for example, at least a 20%, 30%, 40%, 50%, 60%, or 70% reduction in the level of LHC transcripts.

Further, an algal mutant as provided herein having an attenuated SGI1 gene can have increased abundance of a Rubisco Activase (RA) polypeptide. The level of RA protein can be, for example, 1.5 fold, 2 fold, 2.5 fold, or greater than 2.5 fold the level of a control or wild type cell. One or both of an RA alpha isozyme or an RA beta isozyme can be increased in a high productivity mutant as provided herein. The level of an RA transcript can also be elevated in an algal mutant as provided herein, for example, from about 1.2 fold to 10 fold wild type levels or more. Provided herein in some embodiments is a low chlorophyll algal mutant having reduced PSII antenna size and increased expression of RA. The reduction in PSII antenna size can be for example, at least 20% or at least 30% with respect to wild type PSII antenna size, and the increase in RA protein level can be at least two-fold wild type.

In various embodiments a high productivity algal mutant as provided herein that has an attenuated SGI1 gene has at least 10%, at least 12%, at least 14%, at least 15%, at least 17%, or at least 20% more protein on a per TOC basis than a control alga. For example, the high productivity algal mutant can produce at least 10%, at least 20%, at least 25%, at least 30%, at least 35%, at least 40%, at least 45%, at least 50%, of at least 60% more protein than a control cell on a daily basis in a batch, continuous, or semi-continuous culture system.

A mutant algal microorganism as provided herein can be any eukaryotic microoalga, such as but not limited to a Chlorophyte or Charyophyte alga. For example, the mutant microalga can be a Chlorophyte alga of the the Chlorophyceace, the Chlorodendrophyceae, the Prasinophyceace, or the Trebouxiophyceae class. In some embodiments, the mutant microalga can be a member of the Chlorophyceace, such as a species of *Asteromonas, Ankistrodesmus, Carteria, Chlamydomonas, Chlorococcum, Chlorogonium, Chrysosphaera, Dunaliella, Haematococcus, Monoraphidium, Neochloris, Oedogonium, Pelagomonas, Pleurococcus, Pyrobotrys, Scenedesmus*, or *Volvox*. In alternative embodiments, the mutant microalga can be a member of the Chlorodendrophyceae, such as a species of *Prasinocladus, Scherffelia*, or *Tetraselmis*. In further alternative embodiments, the mutant alga can be a member of the Prasinophyceace, optionally a species of *Ostreococcus* or *Micromonas*. Further alternatively, the mutant microalga can be a member of the Chlorodendrophyceae, such as a species of *Prasinocladus, Scherffelia*, or *Tetraselmis*, or can be a member of the Trebouxiophyceae, optionally a species of a genus selected from the group consisting of *Botryococcus, Chlorella, Auxenochlorella, Heveochlorella, Marinichlorella, Parachlorella, Pseudochlorella, Tetrachlorella, Eremosphaera, Franceia, Micractinium, Nannochloris, Oocystis, Picochlorum, Prototheca, Stichococcus*, or *Viridiella*.

A further aspect of the invention is a method of making a bioproduct, where the method includes culturing an mutant photosynthetic mutant as provided herein that has an attenuated SGI1 gene to produce the bioproduct. The method can further include recovering the bioproduct from the culture or organism. For example, the product can be recovered from the culture medium, harvested algal cells, or whole culture, or can be isolated from plants by harvesting or homogenizing plant tissue, for example. The bioproduct can be, for example, biomass, protein, lipid, or carbohydrate. Further, the product can be one or more lipids, proteins, polyketides, terpenoids, pigments, antioxidants, vitamins, nucleotides, nucleic acids, amino acids, carbohydrates, alcohols, hormones, cytokines, peptides, or polymers. In some embodiments, the product is a high protein biomass, where protein constitutes at least 50% of the TOC of the photosynthetic organism or tissue therefrom. In alternative embodiments, the product is lipid, and may be, for example, triglyceride.

The method can include culturing an algal SGI1 mutant in batch, semi-continuous, or continuous culture where the culture medium may be nutrient replete, or may be, for example, nitrogen deplete. The culturing can be under photoautotrophic conditions, in which inorganic carbon, e.g., carbon dioxide or carbonate, is substantially the sole carbon source in the culture medium for the production of organic molecules by the algal mutant.

Yet another aspect of the invention is a method of isolating a mutant alga having higher productivity with respect to the progenitor alga from which it is derived. The method includes: culturing an algal strain under semi-continuous or continuous photoautotrophic conditions for at least twenty generations and isolating at least one mutant line from the culture, where the isolated line has a higher growth rate than the progenitor algal strain. The method can include a mutagenesis step prior to the culturing. Mutagenesis can be by UV, gamma irradiation, chemical mutagens, random insertional mutagenesis, or targeted mutagenesis, for example. In various embodiments, the algae are exposed to constant light during the culturing. In various embodiments, the light intensity to which the algae are exposed during the culturing is at least 500 uE, at least 600 uE, at least 700 uE, at least 800 uD, at least 900 uE, at least 1000 uE, at least 1100 uE, at least 1200 uD, at least 1400 uE, at least 1600 uE, at least 1800 uE, at least 2000 uE, at least 2200 uE, at least 2500 uE, or at least 3000 uE.

The isolated line having a higher growth rate can be assayed for higher productivity with respect to the progenitor line, for example, in batch, semicontinuous, or continuous culture. Isolating a high productivity mutant can optionally further include: measuring one or more of Fv/Fm, sigma, PSII, PSI, or Pmax (C) (Pmax for carbon fixation).

The method can further include sequencing the genome of the isolated high productivity mutant to identify the mutation.

Yet another aspect of the invention is a method of selecting for high productivity algal mutants, where the method includes: mutagenizing a population of algae, selecting low chlorophyll cells using fluorescence activated cell sorting (FACS), distributing isolated lines of the selected low chlorophyll fluorescence cells in multiwell plates, screening the low chlorophyll fluorescence cells in multiwell plates for photosystem II (PSII) antenna size, Fv/Fm, and selecting at least one cell line having reduced PSII antenna size, increased Fv/Fm, and increased with respect to wild type cells, to select a high productivity mutant. The method can optionally further include measuring Pmax. The isolated line having a higher growth rate can be assayed for higher productivity with respect to the progenitor line, for example, in batch, semicontinuous, or continuous culture. The method can further include performing PCR and/or sequencing at least a portion of the genome of the isolated high productivity mutant to identify the mutation.

BRIEF DESCRIPTION OF THE DRAWINGS

FIG. 4 is an alignment of the Response Regulator receiver (RR) domain of algal SGI1 polypeptides. The sequences shown are *Parachlorella* sp. WT-1185 (SEQ ID NO:58), *Coccomyxa subellipsoidea* (SEQ ID NO:59), *Ostreococcus lucimarinus* (SEQ ID NO:60), *Chlamydomonas reinhardtii* (SEQ ID NO:61), *Chromochloris zofingiensis* (SEQ ID NO:62), *Volvox carteri* (SEQ ID NO:63), *Tetraselmis* sp. 105 (SEQ ID NO:64), *Oocystis* sp. (SEQ ID NO:65), and *Micromonas* sp. RCC299 (SEQ ID NO:66).

FIG. 5 is an alignment of the myb domain of algal SGI1 polypeptides. The sequences shown are *Parachlorella* sp. WT-1185 (SEQ ID NO:40), *Coccomyxa subellipsoidea* (SEQ ID NO:41), *Ostreococcus lucimarinus* (SEQ ID NO:42), *Chlamydomonas reinhardtii* (SEQ ID NO:43), *Chromochloris zofingiensis* (SEQ ID NO:44), *Volvox carteri* (SEQ ID NO:45), *Tetraselmis* sp. 105 (SEQ ID NO:46), *Oocystis* sp. (SEQ ID NO:47), and *Micromonas* sp. RCC299 (SEQ ID NO:48).

FIGS. 17A-17D provides graphs showing photophysiological measurements of the Cas9 targeted *Tetraselmis* SGI1 mutants A) PSII cross-section measured at 450 nm, B) PSII cross-section measured at 520 nm, C) Fv/Fm, and D) PSII turnover rate.

FIGS. 18A-18C provides graphs showing photophysiological measurements of the Cas9 targeted *Tetraselmis* SGI1 mutants A) 14C Pmax per cell, B) 14C Pmax per TOC, and C) growth rate.

DETAILED DESCRIPTION OF THE INVENTION

Figures 1A, 1B:
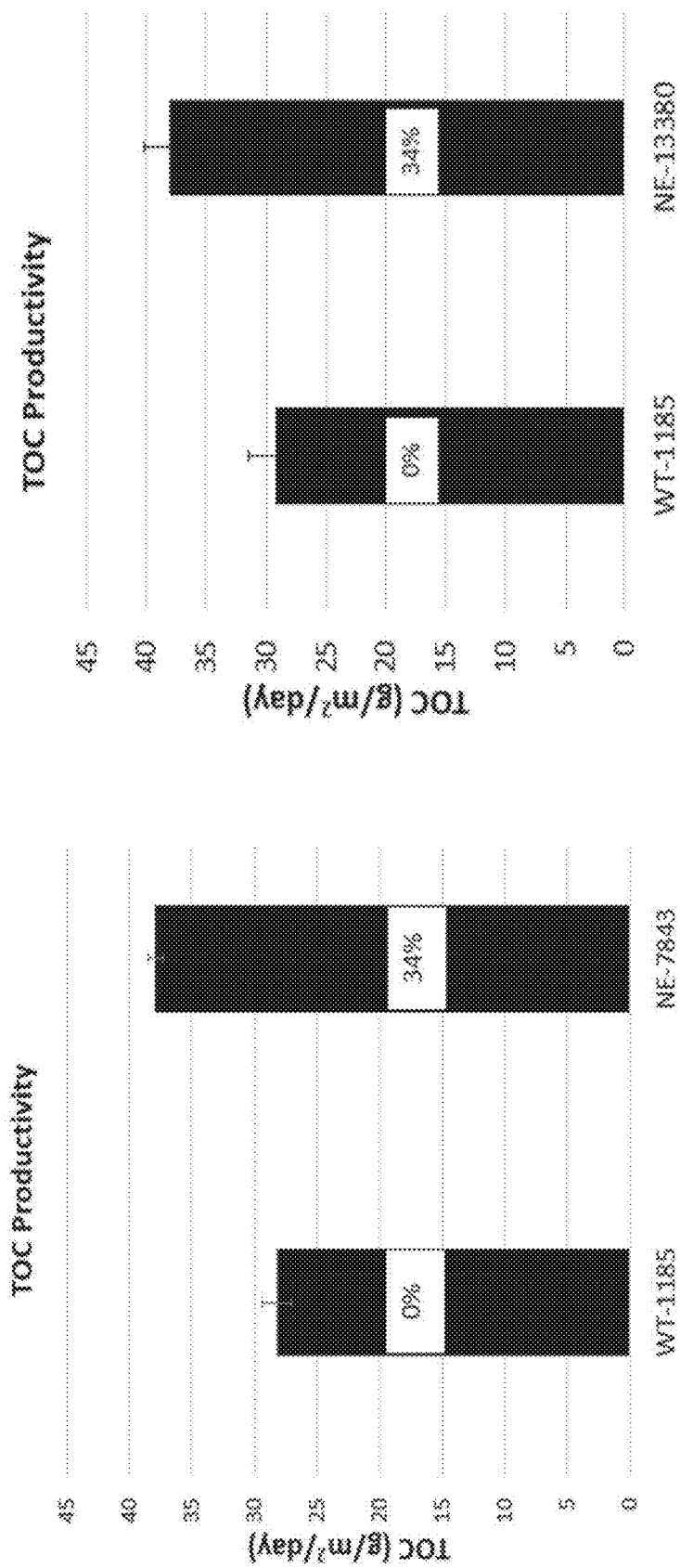
FIGS. 1A-1B provides graphs showing TOC productivity improvement of *Parachlorella* classical mutants A) NE-7843 and B) NE-13380 over WT-1185 under continuous light semicontinuous culture conditions (65% daily dilution, 2000uE, 1% CO2). The represented data is from biological duplicate cultures.

Provided herein are algal mutants having reduced chlorophyll and higher photosynthetic efficiency with respect to control algae, in which the algal mutants have attenuated expression of a gene encoding a polypeptide having a Response Receiver Domain and a homeodomain. The bacterial CheY protein is a known member of a two component system that effects transcriptional change in response to environmental signals.

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All ranges provided within the application are inclusive of the values of the upper and lower ends of the range unless specifically indicated otherwise.

All publications, patents and other references mentioned herein are incorporated by reference in their entireties for all purposes as if each individual publication or patent application were specifically and individually indicated to be incorporated by reference.

The term "and/or" as used in a phrase such as "A and/or B" herein is intended to include "A and B", "A or B", "A", and "B".

"About" means either within 10% of the stated value, or within 5% of the stated value, or in some cases within 2.5% of the stated value, or, "about" can mean rounded to the nearest significant digit.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, "gene" may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single stranded nucleic acid molecule that comprises a gene or a portion thereof can be a coding (sense) strand or a non-coding (antisense) strand.

A nucleic acid molecule or polypeptide may be "derived from" an indicated source, which includes the isolation (in whole or in part) of a nucleic acid segment or polypeptide from an indicated source. A nucleic acid molecule may also be derived from an indicated source by, for example, direct cloning, PCR amplification, or artificial synthesis from the indicated polynucleotide source or based on a sequence associated with the indicated polynucleotide source, which may be, for example, a species of organism.

Genes or nucleic acid molecules derived from a particular source or species also include genes or nucleic acid molecules having sequence modifications with respect to the source nucleic acid molecules, that is, the sequence of the gene or nucleic acid molecule is derived from the sequence of a gene or nucleic acid molecule from the referenced source or species but may have modifications. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 65%, at least 70%, at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

Similarly, a polypeptide or protein derived from a particular source or species includes polypeptides or proteins having sequence modifications with respect to the source prolypeptide, that is, the polpeptide is derived from the sequence of a polypeptide from the referenced source or species but may have modifications. For example, a polypeptide or protein derived from a source (e.g., a particular referenced protein) can include one or more mutations (amino acid differences) with respect to the source polypeptide that are unintended or that are deliberately introduced (for example, by mutation of the encoding nucleic acid molecule). A polypeptide that is derived from a referenced polypeptide can have at least 60%, at least 65%, at least 70%, at least 75%, at least 80%, at least 85%, at least 90%, or at least 95% sequence identity with the referenced or source polypeptide, or to a functional fragment thereof. For example, a polypeptide that is derived from a referenced polypeptide can have at least 80%, or at least 85%, at least 90%, at least 95%, at least 96%, at least 97%, at least 98%, or at least 99% sequence identity with the referenced or source polypeptide, or a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be substantially free of chemicals beyond buffer or solvent, for example. "Substantially free" is not intended to mean that other components beyond the novel nucleic acid molecules are undetectable.

The terms "naturally-occurring" and "wild type" refer to a form found in nature. For example, a naturally occurring or wild type nucleic acid molecule, nucleotide sequence or protein may be present in and isolated from a natural source, and is not intentionally modified by human manipulation.

As used herein "attenuated" means reduced in amount, degree, intensity, or strength. An attenuated gene is a gene that produces less of its encoded product and/or produces a less functional encoded product, with respect to a non-attenuated, or wild type, gene. An attenuated gene can in some examples produces none of its encoded product, or can produce a gene product (polypeptide) that is completely inactive. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, truncation, frameshifting, or insertional mutation) that does not encode a complete functional open reading frame or that has decreased expression due to alteration or disruption of gene regulatory sequences. An attenuated gene can also be a gene that has one or more mutations affecting the amino acid sequence of the encoded polypeptide, where the encoded polypeptide is reduced in amount and/or activity by the mutation(s). An attenuated gene may also be a gene targeted by a construct that reduces expression of the gene, such as, for example, an antisense RNA, microRNA, RNAi molecule, or ribozyme. Attenuated gene expression can be gene expression that is eliminated, for example, reduced to an amount that is insignificant or undetectable. Attenuated gene expression can also be gene expression that results in an RNA or protein that is not fully functional or nonfunctional, for example, attenuated gene expression can be gene expression that results in a truncated RNA and/or polypeptide.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene or nucleic acid molecule may be derived from a different species (and so "heterologous"), or from the same species (and so "homologous"), relative to the cell being transformed. An "endogenous" nucleic acid molecule, gene or protein is a native nucleic acid molecule, gene, or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. Thus, a "non-native" nucleic acid molecule is a nucleic molecule that is not naturally present in the host cell, for example, the non-native nucleic acid molecule is exogenous to the host cell or microorganism into which it is introduced, and may be heterologous with respect to the host cell or microorganism. Additionally, a nucleic acid sequence or amino acid sequence that has been removed from a cell, subjected to laboratory manipulation, and introduced or reintroduced into a host cell such that it differs in sequence or location in the genome with respect to its position in a non-manipulated organism (i.e., is juxtaposed with or operably linked to sequences it is not juxtaposed with or operably linked to in a non-transformed organism) is considered "non-native". Non-native genes also include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering regardless of whether the amino acid varies from that of a wild-type protein.

When applied to organisms, the term recombinant, engineered, or genetically engineered refers to organisms that have been manipulated by introduction of a heterologous or exogenous recombinant nucleic acid sequence into the organism (e.g., a non-native nucleic acid sequence), and includes gene knockouts, targeted mutations, gene replacement, and promoter replacement, deletion, disruption, or insertion, as well as introduction of transgenes or synthetic genes or nucleic acid sequences into the organism. That is, recombinant, engineered, or genetically engineered refers to organisms that have been altered by human intervention. Recombinant or genetically engineered organisms can also be organisms into which constructs for gene "knockdown" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or cas/CRISPR systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain $-10$ and $-35$ prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within 1 kb, 2 kb, 3 kb, 4 kb, 5 kb or more of the transcriptional start site of a gene, where the additional sequences can influence the rate of transcription of the downstream gene and optionally the responsiveness of the promoter to developmental, environmental, or biochemical (e.g., metabolic) conditions.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" [of a gene product] includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination or targeted integration or mutation using a cas/CRISPR system to knockout a particular gene of interest. In still other embodiments, targeted insertion into or mutation of a gene regulatory region using a cas/CRISPR system, RNAi, or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, "mutant" refers to an organism that has a mutation in a gene that is the result of classical mutagenesis, for example, using gamma irradiation, UV, or chemical mutagens, or is a recombinant organism that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, TALENs, and/or CRISPR technologies, and the like. A mutant is therefore not a naturally-occurring organism and is the result of human intervention. A mutant organism of interest will typically have a phenotype different than that of the corresponding wild type or progenitor strain that lacks the mutation, where the phenotype can be assessed by growth assays, product analysis, photosynthetic properties, biochemical assays, etc. When referring to a gene "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region, e.g., within 2 kb of the transcriptional start site or within 3 kb or the translational start site. For example, a mutant having attenuated expression of a gene as disclosed herein can have a mutation, which can be one or more nucleobase changes and/or one or more nucleobase deletions and/or one or more nucleobase insertions, into the region of a gene 5' of the transcriptional start site, such as, in non-limiting examples, within 2 kb, within 1.5 kb, within 1 kb, or within 0.5 kb of the known or putative transcriptional start site, or within 3 kb, within 2.5 kb, within 2 kb, within 1.5 kb, within 1 kb, or within 0.5 kb of the translational start site. As nonlimiting examples, a mutant gene can be a gene that has a mutation, insertion, or deletion within the promoter region that can either increase or decrease expression of the gene; can be a gene that has a deletion that results in production of a nonfunctional protein, truncated protein, dominant negative protein, or no protein; can be a gene that has one or more point mutations leading to a change in the amino acid of the encoded protein or results in aberrant splicing of the gene transcript, etc.

Conserved domains of polypeptides include those identified in the "cd" (conserved domain) database, the COG database, the SMART database, the PRK database, the TIGRFAM database, the InterPro database (ebi.ac.uk/interpro/) or others known the art. The National Center for Biotechnology Information website (ncbi.nlm nih.gov/Structure/cdd/wrpsb.cgi) sponsored by the U.S. National Institutes of Health includes a conserved domain database (CDD) which it describes as "a protein annotation resource that consists of a collection of well-annotated multiple sequence alignment models for ancient domains and full-length proteins. These are available as position-specific score matrices (PSSMs) for fast identification of conserved domains in protein sequences via RPS-BLAST. CDD content includes NCBI-curated domains, which use 3D-structure information to explicitly define domain boundaries and provide insights into sequence/structure/function relationships, as well as domain models imported from a number of external source databases (Pfam, SMART, COG, PRK, TIGRFAM)."

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. The latest release of Pfam is Pfam 30.0 (May 2016). Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) Nucleic Acids Research 26, 263-266; Bateman (2004) *Nucleic Acids Research* 32, Database Issue, D138-D141; Finn (2006) *Nucleic Acids Research* Database Issue 34, D247-251; Finn (2010) *Nucleic Acids Research* Database Issue 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be double stranded or single stranded and can be, for example, the complement of the mRNA sequence. In preferred examples, a cDNA does not include one or more intron sequences that occur in the naturally-occurring gene that the cDNA corresponds to (i.e., the gene as it occurs in the genome of an organism). For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences multiple partial cDNAs.

Reference to properties that are "substantially the same" or "substantially identical" without further explanation of the intended meaning, is intended to mean the properties are within 10%, and preferably within 5%, and may be within 2.5%, of the reference value. Where the intended meaning of "substantially" in a particular context is not set forth, the term is used to include minor and irrelevant deviations that are not material to the characteristics considered important in the context of the invention.

A "control cell" "control organism" or "control microorganism" is either a wild type cell, organism, or microorganism from which a mutant cell, organism, or microorganism (genetically engineered or mutagenized cell, organism, or microorganism) is directly or indirectly derived, or is a cell, organism, or microorganism that is substantially identical to the mutant cell, organism, or microorganism referred to, with the exception that the control cell, organism, or microorganism does not have the mutation resulting in increased productivity, for example, the control cell, organism, or microorganism has not been genetically engineered or mutagenized to attenuate an SGI1 gene. For example, where the recombinant alga comprises mutation in an SGI1 gene, a control alga can be substantially identical to the recombinant alga with the exception that the control alga does not comprise a mutation in the SGI1 gene.

"The same conditions" or "the same culture conditions", as used herein, means substantially the same conditions, that is, any differences between the referenced conditions that may be present are minor and not relevant to the function or properties of the microorganism that are material to the invention, including lipid production or biomass production.

As used herein "lipid" or "lipids" refers to fats, waxes, fatty acids, fatty acid derivatives such as fatty alcohols, wax esters, alkanes, and alkenes, sterols, monoglycerides, diglycerides, triglycerides, phospholipids, sphingolipids, saccharolipids, and glycerolipids. "FAME lipids" or "FAME" refers to lipids having acyl moieties that can be derivatized to fatty acid methyl esters, such as, for example, monoacylglycerides, diacylglycerides, triacylglycerides, wax esters, and membrane lipids such as phospholipids, galactolipids, etc. Lipid productivity can be assessed as FAME productivity in milligrams per liter (mg/L) and for algae, may be reported as grams per meter$^2$ per day (g/m$^2$/day). In the semi-continuous assays provided herein, mg/L values are converted to g/m2/day by taking into account the area of incident irradiance (the SCPA flask rack aperture of 1½"× 3⅜", or 0.003145 m$^2$) and the volume of the culture (550 ml). To obtain productivity values in g/m$^2$/day, mg/L values are multiplied by the daily dilution rate (30%) and a conversion factor of 0.175. Where lipid or subcategories thereof (for example, TAG or FAME) are referred to as a percentage, the percentage is a weight percent unless indicated otherwise.

As used herein, the term "fatty acid product" includes free fatty acids, mono-di- or triglycerdes, fatty aldehydes, fatty alcohols, fatty acid esters (including, but not limited to, wax esters); and hydrocarbons, including, but not limited to, alkanes and alkenes).

"Biomass" refers to cellular mass, whether of living or dead cells, and can be assessed, for example, as wet weight or aspirated pellet weight, or as dry weight (e.g., lyophilate of a culture sample or pelleted cells), ash-free dry weight (AFDW), or total organic carbon (TOC), using methods known in the art. Biomass increases during the growth of a culture under growth permissive conditions and may be referred to as "biomass accumulation" in batch cultures, for example. In continuous or semi-continuous cultures that undergo steady or regular dilution, biomass that is produced that would otherwise accumulate in the culture is removed during culture dilution. Thus, daily biomass productivity (increases in biomass) by these cultures can also be referred to as "biomass accumulation". Biomass productivity can be assessed as TOC productivity in milligrams per liter (mg/L) and for algae, may be reported as grams per meter$^2$ per day (g/m$^2$/day). In the semi-continuous assays provided herein, mg/L values are converted to g/m2/day by taking into account the area of incident irradiance (the SCPA flask rack aperture of 1½"×3⅜", or 0.003145 m$^2$) and the volume of the culture (550 ml). To obtain productivity values in g/m$^2$/day, mg/L values are multiplied by the daily dilution rate (30%) and a conversion factor of 0.175. Where biomass is expressed as a percentage, the percentage is a weight percent unless indicated otherwise.

In the context of the invention, a "nitrogen source" is a source of nitrogen that can be taken up and metabolized by the subject microorganism and incorporated into biomolecules for growth and propagation. For example, compounds including nitrogen that cannot be taken up and/or metabolized by the microorganism for growth (e.g., nitrogen-containing biological buffers such as Hepes, Tris, etc.) are not considered nitrogen sources in the context of the invention.

"Reduced nitrogen", as used herein, is nitrogen in the chemical form of ammonium, ammonia, urea, or an amino acid that can be taken up and metabolized by the microorganism being cultured to provide a source of nitrogen for incorporation into biomolecules, thereby supporting growth. For example, in addition to ammonium/ammonia and urea, reduced nitrogen can include various amino acids where the amino acid(s) can serve as a nitrogen source to the subject microorganism. Examples of amino acids can include, without limitation, glutamate, glutamine, histidine, lysine, arginine, asparagine, alanine, and glycine. "Non-reduced nitrogen" in the context of a nitrogen source that can be present in a culture medium for microorganisms refers to nitrate or nitrite that must be reduced prior to assimilation into organic compounds by the microorganism.

"The sole source of nitrogen [in the culture medium]" is used interchangeably with "substantially the sole source of nitrogen" and indicates that no other nitrogen source is intentionally added to the culture medium, or that no other nitrogen source is present in an amount sufficient to significantly increase the growth of the microorganisms or cells cultured in the referenced medium. Throughout this application, for brevity, the terms "nitrate-only" is used to characterize culture media in which nitrate is the only source of nitrogen that is available to the microorganisms for supporting growth.

Similarly, "the sole source of carbon [in the culture medium]" is used interchangeably with "substantially the sole source of carbon" and indicates that no other carbon source is present in an amount sufficient to increase the productivity, growth, or propagation of the microorganisms or cells cultured in the referenced medium or become incorporated into biomolecules such as lipids produced by the microorganisms or cells.

"Nitrogen replete" conditions refer to media conditions in which no further growth or propagation benefit is conferred by adding additional nitrogen (in a form that can be used by the microorganism) to the medium. Similarly, "nutrient replete" conditions refer to media conditions in which no nutrient is limiting to growth or propagation, that is, when a medium is nutrient replete, adding additional nutrient(s) to the medium does not result in an improved growth or propagation rate. In the context of "nutrient replete", "nutrients" includes, as nonlimiting examples, phosphate, sulfur, iron, and optionally silica, but excludes carbon sources such as sugars or organic acids that may be used by the organism as an energy source.

SGI1 Polypeptides

As described herein, SGI1 or "Significant Growth Improvement 1" polypeptides are polypeptides that include a Response Regulator receiver or "RR" domain (pfam PF00072) and a Myb-like binding domain, referred to herein simply as a "myb" domain (pfam PF00249), where the RR domain is positioned N-terminal to the myb domain. The amino acid sequence of an SGI1 polypeptide that encompasses the RR domain and myb domain includes a stretch of amino acids that occurs between the RR and myb domains that is found to be poorly conserved or not conserved among SGI1 polypeptides. The amino acid sequence occurring between the RR domain and myb domain may be referred to herein as a linker between the two domains. The linker may be of any length, and in various examples may range in length from one to about 300 amino acids, from ten to about 200 amino acids, or from twenty to about 150 amino acids in length. The linker region can optionally include a nuclear localization sequence (NLS).

An RR domain within an SGI1 protein can be characterized as pfam PF00072, or as a "signal receiver domain" or simply "receiver domain", and/or can be classified as cd00156 in the conseved domain database (CDD), as COG0784 in the Clusters of Orthologous Groups of proteins database, or as an Interpro "CheY-like superfamily" domain, IPR011006. The RR domain is found in bacterial two-component regulatory systems (like the bacterial chemotaxis two-component system that includes a polypeptide known as CheY), in which it receives a signal from a sensor partner. The RR domain of such systems is often found N-terminal to a DNA binding domain and can include a phosphoacceptor site. FIG. 4 provides an alignment of the RR domains of *Parachlorella* sp. WT-1185 (SEQ ID NO:58), *Coccomyxa subellipsoidea* (SEQ ID NO:59), *Ostreococcus lucimarinus* (SEQ ID NO:60), *Chlamydomonas reinhardtii* (SEQ ID NO:61), *Chromochloris zofingiensis* (SEQ ID NO:62), *Volvox carteri* (SEQ ID NO:63), *Tetraselmis* sp. 105 (SEQ ID NO:64), *Oocystis* sp. WT-4183 (SEQ ID NO:65), and *Micromonas* sp. RCC299 (SEQ ID NO:66).

A myb domain within an SGI1 protein can be characterized, for example, as pfamPF00249: "Myb-like DNA-binding domain", and/or may be identified as conserved domain TIGR01557 "myb-like DNA-binding domain, SHAQKYF class", or as an Interpro Homeobox-like domain superfamily domain (IPR009057) and/or an Interpro Myb domain (IPR017930).

In addition to having an RR domain N-terminal to a myb domain, an SGI1 protein as provided herein can have a score of 300 or higher, 320 or higher, 340 or higher, 350 or higher, 360 or higher, or 370 or higher with an e-value of less than about 1e-10, 1e50, 1e-70, or 1e-100, when scanned with a Hidden Markov Model (HMM) designed to score proteins on the basis of how well a protein's amino acid sequence matches the conserved amino acids of a region of SGI1 homologs in algae (see Example 6). The region of SGI1 polypeptides used to develop the HMM is the amino acids sequence that includes (proceeding in the N-terminal to C-terminal direction) the RR domain, the linker, and the myb domain. In an HMM, highly conserved amino acid positions are weighted more heavily than poorly conserved amino acid positions within a compared region of the polypeptides to arrive at the score. Polypeptides having scores of at least about 300, or of 350 or greater, such as for example 370 or greater, when scanned with an HMM model based on protein sequences of algal SGI1 polypeptides that include a single continuous sequence that includes the RR domain, linker, and myb domain developed using include, without limitation, polypeptides of the algal and plant species *Parachlorella* sp. 1185 (SEQ ID NO:3), *Coccomyxa subellipsoidea* (SEQ ID NO:9), *Ostreococcus lucimarinus* (SEQ ID NO:10), *Chlamydomonas reinhardtii* (SEQ ID NO:11), *Volvox carteri* (SEQ ID NO:13), *Tetraselmis* sp. 105 (SEQ ID NOs:14, 15, and 16), *Oocystis* sp. (SEQ ID NO:17), *Micromonas* sp. RCC299 (SEQ ID NO:18), *Micromonas pusilla* (SEQ ID NO:19), *Sphagnum fallax* (SEQ ID NO:20), *Physcomitrella patens* (SEQ ID NO:21), *Arabidopsis thaliana* (SEQ ID NO:22), *Arabidopsis halleri* (SEQ ID NO:23), *Arabidopsis lyrata* (SEQ ID NO:24), *Helianthus annuus* (SEQ ID NO:25), *Vitis vinifera* (SEQ ID NO:26), *Amborella trichopoda* (SEQ ID NO:27), *Ricinus communis* (SEQ ID NO:28), *Solanum lycopersicum* (SEQ ID NO:29), *Solanum tuberosum* (SEQ ID NO:30), *Gossypium hirsutum* (SEQ ID NO:31), *Theobroma cacao* (SEQ ID NO:32), *Phaeolis vulgaris* (SEQ ID NO:33), *Glycine max* (SEQ ID NO:34), *Chenopodium quinoa* (SEQ ID NO:35), *Malus domesticus* (SEQ ID NO:36), *Zea mays* (SEQ ID NO:37), *Brassica rapa* (SEQ ID NO:38), and *Oryza sativa* (SEQ ID NO:39). Also included as SGI1 polypeptides polypeptides having at least 50%, at least 55%, at least 60%, at least 65%, at least 70%, at least 75%, at least 80%, at least 85%, at least 90%, at least 95%, at least 96%, at least 97%, at least 98%, or at least 99% identity to any of the aforegoing, where the polypeptide has an RR domain and a myb domain, and the RR domain is N-terminal to the myb domain, where the SGI1 polypeptide is a naturally-occurring polypeptide or a variant thereof. In various embodiments, the SGI1 polypeptide is from a plant or algal species, i.e., is a naturally-occurring polypeptide of a plant or algal species. A gene encoding an SGI1 polypeptide as provided herein, for example a gene that is disrupted or whose expression is attenuated in a mutant as provided herein can be, in various embodiments, a naturally-occurring gene of a plant or algal species that encodes a polypeptide as disclosed herein.

In some embodiments, an SGI1 polypeptide as provided herein is an algal SGI1 polypeptide, for example, having the sequence of a naturally-occurring algal SGI1 polypeptide, where the algal polypeptide includes an RR domain and a myb domain, and the RR domain is N-terminal to the myb domain. The algal polypeptide can optionally have at least 50%, at least 55%, at least 60%, at least 65%, at least 70%, at least 75%, at least 80%, at least 85%, at least 90%, at least 95%, at least 96%, at least 97%, at least 98%, or at least 99% identity to any of the algal SGI1 polypeptides disclosed herein. In some embodiments, an SGI1 gene can be a gene encoding an algal SGI1 polypeptide, such as for example, a polypeptide having the sequence of a naturally-occurring algal SGI1 polypeptide. An SGI1 gene that encodes a polypeptide having the sequence of a naturally-occurring algal SGI polypeptide can be a gene having a naturally-occurring gene sequence of gene-encoding sequence, or can have a sequence that varies from the sequence of a naturally-occurring gene. In various embodiments, an SGI1 gene that is attenuated, mutated, or disrupted in a mutant photosynthetic organism as disclosed herein can be a gene that is identified through BLAST, for example, using one or more sequences disclosed herein as queries, and/or by HMM scanning, where the HMM is built from amino acid sequences, for example upon multiple alignment of at least six SGI1 polypeptides, where the amino acid sequences include an RR domain and a myb domain, where the RR domain is N-terminal to the myb domain, and where there is a linker sequence between the RR and myb domains that does not belong to either domain.

In some embodiments, an SGI1 polypeptide has the sequence of an algal SGI1 polypeptide or is a variant of a naturally-occurring algal SGI1 polypeptide having at least 85%, at least 90%, or at least 95% identity to an RR domain of a naturally-occurring algal SGI1 polypeptide and/or has at least 50%, at least 55%, at least 60%, at least 65%, at least 70%, at least 75%, at least 80%, at least 85%, at least 90%, at least 95%, at least 96%, at least 97%, at least 98%, or at least 99% identity to any of SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49. In some embodiments, an SGI1 polypeptide has the sequence of an algal SGI1 polypeptide or is a variant of a naturally-occurring algal SGI1 polypeptide having at least 85%, at least 90%, or at least 95% identity to a myb domain of a naturally-occurring algal SGI1 polypeptide and/or has at least 50%, at least 55%, at least 60%, at least 65%, at least 70%, at least 75%, at least 80%, at least 85%, at least 90%, at least 95%, at least 96%, at least 97%, or at least 98%, or at least 99% identity to any of SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67.

In some embodiments, an SGI1 polypeptide has the sequence of an algal SGI1 polypeptide or is a variant of a naturally-occurring algal SGI1 polypeptide having at least 85%, at least 90%, or at least 95% identity to a naturally-occurring algal SGI1 polypeptide and/or has at least 50%, at least 55%, at least 60%, at least 65%, at least 70%, at least 75%, at least 80%, at least 85%, at least 90%, at least 95%, at least 96%, at least 97%, at least 98%, or at least 99% identity to any of SEQ ID NO:3, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

In some embodiments, an SGI polypeptide has the sequence of a plant SGI1 polypeptide or is a variant of a naturally-occurring plant SGI1 polypeptide having at least 85%, at least 90%, or at least 95% identity to a naturally-occurring algal SGI polypeptide and/or has at least 50%, at least 55%, at least 60%, at least 65%, at least 70%, at least 75%, at least 80%, at least 85%, at least 90%, at least 95%, at least 96%, at least 97%, at least 98%, or at least 99% identity to an RR domain of, SEQ ID NO:50, SEQ ID NO:51, SEQ ID NO:52, SEQ ID NO:53, SEQ ID NO:54, SEQ ID NO:55, SEQ ID NO:56, or SEQ ID NO:57. In some embodiments, an SGI polypeptide has the sequence of a plant SGI1 polypeptide or is a variant of a naturally-occurring plant SGI1 polypeptide having at least 85%, at least 90%, or at least 95% identity to a naturally-occurring algal SGI polypeptide and/or has at least 50%, at least 55%, at least 60%, at least 65%, at least 70%, at least 75%, at least 80%, at least 85%, at least 90%, at least 95%, at least 96%, at least 97%, at least 98%, or at least 99% identity to a myb domain of SEQ ID NO:68, SEQ ID NO:69, SEQ ID NO:70, SEQ ID NO:71, SEQ ID NO:72, SEQ ID NO:73, SEQ ID NO:74, or SEQ ID NO:75.

In some embodiments, an SGI polypeptide has the sequence of a plant SGI1 polypeptide or is a variant of a naturally-occurring plant SGI1 polypeptide having at least 85%, at least 90%, or at least 95% identity to a naturally-occurring algal SGI polypeptide and/or has at least 50%, at least 55%, at least 60%, at least 65%, at least 70%, at least 75%, at least 80%, at least 85%, at least 90%, at least 95%, at least 96%, at least 97%, at least 98%, or at least 99% identity to any of SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, or SEQ ID NO:39.

Mutant Strains

Mutants provided herein that have an attenuated SGI1 gene include photosynthetic organisms, such as eukaryotic photosynthetic organisms, including plants and algae, such as single celled eukaryotic algae (microalgae).

An algal strain having a mutated SGI1 gene which can be, in various examples, a strain genetically engineered to have attenuated expression of an SGI1 gene, can be any eukaryotic algal strain such as, for example, a species of any of the genera *Achnanthes, Amphiprora, Amphora, Ankistrodesmus, Asteromonas, Boekelovia, Bolidomonas, Borodinella,*

*Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phwodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*.

For example, an alga having a mutation in an SGI1 gene as disclosed herein can be a species belonging to any of the phyla ochrophyta (including members of the bacillariophyceae, coscinodiscophyceae, fragilariophyceae, eustigmatophyceae, xanthophyceae, pelagophyceae, chrysophyceae, raphidophyceae, and synurophyceae), haptophyta (including members of the coccolithophyceae and pavlophyceae), and chlorophyta (including members of the trebouxiophyceae, chlorophyceae, nephrophyceae, pyramimonadophyceae, ulvophyceae, mamiellophyceae, and chlorodendrophyceae), as well as the charyophyta, euglenoids, and dinoflagellates.

In some embodiments of the present application, preferred microorganisms that may be mutated or genetically engineered include, but are not limited to, chlorophyte species such as *Chlorella, Parachlorella, Pseudochlorella, Tetrachlorella, Auxenochlorella, Prototheca, Oocystis, Franceia, Micratinium, Picochlorum, Nannochloris, Schizochlamydella, Eremosphaera, Stichococcus, Botryococcus, Viridiella, Parietochloris Borodinella, Bracteacoccus, Neochloris, Monoraphidium, Desmodesmus, Scenedesmus, Ankistrodesmus, Carteria, Chlamydomonas, Chlorococcum, Chlorogonium, Volvox, Platymonas, Dunaliella, Haematococcus, Asteromonas, Pyrobotrys, Oedogonium, Nephroselmis, Pleurococcus, Pyramimonas, Pseudoneochloris, Ostreococcus, Tetraselmis*, and *Staurastrum*.

In other examples, mutants can be engineered or isolated using a heterokont algal species such as a diatom species such as, for example, a species of any of the genera *Amphora, Chaetoceros, Cyclotella, Fragilaria, Fragilaropsis, Hantzschia, Navicula, Nitzschia, Phæodactylum*, or *Thalassiosira*. In further examples a mutant as disclosed herein is a species of the Eustigmatophyceae class, such as, for example, a species of *Ellipsoidion, Eustigmatos, Vischeria, Monodus, Nannochloropsis*, or *Pseudostaurastrum*. Other genera of the Ochrophyta that may be considered include, without limitation, *Boldimonas, Botrydium, Baucheria, Tribonema, Monodus, Aureococcus, Bigeloweilla, Pelagomomas, Chrysosphaera, Ochromonas, Heterosigma, Nephrochloris, Boekelovia, Cricosphaera, Hymenomonas, Isochrysis, Pleurochrysis*, and *Pavlova*.

In additional embodiments, organisms that may be mutated or engineered to include a mutated or attenuated SGI1 gene include plant species. A wide variety of plants and plant cell systems may be mutated or engineered to attenuate expression of an SGI gene, for example using nucleic acid constructs and various transformation methods known in the art (See Guerineau F., *Methods Mol Biol.* (1995) 49:1-32). In preferred embodiments, target plants and plant cells include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot potato, sugar beets, yarn), leafy vegetable crops (e.g., lettuce, spinach); flowering plants (e.g., petunia, rose, chrysanthemum), conifers and pine trees (e.g., pine fir, spruce), plants used in phytoremediation (e.g., heavy metal accumulating plants); oil crops (e.g., sunflower, rape seed) and plants used for experimental purposes (e.g., *Arabidopsis*). Thus, SGH mutants can be generated in a broad range of plants, such as for example with dicotyledonous plants belonging to the orders Magniolales, Miciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. SGH mutants can also be generated in monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales, or with plants belonging to Gymnospermae, e.g. those belonging to the orders Pinales, Ginkgoales, Cycadales, Araucariales, Cupressales and Gnetales, or with plants classified as mosses (Bryophyta), for example, Sphagnales and Funariales.

Exemplary and nonlimiting plant species that may have an attenuated SGI1 gene include *Sphagnum fallax, Physcomitrella patens, Arabidopsis thaliana, Arabidopsis halleri, Arabidopsis lyrata, Helianthus annuus, Vitis vinifera, Amborella trichopoda, Ricinus communis, Solanum lycopersicum, Solanum tuberosum, Gossypium hirsutum, Theobroma cacao, Phaeolis vulgaris, Glycine max, Chenopodium quinoa, Malus domesticus, Zea mays, Brassica rapa*, and *Oryza sativa*.

Gene Attenuation

A mutant microorganism as provided herein having an attenuated SGI1 gene is a mutant generated by human intervention, for example, by classical mutagenesis or genetic engineering. For example, a mutant microorganism as provided herein can be a mutant generated by any feasible mutagenesis method, including but not limited to UV irradiation, gamma irradiation, or chemical mutagenesis, and screening for mutants having reduced chlorophyll and increased productivity, for example using the methods disclosed herein. For example, screening for reduced chlorophyll mutants can use fluorescence activated cell sorting (FACS), visual inspection, and/or extraction and measurement of chlorophyll absorption. Increased productivity can be assessed by growth of mutants and measurement of dry weight, wet weight, ash-free dry weight, or total organic carbon (TOC). Methods for generating mutants of photosynthetic organisms using classical mutagenesis and genetic engineering are well-known.

Examples of attenuated genes include, without limitation, genes that have one or more nucleotide substitutions that change the sequence of one or more amino acids resulting in reduced or abolished activity of the encoded protein; insertions or deletions (indels) in the gene that change the amino acid sequence of the protein by frameshifting and/or introducing stop codons; large insertions into the gene that result in frameshifting or truncation of the encoded polypeptide or instability of the RNA transcribed by the gene, large deletions that result in no functional protein being made; insertions, deletions, or point mutations in regions of the gene 5' or 3' of the coding region that affect transcription; and insertions, deletions, or point mutations in introns or at intron/exon junctions that affect may affect transcription, splicing, or RNA stability. An attenuated gene can also be a gene whose transcript is targeted by, for example, RNAi, antisense RNA, ribozymes, or the like. A photosynthetic organism having an attenuated SGI1 gene is referred to herein as "an SGI1 mutant" regardless of the mechanism of attenuation of the SGI1 gene. SGI1 mutants can be isolated by methods disclosed herein, including mutagenesis and screening procedures disclosed herein as well as by genetic engineering.

Thus, a mutant can be a genetically engineered mutant, for example, a mutant in which an SGI1 gene has been targeted by homologous recombination for knock-out, knockdown, and/or gene replacement (for example with mutated form of the gene that may encode a polypeptide having reduced activity with respect to the wild type polypeptide). For example, a photosynthetic organism of interest may be engineered by site directed homologous recombination to insert a sequence into a genomic locus and thereby alter a gene and/or its expression, and/or to insert a promoter into a genetic locus of the host microorganism to affect the expression of a gene at the locus.

For example, gene knockout, gene knockdown, or gene replacement by homologous recombination can be by transformation of a nucleic acid (e.g., DNA) fragment that includes a sequence homologous to the region of the genome to be altered, where the homologous sequence is interrupted by a foreign sequence, typically a selectable marker gene that allows selection for the integrated construct. The genome-homologous flanking sequences on either side of the foreign sequence or mutated gene sequence can be for example, at least about 50, at least about 100, at least about 200, at least about 300, at least about 400, at least about 500, at least about 600, at least about 700, at least about 800, at least about 900, at least about 1,000, at least about 1,200, at least about 1,500, at least about 1,750, or at least about 2,000 (e.g., at least any of 50, 100, 200, 500, 1000, 1500 or 2000) nucleotides in length. A gene knockout or gene "knock in" construct in which a foreign sequence is flanked by target gene sequences, can be provided in a vector that can optionally be linearized, for example, outside of the region that is to undergo homologous recombination, or can be provided as a linear fragment that is not in the context of a vector, for example, the knock-out or knock-in construct can be an isolated or synthesized fragment, including but not limited to a PCR product. In some instances, a split marker system can be used to generate gene knock-outs by homologous recombination, where two DNA fragments can be introduced that can regenerate a selectable marker and disrupt the gene locus of interest via three crossover events (Jeong et al. (2007) *FEMS Microbiol Lett* 273: 157-163).

In one aspect this disclosure provides genetically modified organisms, e.g., microorganisms having one or more genetic modifications or mutations for attenuating expression of an SGI1 gene. As used herein "attenuating" or "altering" the expression and/or function" of a gene (e.g. an SGI1 gene) means reducing or eliminating expression of the gene in any manner that reduces production, expression and/or function of the normally expressed fully functional protein. Means for attenuating a gene such as an SGI1 gene include, for example, homologous recombination constructs; CRISPR systems, including guide RNAs, Cas9 or other cas enzymes, e.g., Cpf1, Cms1, Csm1, or others, and optionally, donor fragments for insertion into the targeted site; RNAi constructs, including shRNAs, antisense RNA constructs; ribozyme constructs; TALENS, Zinc Finger nucleases; and meganucleases. For instance, in some embodiments, the gene can be disrupted by, for example, an insertion or gene replacement mediated by homologous recombination and/or by the activity of a double strand break inducing agent such as meganuclease (see, e.g., WO2012017329 (US20130164850 and US20160272980), zinc finger nuclease (Perez-Pinera et al. (2012) *Curr. Opin. Chem. Biol.* 16:268-277; WO2012017329 (US20130164850 and US20120324603), TALEN (WO2014/207043 (US20160130599); WO 2014/076571 (US20160272980)), or a cas protein (e.g., a Cas9 protein, Cpf1 effector protein, or Csm1 effector protein) of a CRISPR system (see e.g., U.S. Pat. Nos. 8,697,359; 8,795,965; 8,889,356; US 2016/0304893; US 2016/0090603; US2014/0068797; US 2016/0208243; US 2017/0233756). Other methods of disruption are known in the art and would be suitable here as would be understood by those of ordinary skill in the art.

In some embodiments, the mutant microorganism has one or more mutations that are present in, or one or more mutations affecting the expression of, an SGI1 gene. A recombinant microorganism engineered to have attenuated expression of an SGI1 gene can have a disrupted SGI1 gene that includes as least one insertion, mutation, or deletion that reduces or abolishes expression of the gene such that a fully functional SGI1 gene is not produced or is produced in lower amounts than is produced by a control microorganism that does not include a disrupted SGI1 gene. For instance, in some embodiments, one or more mutations (change, deletion, and/or insertion of one or more nucleotides) can be in the coding region of the gene or can be in an intron, 3' UTR, 5' UTR, or promoter region, e.g., within about 1 kb of the transcriptional start site, within about 2 kb of the transcriptional start site or within about 3 kb of the translational start site. In some embodiments, for example, a mutant microorganism having attenuated expression of a gene as disclosed herein can have one or more mutations, which can be one or more nucleobase changes and/or one or more nucleobase deletions and/or one or more nucleobase insertions, into the region of a gene 5' of the transcriptional start site, such as, in non-limiting examples, within about 2 kb, within about 1.5 kb, within about 1 kb, or within about 0.5 kb of the known or putative transcriptional start site, or within about 3 kb, within about 2.5 kb, within about 2 kb, within about 1.5 kb, within about 1 kb, or within about 0.5 kb of the translational start site. As nonlimiting examples, a mutant gene can be a gene that has a mutation, insertion, or deletion within the promoter region that can either increase or decrease expression of the gene; can be a gene that has a deletion that results in production of a nonfunctional protein, truncated protein, dominant negative protein, or no protein; can be a gene that has one or more point mutations leading to a change in the amino acid of the encoded protein or results in aberrant splicing of the gene transcript, etc.

The CRISPR systems referred to herein, and reviewed by Hsu et al. (*Cell* 157:1262-1278, 2014) include, in addition to the cas nuclease polypeptide or complex, a targeting RNA, often denoted "crRNA", that interacts with the genome target site by complementarity with a target site sequence, a trans-activating ("tracr") RNA that complexes with the cas polypeptide and also includes a region that binds (by complementarity) the targeting crRNA. This disclosure contemplates the use of two RNA molecules (a "crRNA" and a "tracrRNA") that can be co-transformed into a host strain (or expressed in a host strain) that expresses or is transfected with a cas protein for genome editing, or the use of a single guide RNA that includes a sequence complementary to a target sequence as well as a sequence that interacts with a cas protein. That is, in some strategies a CRISPR system as used herein can comprise two separate RNA molecules (RNA polynucleotides: a "tracr-RNA" and a "targeter-RNA" or "crRNA", see below) and referred to herein as a "double-molecule DNA-targeting RNA" or a "two-molecule DNA-targeting RNA." Alternatively, as illustrated in the examples, the DNA-targeting RNA can also include the trans-activating sequence for interaction with the cas protein (in addition to the target-homologous ("cr") sequences), that is, the DNA-targeting RNA can be a single RNA molecule (single RNA polynucleotide) and is referred to herein as a "chimeric guide RNA," a "single-guide RNA," or an "sgRNA." The terms "DNA-targeting RNA" and "gRNA" are inclusive, referring both to double-molecule DNA-targeting RNAs and to single-molecule DNA-targeting RNAs (i.e., sgRNAs). Both single-molecule guide RNAs and two RNA systems have been described in detail in the literature and for example, in U.S. Patent Application Publication No. US 2014/0068797, incorporated by reference herein in its entirety. Some embodiments of the methods and compositions presented herein include a guide RNA that has a sequence corresponding to a target sequence in an SGI1 gene. In some embodiments, the guide RNA is a chimeric guide. In other embodiments, the guide RNA does not include a tracr sequence. In some examples, both a crRNA for targeting the gene locus and a tracrRNA are employed in the cas-mediated mutagenesis. In some embodiments a cas protein is expressed in the target cell or organism, and in some alternative embodiments a cas protein may be introduced in to the cell, for example, as a ribonucleoprotein complex that includes a guide RNA, which may be a chimeric guide RNA or a crRNA and, in some embodiments, a tracrRNA. Any cas protein can be used in the methods herein, e.g., Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm1, Csm2, Csm3, Csm4, Csm5, Csm6, Cmr1, Cmr3, Cmr4, Cmr5, Cmr6, Cms1, Cpf1, Csb1, Csb2, Csb3, Csx17, Csx14, Csx10, Csx16, CsaX, Csx3, Csx1, Csx15, Csf1, Csf2, Csf3, Csf4, C2c1, C2c2, C2c3, and homologs thereof, or modified versions thereof. The cas protein can be a Cas9 protein, such as a Cas9 protein of *Staphylococcus pyogenes, S. thermophilus, S. pneumonia, S. aureus*, or *Neisseria meningitidis*, as nonlimiting examples. Also considered are the Cas9 proteins provided as SEQ ID NOs:1-256 and 795-1346 in U.S. Patent Application Publication No. US 2014/0068797, incorporated herein by reference in its entirety, and chimeric Cas9 proteins that may combine domains from more than one Cas9 protein, as well variants and mutants of identified Cas9 proteins. The RNA-guided nuclease can be, for example, a Cpf1 protein (see, for example, US 2016/0208243) or a Csm1 protein (see, for example, US 2017/0233756).

Cas nuclease activity cleaves target DNA to produce double strand breaks. These breaks are then repaired by the cell in one of two ways: non-homologous end joining or homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion, or altered, often resulting in mutation. In homology-directed repair, a donor polynucleotide (sometimes referred to as a "donor DNA" or "editing DNA") which may have homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. The modifications of the target DNA due to NHEJ and/or homology-directed repair (for example using a donor DNA molecule) can lead to, for example, gene correction, gene replacement, gene tagging, transgene insertion, nucleotide deletion, gene disruption, gene mutation, etc.

In some instances, cleavage of DNA by a site-directed modifying polypeptide (e.g., a cas nuclease, zinc finger nuclease, meganuclease, or TALEN) may be used to delete nucleic acid material from a target DNA sequence by cleaving the target DNA sequence and allowing the cell to repair the sequence in the absence of an exogenously provided donor polynucleotide. Such NHEJ events can result in mutations ("mis-repair") at the site of rejoining of the cleaved ends that can resulting in gene disruption.

Alternatively, if a DNA-targeting RNA is co-administered to cells that express a cas nuclease along with a donor DNA, the subject methods may be used to add, i.e. insert or replace, nucleic acid material to a target DNA sequence (e.g., "knock out" by insertional mutagenesis, or "knock in" a nucleic acid that encodes a protein (e.g., a selectable marker and/or any protein of interest), an siRNA, a miRNA, etc., to modify a nucleic acid sequence (e.g., introduce a mutation), and the like.

A donor DNA can in particular embodiments include a gene regulatory sequence (e.g., a promoter) that can, using CRISPR targeting, be inserted upstream of the coding regions of the gene and upstream of the presumed proximal promoter region of the gene, for example, at least about 50 bp, at least about 100 bp, at least about 120 bp, at least about 150 bp, at least about 200 bp, at least about 250 bp, at least about 300 bp, at least about 350 bp, at least about 400 bp, at least about 450 bp, or at least about 500 bp (e.g., at least 50, 100, 200, 300, 400 or 500 bp) upstream of the initiating ATG of the coding region of the SGI1 gene. The donor DNA can include a sequence, such as for example a selectable marker or any convenient sequence, that may be interfere with the native promoter. The additional sequence inserted upstream of the initiating ATG of the SGI1 open reading frame (e.g., in the 5'UTR or upstream of the transcriptional start site of the SGI! gene) can decrease or even eliminate expression of the endogenous SGI1 gene. Alternatively, or in addition, the native SGI1 gene can have its endogenous promoter wholly or partially replaced by a weaker or differently regulated promoter, or a non-promoter sequence.

In some examples, a nucleic acid molecule introduced into a host cell for generating a high efficiency genome editing cell line encodes a Cas9 enzyme that is mutated to with respect to the corresponding wild-type enzyme such that the mutated Cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (an enzyme that cleaves a single strand). Other examples of mutations that render Cas9 a nickase include, without limitation, H840A, N854A, and N863A. In some embodiments, a Cas9 nickase may be used in combination with guide sequence(s), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strains at staggered positions can also reduce nontarget cleavage, as both strands must be accurately and specifically cleaved to achieve genome mutation. In additional examples, a mutant Cas9 enzyme that is impaired in its ability to cleave DNA can be expressed in the cell, where one or more guide RNAs that target a sequence upstream of the transcriptional or translational start site of the targeted gene are also introduced. In this case, the cas enzyme may bind the target sequence and block transcription of the targeted gene (Qi et al. (2013) *Cell* 152:1173-1183). This CRISPR interference of gene expression can be referred to as RNAi and is also described in detail in Larson et al. (2013) *Nat. Protoc.* 8: 2180-2196. In some cases, a cas polypeptide such as a Cas9 polypeptide is a fusion polypeptide, comprising, e.g.: i) a Cas9 polypeptide (which can optionally be variant Cas9 polypeptide as described above); and b) a covalently linked heterologous polypeptide (also referred to as a "fusion partner"). A heterologous nucleic acid sequence may be linked to another nucleic acid sequence (e.g., by genetic engineering) to generate a chimeric nucleotide sequence encoding a chimeric polypeptide. In some embodiments, a Cas9 fusion polypeptide is generated by fusing a Cas9 polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a hemagglutinin (HA) tag; a FLAG tag; a Myc tag; and the like).

Host cells can be genetically engineered (e.g., transduced or transformed or transfected) with, for example, a vector construct that can be, for example, a vector for homologous recombination that includes nucleic acid sequences homologous to a portion of an SGI1 gene locus of the host cell or to regions adjacent thereto, or can be an expression vector for the expression of any or a combination of: a cas protein (e.g., a Cas9 protein), a CRISPR chimeric guide RNA, a crRNA, and/or a tracrRNA, an RNAi construct (e.g., a shRNA), an antisense RNA, or a ribozyme. The vector can be, for example, in the form of a plasmid, a viral particle, a phage, etc. A vector for expression of a polypeptide or RNA for genome editing can also be designed for integration into the host, e.g., by homologous recombination. A vector containing a polynucleotide sequence as described herein, e.g., sequences having homology to host SGI1 gene sequences (including sequences that are upstream and downstream of the SGI1 polypeptide-encoding sequences), as well as, optionally, a selectable marker or reporter gene, can be employed to transform an appropriate host to cause attenuation of an SGI1 gene.

The recombinant microorganism in some examples can have reduced but not abolished expression of the SGI1 gene, and the recombinant microorganism can have an increase in lipid production of from about 25% to about 200% or more, for example. For example, the increase in lipid production can be between about 25% more to about 200% more, about 25% more to about 175% more, about 25% more to about 150% more, about 25% more to about 125% more, about 50% more to about 200% more, about 50% more to about 175% more, about 50% more to about 150% more, about 50% more to about 125% more, about 75% more to about 200% more, or about 75% more to about 175% more, about 75% more to about 150%, or about 75% more to about 125% more (e.g., 25-200% more) with respect to a control microorganism. A genetically modified photosynthetic organism as provided herein can in some examples include a nucleic acid construct for attenuating the expression of an SGI1 gene. In some embodiments, genetically modified microorganism as provided herein can include a nucleic acid construct for attenuating the expression of an SGI1 polypeptide. For example, a host microorganism can include a construct for expressing an RNAi molecule, ribozyme, or antisense molecule that reduces expression of an SGI1 gene. In some examples, a recombinant microorganism as provided herein can include at least one introduced (exogenous or non-native) construct for reducing expression of an SGI1 gene.

In some examples, genetically engineered strains can be screened for expression of an SGI1 gene that is decreased with respect to a control cell that does not include a genetic modification for attenuating SGI1 gene expression, but not eliminated, using methods known in the art, such as, for example, RNA-Seq or reverse transcription-PCR (RT-PCR). A genetically engineered strain as provided herein can be engineered to include a construct for attenuating gene expression by reducing the amount, stability, or translatability of mRNA of a gene encoding an SGI1 polypeptide. For example, a microorganism such as an algal or heterokont strain can be transformed with an antisense RNA, RNAi, or ribozyme construct targeting an mRNA of an SGI1 gene using methods known in the art. For example, an antisense RNA construct that includes all or a portion of the transcribed region of a gene can be introduced into a microorganism to decrease gene expression (Shroda et al. (1999) *The Plant Cell* 11:1165-78; Ngiam et al. (2000) *Appl. Environ. Microbiol.* 66: 775-782; Ohnuma et al. (2009) *Protoplasma* 236: 107-112; Lavaud et al. (2012) *PLoS One* 7:e36806). Alternatively or in addition, an RNAi construct (for example, a construct encoding a short hairpin RNA) targeting a gene having a TPR domain can be introduced into a phohtosynthetic organism such as an alga or plant for reducing expression of the SGI1 gene (see, for example, Cerruti et al. (2011) *Eukaryotic Cell* (2011) 10: 1164-1172; Shroda et al. (2006) *Curr. Genet.* 49:69-84).

Ribozymes are RNA-protein complexes that cleave nucleic acids in a site-specific fashion. Ribozymes have specific catalytic domains that possess endonuclease activity. For example, U.S. Pat. No. 5,354,855 (incorporated herein in its entirety by reference) reports that certain ribozymes can act as endonucleases with a sequence specificity greater than that of known ribonucleases and approaching that of the DNA restriction enzymes. Catalytic RNA constructs (ribozymes) can be designed to base pair with an mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) *Nature* 334:585-591. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A, C or U) (Thompson et al., (1995) *Nucl Acids Res* 23:2250-68). The frequency of this dinucleotide occurring in any given RNA is statistically 3 out of 16. Therefore, for a given target messenger RNA of 1,000 bases, 187 dinucleotide cleavage sites are statistically possible.

The general design and optimization of ribozyme directed RNA cleavage activity has been discussed in detail (Haseloff and Gerlach (1988) *Nature* 334:585-591; Symons (1992) *Ann Rev Biochem* 61: 641-71; Chowrira et al. (1994) *J Biol Chem* 269:25856-64; Thompson et al. (1995) supra), all incorporated by reference in their entireties. Designing and testing ribozymes for efficient cleavage of a target RNA is a process well known to those skilled in the art. Examples of scientific methods for designing and testing ribozymes are described by Chowrira et al., (1994) supra and Lieber and Strauss (1995) *Mol Cell Biol.* 15: 540-51, each incorporated by reference. The identification of operative and preferred sequences for use in down regulating a given gene is a matter of preparing and testing a given sequence, and is a routinely practiced "screening" method known to those of skill in the art. The use of RNAi constructs is described in literature cited above as well as in US2005/0166289 and WO 2013/016267 (both of which are incorporated herein by reference), for example A double stranded RNA with homology to the target gene is delivered to the cell or produced in the cell by expression of an RNAi construct, for example, an RNAi short hairpin (sh) construct. The construct can include a sequence that is identical to the target gene, or at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identical to a sequence of the target gene. The construct can have at least about 20, at least about 30, at least about 40, at least about 50, at least about 100, at least about 200, at least about 300, at least about 400, at least about 500, at least about 600, at least about 700, at least about 800, at least about 900, or at least about 1 kb of sequence (e.g., at least 20, 50, 100, 200, 400, 600, 800 or 1 kb of sequence) homologous to the target gene. Expression vectors can be engineered using promoters selected for continuous or inducible expression of an RNAi construct, such as a construct that produces an shRNA.

Promoters used in antisense, RNAi, or ribozyme constructs can be any that are functional in the host organism and that are suitable for the levels of expression required for reducing expression of the target gene to a desired amount. Promoters functional in algae and plants are known in the art and disclosed herein. The construct can be transformed into algae or plants using any feasible method, include any disclosed herein. A recombinant organism or microorganism transformed with a nucleic acid molecule for attenuating SGI1 gene expression, such as but not limited to an antisense, RNAi, or ribozyme construct, can have the properties of an SGI1 mutant as described herein, including, for example, reduced chlorophyll, increased photosynthetic efficiency, and increased productivity in culture, with respect to a host organism or microorganism that does not include the exogenous nucleic acid molecule that results in attenuated gene expression.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/ or expression of transgenes, constructs from either the nucleus or the plastid, and in some cases can result in transient expression of transgenes. The transformation methods can also be used for the introduction of guide RNAs or editing DNAs. Genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell*, 2010; and Gong et al., *J. Ind. Microbiol. Biotechnol.*, 2011). Non-limiting examples of such useful transformation methods include agitation of cells in the presence of glass beads or silicon carbide whiskers as reported by, for example, Dunahay, *Biotechniques*, 15(3):452-460, 1993; Kindle, *Proc. Natl. Acad. Sci. U.S.A.*, 1990; Michael and Miller, *Plant J.*, 13, 427-435, 1998. Electroporation techniques have been successfully used for genetic transformation of several microalgal species including *Nannochloropsis* sp. (see, e.g., Chen et al., *J. Phycol.*, 44:768-76, 2008), *Chlorella* sp. (see, e.g., Chen et al., *Curr. Genet.*, 39:365-370, 2001; Chow and Tung, *Plant Cell Rep.* Vol. 18, No. 9, 778-780, 1999), *Chlamydomonas* (Shimogawara et al., *Genetics*, 148: 1821-1828, 1998), and *Dunaliella* (Sun et al., *Mol. Biotechnol.* 30(3): 185-192, 2005), for example. Micro-projectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.*, 252:572-579, 1996), Cyclotella and Navicula (Dunahay et al., *J. Phycol.*, 31:1004-1012, 1995), *Cylindrotheca* (Fischer et al., *J. Phycol.*, 35:113-120, 1999), and Chaetoceros sp. (Miyagawa-Yamaguchi et al., *Phycol. Res.* 59: 113-119, 2011), as well as green algal species such as *Chlorella* (El-Sheekh, *Biologia Plantarum*, Vol. 42, No. 2: 209-216, 1999), and *Volvox* species (Jakobiak et al., *Protist*, 155:381-93, 2004). Additionally, *Agrobacterium*-mediated gene transfer techniques can also be useful for genetic transformation of microalgae, as has been reported by, for example, Kumar, *Plant Sci.*, 166(3):731-738, 2004, and Cheney et al., *J. Phycol.*, Vol. 37, Suppl. 11, 2001. Conjugation with bacterial species has also been employed for transfer of genes and constructs to algae, as disclosed for example in US 2016/0244770, incorporated herein by reference.

A transformation vector or construct as described herein will typically comprise a marker gene that confers a selectable or scorable phenotype on target host cells, e.g., algal cells or may be co-transformed with a construct that includes a marker. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocidin, bleomycin (see, for example, Apt et al., 1996, supra; Fischer et al., 1999, supra; Fuhrmann et al., *Plant J.,* 19, 353-61, 1999, Lumbreras et al., *Plant J.,* 14(4):441-447, 1998; Zaslayskaia et al., *J. Phycol.,* 36:379-386, 2000), spectinomycin (Cerutti et al., *Genetics,* 145: 97-110, 1997; Doetsch et al., *Curr. Genet.,* 39, 49-60, 2001; Fargo, *Mol. Cell. Biol.,* 19:6980-90, 1999), streptomycin (Berthold et al., *Protist,* 153:401-412, 2002), paromomycin (Jakobiak et al., *Protist,* supra.; Sizova et al., *Gene,* 277: 221-229, 2001), nourseothricin (Zaslayskaia et al., 2000, supra), G418 (Dunahay et al., 1995, supra; Poulsen and Kroger, *FEBS Lett.,* 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paromomycin and neomycin resistance (Sizova et al., 2001, supra). Other fluorescent or chromogenic markers that have been used include luciferase (Falciatore et al., *J. Mar. Biotechnol.,* 1: 239-251, 1999; Fuhrmann et al., *Plant Mol. Biol.,* 2004; Jarvis and Brown, *Curr. Genet.,* 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.,* 1:165-169, 1994), β-galactosidase (Gan et al., *J. Appl. Phycol.,* 15:345-349, 2003; Jiang et al., *Plant Cell Rep.,* 21:1211-1216, 2003; Qin et al., *High Technol. Lett.,* 13:87-89, 2003), and green fluorescent protein (GFP) (Cheney et al., 2001, supra; Ender et al., *Plant Cell,* 2002, Franklin et al., *Plant J.,* 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.,* 18:778-780, 1999; Jarvis and Brown, *Curr. Genet.,* 317-321, 1991; Lohuis and Miller, *Plant J.,* 13:427-435, 1998). The SV40 promoter from simian virus has also reported to be active in several algae (Gan et al., *J. Appl. Phycol.,* 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.,* 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.,* 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.,* 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482, incorporated by reference herein). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272:3413-3423, 2005), thus gene expression can be switched off or on when microalgal cells are grown in the presence of ammonium/nitrate. An ammonium-repressible *Nannochloropsis* promoter referred to as the "Ammonia repressible Nitrite/Sulfite Reductase" promoter is disclosed in US 2017/0073695, incorporated herein by reference. Additional algal promoters that can find use in the constructs and transformation systems provided herein include those disclosed in U.S. Pat. Nos. 8,835,419; 8,883,993; U.S. Patent Appl. Pub. No. US 2013/0023035; U.S. Patent Application Pub. No. US 2013/0323780; U.S. Patent Application Pub. No. US 2014/0363892, U.S. Patent Application Pub. No. US 2017/0152520, and U.S. Patent Application Pub. No. US 2017/0114107, all incorporated herein by reference in their entireties.

Host cells or organisms can be either untransformed cells or organisms or can be cells or organisms that are already transfected with at least one exogenous nucleic acid molecule. For example, an algal or plant host cell that is engineered to have attenuated expression of an SGI1 gene can further include one or more transgenes that may confer or contribute to any desirable trait, such as, but not limited to, increased production of biomolecules of interest, such as one or more proteins, pigments, alcohols, or lipids.

Transformation of algal cells by microbombardment is described, for example, in U.S. Pat. No. 8,883,993 and US Patent Application publication no. US 2017/0130238, both of which are incorporated by reference in their entireties. Bombardment of cells using the BioRad Helios® Gene Gun is also described in the Helios Gene Gun System Instruction Manual, M1652411 available at bio-rad.com/en-us/product/helios-gene-gun-system?tab=Documents).

In various aspects, gene-attenuating mutations are generated in a plant. The methods include, for example introducing CRISPR system as described herein to target one or more plant SGI1 genes. A wide variety of plants and plant cell systems may be engineered for the desired physiological and agronomic characteristics described herein using the nucleic acid constructs of the present disclosure and the various transformation methods known in the art (See Guerineau F., Methods Mol Biol. (1995) 49:1-32). In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot potato, sugar beets, yarn), leafy vegetable crops (e.g., lettuce, spinach); flowering plants (e.g., petunia, rose, chrysanthemum), conifers and pine trees (e.g., pine fir, spruce), plants used in phytoremediation (e.g., heavy metal accumulating plants); oil crops (e.g., sunflower, rape seed) and plants used for experimental purposes (e.g., *Arabidopsis*). Thus, SGI1 mutants can be generated in a broad range of plants, such as for example with dicotyledonous plants belonging to the orders Magniolales, Miciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales.

SGI1 mutants can be also be generated in monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales, or with plants belonging to Gymnospermae, e.g. those belonging to the orders Pinales, Ginkgoales, Cycadales, Araucariales, Cupressales and Gnetales.

Alternatively or in addition to any of the embodiments set forth above, included herein are the following embodiments: Embodiment 1 is a mutant photosynthetic organism having an attenuated gene encoding an SGI1 polypeptide, wherein the the photosynthetic organism produces more biomass or more of at least one bioproduct than a control photosynthetic organism grown or cultured under the substantially the same conditions, optionally wherein one or more of the following are satisfied:

a) the mutant photosynthetic organism has reduced chlorophyll with respect to the control photosynthetic microorganism;

b) the mutant photosynthetic organism has an increased chlorophyll a:b ratio with respect to the control photosynthetic organism;

c) the mutant photosynthetic organism has a reduced photosystem II (PSII) antenna size with respect to the control photosynthetic organism;

d) the mutant photosynthetic organism according to claim 1, wherein the mutant photosynthetic organism has a higher $^{14}$C Pmax with respect to the control photosynthetic organism;

e) the mutant photosynthetic organism according to claim 1, wherein the mutant photosynthetic organism has a higher Fv/Fm than the control organism;

f) the mutant photosynthetic organism has a higher protein content than the control organism; and g) the the mutant photosynthetic organism has a higher rubisco activase content than the control organism.

Embodiment 2 is a mutant photosynthetic organism according to embodiment 1, wherein the mutant photosynthetic organism produces at least 10%, at least 15%, at least 20%, at least 25%, at least 30%, at least 35%, at least 40%, at least 45%, at least 50%, at least 60%, at least 70%, at least 80%, at least 90% or at least 100% more biomass or at least 10%, at least 15%, at least 20%, at least 25%, at least 30%, at least 35%, at least 40%, at least 45%, at least 50%, at least 60%, at least 70%, at least 80%, at least 90% or at least 100% more of at least one bioproduct than a control photosynthetic organism grown or cultured under the substantially the same conditions, optionally wherein the bioproduct is one or more lipids, one or more carbohydrates, one or more proteins or peptides, one or more nucleic acids, one or more sugars, one or more alcohols, one or more amino acids, one or more nucleotides, one or more antioxidants, one or more pigments or colorants, one or more vitamins, one or more terpenoids, or one or more polymers.

Embodiment 3 is a mutant photosynthetic organism according to embodiment 1 or embodiment 2, wherein the SGI1 gene encodes an SGI polypeptide having a myb domain C-terminal to a Response Regulator receiver domain, optionally wherein the SGI1 polypeptide:

a) comprises an amino acid sequence that encodes a Response Regulator receiver (RR) domain having least 50%, at least 55%, at least 60%, at least 65%, at least 70%, at least 75%, at least 80%, at least 85%, at least 90%, or at least 95% identity to any of SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, or SEQ ID NO:57; and/or b) comprises an amino acid sequence that encodes a myb domain having least 50%, at least 55%, at least 60%, at least 65%, at least 70%, at least 75%, at least 80%, at least 85%, at least 90%, or at least 95% identity to any of SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, or SEQ ID NO:75.

Embodiment 4 is a mutant photosynthetic organism according to any of embodiments 1-3, wherein the SGI1 gene is mutated, optionally wherein:

a) the SGI1 gene comprises an indel that inactivates the gene;

b) the SGI1 gene comprises a mutation that changes at least one amino acid of the SGI1 polypeptide encoded by the gene;

c) the SGI1 gene comprises an insertion of an introduced DNA fragment that inactivates the gene;

d) the SGI1 gene comprises an insertion of an introduced DNA fragment in the 5' or 3' untranslated region of the gene that reduces expression of the gene; and/or e) the SGI1 gene comprises an indel in the 5' or 3' untranslated region of the gene that reduces expression of the gene.

Embodiment 5 is a mutant photosynthetic organism according to any of embodiments 1-3, wherein the mutant photosynthetic organism comprises an RNAi construct, an antisense construct, or a ribozyme construct that targets the SGI1 gene transcript.

Embodiment 6 is a mutant photosynthetic organism according to any of embodiments 1-5, wherein the mutant photosynthetic organism is a plant, optionally a monocot, dicot, or moss.

Embodiment 7 is a mutant photosynthetic organism according to any of embodiments 1-5, wherein the mutant photosynthetic organism is an alga, optionally a microalga, optionally a Chlorophyte or Charyophyte alga.

Embodiment 7 is a mutant photosynthetic organism according to embodiment 7, wherein the mutant photosynthetic microorganism is a Chlorophyte alga of the Chlorophyceace, the Chlorodendrophyceae, the Prasinophyceae, or the Trebouxiophyceae class.

Embodiment 8 is a biomass comprising a mutant photosynthetic organism of any of the above embodiments.

Embodiment 9 is a method of producing biomass or a bioproduct comprising cultivating any of the mutant photosynthetic organisms of embodiments 1-7 and isolating biomass.

EXAMPLES

Media

PM119 is a nutrient replete medium that includes: 35 ppt Instant Ocean Salts (Aquatic Eco Systems; Apopka, Fla.), 5× Guillard's F/2 marine water enrichment solution (SOX stock from Sigma-Aldrich, St. Louis, Mo., cat. No. G0154; final concentrations of components in media: 4.413 mM Sodium nitrate; 0.16 mM Sodium phosphate monobasic; 0.103 µM Biotin; 0.240 µM Cobalt chloride.$6H_2O$; 0.200 µM Cupric sulfate.$5H_2O$; 0.0585 mM Disodium EDTA.$2H_2O$; 4.54 µM Manganese chloride.$4H_2O$; 0.124 µM Sodium molybdate.$2H_2O$; 1.48 µM Thiamine.HCl; 0.0185 µM Vitamin $B_{12}$, 0.382 µM Zinc sulfate.$7H_2O$).

PM074 is a nutrient replete medium that is made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM $NaNO_3$, 0.361 mM $NaH_2PO_4.H_2O$, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

PM147 is a nutrient replete medium that is based on PM074 but has 50% of the salt. It is made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (17.5 g/L) (Aquatic Eco Systems, Apopka, Fla.).

PM153 is a nutrient replete medium that is based on PM074 but includes urea instead of nitrate as the nitrogen source. It is made by adding 1.3 ml PROLINE® F/2 Algae Feed Part A (Aquatic Eco-Systems) and 1.3 ml 'Solution C' to a final volume of 1 liter of a solution of Instant Ocean salts (17.5 g/L) (Aquatic Eco Systems, Apopka, Fla.), and then adding 4 ml if 1.1 M filter-sterilized urea. Solution C is 38.75 g/L $NaH_2PO_4$ $H_2O$, 758 mg/L Thiamine HCl, 3.88 mg/L vitamin B12, and 3.84 mg/L biotin.

Example 1. UV Mutagenesis of a *Parachlorella* Strain

To isolate mutants from a chlorophyte, or green algal species, cells of *Parachlorella* strain WT-1185 were mutagenized with UV and selected based on low chlorophyll fluorescence after low light acclimation. The *Parachlorella* strain used for mutagenesis, WT-1185, was isolated from a marine environment. *Parachlorella* WT-1185 cells were grown to mid-log phase and then diluted to $1 \times 10^6$ cells/mL with growth medium PM119. The cell suspensions were transferred by pipet to a 100 mm Petri dish and placed within a STRATALINKER® 2400 UV crosslinker (Agilent Technologies, Santa Clara, Calif.) with the plate lid removed. UV irradiation was carried out with 10,000, 25,000, and 50,000 µJ/$cm^2$. After irradiation, cell suspensions were pipetted into a shake flask wrapped in foil to prevent light exposure for twenty-four hours during recovery.

Example 2. Screens for Low Chlorophyll *Parachlorella* Sp. Strain WT-1185 Mutants Following mutagenesis and recovery as described in Example 1, cells from pale-colored colonies were selected and allowed to grow from between one and five days in low (100 µmol photons $m^{-2}$ $sec^{-1}$) light, after which they were sorted by flow cytometry using a BD FACSAria II flow cytometer (BD Biosciences, San Jose, Calif.) to select cells having low chlorophyll fluorescence. In general, the portion of cells with the lowest approximately 0.5 to 2% of chlorophyll fluorescence compared to the total population of cells was selected. Further primary screening of antenna-reduced lines isolated through flow cytometry was conducted through the selection of pale green or yellow colonies visually after sorted cells were plated. In order to screen putative antenna-reduced lines from other reduced pigment mutants and false positives, selected colonies were subjected to a medium-throughput secondary cultivation screen to acclimate the isolates to low light conditions prior to photophysiological measurements. Chlorophyll fluorescence was monitored during low light acclimation to select colonies that retained the reduced chlorophyll fluorescence characteristic of the high light acclimated state. Clones that were selected demonstrated only small increases in chlorophyll (relative to wild type cells) when transferred from high to low light.

Semicontinuous culture assays in constant high light (approximately 1,700 µmol photons $m^{-2}$ $sec^{-1}$) using 165 ml cultures in 75 $cm^2$ tissue culture flasks were performed to identify strains having increased productivity (increased rate of biomass production, measured as TOC accumulation) with respect to the wild type progenitor strain WT-1185. Two 75 $cm^2$ flasks were inoculated with seed culture of a given mutant strain. The flasks had stoppers having tubing connected with syringe filters for delivering $CO_2$-enriched air (1% $CO_2$) that was bubbled through the cultures. The flasks were aligned with the width (narrowest dimension) against an LED light bank. The depth of the cultures (the distance from the wall of the flask nearest the light source to the wall at back of the flask) was approximately 8.0 cm. The cultures were diluted daily at the beginning of the light period by removing 65% of the culture volume and replacing it with fresh PM119 media diluted to adjust for the increase in salinity due to evaporation occurring in the cultures (212 ml di $H_2O$ to 1 L PM119 medium). Samples for TOC analysis were taken from the culture removed for the dilution. Two isolates, NE-7843 and NE-13380, that were identified in this assay as having increased productivity were analyzed further.

Example 3. Semi-Continuous Productivity Assays of Algal Mutants NE-7843 and NE-13380

Among the *Parachlorella* strains that were found to have reduced chlorophyll under low light conditions were two isolates that were analyzed for increased productivity: mutants NE-7843 and NE-13380. In the productivity assay, photoautotrophic cultures of the mutants were grown over several days in constant light semi-continuous mode (CL-SCPA) with culture samples removed daily for biomass determination. The light was kept at a constant 1900-2000 µmol photons $m^{-2}$ $sec^{-1}$ for 24 hours per day. In this assay PM119 culture medium in a 225 $cm^2$ flask was inoculated with seed culture of a given mutant strain. Three cultures were initiated per strain. The flasks included stir bars and had stoppers having tubing connected with syringe filters for delivering $CO_2$ enriched air (1% $CO_2$) that was bubbled through the cultures. The flasks were aligned with the width (narrowest dimension) against an LED light bank. The "depth" dimension of the flasks, extending back from the light source, was 13.7 cm. Taking into account the positioning of the flasks the farthest distance of the cells in the flasks from the surface of the light source was approximately 15.5 cm. The cultures were diluted daily by removing 65% of the culture volume and replacing it with fresh PM119 culture medium diluted to adjust for the increase in salinity due to evaporation occurring in the cultures. Samples for TOC analysis were taken from the culture removed for the dilution. The semi-continuous productivity assay was run for 12 days once the cultures had reached steady state.

Productivity for the assay was assessed by measuring total organic carbon (TOC) from the samples that were removed daily. Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of $r^2 > 0.999$.

Exemplary results of the small-scale productivity assays are provided in FIG. 1A for mutant NE-7843 and FIG. 1B for mutant NE-13380, where the average daily productivity of duplicate cultures over 12 days of the culturing is shown. FIGS. 1A and 1B demonstrate that mutants NE-7843 and NE-13380, respectively, had higher productivity in this CLSCPA assay, each demonstrating an average 34% increase over wild type in TOC over the course of the 12 day assay.

Example 4. Genotyping of Parachlorella LIHLA Mutants

The genomes of NE-13380 and NE-7843 were sequenced to identify mutations such as single nucleotide polymorphisms (SNPs) or insertion/deletion mutations (indels), any of which could form the genetic basis for the phenotypes observed in these two strains. SNPs were identified in the genome of NE-13380 that caused mutations in the coding regions of four different genes (first four rows of Table 1).

TABLE 1

SNPs in NE-13380 Genome

| Mutated Gene(s) | Description | SNP Type | Coding Sequence Modification |
|---|---|---|---|
| T-0699 | Winged helix DNA-binding domain | Missense variant | Trp13Arg |
| T-4339 | chain C domain 1 conserved predicted protein | Stop-gained | Arg575Stop |
| T-0841, T-1004 | Flagellar-associated protein calcium transporting ATPase | Missense variant | Ser1019Leu |
| T-2261 | CheY-like protein | Splice acceptor variant & intron variant | potential intron retention |
| T-0898, T-0899, T-0900 | Conserved predicted protein Dynein light chain 4 axonemal | intergenic region | none |
| T-2627 | RNA helicase ATP-dependent SK12/DOB1 protein isoform 1 | intron variant | none |
| T-9629 | ADP-ribosylation factor GTPase-activating protein AGD5 isoform 1 and conserved predicted protein | Upstream gene variant, intron variant | none |

While this analysis of NE-13380 mutations was underway, analysis of the NE-7843 genome revealed that this strain also harbored distinct SNPs (Table 2), including an SNP in the T-2261 gene (gene sequence provided as SEQ ID NO:1; coding sequence provided as SEQ ID NO:2 encoding the protein sequence of SEQ ID NO:3), a gene also mutated in NE-13380 (row 4 of Table 1)—providing strong evidence that mutations in the T-2261 gene were the cause of the highly desirable high productivity phenotype of these strains.

TABLE 2

SNPs in NE-7843 Genome

| Mutated Gene(s) | Description | SNP Type | Coding Sequence Modification |
|---|---|---|---|
| T-0936 | Zn finger Ran-binding family protein | Stop-gained | *329Lys |
| T-4448 | Cytochrome P450 CYP 711clan | Missense variant | Leu508Cys |
| T-2261 | Type b response regulator Sensor histidine kinase/CheY | Missense variant | Leu250Pro |
| T-3935 | Pyruvate-flavodoxin oxidoreductase | Missense variant | Lys577Glu |
| T-8682 | Dynein light chain LC8 type 2 | Missense variant | Tyr77His |
| T-4805 | Sm-like ribonucleoproteins | Missense variant | Asp32Asn |
| T-5398 | Aldolase class I | Missense variant | Gly26Cys |

Figure 2:
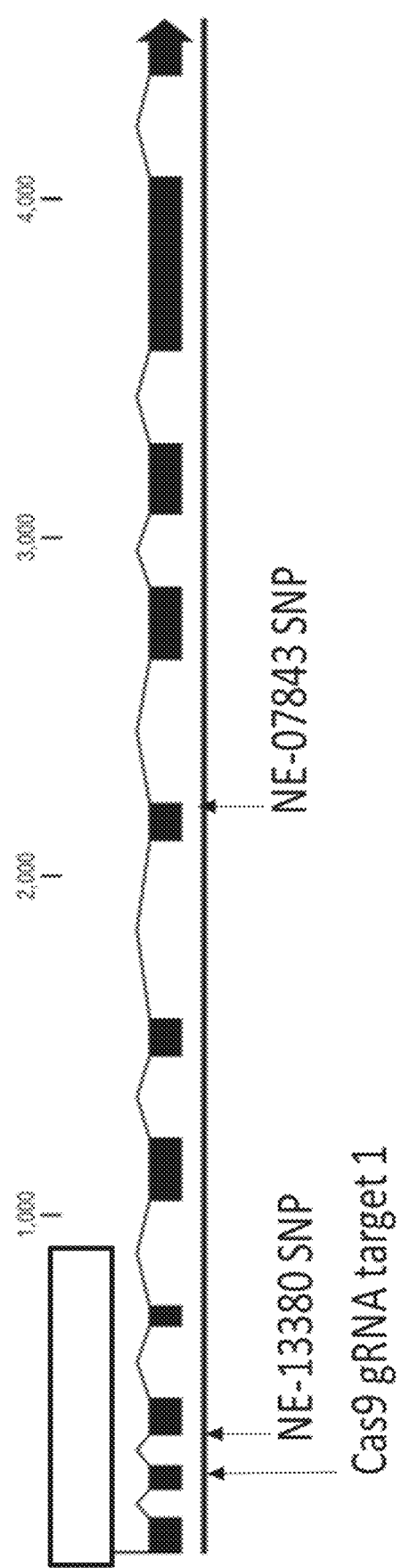
FIG. 2 is a diagram of the *Parachlorella* T-2261 (SGI1) gene structure depicting locations of SNPs detected by genome sequencing of NE-7843 and NE-13380. The location targeted by a guide RNA for Cas9-mediated insertional mutagenesis is also shown.

FIG. 2 shows the location of the nutations in the Parachlorella T-2661 gene having a response regulator CheY-like domain.

Example 5. Generating Targeted Mutations in the Parachlorella T-2661 "Response Regulator CheY-Like Protein" Gene To definitively demonstrate that mutation of the T-2261 gene resulted in the high productivity phenotype, three strains were generated in which the T-2261 gene was knocked out by Cas9-mediated insertional mutagenesis with a guide RNA targeting the 3'end of the second exon of the T-2261 gene (FIG. 2). The single guide RNA (sg RNA) (SEQ ID NO:5) included the target sequence of SEQ ID NO:4 (i.e., the CRISPR sequence or sequence corresponding to the target sequence of the T-2261 gene), and was produced by annealing two complementary DNA oligomers that incorporated the sequence of the T7 promoter to generate a double-stranded template for in vitro transcription. In vitro transcription reactions were performed using the MEGAshortscript™ T7 Kit (Life Technologies cat #AM1354M;

Carlsbad, Calif.) according to the manufacturer's protocol. The resulting RNA was purified using Zymo-Spin™ V-E columns (Zymo Research; Irvine, Calif.; cat #C1024-25) according to the manufacturer's protocol.

Purified guide RNA was transformed into cells of the *Parachlorella* Cas9-expressing Editor cell line GE-15699. The Cas9-expressing Editor line was produced by transforming wild type *Parachlorella* strain WT-1185 with a construct that included: 1) a Cas9 expression cassette which contained an engineered Cas9 gene codon optimized for *Parachlorella* and containing introns from *Parachlorella*, that also included an N-terminal FLAG tag, nuclear localization signal, and peptide linker (SEQ ID NO:76) operably linked to the *Parachlorella* RPS17 promoter (SEQ ID NO:77) and the *Parachlorella* RPS17 terminator (SEQ ID NO:78); 2) a selectable marker expression cassette, which contained the blasticidin resistance gene from *Aspergillus terreus* codon optimized for *Parachlorella* and containing *Parachlorella* introns (SEQ ID NO:79), operably linked to the *Parachlorella* RPS4 promoter (SEQ ID NO:80) and the *Parachlorella* RPS4 terminator (SEQ ID NO:81); and 3) a GFP reporter expression cassette, which contained the TurboGFP gene (Evrogen, Moscow, Russia) (SEQ ID NO:82), driven by the *Parachlorella* ACP1 promoter (SEQ ID NO:83) and terminated by the *Parachlorella* ACP1 terminator (SEQ ID:84). (See for example copending commonly-owned US Patent application publication US 2016/0304896 as well as US patent application publication US 2017/0073695 and US patent application publication US 2017/0152520, all of which are incorporated herein by reference in their entireties.)

The guide RNA (SEQ ID NO:5) was transformed in Editor line GE-15699 along with a DNA donor fragment that included a bleomycin resistance "BleR" gene codon-optimized for *Parachlorella* and containing *Parachlorella* introns (SEQ ID NO:6) operably linked to the *Parachlorella* RPS4 promoter (SEQ ID NO:7) and the *Parachlorella* RPS4 terminator (SEQ ID NO:8). Transformation was by electroporation, essentially as described in US 2016/0304896. Following electroporation, cells were plated on agar medium containing 250 µg/ml zeocin to select for transformants that incorporated the BleR cassette. Transformants were screened by colony PCR using primers designed to amplify across the native targeted locus and three strains were selected that demonstrated the insertion of the BleR cassette into the T-2661 gene locus: GE-16391, GE-16392, and GE-16393.

Figure 3:
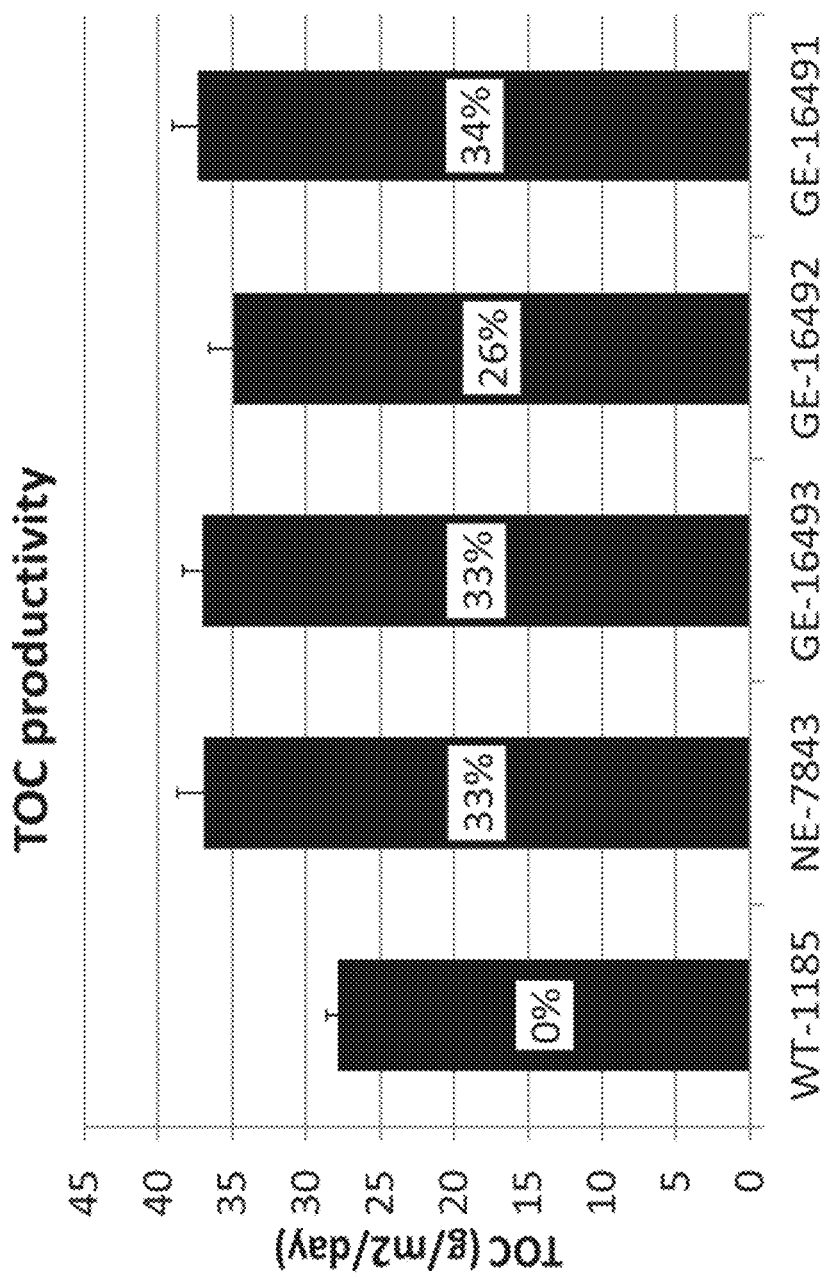
FIG. 3 is a graph showing TOC productivities of *Parachlorella* T-2261 (SGI1) knockout mutants generated by Cas9. Data represent the average and standard deviation from three biological replicates assessed under continuous light (2000 µE) semicontinuous culture conditions.

Cas9-engineered mutants GE-16391, GE-16392, and GE-16393, and classically-derived mutant NE-7843 were assayed under continuous light in a semi-continuous dilution productivity assay (SCPA) under conditions described in Example 3 (the CL2000 assay: the light was kept at a constant 1900-2000 µmol photons $m^{-2}$ $sec^{-1}$ for 24 hours per day and the culture was diluted back by 65% daily). The Cas9-engineered mutants were found to exhibit TOC productivity increases over wild type strains at a magnitude essentially identical to that observed in the original strains isolated from classical mutagenesis (FIG. 3), with the GE-16392 demonstrating about a 26% increase in biomass productivity and the GE-16391 and GE-16393 mutants demonstrating biomass productivity increases of 33% and 34%. From this it was concluded that knockout or severe reduction of T-2661 expression or function in *Parachlorella* WT1185 can lead to 25-35% increases in biomass productivity under continuous high light conditions. Because of its influence on productivity, the T-2661 gene was named SGI1, or Significant Growth Improvement 1.

Example 6. *Parachlorella* SGI1 (T-2661) Gene and Orthologs in Other Photosynthetic Organisms The *Parachlorella* SGI1 gene (SEQ ID NO:1, coding sequence provided as SEQ ID NO:2) was found to encode a polypeptide (SEQ ID NO:3) that includes two major functional domains, both occurring in the N-terminal half of the 619 amino acid protein. The presence of a Response Regulator receiver or "RR" domain (Pfam PF00072), extending from approximately amino acid 36 to amino acid 148 of the *Parachlorella* SGI1 polypeptide (SEQ ID NO:3), is responsible for the bioinformatic annotation of SGI1 as a CheY-like polypeptide (see Tables 1 and 2). This RR domain is also characterized as a "signal receiver domain", cd00156, in the consved domain database (CDD), extending approximately from amino acid 37 through amino acid 154. This domain is also characterized as a "CheY-like receiver (REC) domain", COG0784, in the Clusters of Orthologous Groups of proteins database and as an Interpro "CheY-like superfamily" domain, IPR011006, with both of these characterized domains extending from approximately amino acid 33 to approximately amino acid 161 of the *Parachlorella* SGH polypeptide of SEQ ID NO:3. The RR domain (sometimes referred to as a "receiver" or often, a "REC" domain) is found in bacterial two-component regulatory systems (like the bacterial chemotaxis two-component system that includes a polypeptide known as CheY), in which it receives a signal from a sensor partner. The RR domain of such systems is often found N-terminal to a DNA binding domain and typically includes a phosphoacceptor site that can be phosphorylated, where phosphorylation may be responsible for its activation or deactivation.

The *Parachlorella* SGI1 gene (T-2661 gene) also has a myb domain, positioned C-terminal to the RR domain. The myb domain is identified as pfam PF00249: "Myb-like DNA-binding domain", extending from approximately amino acid position 204 to approximately amino acid position 254 of SEQ ID NO:3, and is also identified as conserved domain TIGRO1557 "myb-like DNA-binding domain, SHAQKYF class", which extends from approximately amino acid position 202 to amino acid position 255 of SEQ ID NO:3 (*Parachlorella* SGI1 polypeptide). When SEQ ID NO:3 is queried against the Interpro protein sequence analysis and classification database, an Interpro Homeobox-like domain superfamily domain (IPR009057), extending from amino acid position 201 to amino acid position 259 of SEQ ID NO:3, and an Interpro Myb domain (IPR017930), extending from amino acid position 199 to amino acid position 258 of SEQ ID NO:3, are identified.

In addition, a nuclear localization signal could be identified in the *Parachlorella* SGI1 polypeptide positioned between the RR domain and the Myb domain, within a region of low amino acid conservation referred to herein as the linker between the conserved domains.

No conserved protein domains could be found in the region of the *Parachlorella* SGI1 polypeptide C-terminal to the myb domain. In contrast, the SGI1 architecture of an RR and a myb domains, where the myb domain is positioned C-terminal to the RR domain, can be found in many proteins coded for in *Viridiplantae* genomes. Bioinformatic analysis was used to identify likely orthologs of *Parachlorella* SGI1 in additional plant and algal species based on this conserved architecture.

To identify a class of SGI1 proteins in additional photosynthetic organisms, a Hidden Markov Model (HMM) was built for the 'RR domain-myb domain' architecture found in the *Parachlorella* SGI1 polypeptide. The amino acid sequence used to develop the HMM included the contiguous stretch of amino acids sequence that included both the RR domain and the myb domain, as well as the linker region between the two domains.

As a first step, the *Parachlorella* SGI1 polypeptide sequence (SEQ ID NO:3) was used to BLAST search the JGI Phytozome database v.12 that included the genomes of plants and algae. Three proprietary algal genomes (from *Parachlorella, Tetraselmis,* and *Oocystis* species) were also added to the database that was searched. The search was halted when it reached approximately 2,000 hits. These results were then analyzed by InterProScan (available from the EMBL-EBI [European Molecular Biolgy Laboratories-European Bioinformatics Institute, for example, at ebi-.ac.uk]) to ensure that selected results had both the Interpro CheY-like superfamily domain (IPR011006) and the Interpro Homeobox-like or Myb domain (IPR009057 or IPR017930). Candidates that did not have both domains were eliminated. This step reduced the number of selected hits to between 900 and 1,000, with polypeptides having the two domain architecture (RR domain N-terminal to myb domain) clearly identifed in polypeptides of both algae and higher plants. The resulting sequences were used to assemble a phylogenetic tree based on sequence homology. The phylogenetic tree showed a clear grouping of SGI1-homologous polypeptides from algal species.

In a given species of algae, the number of SGI-like genes is low. Typically a single gene was identified in a given algal species, although in *Tetraselmis* three highly homologous genes were identified, which were in all likelihood alleles of the same gene the strain that was assessed to be triploid. The low number of SGI1 genes in a given algal species indicates that the identified SGI1 gene or genes in that algal species is in fact the functional SGI1 gene of that species, as the function of the single SGI1 polypeptide found in *Parachlorella*, which is haploid, and the three highly similar SGI1 polypeptides identified in *Tetraselmis*, which is thought to be triploid, were functionally validated (see Examples 5 and 7 and 16-18). (The *Parachlorella* and *Tetraselmis* genomes were sequenced in-house.)

To establish a criterion for likely SGI1 orthologs in other photosynthetic organisms then, a Hidden Markov Model (HMM) was developed based on the algal cluster of SGI1 polypeptide sequences. The HMM was developed based on the N-terminal portion of the SGI1 polypeptide that encompasses both the RR and myb domains, including the linker region between the two conserved domains. The sequence of the polypeptides C-terminal to the myb domain that did not include any recognizable conserved structure were excluded from the model-building. HMMER 3.1b2 was used to build the HMM using Multiple Sequence Alignments (MSAs) from proprietary sequences of *Parachlorella, Oocystis,* and *Tetraselmis* polypeptides as well as sequences of public databases of polypeptides of *Chlamydomonas reinhardtii, Volvox carteri, Chromochloris zofingiensis, Coccomyxa subellipsoidea, Micromonas* sp. RCC299, and *Ostreococcus luminarinus*. Multiple sequence alignments (MSAs) of the N-terminal portions of the proteins as described above were generated using the ETE3 toolkit and eggnog4l workflow. This program internally uses the programs Muscle, MAFFT, Clustal Omega, and M-coffee for alignment, trimA1 for alignment trimming, and PhyML for phylogeny interference. All of these programs are publicly available. An HMM, unlike a single protein sequence used for homology comparison, for example, captures information from multiple protein sequences and is therefore able to distinguish highly conserved from highly divergent residues within a polypeptide sequence and take that into account when determining relatedness of sequences. When an HMM is used to score a sequence, highly conserved residues receive more weight that highly divergent residues, thereby providing superior sensitivity and accuracy than simpler PSAs.

The SGI1 HMM was used to assign a score to the polypeptides identified in the BLAST search that also were verified as having the two conserved domains (RR and myb). The highest scores (with the exception of the very high-scoring *Arabidopsis halleri* homolog, SEQ ID NO:23) were found in algal species, with HMM scores for putative orthologs ranged from about 475 to less than 200 in the photosynthetic organism database. Algal homolog HMM scores in this sample generally ranged from about 400 to about 450. As shown in Table 3, the SGI1 homologs in *Oocystis, Tetraselmis, Parachlorella* and almost all additional algal homologs queried had scores of about 400 or greater. The unusually low score of the *Chromochloris zofingiensis* polypeptide is likely to be the result of flawed genome annotation; an alignment of RR domains of algal SGI1 polypeptides (FIG. 4) shows the sequence of the *C. zofingiensis* RR domain (SEQ ID NO:44) appears to be missing a continuous stretch of amino acids at the N-terminal region of this domain Sequence homologies of the RR domains of the algal SGI1 homologs shown in FIG. 4 with the *Parachlorella* SGI1 RR domain (SEQ ID NO:40) ranged from about 55% to about 80% amino acid sequence identity. FIG. 5 provides an alignment of myb domain sequences of algal SGI1 polypeptides, with sequence homologies with the *Parachlorella* myb domain (SEQ ID NO: 58) ranging from about 85% to about 97% amino acid sequence identity among this set of algal homologs.

TABLE 3

SGI1 Orthologs in Algal species

| Organism | Polypeptide Sequence | RR domain | Myb domain | HMM Score | E value |
| --- | --- | --- | --- | --- | --- |
| *Parachlorella* sp. 1185 | SEQ ID NO: 3 | SEQ ID NO: 40 | SEQ ID NO: 58 | 400.20 | 8.5e−118 |
| *Coccomyxa subellipsoidea* | SEQ ID NO: 9 | SEQ ID NO: 41 | SEQ ID NO: 59 | 403.0 | 1.2e−118 |
| *Ostreococcus lucimarinus* | SEQ ID NO: 10 | SEQ ID NO: 42 | SEQ ID NO: 60 | 425.8 | 1.4e−125 |
| *Chlamydomonas reinhardtii* | SEQ ID NO: 11 | SEQ ID NO: 43 | SEQ ID NO: 61 | 413.3 | 8.4e−122 |
| *Chromochloris zofingiensis* | SEQ ID NO: 12 | SEQ ID NO: 44 | SEQ ID NO: 62 | 292.6 | 6.1e−85 |
| *Volvox carteri* | SEQ ID NO: 13 | SEQ ID NO: 45 | SEQ ID NO: 63 | 441.4 | 2.3e−130 |

TABLE 3-continued

SGI1 Orthologs in Algal species

| Organism | Polypeptide Sequence | RR domain | Myb domain | HMM Score | E value |
|---|---|---|---|---|---|
| *Tetraselmis* sp. 105 (T-5172) | SEQ ID NO: 14 | SEQ ID NO: 46 | SEQ ID NO: 64 | 403.6 | 7.9e−119 |
| *Tetraselmis* sp. 105 (T-5185) | SEQ ID NO: 15 | SEQ ID NO: 46 | SEQ ID NO: 64 | 403.0 | 1.2e−118 |
| *Tetraselmis* sp. 105 (T-5230) | SEQ ID NO: 16 | SEQ ID NO: 46 | SEQ ID NO: 64 | 402.9 | 1.3e−118 |
| *Oocystis* sp. | SEQ ID NO: 17 | SEQ ID NO: 47 | SEQ ID NO: 65 | 426.9 | 6e−126 |
| *Micromonas* sp. RC299 | SEQ ID NO: 18 | SEQ ID NO: 48 | SEQ ID NO: 66 | 418.4 | 2.4e−123 |
| *Micromonas pusilla* | SEQ ID NO: 19 | SEQ ID NO: 49 | SEQ ID NO: 67 | 405.9 | 1.6e−119 |

Plant species had homologs whose HMM scores ranged from 475.9 (*Arabidopsis halleri*) to below 200. Examples of plant homologs having HMM scores of 370 or greater are provided in Table 4. Growth effects on plants having a mutation in a gene encoding one of these homologs, the *Arabidopsis gaditana* "ARR2" gene having an HMM score of 371, is demonstrated in Example 19.

TABLE 4

SGI1 Homologs in Plant species

| Organism | Polypeptide Sequence | RR domain | Myb domain | HMM Score | E value |
|---|---|---|---|---|---|
| *Sphagnum fallax* | SEQ ID NO: 20 | SEQ ID NO: 50 | SEQ ID NO: 68 | 397.3 | 6.8e−117 |
| *Physcomitrella patens* | SEQ ID NO: 21 | SEQ ID NO: 51 | SEQ ID NO: 69 | 372.3 | 2.8e−109 |
| Arabidopsis_thaliana | SEQ ID NO: 22 | SEQ ID NO: 52 | SEQ ID NO: 70 | 371.1 | 6.4e−109 |
| *Arabidopsis halleri* | SEQ ID NO: 23 | SEQ ID NO: 53 | SEQ ID NO: 71 | 475.9 | 6.9e−141 |
| *Arabidopsis lyrata* | SEQ ID NO: 24 | | SEQ ID NO: 71 | 395.5 | 2.4e−116 |
| *Helianthus annus* | SEQ ID NO: 25 | | | 391.2 | 4.9e−115 |
| *Vitis vinifera* | SEQ ID NO: 26 | SEQ ID NO: 54 | SEQ ID NO: 72 | 390.6 | 7.3e−115 |
| *Amborella trichopoda* | SEQ ID NO: 27 | | | 390.1 | 1e−114 |
| *Ricinus communis* | SEQ ID NO: 28 | | | 390.1 | 1.1e−114 |
| *Solanum lycopersicum* | SEQ ID NO: 29 | | | 388.4 | 3.4e−114 |
| *Solanum tuberosum* | SEQ ID NO: 30 | | | 387.2 | 7.9e−114 |
| *Gossypium hirsutum* | SEQ ID NO: 31 | | | 385.8 | 2.1e−113 |
| *Theobroma cacao* | SEQ ID NO: 32 | | | 383.0 | 1.6e−112 |
| *Phaseolus vulgaris* | SEQ ID NO: 33 | | | 381.6 | 4.2e−112 |
| *Glycine max* | SEQ ID NO: 34 | SEQ ID NO: 55 | SEQ ID NO: 73 | 381.4 | 4.6e−112 |
| *Chenopodium quinoa* | SEQ ID NO: 35 | | | 373.7 | 1.1e−109 |
| *Malus domestica* | SEQ ID NO: 36 | | | 372.6 | 2.4e−109 |
| *Zea mays* | SEQ ID NO: 37 | SEQ ID NO: 56 | SEQ ID NO: 74 | 371.5 | 4.9e−109 |
| *Brassica rapa* | SEQ ID NO: 38 | | | 370.5 | 1e−108 |
| *Oryza sativa* | SEQ ID NO: 39 | SEQ ID NO: 57 | SEQ ID NO: 75 | 369.6 | 1.9e−108 |

In all of the algal and plant homologs listed in Tables 2 and 3, the RR and myb domains occur within the first (N-terminal-most) amino acids of the polypeptide sequences as annotated in the JGI genomes, and no conserved domains are identified carboxy-terminal to the myb domain in these SGI1 homologs.

Example 7. Chlorophyll Content, Antenna Size, and Photophysiology of SGI1 Mutants NE-7843 and NE-13380

Chlorophyll content of the high productivity mutants was determined by extracting cells with methanol and analyzing the supernatant by spectrophotometry. Briefly, 500 µl aliquots of culture were pipetted into 2.0 ml twist top tubes and pelleted using a table top microcentrifuge at 15,000 rpm for 10 minutes. The supernatants were aspirated from the pellets, and each pellet was resuspended in 1.5 ml 99.8% methanol (previously neutralized with magnesium carbonate). 0.2 ml of glass beads (0.1 mm diameter) were added to each vial and bead beat for 3 min 1.0 ml of supernatant was transferred to new 1.7 ml flip-top tubes and were centrifuged in a table top microcentrifuge at 15,000 rpm for 10 minutes. The resulting pellets were white indicating that a complete extraction had been performed. 0.8 ml of each supernatant was pipetted into an optical glass cuvette and absorption wavelengths were read immediately at 720 nm, 665 nm and 652 nm wavelengths. Spectrophotometric measurements were carried out in dual-beam mode using a 99.8% methanol blank. The following equations were used to calculate the concentration of chlorophyll: Chlorophyll a [g m$^{-3}$]=16.72 (A665−A720)+9.16 (A652−A720) and Chlorophyll b [g m-3]=34.09(A652−A720)−15.28(A665−A720). The amount of chlorophylls a and be were standardized on a per cell and per TOC basis. Table 5 shows that while the amount of total chlorophyll per cell varied somewhat among the SGI1 mutants, it was universally decreased with respect to wild type cells by an amount ranging from about 30% to about 65%, consistent with the observed reduction in antenna size. On a per TOC basis, the reduction in total chlorophyll in SGI1 mutants with respect to wild type cells ranged from about 30% to about 50%.

TABLE 5

Chlorophyll content of SGI1 Mutants and Wild Type Algae

| Strain | Chl a/ cell, pg | Chl a, % change | Chl b/ cell, pg | Chl b, % change | Total Chl/ TOC (%) | Total Chl/ TOC % change |
|---|---|---|---|---|---|---|
| WT-1185 | 0.284 | 0% | 0.097 | 0% | 6.9% | 0% |
| NE-7843 | 0.306 | 8% | 0.058 | −40% | 4.7% | −32% |
| NE-13380 | 0.287 | 1% | 0.063 | −35% | 4.4% | −36% |
| GE-16491 | 0.250 | −12% | 0.045 | −54% | 3.7% | −46% |
| GE-16492 | 0.211 | −26% | 0.035 | −64% | 3.4% | −50% |
| GE-16493 | 0.246 | −14% | 0.043 | −55% | 3.6% | −47% |

In addition to chlorophyll content, SGI1 knockout strains NE-7843, NE-13380, GE-16391, GE-16392, and GE-16393 were analyzed for PSII antenna size, PSI antenna size, $1/\tau'_{Qa}$ (the light saturated rate of electron transport on the acceptor side of photosystem II at light saturation, a measure of the efficiency of linear photosynthetic electron transport) as well as a Pmax for carbon fixation. Cells of the wild type and SGI1 mutant strains were cultured in the constant light semicontinuous culture assay (CL-SCPA) described in Example 3. Data on *Parachlorella* wild type and SGI1 classical mutants (NE-7843 and NE-13380) were obtained in separate experiments from the that included the three targeted SGI1 knockouts (GE-16491, GE-16492, GE-16493). Analysis of various photosynthetic parameters was performed using the Fluorescence Induction and Relaxation (FIRe) technique developed to measure a comprehensive series of photosynthetic and physiological characteristics of photosynthetic organisms (Gorbunov and Falkowski (2005) "Fluorescence Induction and Relaxation (FIRe) Technique and Instrumentation for Monitoring Photosynthetic Processes and Primary Production in Aquatic Ecosystems" in: Photosynthesis: Fundamental Aspects to Global Perspectives, Proc. 13th International Congress of Photosynthesis, Montreal, Aug. 29-Sep. 3, 2004. (Eds: A. van der Est and D. Bruce), Allen Press, V.2, pp. 1029-1031). The FIRe technique relies on measurement and analysis of chlorophyll "variable fluorescence" profiles (reviewed by Falkowski et. al., 2004 "Development and Application of Variable Chlorophyll Fluorescence Techniques in Marine Ecosystems" in: Chlorophyll a Fluorescence: A Signature of Photosynthesis (C. Papageorgiou and Govingjee, eds), Springer, pp. 757-778) which depend on the relationship between chlorophyll fluorescence and the efficiency of photosynthetic processes. This technique provides a set of parameters that characterize photosynthetic light-harvesting processes, the photochemistry in Photosystem II (PSII), and photosynthetic electron transport down to carbon fixation. The measurements performed herein used a mini-FIRe device produced by Maxim Gorbunov of Rutgers University, East Brunswick, N.J. A commercially available FIRe device is available from Sea-Bird Scientific (Halifax, Canada, satlantic.com and planet-ocean.co.uk). Further information regarding the use of the FIRe device is available in company manuals. All measurements were taken using constant light (2000 µmol photons·m$^{-2}$·sec$^{-1}$) semicontinuous cultures (CL-SCPA) cultures (see Example 3). To obtain $F_V/F_M$ and $\sigma_{PSII}$ measurements of Fluorescence Induction and Relaxation (FIRe) kinetics were performed in the dark. The values for Fv/Fm and $\sigma_{PSII}$ presented in Table 7 were calculated as an average of 6 measurements (3 measurements of each of the 2 biological replicates), errors for these parameters did not exceed 5%.

Measurements of PSI cross-section were performed using a modified JTS-10 spectrometer with a filter set to measure the electrochromic shift (ECS) at 520 nm equipped with a custom-built single turnover flasher (STF). The peak power density in the sample chamber was high enough to ensure full closure of reaction centers within approximately 10 µs. The resulting excitation rate was ~1 to 3 hits per reaction center per 10 µs (depending on the functional absorption cross section of the photosystem). The STF generated short ultra-bright pulses of blue light (455 nm, with 30 nm half bandwidth), and the pulse timing was controlled by the trigger from the JTS-10 Spectrometer. The pulse duration was controlled by the STF Pulse Control Box and was adjustable in the range from 1 µs to 50 µs using the potentiometer on the front panel. To measure the PSI cross-section, we diluted cultures to an OD of about 0.2 at the chlorophyll maximum (~440 nm) based on measurement of absorption spectra of cell suspension using a Perkin Elmer Lambda 650 spectrophotometer equipped with an integrating sphere. The ECS was measured using 10 µs flashes with intensities ranging from 4000 to 120,000 µmol photons m$^{-2}$ s$^{-1}$ in the presence of DCMU and hydroxylamine. The experimental curve was fitted with a simple exponential function $$ECS = ECS_M \times (1 - e^{It \times \sigma PSI})$$

where $ECS_M$ is the maximal ECS signal; It is photon density in photons/m$^2$; and $\sigma_{PSI}$ is functional cross-section of PSI. Obtained values for functional cross-section of PSI for the wild type of *Parachlorella* (WT-1185) was $(4.0 \pm 0.5) \times 10^{-18}$ m$^2$. These values are close to those obtained for the functional cross-section of PSII grown under the same conditions ($\sigma_{PSII} = (4.3 \pm 0.1) \times 10^{-18}$ m$^2$). Errors for these parameters were estimated not to exceed 20%.

Carbon fixation rates ($C^{14}$ $P_{max}$) were measured using cultures normalized to 5 µg chl ml$^{-1}$ in media containing 0.5 g l$^{-1}$ (5.95 mM) sodium bicarbonate. 20.4 µCi ml$^{-1}$ $C^{14}$ labeled sodium bicarbonate was added to each culture and exposed to 2500 µE for a duration of 10 minutes. Samples were immediately acidified with 2N HCl and allowed to off-gas overnight. The following day samples were measured using a Beckman LS6500 scintillation counter and quantified.

$\tau'_{Qa}$ (the time of electron transport on the acceptor side of PSII measured under saturating light conditions—effectively determined by the slowest step of linear photosynthetic electron transport) was measured from FIRe light curves and dark induced relaxation kinetics (DIRK) profiles. Volumetric PSII concentration relative to wild type was estimated as ($Fv/\sigma^{530}_{PSII}$). Errors for these parameters were estimated not to exceed 15%. Optical absorption cross section (averaged over emission spectrum of a light source) was estimated using the following equation:

$$a_{chl/TOC} = \frac{1}{[Chl/TOC]} \int_{400}^{700} \ln(10) \times \frac{OD(\lambda)}{\Delta l} \times \frac{I(\lambda)}{\int_{400}^{700} I(\lambda) d\lambda} d\lambda$$

where [Chl/TOC] is the chlorophyll/TOC of the sample, OD($\lambda$) is the measured optical density of the sample at wavelength $\lambda$, $\Delta l$ is the measuring beam pathlength in the cuvette (1 cm), I($\lambda$) is the intensity of the light source used to grow algae at wavelength $\lambda$.

TABLE 6

Fluorescent and Photosynthetic Parameters Measured with the FIRe Technique

| FIRe, JTS-10 retrieved parameters | Description |
|---|---|
| Fv/Fm | Maximum quantum yield of photochemistry in PSII, measured in a dark-adapted state (dimensionless). This parameter characterizes the efficiency of primary photosynthetic reactions. |
| $\sigma_{PSII}$ | Functional absorption cross section of PSII (Å$^2$) in a dark-adapted state. The parameter is the product of the optical absorption cross section of PSII (i.e., the physical size of the PSII unit) and the quantum yield of photochemistry in PSII. Could be measured using different excitation wavelengths |
| $\sigma_{PSI}$ | Functional absorption cross section of PSI (Å$^2$) in a dark-adapted state. The parameter is the product of the optical absorption cross section of PSII (i.e., the physical size of the PSI unit) and the quantum yield of photochemistry in PSI. |
| $1/\tau'_{Qa}$ | Light saturated rate of electron transport on the acceptor side of photosystem II. This parameter indicates efficiency of linear photosynthetic electron transport |

Table 7 shows that all of the SGI1 mutants demonstrated increased Fv/Fm (by about 10-14%) while exhibiting reduced antenna cross-sectional size as compared to the wild type strain from which they were derived. The SGI1 mutants also had reduced antenna size of PSII and PSI (down 40-50% with respect to wild type), high rates of electron transport on the acceptor side of PSII ($1/\tau'_{Qa}$) under saturating light (increased between about 35% and about 130%, and by at least approximately 100% with respect to wild type in the engineered mutants) and high rates of carbon uptake ($P_{max}$) (up at least 30-40% with respect to wild type), while, as determined by Multiple Reaction Monitoring protein determination, the number of photosystems on a per TOC basis was maintained (see Example 7). Strains were also characterized by higher chlorophyll a to chlorophyll b ratio compared to the wild type (increased by approximately 70%), which is indicative of loss of peripheral light harvesting complexes and is consistent with the observed reduced size of the functional cross-section of PSII. (Table 7). The recapitulated SGI1 KO mutants (GE-16491, GE-16492, and GE-16493, engineered using CRISPR/Cas9) showed a very similar photophysiological phenotype to the original mutants, but with even greater reductions in the antenna of PSII (up to 55%), faster rates of electron transport on the acceptor side of PSII under saturating light (increased by up to 130%), and higher rates of carbon uptake (up to 80% higher in GE-16491) (Table 7).

In pilot experiments, wild type *Parachlorella* cells (strain WT-1185) were mutagenized by UV as described in Example 1. Mutagenesis can also be effected by chemical mutagens, random insertional mutagenesis (see, for example, US 2014/0220638, incorporated herein by reference) or even targeted mutagenesis, such as by CRISPR/Cas9 (see, for example US 2016/0304896, incorporated herein by reference).

As described in Example 2, mutagenized algal cells were allowed to recover in low light and then subjected to fluorescence activated cell sorting (FACS), where low chlorophyll fluorescence cells having the lowest approximately 0.5 to 2% of chlorophyll fluorescence compared to the total population of cells were selected. (Sticter, less strict, broader, or narrower ranges of chlorophyll fluorescence can be imposed on the FACS selection at the user's discretion.) The FACS sorted cells were plated, and after colonies grew up they were individually picked and inoculated into culture medium (lacking a reduced carbon source) in 96 well plates and the cultures were allowed to grow photoautotrophically in the light (500 µE m-2 s$^{-1}$. Small-scale (approximately 100-200 µl) cultures were initiated in ten 96 well plates, resulting in approximately 960 individual cultures of low chlorophyll-selected lines.

The second phase of the screen for high productivity mutants used the FIRe device with an attached fiber optic cable that transferred light pulses for probing cell fluores-

TABLE 7

Photophysiology of *Parachlorella* SGI Mutants

| | FIRe/JTS-10 | | | | $^{14}$C | |
| --- | --- | --- | --- | --- | --- | --- |
| Strain | $F_V/F_M$ | $\sigma_{PSII}$ (Å$^2$, at 450 nm) | $\sigma_{PSII}$ (Å$^2$, at 530 nm) | $\sigma_{PSI}$ (Å$^2$, at 440 nm) | $1/\tau'_{Qa}$ (s$^{-1}$) | $P_{max}$ (nmol $^{14}$C/µg TOC/hour) | Cell size Cell size, µm$^3$ |
| WT-1185 | 0.598 | 428 | 153 | 380 | 94 | 10.1 | 40 |
| NE-7843 | 0.667 | 277 | 89 | — | 194 | 14.8 | 63 |
| NE-13380 | 0.677 | 261 | 84 | 240 | 197 | 17.3 | 57 |
| GE-16491 | 0.678 | 253 | 75 | — | 211 | 19.6 | 83 |
| GE-16492 | 0.688 | 235 | 69 | — | 225 | 15.4 | 85 |
| GE-16493 | 0.687 | 243 | 71 | — | 250 | 16.2 | 76 |

Example 8. Photophysiological Screening for High Productivity Algal Mutants

Based on the discovery of high productivity mutants NE-7843 and NE-13380 using a screen for reduced antenna strains and productivity assays, and the subsequent discovery that such high productivity mutants had distinctive photophysiological characteristics as set forth in Tables 5 and 6, including higher maxium photosynthetic yield ($F_V/F_M$), reduced PSII antenna size ($\sigma_{PSII}$), and increased PSII turnover rate ($1/\tau'_{Qa}$), a screen for high productivity algal mutants was devised, referred to herein as the "FACS-FIRE" screen. The screen included a selection for low chlorophyll mutants from a progenitor algal population using FACS, and screening of individual lines from the population selected by FACS for low chlorophyll fluorescence using the FIRe device described in Example 6 to determine PSII antenna size ($\sigma_{PSII}$) at one or more wavelengths, $F_V/F_M$, and the rate of electron transport at the acceptor side of PSII ($1/\tau'_{Qa}$). Lines having reduced PSII antenna size, increased $F_V/F_M$ and increased $1/\tau'_{Qa}$ were expanded, re-tested, and assayed for carbon uptake rate (Pm ($^{14}$C)) and productivity in culture.

cence and transmitted collected fluorescence to the instrument detector. The fiber optic cable was held over each individual well to probe and measure fluorescence from isolated cell lines, which was recorded and used to calculate $F_V/F_M$, PSII antenna size ($\sigma_{PSII}$) and PSII turnover rate (rate of electron transport at the acceptor side of PSII, $1/\tau'_{Qa}$) by the FIRe device. Lines exhibiting $F_V/F_M$ increased by at least 10%, PSII antenna size reduced by at least 30%, and PSII turnover rate increased by at least 50% were selected for further study. Cutoff values for such parameters can be set to different values at the user's discretion, for example, $F_V/F_M$ increased by at least 5%, PSII antenna size reduced by at least 20%, and PSII turnover rate increased by at least 20% or stricter criteria can be used for selecting strains of interest.

Figure 6:
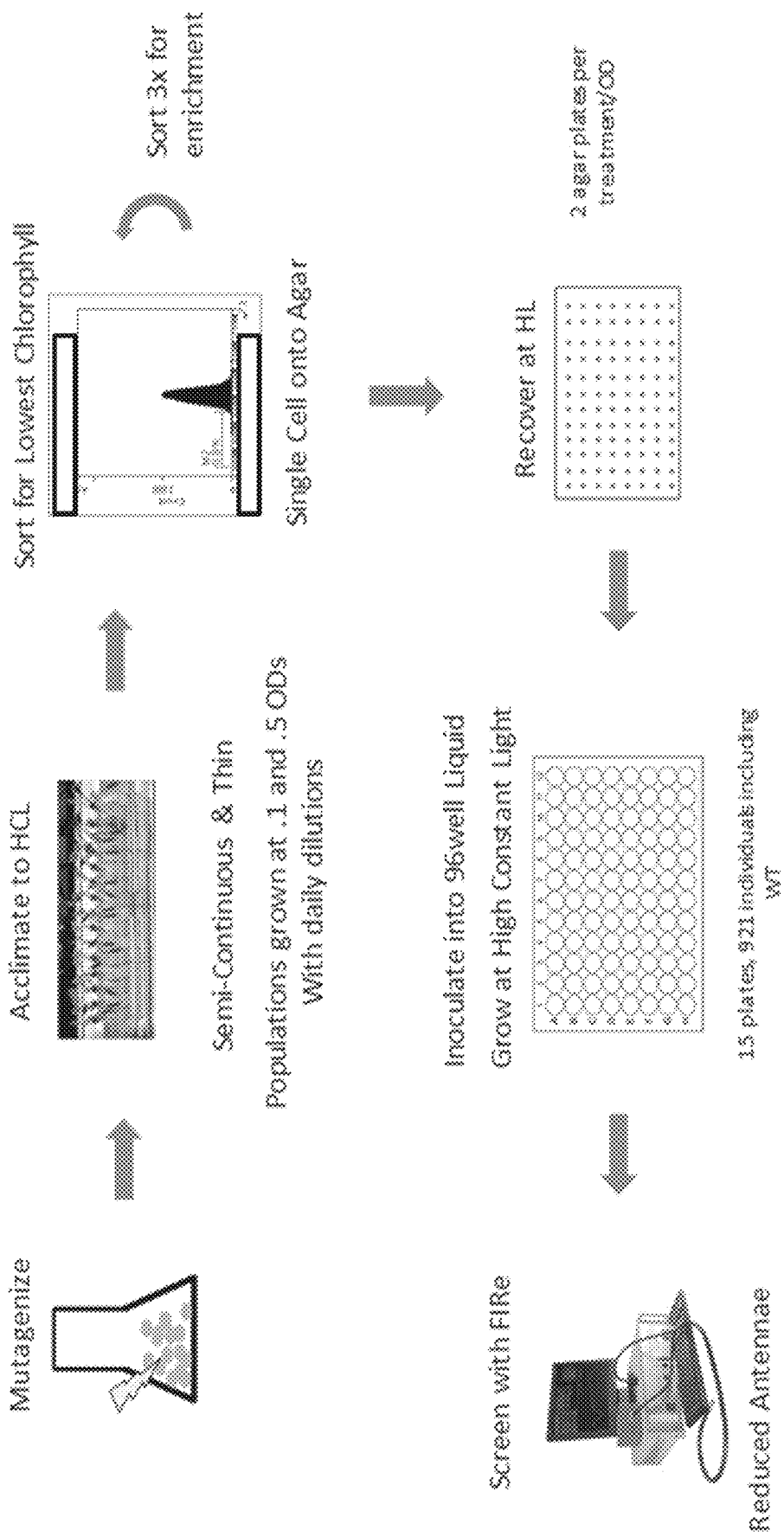
FIG. 6 is a schematic diagram of the FACS-FIRe screening method. Not shown is mutagenesis, which can be performed prior to FACS. The method can further include productivity testing.

A schematic of the screening process is shown in FIG. 6. The screen, involving FACS-based selection of low chlorophyll lines and FIRe-based screening of small scale culture can be further automated, for example, by the FACS device directing low chlorophyll cells directly into wells of multi-well plates and/or by an automated mechanical arm to successively position the FIRe fiber optic cable or an emitting LED with fluorescence detector system—or another system capable of providing microsecond high intensity light flashes and collecting fluorescence signals over individual wells of multiwell plates.

Algal lines demonstrating low chlorophyll fluorescence and reduced antenna size, increased $F_V/F_M$, and increased PSII turnover rate ($1/\tau'_{Qa}$) can be further assessed as provided in Example 6, above, for example, for low chlorophyll b content and/or increased carbon uptake and for higher productivity in culture, for example, in semicontinuous culture (e.g., Example 3).

Figure 7:
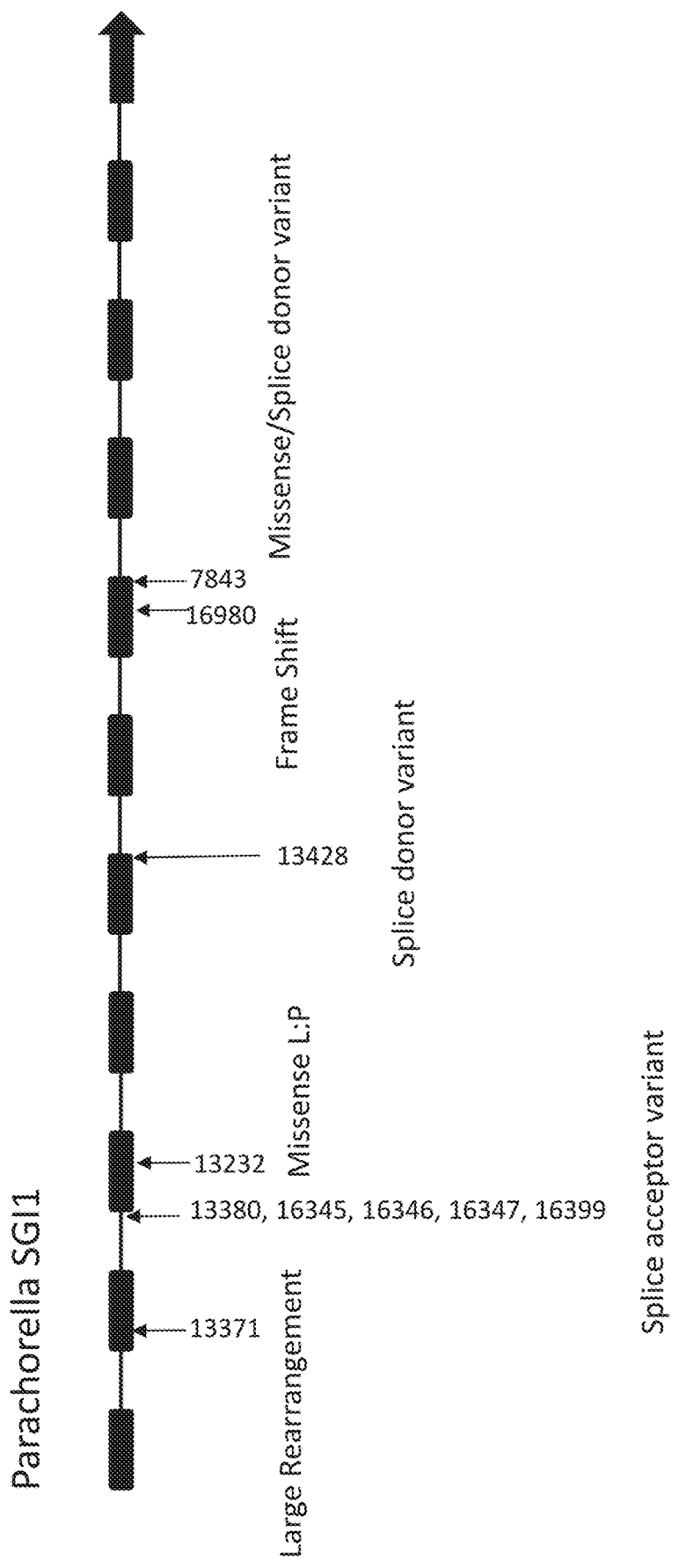
FIG. 7 is a diagram of the *Parachlorella* SGI1 gene structure depicting locations of SNPs detected by genome sequencing of NE-07843 and NE-13380 and targeted mutations GE-13371, GE13380, GE-16345, GE-16346, GE-16347, GE-16399, GE-13232, GE-13428, and GE-16980 resulting from Cas9-mediated mutagenesis. The locations of the guide RNAs are shown by arrows.

Several mutant strains were identified using the FACS-FIRE screening methods, among them NE-16980, whose genome was sequenced. NE-16980 was found to have a frameshift mutation in the SGI1 (T-2661) gene (FIG. 7).

Example 9. Microproximate Analysis of SGI1 Mutants NE-7843 and NE-13380

To determine the overall biomass composition of the SGI1 attenuation mutants, quantitative analysis of samples from cultures grown in semicontinuous mode with 40% daily dilution was performed to determine the lipid, protein, and carbohydrate content of the cells in semi-continuous culture. After the cultures reached steady state, aliquots of the culture removed for daily dilution was used for analysis of lipid, protein, and carbohydrate. Total organic carbon (TOC) of the algal culture samples was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of $r^2 > 0.999$.

To determine lipid content, FAME analysis was performed on 2 mL samples that were dried using a GeneVac HT-4X. To the dried pellets the following was added: 500 µL of 500 mM KOH in methanol, 200 µL of tetrahydrofuran containing 0.05% butylated hydroxyl toluene, 40 µL of a 2 mg/ml C11:0 free fatty acid/C13:0 triglyceride/C23:0 fatty acid methyl ester internal standard mix and 500 µL of glass beads (425-600 µm diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were then vortexed for five minutes at 2 krpm and finally centrifuged for three minutes at 1 krpm. The heptane layer was sampled using a Gerstel MPS Autosampler. Quantitation used the 80 µg of C23:0 FAME internal standard.

To determine protein content, isolated biomass samples were hydrolyzed and the amino acids were derivatized to propoxycarbonyl propyl esters (AAPE's), analyzed via GC/MS, and quantitated against an internal standard, as detailed below. Aliquots (0.5 ml) of wild type *Parachlorella* (WT-1185) and SGI1 knockout strain GE-13380 from the semicontinuous cultures were centrifuged and the pellets were washed twice with phosphate buffered saline (PBS). The cells were finally resuspended to a final volume of 0.5 ml (the starting volume) and transferred to a 4 ml glass vial. To the culture sample, 800 µl of 6M HCl with TGA was added (400 µl of thioglycolic acid (TGA) was added to 19.6 ml of 6M HCl just before use). Ten µl of beta mercapto-ethanol were then added to the vial, followed by 200 µl of 20 mM norvaline, used as an internal standard. Each vial was blanketed with $N_2$ for 10 seconds, after which the vials were vortexed for 1 min at 2500 rpm to homogenize the samples. The vials were then placed in a 110° C. oven for 22 hours. At the end of the hydrolysis incubation, the vials were vortexed for 10 min at 2500 rpm, and then centrifuged up to 1000 rpm after which the centrifuge was stopped. A 50 aliquot was removed from each vial and dried by placing in an acid safe EZ-2 Genevac which was run on the HCl method for at least 3 hours prior to derivatization.

For derivativization, 250 µl of milli-Q $H_2O$ was added to the dried acid hydrolysates, followed by 10 µl of antioxidant mix and then 120 µl of 0.5M NaOH. The antioxidant mix was made by adding 0.25 ml of n-propanol, 50 µl of thiodiglycol, and a few granules of phenol to 2.20 ml of Milli-Q $H_2O$, and vortexing. 80 µl of the catalyst, a 4:1 mix of pyridine and n-propanol was then added, and the vial was capped and vortexed at 2500 rpm for 1 min 50 µl of propyl chloroformate was then added, and the vial was capped and vortexed at 2500 rpm for 1 min After a 1 min incubation, the vial was again vortexed at 2500 rpm for 1 min 500 µl of a 4:1 mixture of isooctane and chloroform was then added to the vial which was again capped and vortexed at 2500 rpm for 1 min. The rack of sample vials was then covered with another sample rack and shaken 20 times to ensure emulsion of the samples. The samples were then centrifuged until the centrifuge reached 1000 rpm and then the centrifuge was stopped. 200 µl of the organic layer was removed into a new GC vial with a glass insert and analyzed by GC/MS.

The samples were analyzed by GC/MS using a ZB-AAA 10×0.25 mm ID Amino Acid Analysis GC column and quantitated using the internal norvaline standard. The needle Wash 1 solvent was acetone and the needle Wash 2 solvent was isooctane/chloroform (80/20) with a program of 110° C., hold 0 min, 30° C./min to 320° C., hold 0.5 min, using a 4 µl injection at 15:1 split, 250° C. at 1.1 ml/min with a 300° C. transfer line.

The GC-MS data was multiplied by 0.0005 L to obtain µmol values, and multiplied by the molecular weight of the amino acid. The value was divided by 5 to correct for the volume to obtain µg/ml of each amino acid. Asparagine is converted to aspartic acid during acid hydrolysis, thus asparagine plus aspartic acid are determined as aspartic acid in these methods. Tryptophan is not measured by these methods but does not make up a significant fraction of the amino acids in *Parachlorella* proteins.

For total carbohydrate quantitation, biomass was hydrolyzed for one hour in 6N hydrochloric acid to convert polysaccharides to monosaccharides. The resulting monosaccharides were converted to trimethylsilyl ethers using MSTFA N-methyl-N-trinethylsilyltrifluoroacetamide with 1% trimethylchlorosilane, and the ethers were resolved and quantitated using GC-MS analysis.

For acid hydrolysis of culture samples, 500 µl of Milli-Q $H_2O$ was added to 500 µl culture samples in 4 ml vials, or, where the culture sample was more concentrated (higher TOC), 800 µl of Milli-Q $H_2O$ was added to 200 µl of culture sample. 20 µl of 2.5 mg/ml ribitol and U-$^{13}$C-glucose as an internal standard was added to the 1 ml diluted culture samples in 4 ml vials. 1 ml of concentrated HCl was then added to each of the vials, the vials were capped and placed in a 105° C. dry bath for 1 hour. The samples were then allowed to cool to room temperature, and 100 µl was transferred to a glass insert inside a 1.5 ml microcentrifuge tube.

For derivatization, the microfuge tubes that included glass inserts containing the samples were place in an acid safe EZ-2 Genevac which was run on the HCl method for at least 3 hours. After drying, 100 µl of the derivatization reagent, which consisted of 800 µl of dry pyridine added to 1 ml of freshly opened MFSTA-1% TMCS, was added to each sample. The samples were incubated for 1 hour at 40° C. while mixing at 1000 rpm in an Eppendorf Thermomixer. Following incubation, the samples were directly analyzed by GC/MS.

The samples were analyzed by GC/MS using a DB5-MS 30 m×250 µm×25 µm GC column and quantitated using the internal U-$^{13}$C-glucose standard. The needle wash solvent was pyridine with a program of 1 min equilibration, 170° C. for 8 min, 10° C./min to 210° C. for 0 min, then 50° C./min to 325° C. for 2 min (total run time 16.3 min).

Figure 8:
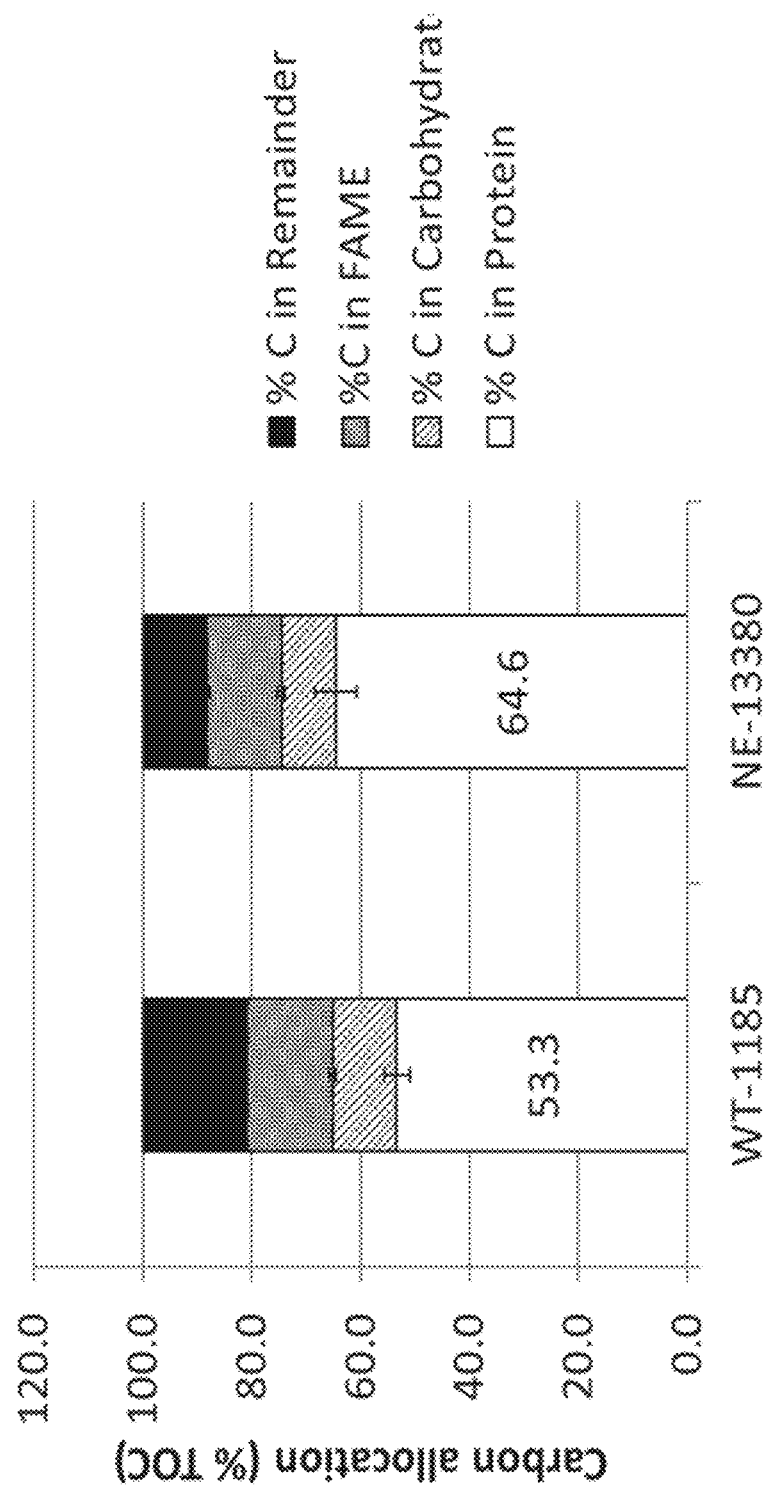
FIG. 8 is a graph showing the results of microproximate analysis of biomass of *Parachlorella* wild type strain WT-1185 and classical mutant NE-13380 to determine lipid, protein and carbohydrate content. Samples were acquired from cultures adapted to steady state 40% daily dilution in a semicontinuous system. FAMEs, carbohydrates, and amino acids are represented as the % of TOC allocated to each fraction calculated by the carbon content of each class of analyte. The inset numbers in the % C in protein indicate the actual percentage value.

FIG. 8 shows the results of this analysis on the wild type *Parachlorella* strain as well as the SGH gene attenuation knockout mutants GE-13380. Unexpectedly, SGH knockout mutant NE-13380 was observed to have had an increased percentage of its total organic carbon as protein with respect to wild type, demonstrating an approximately 20% increase in protein on a per TOC basis with respect to the wild type strain (WT-1185). The SGH mutant, which as demonstrated in Example 3 had increased total organic carbon accumulation as compared to wild type in the semi-continuous assay, demonstrated correspondingly reduced lipid and carbohydrate. The amino acid composition of the protein of SGH mutants was found to be highly similar to that of wild type cells. The SGH mutant strains therefore provide a genetic means of increasing the protein content of algae and algal biomass. Depending on culture conditions, an increase of approximately 40% to approximately 60% in areal protein productivity can be anticipated when compounding the increased percentage of protein with the increased biomass productivity demonstrated by the SGI1 mutants.

Example 10. Transcriptomics and Proteomics of SGI1 Mutants NE-7843 and NE-13380

Figure 9:
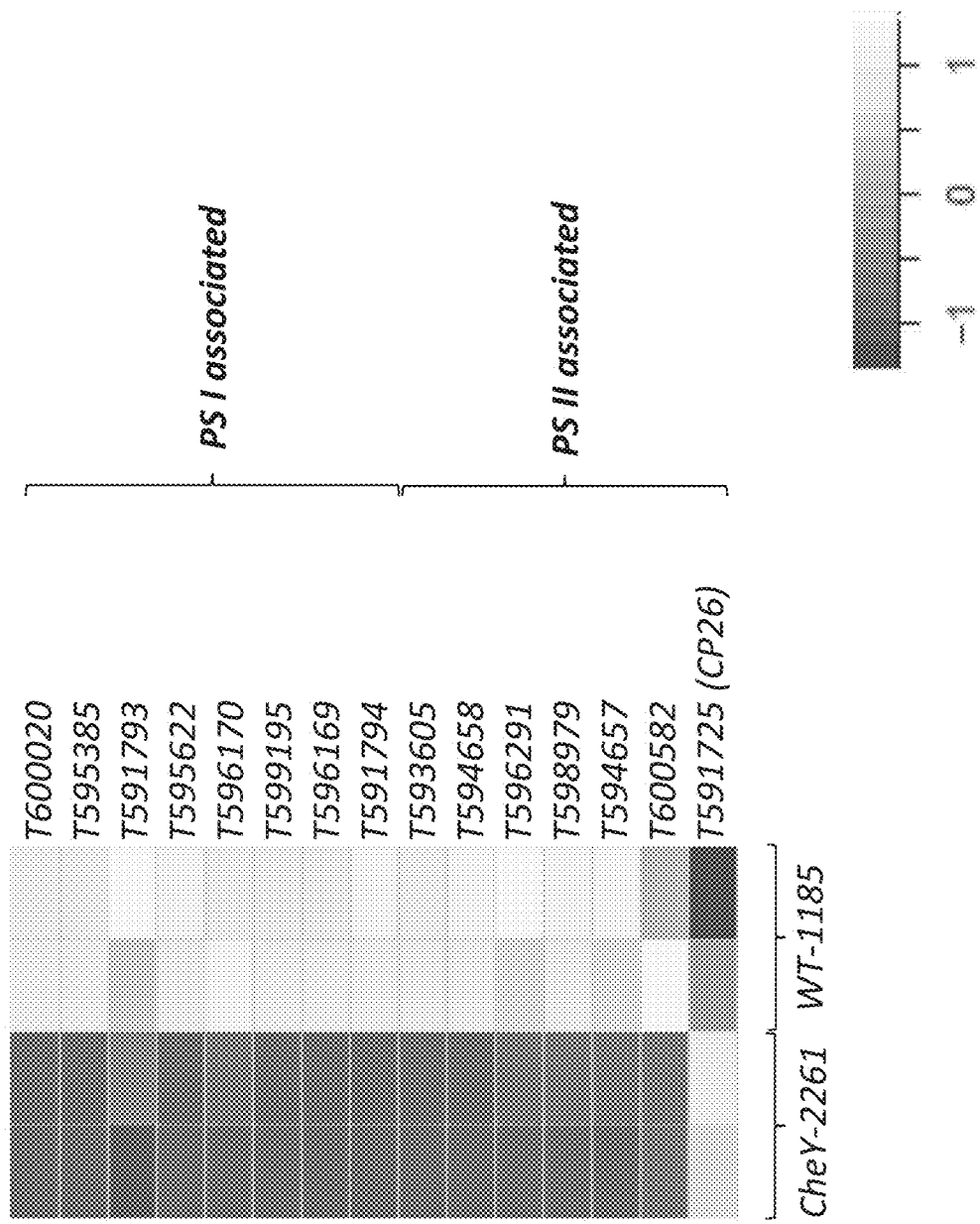
FIG. 9 is a heat map based on transcriptomics data for 15 LHC genes of *Parachlorella* that (with the exception of CP26) are downregulated in the SGI1 mutant NE-7843 with respect to the parental wild type strain WT-1185.

Transcriptomic analysis was performed on mRNA extracts of the wild type and SGH mutant strains NE-7843 and NE-13380 cultured in the constant light semicontinuous culture assay (CL-SCPA or "CL2000" assay) described in Example 3. Transcriptomic analysis of SGH mutants showed a large number of differentially regulated genes with respect to wild type. As the SGI1 mutants demonstrated reduced chlorophyll and reduced photosynthetic antenna, it was of interest to see whether the light harvesting chlorophyll-binding protein (LHC) genes had lower transcript abundance in the mutants with respect to the wild type progenitor strain. Fifteen LHC genes were identified in the *Parachlorella* genome, and strikingly, with the exception of the gene encoding CP26, an LHC polypeptide associated with the PSII reaction center, all of the identified *Parachlorella* LHC genes were found to be downregulated in the SGH mutants with respect to wild type expression levels (FIG. 9). On average, the LHCs mRNAs showed about a 1.7 fold reduction in abundance in SGH relative to WT-1185. Another striking observation from these transcriptomics data was that Rubisco activase was found to have approximately 6 fold higher transcript abundance in the SGH mutant.

Global proteomic analysis was also performed for the WT-1185 and SGH mutant NE-7843 cultured in the constant light semicontinuous culture assay (CL-SCPA or "CL2000" assay) described in Example 3. Mass spectrometry analysis (Michigan State University Proteomics Core Facility, East Lansing, Mich.) was performed to determine global protein abundance. Consistent with the transcriptomics dataset, the SGI1 mutant showed reduced LHC protein abundance and elevated Rubisco activase abundance with respect to wild type cells.

Figures 10A, 10B, 10C, 10D:
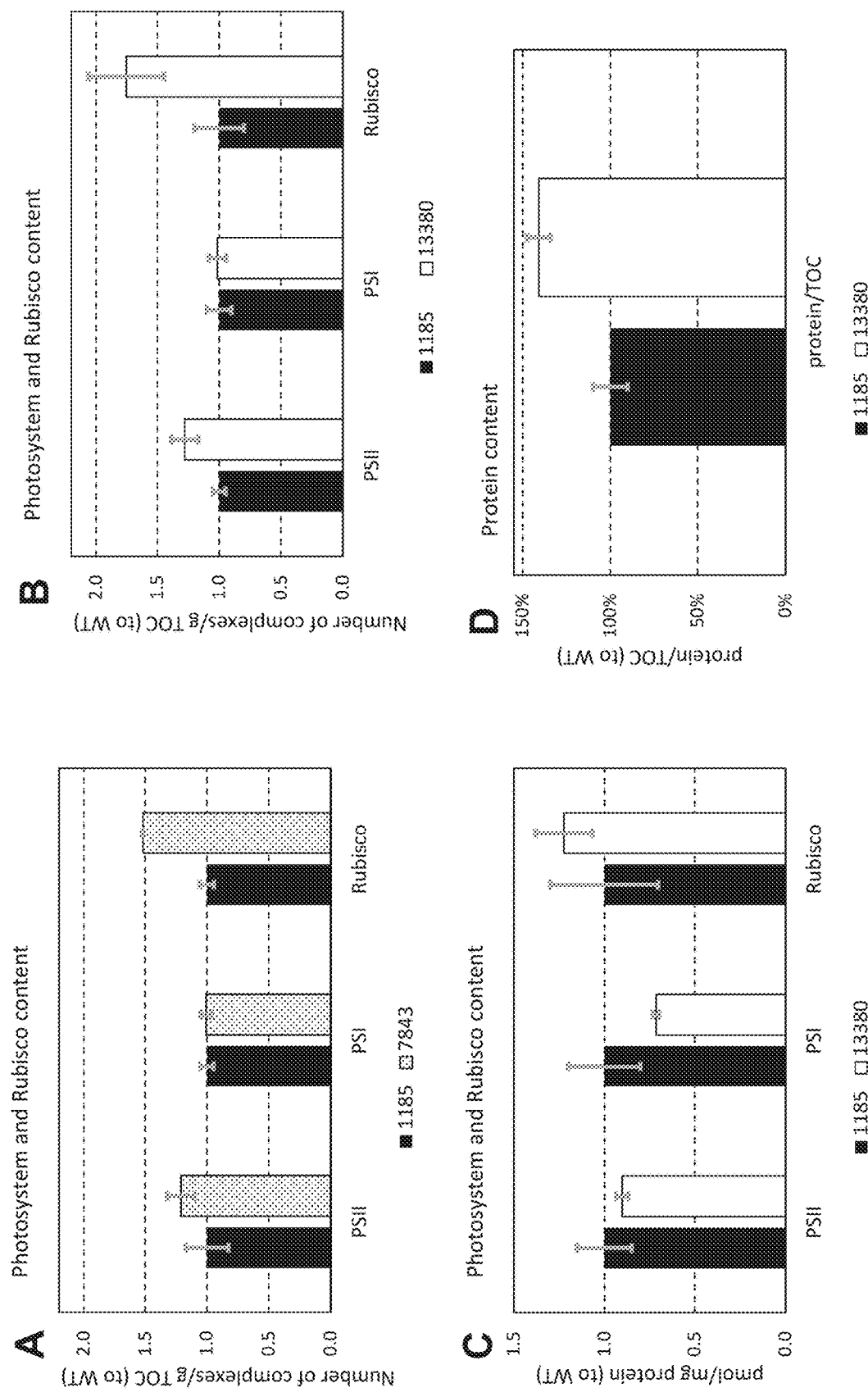
FIGS. 10A-10D provides graphs showing the results of MRM analysis of PSII, PSI and Rubisco content of *Parachlorella* wild type (WT-1185) and SGI1 classical mutants (NE-7843 and NE-13380). A) the number of PSI, PSII, and Rubisco protein complexes per TOC in wild type WT-1185 and mutant NE-7843, B) the number of PSI, PSII, and Rubisco protein complexes per TOC in wild type WT-1185 and mutant NE-13380, and C) the number of the number of PSI, PSII, and Rubisco protein complexes in wild type WT-1185 and mutant NE-13380 on a per gram protein basis. D) Lower protein per TOC in MRM analysis compared to microproximate analysis (FIG. 8) to is related to non-ideal extraction efficiency.

Targeted proteomic analysis was also performed for wild type and SGI1 mutant strains (NE-7843 and NE-13380) cultured in the constant light semicontinuous culture assay (CL-SCPA or "CL2000" assay) described in Example 3. Proteomic analysis was performed using Multiple Reaction Monitoring (MRM), a mass spectrometry approach than enables targeted quantification of proteins of interest with high specificity and sensitivity using internal standards for each protein of interest (see, for example, Qu et al. (2006) *Anal Chem.* 78:4543-4552; Domon et al. (2006) *Mol. Cell. Proteomics* 5:1921-1926; Wolf-Yadlin et al (2007) *Proc. Natl. Acad. Sci. USA* 104:5860-5865; Stahl-Zeng et al. (2007) *Mol. Cell. Proteomics* 6:1809-1817). High quality peptides from PsaD (a PS I subunit) PsbB (a PS II subunit) and RbcL (the Rubisco large subunit), were used to quantitate PSI, PSII and Rubisco abundance in wild type *Parachlorella* (WT-1185) and SGI1 mutants (NE-7843 and NE-13380). The results of the MRM proteomics analysis (JadeBio, La Jolla, Calif.) indicated that the SGI1 mutants are characterized by a slightly elevated PSII/TOC content and PSII:PSI ratio (FIGS. 10A and 10B). Higher Rubisco/TOC content was also observed in the SGI1 mutants compared to the wild type (FIGS. 10A and 10B), which, consistent with the microproximate analysis (Example 6), had higher protein content per TOC. However, quantitative Westerns comparing the levels for PsbD (a PS II polypeptide), the Rubisco large subunit, and Rubisco activase showed that, when normalized to total protein, PS II and Rubisco levels were comparable in wild type and SGI1 mutants, as the SGI1 mutant has a higher protein/TOC content overall (FIGS. 10C and 10D).

Figures 11A, 11B:
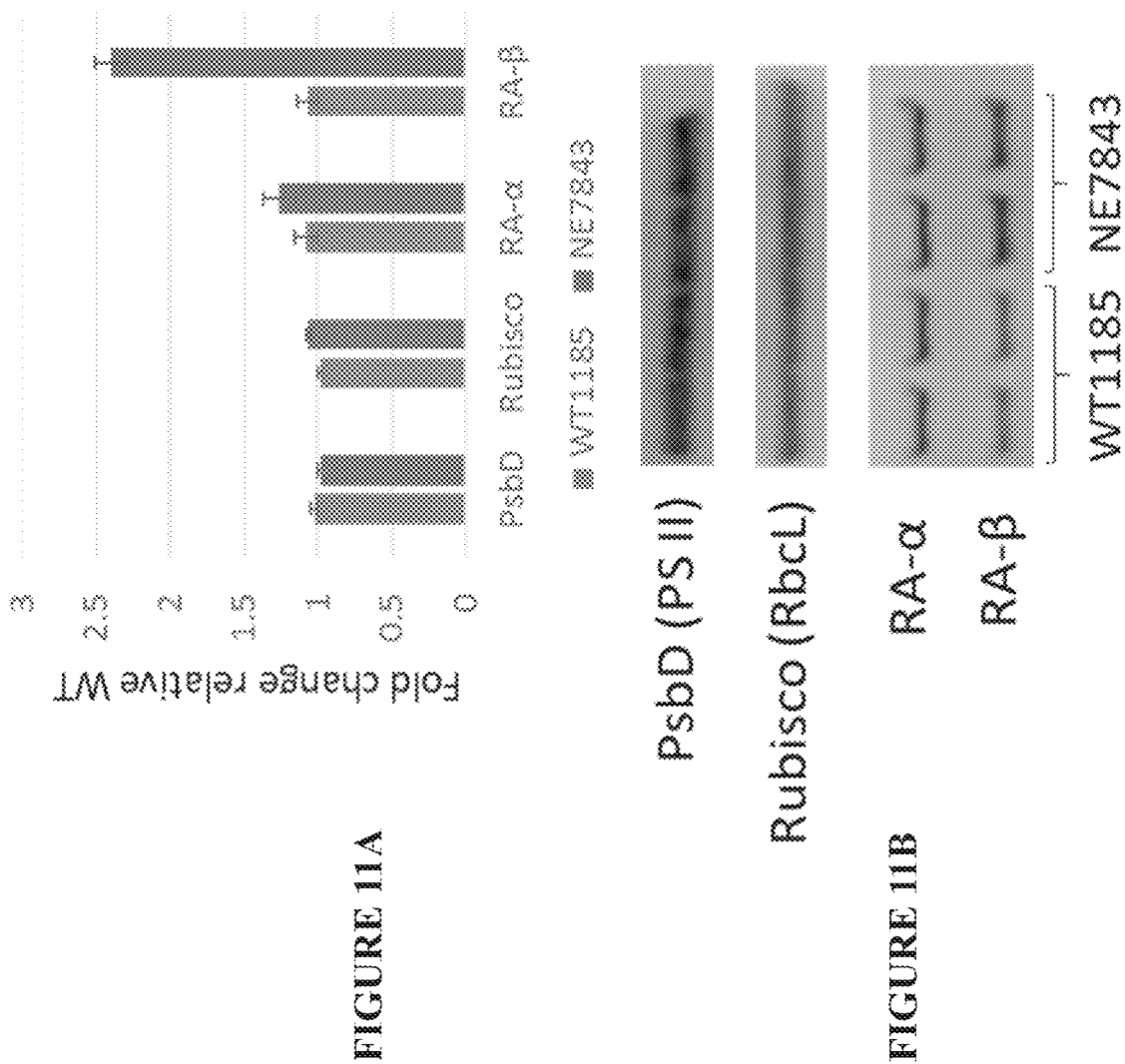
FIG. 11A is a graph showing the difference in PSII, PSI and Rubisco Activase (RA) content of *Parachlorella* wild type (WT-1185) and SGI1 classical mutant NE-7843 by microanalysis.
FIG. 11B provides Western blots used for quantitating PSII, PSI and Rubisco Activase (RA) in *Parachlorella* wild type (WT-1185) and SGI1 classical mutant NE-7843.

An increase in the abundance of the Rubisco activase (RA) protein was observed in both transcriptomics and proteomics analysis (FIGS. 11A and 11B). These observations were confirmed through quantitative Western analysis. The two Rubisco activase isozymes (alpha and beta) mainly differ in their N-termini, with RA-α having an extended N-terminus with respect to RA-β. FIG. 11B shows a Western blot in which the alpha isozyme of the Rubisco activase protein (RA-α) was found to be increased slightly and the beta isozyme of the Rubisco activase protein (RA-β) was found to be significantly increased in abundance to approximately 2.5 fold the wild type protein level, consistent with the increased abundance of the RA transcript in the mutant as determined by transcriptomic analysis.

Example 11. Productivity of SGI1 Mutants in Semicontinuous Culture Simulating Natural Irradiance Conditions To assess productivity of SGI1 mutants in a semicontinuous system under a light regime that mimicked natural daylight conditions on a spring day in Southern California, scale-up cultures were used to inoculate 225 cm$^2$ rectangular tissue culture flasks, each of which contained a final total volume of 550 ml of culture after inoculation. A typical inoculum volume was approximately 200 ml of scale-up culture that was added to approximately 350 ml of PM119 culture medium. Cultures were diluted daily at mid-day, when the light intensity was at its peak, by removing 65% of the volume and replacing it with the same volume of the assay medium plus an additional 10 ml of deionized water to make up for evaporation (included in the make-up medium). Semi-continuous assays were typically run for 10-14 days. Daily lipid and biomass productivities were only calculated for cultures that had reached steady state (where the increase in growth was equal to the dilution factor for the assay).

Three cultures were initiated per strain. The flasks included stir bars and had stoppers having inserted tubing connected with syringe filters for delivering $CO_2$ enriched air (1% $CO_2$, flow rate, 300 ml per min) that was bubbled through the cultures. The flasks were set in a water bath programmed to maintain a constant temperature of 25° C. on stir plates set to 575 rpm during the assay period. Culture flasks were masked with an opaque white plastic to provide a 31.5 cm² rectangular opening for irradiance to reach the culture. The flasks were aligned with the width (narrowest dimension) against an LED light bank that was programmed with a light/dark cycle and light profile that increased until "solar noon" and then declined to the end of the light period. The light profile was designed to mimic a spring day in Southern California: 14 h light:10 h dark, with the light peaking at approximately 2000 µE. The flasks included stir bars and had stoppers with inserted tubing connected with syringe filters for delivering $CO_2$ enriched air (1% $CO_2$, flow rate, 300 ml per min). The flasks were set in a water bath programmed to maintain a constant temperature of 25° C. on stir plates set to 575 rpm during the assay period.

Daily biomass (TOC) productivities were calculated from cultures that had reached steady state. Volumetric TOC productivities in (mg/L/day) were calculated by multiplying the volumetric TOC amounts by the dilution rate. Areal productivities (g/m²/day) were calculated by dividing the total productivity of the culture by the size of the aperture through which irradiance was permitted:

$$\frac{(\text{volumetric productivity}) \text{ mg}}{L * \text{day}} * \frac{0.55 \text{ L}}{0.00315 \text{ m}^2} * \frac{g}{1000 \text{ mg}} = \frac{g}{m^2 * \text{day}}$$

Figure 12:
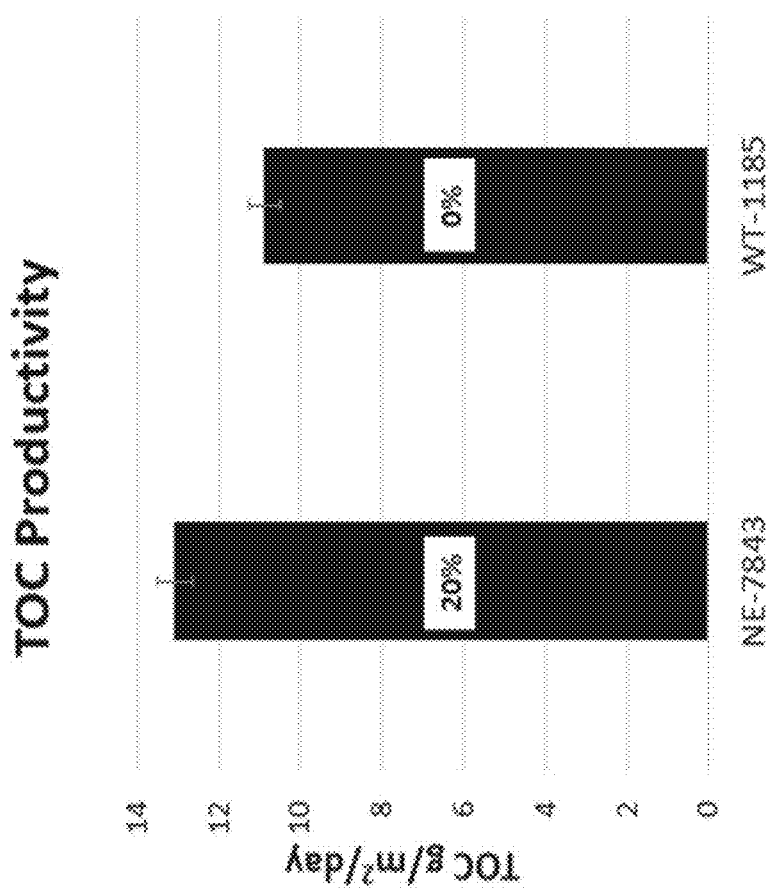
FIG. 12 is a graph showing that SGI1 mutant NE-7843 exhibits increased biomass productivity under SCPA (semi-continuous) culturing in diel light modeled after a typical Imperial Valley, Calif. on May 4th day. Data represents biological triplicates.

FIG. 12 shows the average daily TOC productivity for triplicate cultures of the NE-7843 SGI1 mutant and wild type strain WT-1185 in the semicontinuous diel assay, showing that under these conditions the mutant exhibited a 20% increase in productivity with respect to wild type.

Example 12. Productivity of Batch Cultures Under Nutrient Replete Conditions

Productivity of SGI1 mutant NE-13380 was also assessed over one week while cultured in nitrogen replete batch mode. Cultures of NE-13380 and wild type WT-1185 were inoculated to an initial OD730 of 0.5 from seed (scale-up) cultures that were grown in nitrogen replete culture medium.

After inoculation, SGI1 knockout strain NE-13380 and wild type strain WT-1185 were grown in triplicate cultures in a batch assay in 75 cm² rectangular tissue culture flasks containing 175 ml of PM119 medium for seven days. The flasks were positioned with their narrowest "width" dimension against an LED light source. The culture flasks were masked with an opaque white plastic to provide a 21.1 cm² rectangular opening for irradiance to reach the cultures. Incident irradiance was programmed at a 16 h light:8 hour dark cycle with a linear ramp up of irradiance from 0 to 1200 uE over 4 hours, after which the irradiance was held at for six hours at 1200 uE, and then a linear ramp down in irradiance from 1200 to 0 uE over a 4 h period (increasing or decreasing in 15 min intervals). Deionized $H_2O$ was added to the cultures daily to replace evaporative losses. The temperature of the cultures was regulated by a water bath set at 25° C. Samples (5 mls) were removed on daily for assessing total organic carbon (TOC) as described in Example 3. Sampling was done 30 minutes prior to the end of the light cycle.

Figure 13:
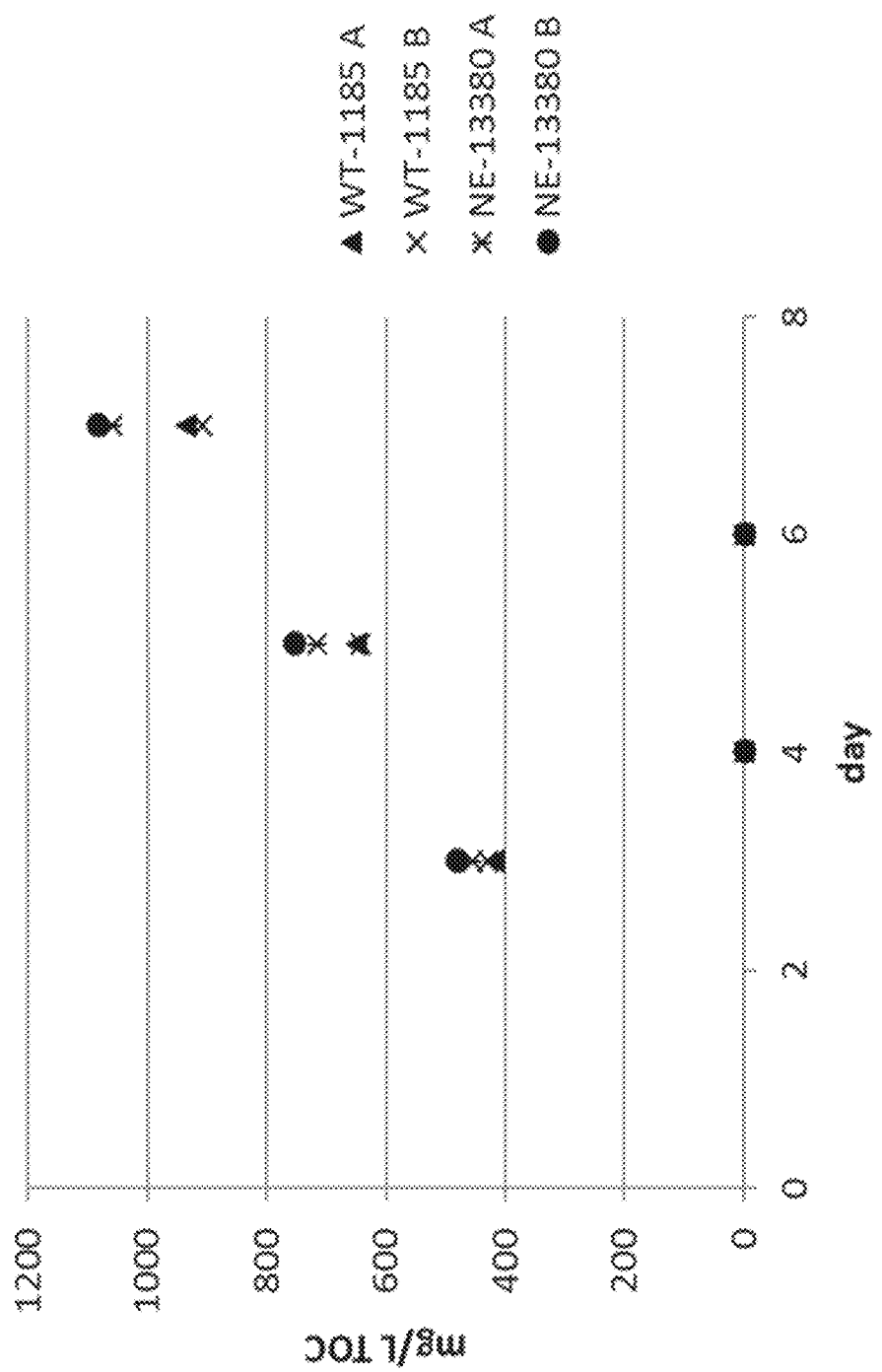
FIG. 13 is a graph showing volumetric TOC accumulation under N-replete batch EPICs diel irradiance conditions. Biological duplicate data are shown individually for WT-1185 and NE-13380.

FIG. 13 shows that under these batch, nitrogen replete conditions the NE-13380 SGI1 mutant outperformed the wild type in biomass accumulation.

Example 13. Toc and Lipid Productivity of Batch Cultures Under Nitrogen Limitation The SGI1 mutant was also assessed for biomass and lipid accumulation under nitrogen limitation. SGI1 knockout strain NE-7843 and the wild type progenitor strain WT-1185 were cultured in a batch productivity assay in nitrogen deplete medium, i.e., the culture medium had no source of nitrogen for cell growth. The production cultures were inoculated to an initial OD730 of 0.5 from seed (scale-up) cultures that were grown in PM074 medium that included 8.8 mM nitrate.

After inoculation, ZnCys knockout strain NE-7843 and wild type strain WT-1185 were grown in triplicate 175 ml cultures in a batch assay in 75 cm² rectangular tissue culture flasks for seven days.

Figure 14A:
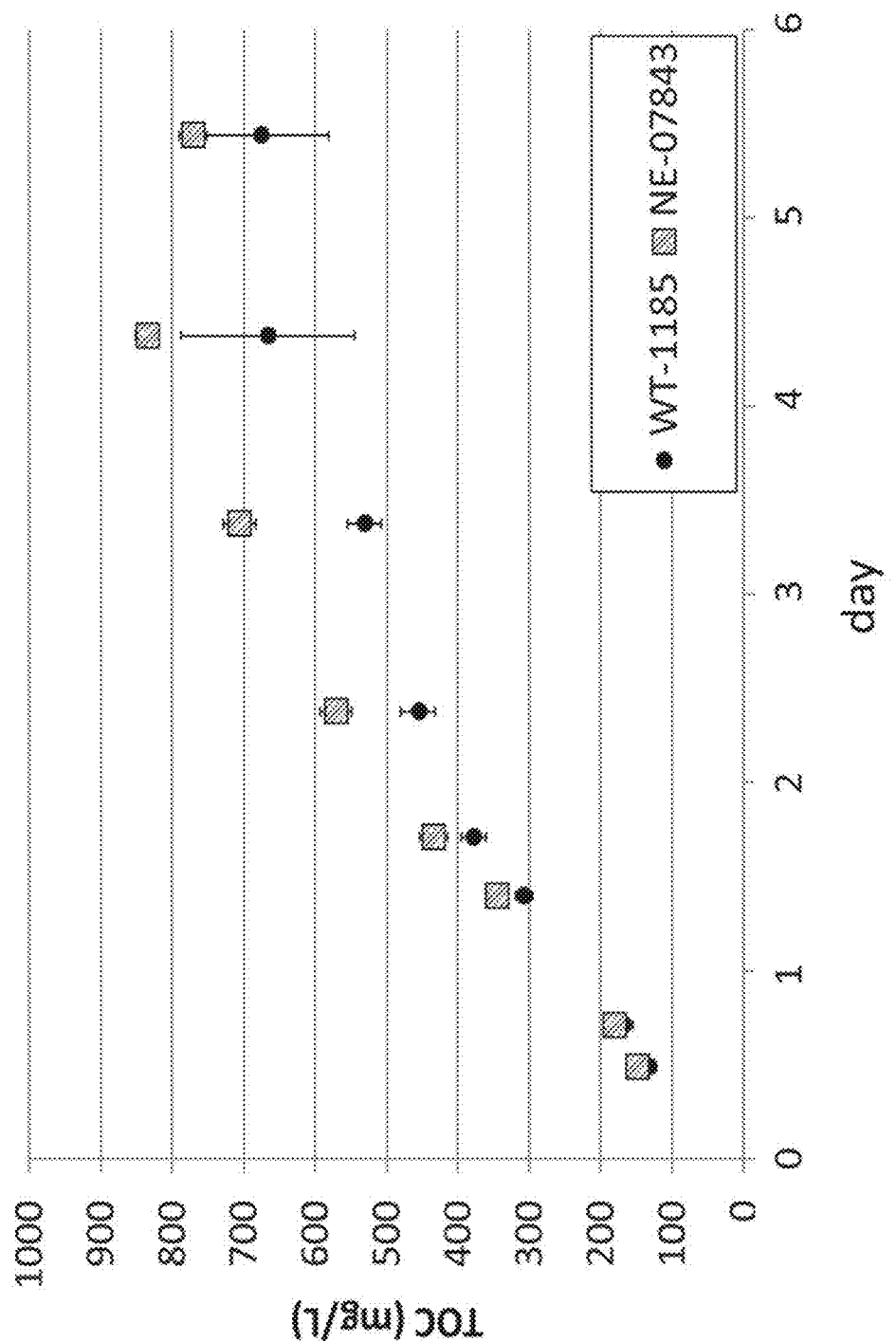
FIG. 14A is a graph showing volumetric TOC productivity under N-free batch AFS mode observed in strain NE-07843 as compared to the wild type stain WT-1185.
Figure 14B:
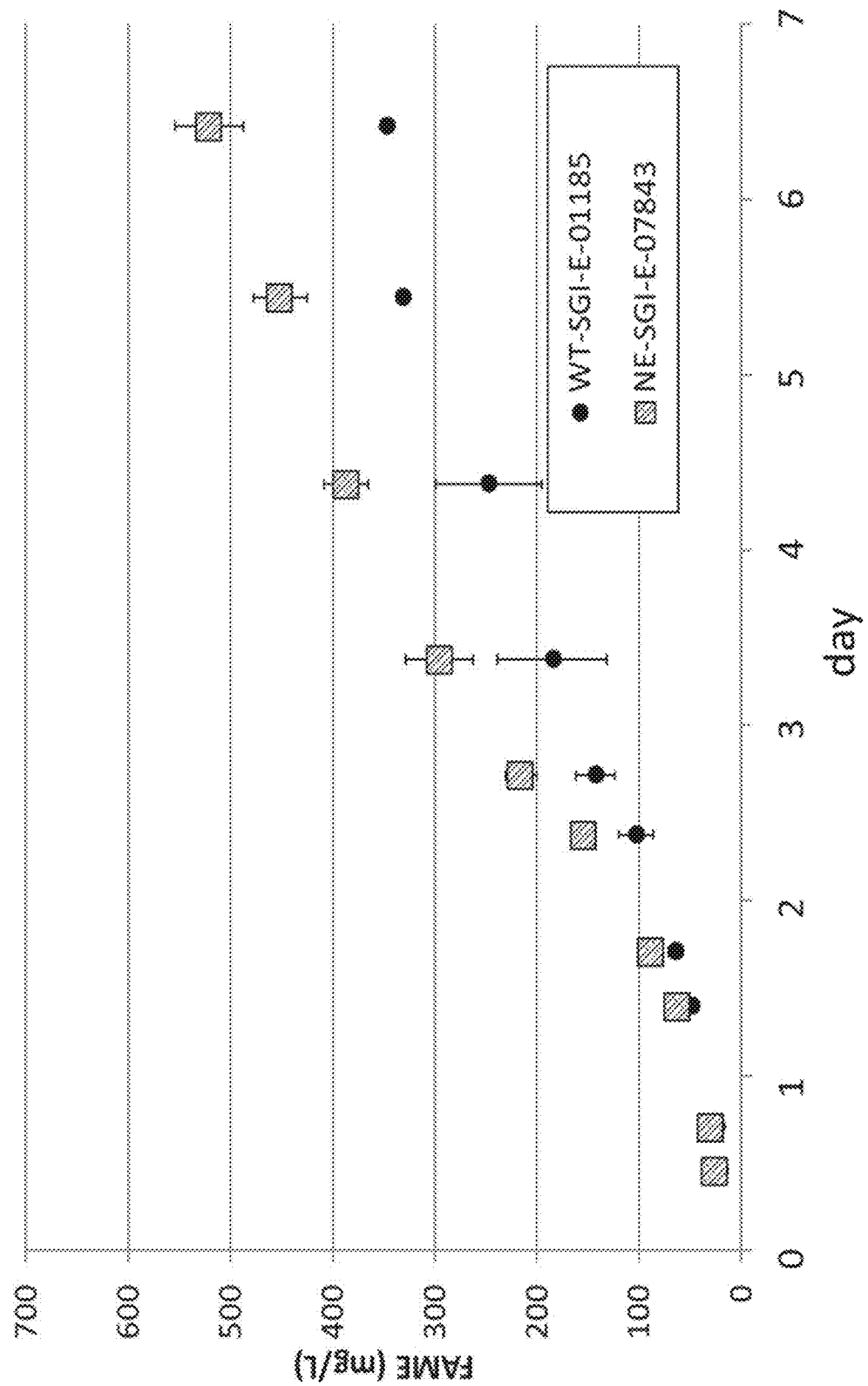
FIG. 14B is a graph showing volumetric FAME productivity under N-free batch AFS mode observed in strain NE-07843 as compared to the wild type stain WT-1185.

FIG. 14A shows the accumulation of volumetric TOC under N-replete batch conditions. Biological duplicate data are shown for WT-1185 and NE-13380, where the NE-13380 mutant outperformed the wild type strain in biomass accumulation. FIG. 14B shows the SGI1 mutants also outperforms the wild type strain in lipid (FAME) accumulation, accumulating approximately 50% more FAME than wild type over the course of the one week assay.

Example 14. High Irradiance Cultures

Growth rate improvements of the SGI1 mutants disclosed herein have been observed in multiple culture conditions (Table 8). Cultures were maintained at high dilution under constant high light by a continuous dilution system that introduced fresh nutrient replete culture medium and discharged an equal volume of culture. Parachlorella SGI1 mutants demonstrated an 18-20% increased growth rate in moderate to high light conditions (500-1,400 µE), and in extremely high light (5,000 µE) the SGI1 mutant was observed to grow at approximately 5-fold the rate of the wildtype progenitor strain (Table 8). The dramatic difference in growth rate under high light conditions can be used to select for SGI1 mutants.

TABLE 8

Growth rates of Parachlorella strains in low density, high light conditions.

| | Specific daily growth rate | | | Rate of division (h) | | |
|---|---|---|---|---|---|---|
| Strain | 500 µE[a] | 1,400 µE[b] | 5,000 µE[c] | 500 µE[a] | 1,400 µE[b] | 5,000 µE[c] |
| WT-1185[d] | 1.75 | 1.92 | 0.16 | 9.5 | 8.7 | 104.0 |
| NE-13380[e] | 2.1 | 2.27 | 0.85 | 7.9 | 7.3 | 19.6 |
| improvement[f] | 20.0% | 18.2% | 431.3% | 20.0% | 18.2% | 431.3% |

[a]Growth rate in shake flask with daily subcultures and 500 µE constant light.
[b]Growth rate in continuous culture kept at low density ($OD_{720}$ = 0.1) with 1,400 µE in T225 photobioreactor (CL-SCPA).
[c]Growth rate in continuous culture kept at low density ($OD_{720}$ = 0.1) with 5,000 µE in FMT150 photobioreactor.
[d]Wildtype Parachlorella.
[e]Parachlorella with SGI1 mutation.
[f]Increase in growth rate in SGI1 mutant in comparison with wildtype parent strain.

A small number of NE-13380 SGI1 mutant cells were inoculated into a photobioreactor with 400×10⁶ wild type *Parachlorella* WT-1185 cells that were being grown in continuous culture in low density conditions (1×10⁶ cells per ml) with high light (1,400 µE). Over a period of 60 days the growth rates slowly increased, such that after 60 days the culture had reached a specific daily growth rate of 2.27. The culture was then plated on agar plates for single colonies. Individual clones were picked and analyzed for growth rate and presence of SGI1 mutation. Remarkably, all of the clones isolated from the plates contained the SGI1 mutation suggesting that it is possible to select for SGI1 type mutations through the use of low density, high light, continuous culture. For example, UV, chemical mutagenesis, random insertional mutagenesis, or other mutagenesis procedures can optionally be performed, followed by low density, high light, continuous culturing for one, two, three, four, five, six, seven, eight, or more weeks to select for high productivity mutants such as SGI1-type mutants.

FIG. 7 shows a map of the SGI1 gene with positions of mutations found in various mutants marked. Strain NE-7843 was isolated in the screens disclosed in Examples 1-6, and strain NE-16980 was isolated using the screen disclosed in Example 7. Several additional mutants whose mutations are identified in FIG. 7 were isolated under the high light, low culture density selection of the present example.

Example 15. Identification and Targeting of the *Tetraselmis* SGI1 Gene

The genome of an environmental isolate of a wild type alga of a *Tetraselmis* species, referred to herein as *Tetraselmis* WT-105, was completely sequenced in-house (Synthetic Genomics, Inc., La Jolla, Calif., USA). Analysis of the genome was most consistent with *Tetraselmis* sp. WT-105 being triploid. Based on reciprocal BLAST using the *Parachlorella* SGI polypeptide sequence as a query for translated sequences of the *Tetraselmis* WT-105 genome, three genes were identified: T-5172 (SEQ ID NO:85, having the protein-encoding sequence (or cDNA sequence) of SEQ ID NO:86), T-5185 (SEQ ID NO:87, having the protein-encoding sequence (or cDNA sequence) of SEQ ID NO:88), and T-5230 (SEQ ID NO:89, having the protein-encoding sequence (or cDNA sequence) of SEQ ID NO:90), considered to be alleles of the *Tetraselmis* WT-105 SGI1 gene. The proteins encoded by alleles T-5185 (SEQ ID NO:14) and T-5230 (SEQ ID NO:16) are highly homologous, demonstrating 98% amino acid sequence identity by BLAST. The protein encoded by the T-5172 allele (SEQ ID NO:15) is 90% identical to the protein encoded by the T-5230 allele (SEQ ID NO:16) and 92% identical to the protein encoded by the T-5185 allele (SEQ ID NO:14) by BLAST analysis. Each allele was determined to have a RR domain and a myb domain (see Table 3). As also provided in Table 3, the *Tetraselmis* SGI1 allelelic polypeptides T-5172, T-5185, and T-5230 were found to have scores of at least 400, namely, 403.0 (e-value 2e-118), 403.6 (e-value 9e-119), and 402.9 (e-value 3e-118), respectively, against an HMM developed for identifying SGI1 polypeptides (Example 6).

Figure 15:
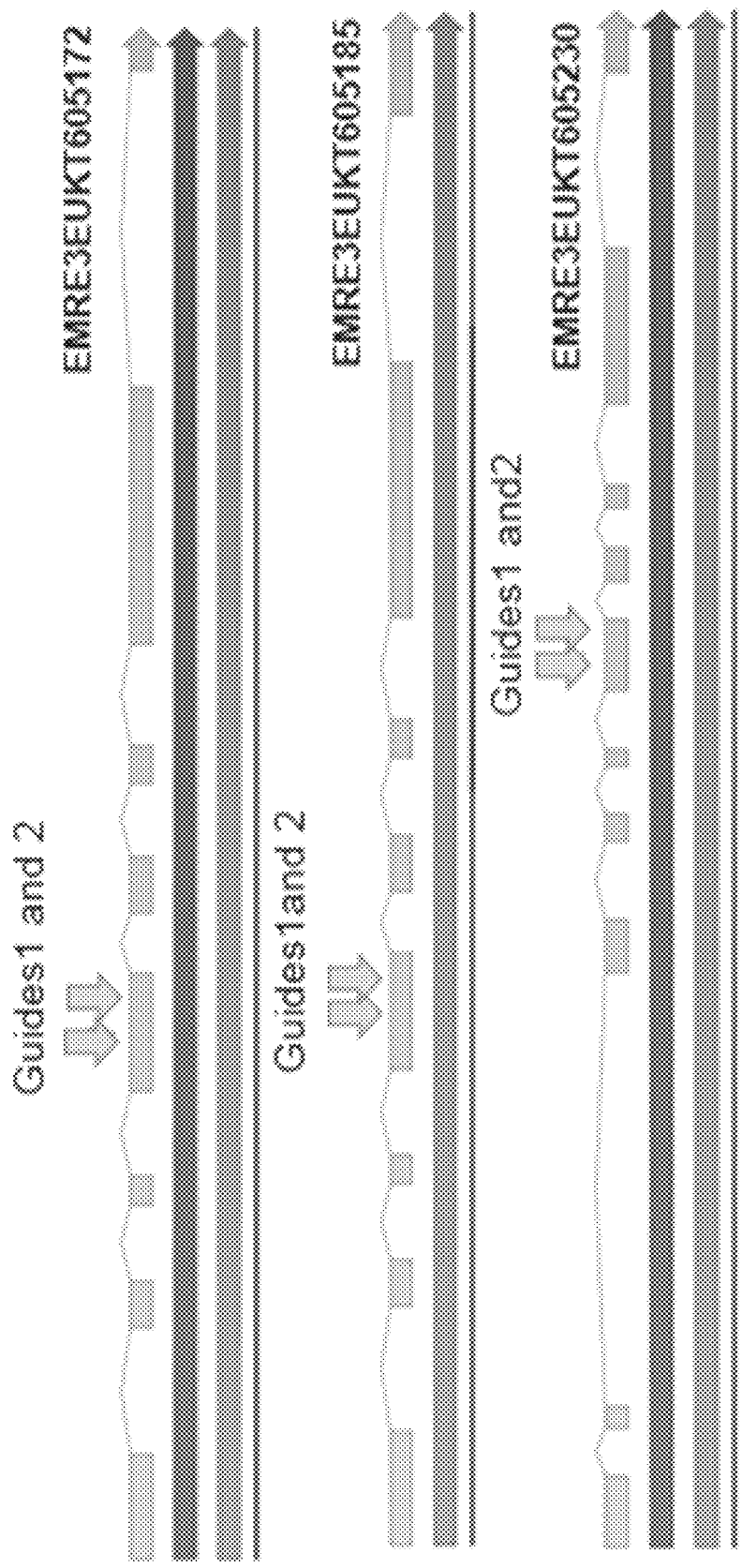
FIG. 15 provides diagrams of the *Tetraselmis* SGI1 alleles and the positions of guide target sequences MA1 (Guide 1) and JC2 (Guide 2).

To generate a *Tetraselmis* SGI knockout strain, a Cas9 ribonucleoprotein complex (RNP) that included a CRISPR-Cas9 guide RNA (crRNA) and a CRISPR-Cas9 tracr RNA (trRNA) complexed with a Cas9 protein was introduced into *Tetraselmis* algal cells by particle bombardment. A selectable marker cassette to select transformants was introduced along with the Cas9 RNP on the gold microparticles. The tracr RNA used to make the RNPs for *Tetraselmis* transformation was a chemically-modified 67 nucleotide Alt-R® CRISPR-Cas9 tracrRNA purchased from IDT (Coralville, Iowa, USA). The crRNAs used in RNP transformations were chemically modified Alt-R® CRISPR-Cas9 crRNAs also purchased from IDT (Coralville, Iowa, USA) that included a 20 nucleotide target sequence (MA1, SEQ ID NO:91 or JC2, SEQ ID NO:92) present in the fourth exon of all three alleles of the SGI1 gene (see FIG. 15). The crRNAs also included a 16 nucleotide sequence complementary to a sequence of the tracrRNA.

Prior to forming the RNP complexes, the crRNAs and tracrRNA were preincubated to allow the crRNAs to hybridize with the tracrRNA. Each RNA was resuspended at a concentration of 100 µM and equal amounts of crRNA and tracrRNA RNA were combined in separate tubes in 20 µM aliquots, such that each RNA had a concentration of 50 µM in each annealing mixture, except that where two crRNAs were used in a single experiment, each crRNA had a concentration of 25 µM in the annealing mixture. The combined RNAs were heated to 95° C. for 5 minutes and then allowed to cool on the benchtop. (Annealed crispr and tracer RNAs that were not used immediately were stored at −20° C.)

A mixture of the annealed crispr and tracrRNAs (10 µl of the annealing mixture) with Cas9 protein was made in phosphate buffered saline (PBS), where the final concentration of Cas9 protein was 100 ug/mL and the final concentration of RNAs was 10 µM. The annealed crRNA(s) and trRNA and Cas9 protein were incubated 15 min at room temperature to form RNPs.

To prepare the gold microparticles, protamine (100 µl of 1 mg/ml solution in PBS, made by heating to 55° C. to 65° C. and cooling to room temperature before use) was added to 5 mg gold particles (0.6 µm, BioRad), and the gold particles/protamine mixture was vortexed and then sonicated. A DNA fragment (SEQ ID NO:93) that included a selectable marker gene operably linked to the *Tetraselmis* RB40 promoter (SEQ ID NO:94) and *Tetraselmis* RB40 terminator (SEQ ID NO:95) was then added to the protamine/gold suspension, and the mixture was vortexed. The selectable marker DNA fragment was a PCR product that included a nourseothricin resistance gene codon optimized for *Tetraselmis* (SEQ ID NO:96) operably linked to the RB40 promoter and terminator. The five 5-most nucleotides of each primer (primer MCA1818, SEQ ID NO:97 and primer MCA1819, SEQ ID NO:98) used to produce the selectable marker cassette by PCR using a plasmid template included phosporothioate groups, such that the final selectable marker cassette fragment used in transformations was phosphorothioate-modified on each end.

The Cas9 RNP preparation (annealed RNAs/Cas9 protein) was added to the gold particles plus selectable marker DNA fragment in protamine solution immediately after addition of the selectable marker DNA fragment to the gold particles and the mixture was vortexed and then placed on ice for 2-4 hours. After the incubation on ice, the gold microparticle preparations were spun down briefly in a microfuge, the supernatant was removed, and 400 µL of 1.5 mg/ml PVP in PBS was added to each microparticle sample. The samples were vortexed, sonicated for 5-10 sec, and again vortexed, after which the PVP-suspended particles were pulled into a pre-dried segment of Tefzel™ tubing by attaching a syringe to flexible tubing that was connected to the Tefzel™ tubing, and drawing the particle mixture into the opposite end of the Tefzel™ tubing by application of suction via the syringe. The Tefzel™ tubing that included the gold particle preparation was set down for 5 min to allow the gold particles to settle, after which the PVP solution was gently pushed back out of the tubing via the syringe. The tubing was then rotated to distribute the gold particles over the inner circumference of the tubing, and allowed to air dry for approximately 5 minutes (during which time the tube was rotated one or more additional times to distribute the particles), after which the Tefzel™ tubing was attached of a nitrogen gas source and nitrogen gas was allowed to flow through the tubing at 0.1 L per min for one minute, and then at from about 0.3 to about 0.4 L per minute for 5-10 minutes to complete the drying. The Tefzel™ tubing coated on the interior surface with gold particles to which the selectable marker DNA and RNPs was adhered was then cut into 0.5 inch segments which were used as cartridges in a BioRad Helios® Gene Gun.

For microbombardment transformation, *Tetraselmis* strain WT-105 was cultured for approximately three days in a volume of 100 mls PM074 culture medium inoculated to an OD730 of 0.2. The starter culture was used to inoculate a 1 liter culture at $3 \times 10^5$ cells/ml, and the one liter culture was allowed to grow out for another 3 days. Cells were resuspended to a concentration of $10^8$ cells per ml, with approximately $10^7$ cells (100 μl) plated within a 4 cm diameter circle on 2% agar PM074 medium plates for each bombardment. Plated cells were allowed to dry in the hood, and were then bombarded with the prepared cartridges from a distance of approximately 5 cm. using helium set at 600 psi. The following day the plates were flooded with PM147 medium and replated on PM147 plates that included 200 μg/ml nourseothricin.

After 10-14 days of growth on selective plates, dozens of colonies were repatched onto selective PM147 plates that included 200 μg/ml nourseothricin. Surviving patches were PCR screened for mutations in the SGI1 locus. It was found that the selectable marker gene cassette (SEQ ID NO:93) did not insert into the Cas9-disrupted locus of transformed *Tetraselmis* cells, therefore, the SGI1-targeted mutations were mostly small insertions or deletions (indels) at the SGI1 target site. PCR fragments generated from the clones were Sanger sequenced to detect these mutation events. Many of the transformants were found to have a mutation at the target site. Ten of these were chosen for cloning of genomic DNA in *E. coli* to sequence each allele. All of the clones in Table 8 were determined by sequencing to be triple knockouts (i.e., homozygous for the mutation) with the exception of clone 8, which was heterozygous for the mutant allele.

TABLE 9

Mutant Alleles in Isolated Tetraselmis Clones after RNP Transformation Using SGI-targeting Guide RNAs

| Clone Number | Strain ID | Guide(s) Used in transformation | Mutation Type |
|---|---|---|---|
| 1 | | MA1 | large insertion |
| 2 | STR24094 | MA1 + JC2 | 7 bp insertion |
| 3 | | MA1 + JC2 | large insertion |
| 4 | | MA1 + JC2 | 5 bp insertion |

TABLE 9-continued

Mutant Alleles in Isolated Tetraselmis Clones after RNP Transformation Using SGI-targeting Guide RNAs

| Clone Number | Strain ID | Guide(s) Used in transformation | Mutation Type |
|---|---|---|---|
| 5 | | MA1 + JC2 | 13 bp insertion |
| 6 | STR24095 | MA1 | 5 bp deletion |
| 7 | STR24096 | MA1 | 9 bp deletion |
| 8 | STR24097 | MA1 | 1 bp insertion |
| 9 | | MA1 + JC2 | large insertion |
| 10 | STR24098 | MA1 + JC2 | 15 bp insertion |

Example 16. Photophysiology of Targeted *Tetraselmis* SGI1 Mutants

Figures 16A, 16B, 16C:
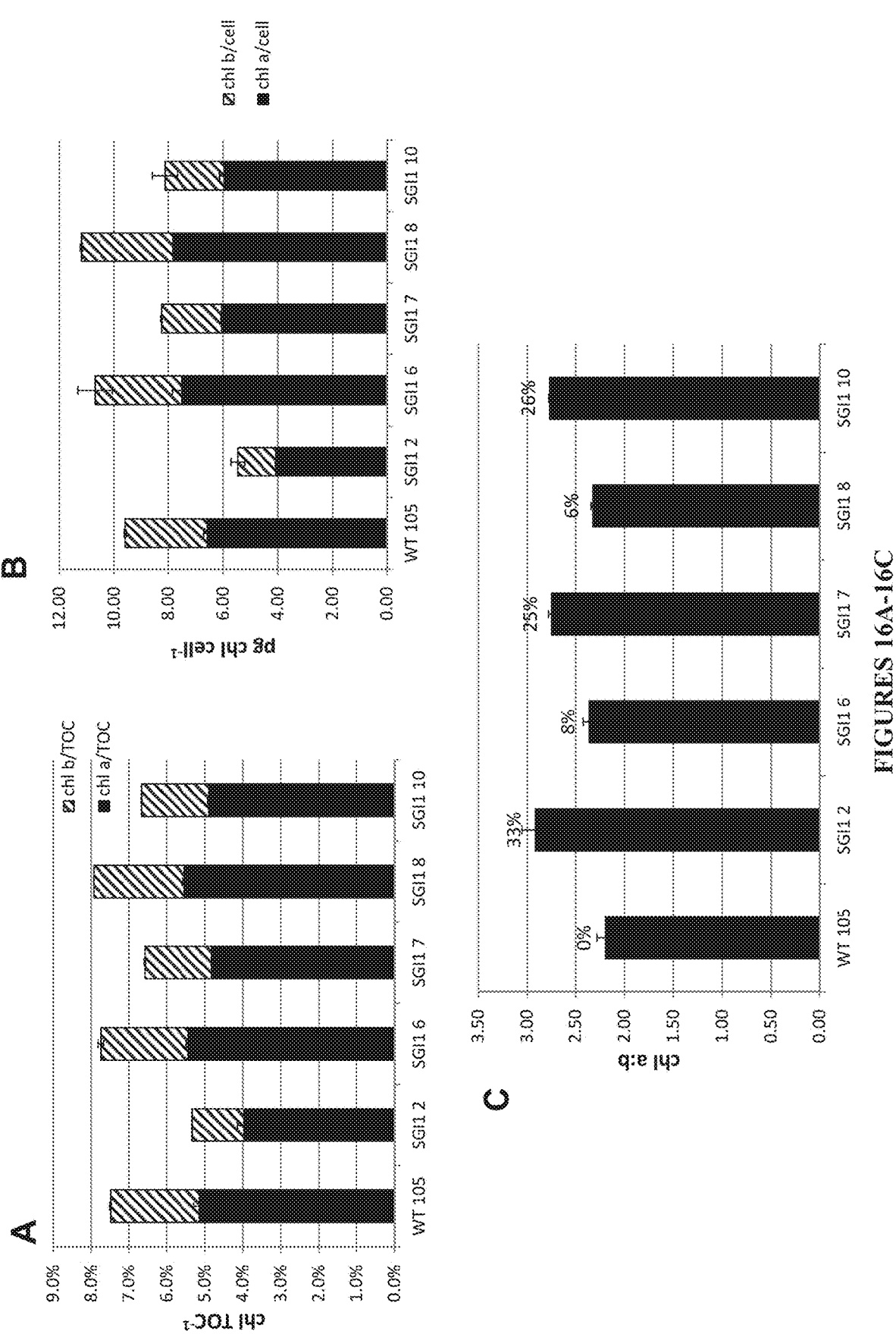
FIGS. 16A-16C provides graphs showing chlorophyll content of Cas9-targeted SGI1 mutants on A) a per TOC basis and B) a per cell basis; C) provides chloropyll a:b ratios of the mutant clones.

To characterize these clones, five of the ten clones listed in Table 8 (clones 2, 6, 7, 8, and 10) were cultured photoautotrophically under low, 24 hour/day light (140 mol photons $m^{-2}s^{-1}$) in replete PM074 culture medium that did not include a reduced carbon source and included nitrate as the nitrogen source. The cultures were diluted daily to maintain a fixed cell number. Chlorophyll was extracted and FIRe and $^{14}C$ $P_{max}$ measurements were performed as described in Example 7. The results are shown in FIGS. 16A, B, and C; FIGS. 17A, B, C; and D, and FIGS. 18A, B, and C. In these low light conditions, the chlorophyll a:b ratio was increased with respect to the wild type strain for all of the mutants (FIG. 16C), with clones 2, 7 and 10 demonstrating decreases in total chlorophyll and particularly in chlorophyll b on both a per TOC (FIG. 16A) and per cell (FIG. 16B) basis. All of the clones demonstrated a reduction in the PSII cross-sectional size measured at both 450 and 520 nm excitation, with clones 2, 7, and 10 showing the greatest reduction in PSII cross-sectional size with respect to wild type (FIGS. 17A and 17B). Clones 2, 7 and 10 also demonstrated the greatest increases in Fv/Fm (FIG. 17C), while all clones demonstrated reduced photosynthetic turnover times PSII (FIG. 17D). $^{14}C$ $P_{max}$ was increased for all clones on both a per cell and per TOC basis (FIGS. 18A and 18B), and all clones had higher growth rates than wild type (FIG. 18C).

Clones 2 and 7, given the strain names STR24094 and STR24096, respectively, were then tested in a semi-continuous assay that used a diel light program with a 14 hour light period that simulated the light intensity of a spring day in Southern California, peaking in intensity at approximately 2,000 mol photons $m^{-2}$ $s^{-1}$ at solar noon. Three biological replicates of each strain were cultured simultaneously and the results of the three cultures were averaged. The culture bottles were partially wrapped in foil to reflect light not initially absorbed back into the cultures. The culture medium was PM153, which included urea as the nitrogen source and did not include a reduced carbon source (i.e., the strains were cultured photoautotrophically), and cultures were diluted back by 60% daily. As summarized in Table 10, that under these conditions, SGI1 mutant strains STR24094 and STR24096 have increased Fv/Fm, reduced PSII antenna size (measured with 520 nm excitation), and increased PSII per TOC. Chlorophyll as a percentage of TOC is reduced in the *Tetraselmis* SGI1 mutants, and the ratio of chlorophyll a to chlorophyll b is increased. The photosynthetic rate, measured as $^{14}C$ incorporation, is increased from about 15 to 20% in these mutants. Productivity, reported as grams TOC produced per meter per day, is increased approximately 6.5% in STR24094 and approximately 10% in STR24096.

TABLE 10

Photophysiology of Tetraselmis SGI1 Mutants in Semi-continuous Diel Cultures

| | FIRe | | | | Chlorophyll | | $^{14}C\ P_{max}$ nmol | |
|---|---|---|---|---|---|---|---|---|
| Strain | Fv/Fm | PSII | τ'Qa (ms) | PSII/TOC | Chl/TOC | Chl a:b | $^{14}C$/ug TOC/h | Productivity $gm^{-2}day^{-1}$ |
| WT-105 | 0.621 | 148 | 5.0 | 17 | 7.8% | 2.0 | 25.6 | 15.5 |
| STR24094 | 0.683 | 108 | 3.6 | 20 | 6.4% | 2.8 | 30.8 | 16.5 |
| | +10% | −27% | −28% | +17.64% | −17.9% | +40% | +20.3% | +6.45% |
| STR24096 | 0.677 | 117 | 4.3 | 21 | 7.6% | 2.5 | 29.7 | 17.1 |
| | +9.0% | −21% | −14% | +23.5% | −2.5% | +25% | +16% | +10.3% |

Example 17. Productivity of *Tetraselmis* SGI1 Mutants in A Constant Light Semi-Continuous Culture System In the CL-SCUBA (Constant Light Semi-Continuous Urea-Based Assay), photoautotrophic cultures of the *Tetraselmis* SGI1 mutants were grown over several days in constant light semi-continuous mode with culture samples removed at the same time each day for biomass determination. The light was programmed at 2000 μmol photons $m^{-2}$ $sec^{-1}$. In this assay 420 ml of PM153 culture medium (that included urea as a nitrogen source) in a 500 ml square flask was inoculated with seed culture of a given strain. Three cultures were initiated per strain. The flasks included stir bars and had stoppers having tubing connected with syringe filters for delivering $CO_2$ enriched air (1% $CO_2$) that was bubbled through the cultures. The flasks were aligned with an aperture of 0.0875 $m^2$ toward the light and "depth" dimension of the flasks, extending back from the light source, was 8 cm. The cultures were diluted daily by removing 40% of the culture volume and replacing it with fresh PM153 culture medium diluted to adjust for the increase in salinity due to evaporation occurring in the cultures. Samples for TOC analysis were taken from the culture removed for the dilution after the cultures had reached steady-state.

Figure 19:
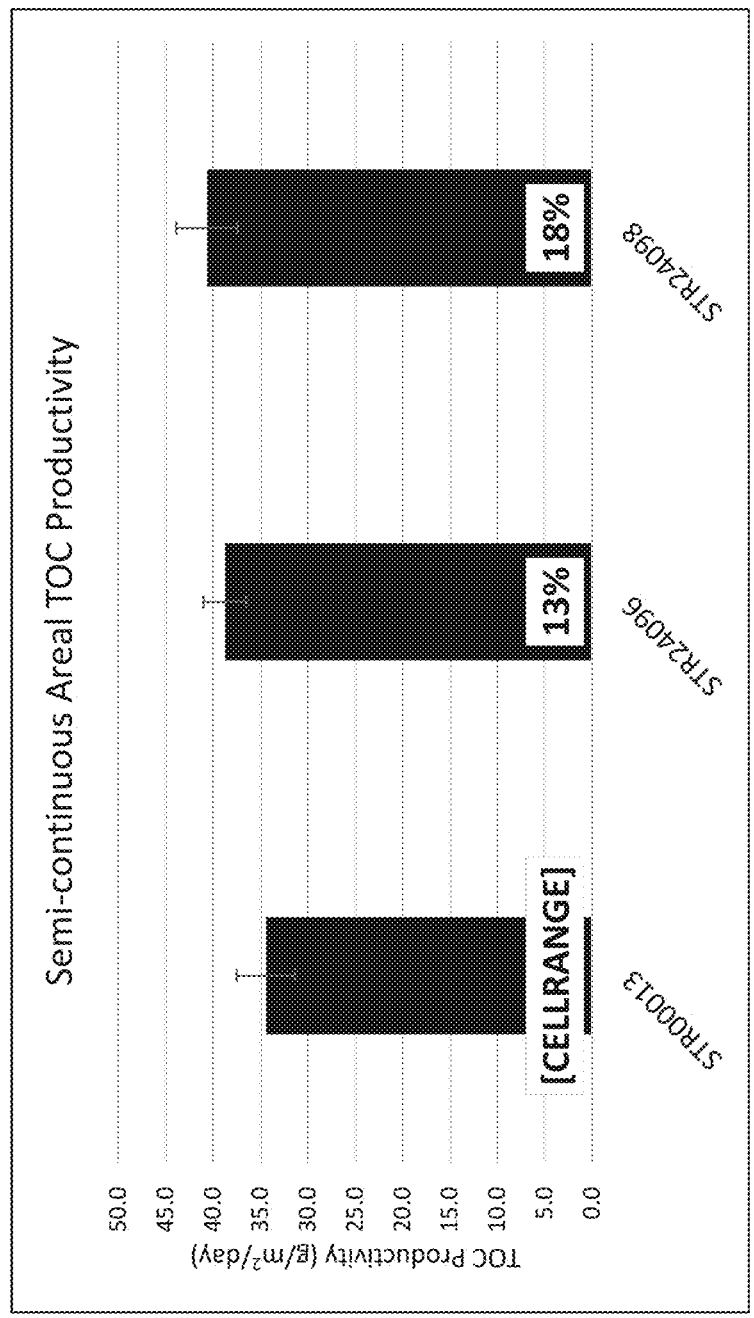
FIG. 19 is a graph providing the areal TOC productivity of two Cas9 targeted *Tetraselmis* SGI1 mutant strains, STR24096 and STR24098 in a semi-continuous twenty-four hour light culture system.

FIG. 19 shows that under these constant light semi-continuous culture conditions, *Tetraselmis* SGI1 mutants STR24096 and STR24096 demonstrated 13% and 18% increased biomass, respectively, with respect to wild type cells (strain STR00013).

Example 18. Productivity of *Tetraselmis* and *Parachlorella* SGI1 Mutants in a Diel Semi-Continuous Culture System In the diel SCUBA (Semi-Continuous Urea Based Assay), photoautotrophic cultures of the mutants were grown over several days in diel light semi-continuous mode. The light was programmed to mimic an average spring day in the Imperial Valley of California ranging from darkness to 2000 μmol photons $m^{-2}$ $sec^{-1}$ at noon. Samples were taken at "dusk" each day. In this assay 420 ml of urea based PM153 culture medium in a 500 ml square flask was inoculated with seed culture of a given mutant strain. Three cultures were initiated per strain. The flasks included stir bars and had stoppers having tubing connected with syringe filters for delivering $CO_2$ enriched air (1% $CO_2$) that was bubbled through the cultures. The flasks were aligned with a aperture towards the light of 0.0875 $m^2$ and "depth" dimension of the flasks, extending back from the light source, was 8 cm. The cultures were diluted daily by removing 40% of the culture volume and replacing it with fresh PM153 culture medium diluted to adjust for the increase in salinity due to evaporation occurring in the cultures. Culture samples removed daily for biomass determination after the cultures had reached steady state. Samples for TOC analysis were taken from the culture removed for the dilution.

Figure 20A:
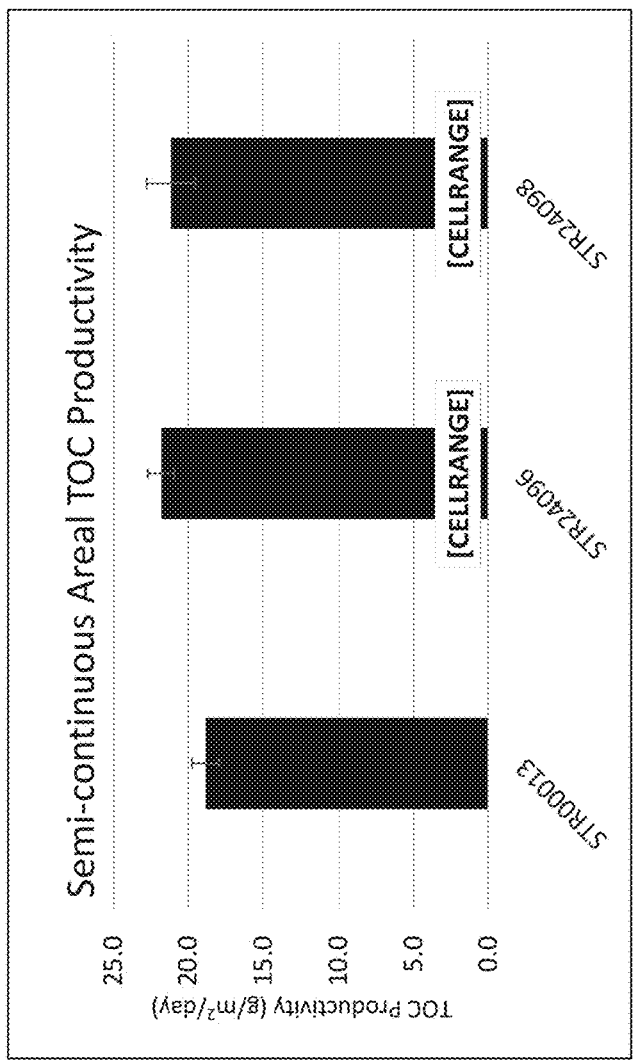
FIG. 20A is a graph providing the areal TOC productivity of two Cas9 targeted *Tetraselmis* SGI1 mutant strains, STR24096 and STR24098 in a semi-continuous diel culture system.

FIG. 20A shows that under these conditions, *Tetraselmis* SGI1 mutants demonstrated between 12% and 16% increased biomass with respect to wild type cells.

Figure 20B:
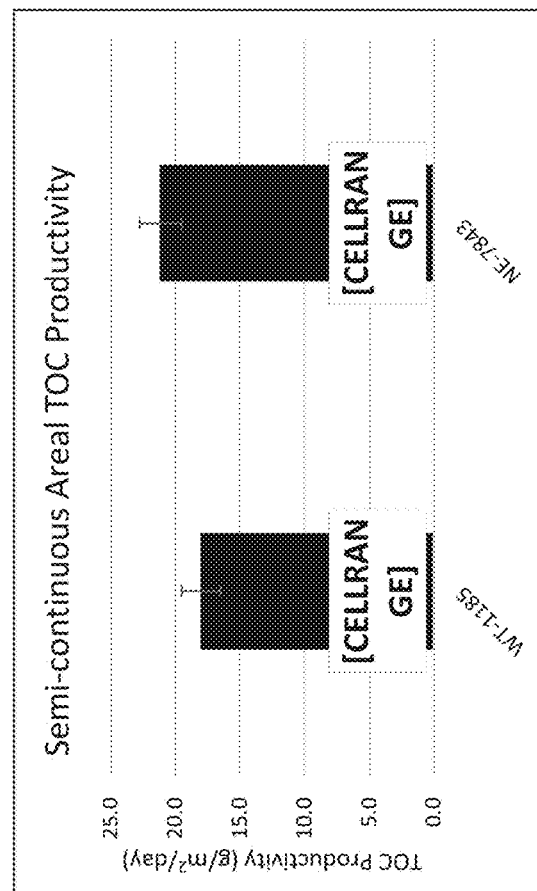
FIG. 20B is a graph providing the areal TOC productivity of a classically-mutagenized *Parachlorella* SGI1 mutant strain, NE-7843, in a semi-continuous diel culture system.

In a parallel diel SCUBA assay performed according to the same protocol, the classically-derived *Parachlorella* SGI1 mutant NE-7843 was tested in triplicate cultures alongside triplicate cultures of the *Parachlorella* wild type strain WT-1185. FIG. 20B shows that under this culture regime, *Parachlorella* SGI1 mutant NE-7843 demonstrates an 18% increase in productivity with respect to the wild type strain.

Example 19. Analysis of *Arabidopsis* SGI1 Mutant

To determine the effects of an SGI1 mutation in higher plants we first identified the closest relatives of the *Parachlorella* SGI1 gene in *Arabidopsis thaliana*. Using the bioinformatic analysis disclosed in Example 6, the closest *A. thaliana* homolog to the *Parachlorella* SGI1 was determined to be ARR2 (SEQ ID NO:22).

Figure 21B:
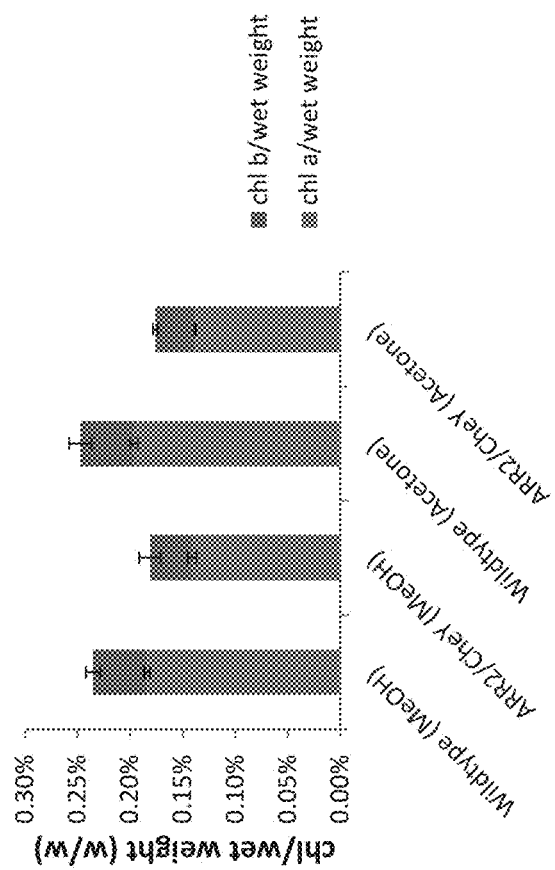
FIG. 21B is a graph showing the chlorophyll a and chlorophyll b content of the *Arabidopsis* wild type and ARR2 mutant plants as a percentage of wet weight.
Figure 21A:
FIG. 21A is a photograph of wild type *Arabidopsis* plants (4 sectors on the left) and ARR2 mutant *Arabidopsis* plants (4 sectors on the right) grown for the same number of days
Figure 22A:
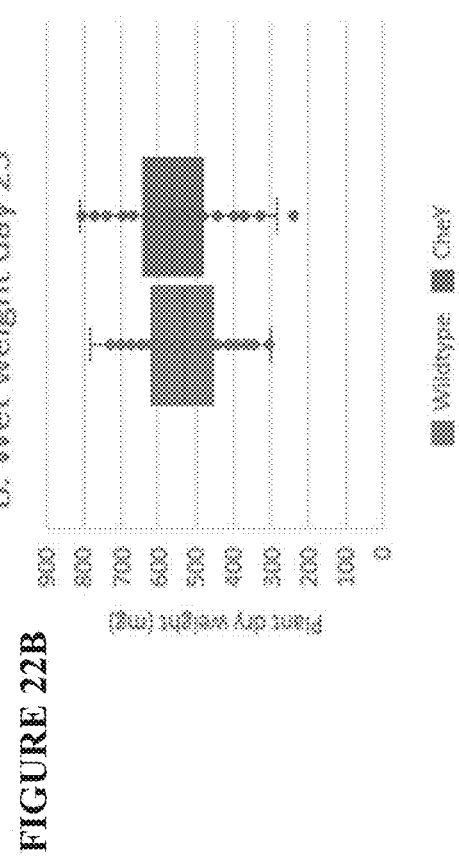
FIG. 22A is a graph of the dry weight of *Arabidopsis* wild type and ARR2 mutant plants at 23 days
Figure 22B:
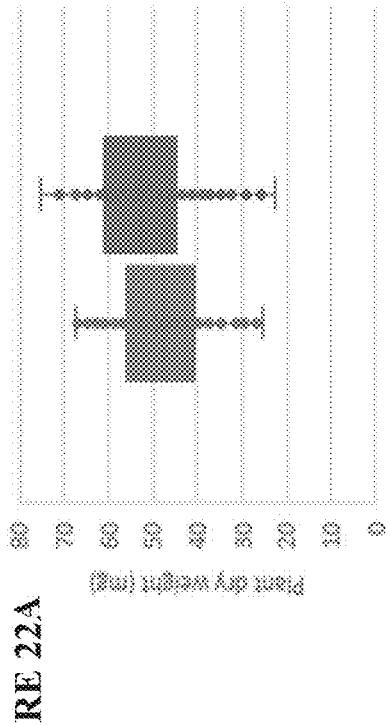
FIG. 22B is a graph of the wet weight of *Arabidopsis* wild type and ARR2 mutant plants at 23 days
Figure 22C:
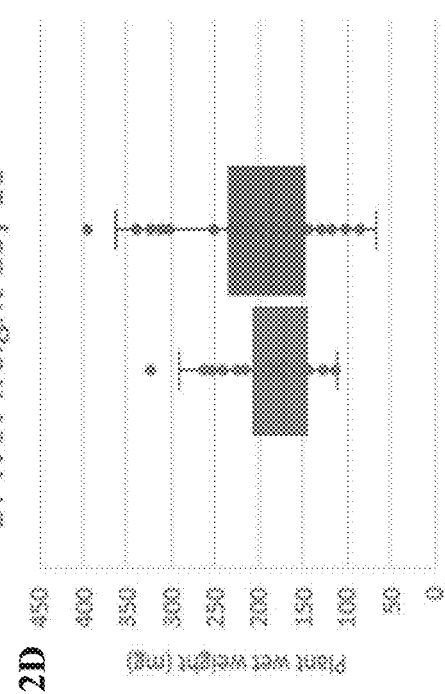
FIG. 22C is a graph of the dry weight of *Arabidopsis* wild type and ARR2 mutant plants at 18 days.
Figure 22D:
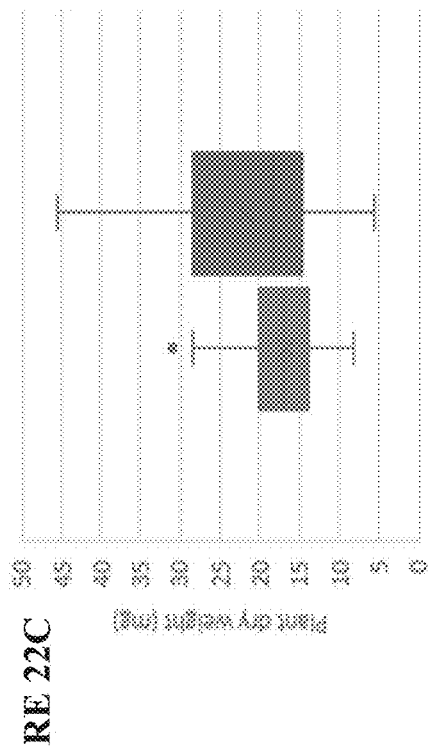
FIG. 22D is a graph of the wet weight of *Arabidopsis* wild type and ARR2 mutant plants at 18 days.

Seeds from *A. thaliana* plants with mutations in ARR1 and ARR2 as well as a wildtype control were obtained from the *Arabidopsis* resource center (ABRC). Seeds were planted in soil (50% MiracleGro fertilized seed starting potting mix, 25% perlite, 25% vermiculite). The planted seeds were vernalized at 4° C. for five days prior to transfer to a conviron for growth. The plants were grown side by side on four different occasions in a conviron set at 25° C. The plants received ~70 μE of light with a 12 hour dark period. Growth of the ARR1 mutant was substantially slower than both the wildtype and the ARR2 plants and we therefore focused on comparisons between the wildtype and ARR2/SGI1 mutant plants (hereafter referred to as SGI1 plants). During the first two growth experiments, we observed a visual improvement in growth of the SGI1 mutant plants (FIG. 21A). *Parachlorella* SGI1 mutants have reduced chlorophyll and we therefore determined the chlorophyll content in *Arabidopsis* wildtype and SGI1 leaves. Chlorophyll was extracted using with both acetone and methanol from three wildtype and three ARR2 mutant plants (two leaves from each plant). We observed a significant reduction in the amount of chlorophyll in the SGI1 mutant plants (FIG. 21B). In the last two growth experiments we harvested plants at day 23 and day 18 to determine wet weights and dry weights of the plant shoots. Although we observed a high variation between individual plants and a high overlap between wild-type and SGI1 plants, the SGI1 plants consistently had a higher average shoot weight of about 10% at 23 days (FIGS. 22A and B) and about 40% at 18 days (FIGS. 22C and D). As found in the green algae (*Parachlorella* and *Tetraselmis*) with SGI1 mutations, we observed reduced chlorophyll and an increase in average biomass during vegetative growth in an *A. thaliana* SGI1 mutant, indicating that SGI mutations can be associated with increased productivity in other higher plants as well.

Although the invention has been described with reference to the above examples, it will be understood that modifications and variations are encompassed within the spirit and scope of the invention. Accordingly, the invention is limited only by the following claims.

What is claimed is:

1. A mutant Chlorophyte algal organism having an attenuated gene encoding an SGI1 polypeptide having at least 80% sequence identity to a polypeptide selected from the group consisting of SEQ ID NO: 3, SEQ ID NO: 14, SEQ ID NO: 15, and SEQ ID NO: 16; and
   wherein the photosynthetic organism produces more biomass than a control organism grown or cultured under the substantially the same conditions, wherein the control photosynthetic organism does not have the attenuated SGI1 gene.

2. A mutant photosynthetic organism according to claim 1, wherein the mutant photosynthetic organism produces at least 15% more lipid than a control photosynthetic organism grown or cultured under the substantially the same conditions.

3. A mutant photosynthetic organism according to claim 1, wherein the mutant photosynthetic organism has reduced chlorophyll with respect to the control photosynthetic microorganism.

4. A mutant photosynthetic organism according to claim 3, wherein the mutant photosynthetic organism has an increased chlorophyll a:b ratio with respect to the control photosynthetic organism.

5. A mutant photosynthetic organism according to claim 1, wherein the mutant photosynthetic organism has a reduced photosystem II (PSII) antenna size with respect to the control photosynthetic organism.

6. A mutant photosynthetic organism according to claim 1, wherein the mutant photosynthetic organism has a higher 14C Pmax with respect to the control photosynthetic organism.

7. A mutant photosynthetic organism according to claim 1, wherein the mutant photosynthetic organism has a higher Fv/Fm than the control organism.

8. A mutant photosynthetic organism according to claim 1, wherein the mutant photosynthetic organism has a higher protein content than the control organism.

9. A mutant photosynthetic organism according to claim 1, wherein the mutant photosynthetic organism has a higher rubisco activase content than the control organism.

10. A mutant algal microorganism according to claim 1, wherein the mutant algal microorganism is a Chlorophyte of the Class Chlorodendrophyceae, or Trebouxiophyceae.

11. A mutant algal microorganism according to claim 10, wherein the mutant algal microorganism has a reduced photosystem II antenna size (PSII) antenna size with respect to the control microorganism.

12. A mutant algal microorganism according to claim 11, wherein the cross-sectional unit size of the PSII antenna size is reduced by at least 25%, with respect to the cross-sectional unit size of the PSII antenna of the control microorganism.

13. A mutant algal microorganism according to claim 12, wherein the mutant algal microorganism has increased Pmax (14C) with respect to the control algal microorganism.

14. A mutant algal microorganism according to claim 13, wherein the Pmax (14C) is increased by at least 25% with respect to the Pmax (14C) of the control microorganism.

15. A mutant algal microorganism according to claim 1, wherein the mutant algal microorganism has a reduced amount of chlorophyll b with respect to the control algal microorganism.

16. A mutant algal microorganism according to claim 1, wherein the mutant algal microorganism has at least 20% less chlorophyll with respect to the control algal microorganism.

17. A mutant algal microorganism according to claim 1, wherein the mutant algal microorganism has at least 20% less chlorophyll b with respect to the control algal microorganism.

18. A mutant algal microorganism according to claim 1, wherein the mutant algal microorganism has a higher protein content than the control algal microorganism.

19. A mutant algal microorganism according to claim 18, wherein the mutant algal microorganism has at least 10% more protein as a percent of total organic carbon than the control algal microorganism.

20. A mutant algal microorganism according to claim 19, wherein the mutant algal microorganism has at least 20% more protein as a percent of total organic carbon than the control algal microorganism.

21. A mutant algal microorganism according to claim 1, wherein the mutant algal microorganism has reduced expression of at least 10 LHC genes with respect to the control algal microorganism.

22. A mutant microorganism according to claim 1, wherein the mutant algal microorganism has increased abundance of a ribulose bisphosphate carboxylase activator (RA) polypeptide with respect to the control algal microorganism.

23. A mutant microorganism according to claim 22, wherein the ribulose bisphosphate carboxylase activator polypeptide is at least 1.5 times, at least 2 times, or at least 2.5 times as abundant in the mutant as in the control algal microorganism.

24. A mutant algal microorganism according to claim 1, wherein the mutant algal microorganism is a Chlorophyte of the Class Chlorodendrophyceae, or Trebouxiophyceae.

25. A mutant algal microorganism according to claim 24, wherein the mutant algal microorganism is a member of the Chlorophyceace, and optionally a species of a genus selected from the group consisting of *Asteromonas, Ankistrodesmus, Carteria, Chlamydomonas, Chlorococcum, Chloro gonium, Chrysosphaera, Dunaliella, Haematococcus, Monoraphidium, Neochloris, Oedogonium, Pelagomonas, Pleurococcus, Pyrobotrys, Scenedesmus*, and *Volvox*.

26. A mutant algal microorganism according to claim 24, wherein the mutant algal microorganism is a member of the Class Chlorodendrophyceae, and optionally a species of a genus selected from the group consisting of *Prasinocladus, Scherffelia*, and *Tetraselmis*.

27. A mutant algal microorganism according to claim 24, wherein the mutant algal microorganism is a member of the Prasinophyceae, optionally a species of *Ostreococcus* or *Micromonas*.

28. A mutant algal microorganism according to claim 24, wherein the mutant algal microorganism is a member of the Class Trebouxiophyceae, and optionally a species of a genus selected from the group consisting of *Botryococcus, Chlorella, Auxenochlorella, Heveochlorella, Marinichlorella, Parachlorella, Pseudochlorella, Tetrachlorella, Eremosphaera, Franceia, Micractinium, Nannochloris, Oocystis, Picochlorum, Prototheca, Stichococcus*, and *Viridiella*.

29. A mutant algal microorganism according to claim 24, wherein the mutant alga is of a genus selected from the group consisting of *Chlorella*, Auxenochlorella, Heveochlorella, Marinichlorella, Parachlorella, and Tetrachlorella.

30. A method of making an algal product comprising culturing the algal mutant of claim 1 to produce the product.

31. A method according to claim 30, further comprising recovering the product from the culture.

32. A method according to claim 30, wherein the product is biomass.

33. A method according to claim 30 wherein the algal product is one or more lipids, proteins, polyketides, terpenoids, pigments, antioxidants, vitamins, nucleotides, nucleic acids, amino acids, carbohydrates, alcohols, hormones, cytokines, peptides, or polymers.

34. A method according to claim 33, wherein the product is one or more lipids.

35. A method according to claim 34, wherein the product is triacylglyceride.

36. A method according to claim 33, wherein the algal product is one or more proteins.

37. A method according to claim 30, wherein said culturing is batch, semi-continuous, or continuous mode.

38. A method according to claim 30, wherein said culturing is in nutrient replete conditions.

39. A method according to claim 30, wherein said culturing is in nitrogen deplete conditions.

40. A mutant algal microorganism according to claim 24, wherein the mutant algal microorganism is a member of a genus selected from the group consisting of *Parachlorella* and *Tetraselmis*.

* * * * *

SEQUENCE LISTING

```
<160> NUMBER OF SEQ ID NOS: 98

<210> SEQ ID NO 1
<211> LENGTH: 4531
<212> TYPE: DNA
<213> ORGANISM: Parachlorella sp.
<220> FEATURE:
<221> NAME/KEY: misc_feature
<223> OTHER INFORMATION: SGI1 gene

<400> SEQUENCE: 1
atgtctggtt cagctggatc gggccaggct actctcagac atgacggtgg ctctgctggc      60
ggcagtgggc ctgtctcaga cggtttttca ccggccggcc tgaaggtaaa gtagaaagac     120
actcatacac atcttggttc ggcgttgaaa gtaggtcatt aacatactct ataaccaata     180
tttgtaggtt ctggtcgtgg acgacgacct catgtgcctt aaggtggtgt cagccatgtt     240
gaagaggtgc agctatcaag gtgaggtctt tactggtgtc tgttattgct gtaacatcat     300
ttcgctgttg cacaatttaa acatttgtaa tttactgttg ttattgcagt ggccacttgt     360
agcagtggca gcgaggcact gacacttcta cgtgaacgca acgaggacgg atcctccgac     420
cagttcgacc tcgtactgtc agatgtttac atgccgggta tgtcgtattc ctttgtaaac     480
tttacaatat gcgtctagtt tgacgcgtac actttgtaca ctttgcaaaa acgcaccctg     540
cgaggtctgc catttggtca ctacaacttg gccaccttgg ttgcaagttt gcaagttcgc     600
tctacgtcaa cgctgcaaaa tgaaccaatt gttttgcact gaccctgcca accttcattt     660
gtggctgcag acatggacgg tttcaagctg cttgaacaca tcggtctaga gttggagctt     720
cccgttatca gtaagttgat cgagccgagt ccagagcgaa gcctgcttct atactattag     780
cagctgtctt ttgatatttg acagcttgac ttgatatggt cacagagcat acttgcaacc     840
aggttacctg ttgaactagc aactgtgccc aagcatctct tcaagcacct ccgtcagtcc     900
atagggtact gttgatttgt actctgcaat actgcactgt aatgcgctgt gaatcactgc     960
ccttcacctc tagatggtgc ttccctggag ccctccccca cctccgcctc aagcccctca    1020
catgcctctc ccccccctgc agtgatgtca tccaacgggg acacgaatgt cgtgctgcgg    1080
ggggtcaccc acggggctgt ggactttctg atcaagcccg ttcgaattga ggagctgcgg    1140
aacgtgtggc agcacgtggt gcgtcgtcgt tccatgcgcg tggccaggac gccagacgag    1200
gggggacact cggacgagga ctctcaggtg cccttggcag cttctgggcg gcttgctgtg    1260
tcggatgcca cttggactgg ggatgcacga ggggtggggg gacaatggga gatgggccat    1320
agtaggccag agttgatggc agtggtggtg gggggagta ggcgggagag aagcagccat    1380
cctggtgttg gttttgatga ttgagtgcat ggggatgatg cacaggtgag ctgactggat    1440
gccttgtctt gctgtgctgc gctgcagcgg cacagtgtga aacgcaagga gtcggagcag    1500
agcccgctgc agctcagcac agagcagggc gggaacaaga agccaagagt ggtgtggtcg    1560
gtggagatgc accaacaggt gtgcttgcgg gcgggtgtat acggggggagg ggggccagct    1620 gctggctgac ctggcgtgcg cggtgcattg cacttggcga tgagggggcgt gcttcagtat    1680
```

```
gtagctggga cgcaattggt tgtgctgtgt gaccagtgca caaaatacat ccctgaattc    1740
cagtgggttg aacagagttg tcctggaggt gggaagcaaa cgcgcacgtg gtagagggga    1800
gcagggtgca gaacagccgc agcaggggtg ttgcgcagtg tgcaggtatc ctgcctccat    1860
gccccgggcc atgggcatac tacgctggta ccgtcaggat gggcgttgag cctggcttgg    1920
ggggcagggg gcgagcgaat gcggaatggg agcggcaggt gctgggaggg tggctgactg    1980
gcttgcagga gcgcaagtcc tgtcggggc gtcgtcctgt tccctcctgc ccgcttcacc    2040
cacgttcact ctcatgcctc cacactcctg ctgctgacac acctgtcgcc acctccgctg    2100
cagtttgtga acgcggtcaa ctccctgggc attgacaagg cggtgcccaa gcggattctg    2160
gacctgatga acgtggaggg gctgacgcgc gagaacgtgg ccagccatct gcaggtgcct    2220
gccatgaccc ctcccaccag ggacctggtg ttttgacacc ctggaactcc tctttgacgg    2280
agcctccagt tcaattccag caatcgaatt gaatcaaaaa gcatgtgcac ccacgtgctg    2340
tttgaatgtc ccatgtggta ggaaacacaa ctgcccccctt gccatttgct ggagggtgcc    2400
cgctgcgcca tgcccgagtg cgctgtgctc agcgttgtgc tgcgccccc gctgactgaa    2460 gctgacagcg tgcggctgag gagggtactg ggggaggggg ggtgggaggc ggccgctggc    2520
ggcggaaggg agggtgtgca cgcatggaca cagggccttt ccgccctgca cggcctctac    2580
tgcaccctgc cacgtgatgt atcgacatgg tgggccatgc tgtgctgtgc cgctgcagaa    2640
gtaccgcctg tacctgaagc gggtggaggg agtgcaatcg ggtgcggcag cctccaagca    2700
gcaccagcac ccgcagtatc accagcagca gcagcagcag caagcgcaac ctcgtgcagc    2760
tgtctcccct gcagcagctt cctttggtgc cctttccttg ggagcccgc agcaggcgca    2820 gcagggcatg ccgcagctgg ggatgcctgt gcaggtgaag actgccccc ccccctccc    2880 cctttccatc ttccctccat cagcctgctg ttccttaccc ttgtcaaccc gtctctcctt    2940
tttcgcaagc agcgcaccac cccccatgca cgccttgcct ggcactgttg tcagctgccc    3000
ccctagaaat acacaaggtg tgggtgcaac tggtgggacc cctccccccc ccccctggg    3060 gctgcagggt ctccctccaa acttggcagc catgggatcc cagccgccgc acatcccctt    3120
ccagcaggcc ctggccatgc aggcggcggc tgcggcggct gcagcagcg gcgcgctccc    3180 cgggagtctg cccccctaca tgccaccccc ggggatgatg ccccccggca tgccgggggg    3240 ggtcccggt atgggagggg tggtgggca tcctcaggta cgggcagcac atgagtgggc    3300 agggtattg gagagggaa gggcaggag gttgcatgtg aggggctgca tggcaaagag    3360
gctgcagcgc aggtgttgct tgcagcactt ccctcggtg gcgcttgcat caaattttga    3420
atcctccccc gatgggcacg cccgtgtgtg ggggggtg ggatgggga tggggtggt    3480 tttgtggcat gtcgggcgct ttcatctacc cgggcccctg cccctgcctg tacgcgtgcg    3540
catgtgtgca gatgcccgcc ccagggatgg actttgcggg tttcaacggg tatggcaacg    3600
ctgcgggggg gctgatgttt ggcgggcagc agcaggcgca gcacgcgcag cagcacgcgt    3660
cagcgcaagc gggctcgctg gcgcagcagc aggcgcagca agtatccatg ggcttgggcc    3720
ttatgccccc ccgttgggg ttccgcccca cctcgctcgc cgcgccagcc ccgcgctccg    3780
cagcaactga gcccgccgca gccccactcc ccctgacgtc ctcgccgcca gctgcttcag    3840
caggcggcag cggcggccca gcagcagctg ctccgcagca cagcagcggc gccgcagcag    3900
cccaagcccc ccatcaccac ccacagtgct cggagcaggg agcggggggg ctcccgcccc    3960
cgctgcccgc gtccagcgcc ccgcagtcct atccctcccc tcccccctcc tcgcaggccg    4020
```

-continued

| | |
|---|---|
| ctttgcatga cccggacgaa cactaccccc caggctcggc agaggtgagc acgtccccc | 4080 |
| gcccctccc cccccccccc ccccttccc ttcaccctgg cttggcgtgc aatgaaaccc | 4140 |
| taaataaccc taaaacctca ttatcagttg caaattggac ccgtgaagcg ggcggggca | 4200 |
| actgcgctct gctggtgtca gcgctgtctc tgccggttcc tgcccagcgt gcgcctgcat | 4260 |
| gcaaggggg atgggggggg ggaggcattt aacaataggc cagtcatctc caatccaccg | 4320 |
| tcaatttcag ccccctcccc ccccctcct catcccttg cagatgcacc accagcacct | 4380 |
| cccagggctg tgtggcttta acccggacga cctgctgggg gggcagctgg gggacatggg | 4440 |
| gttcctgggg gagctggggg gggcggtggg aggaaagcac gaacaggacg acttcctgga | 4500 |
| cctgctgctg aagggggagg aggagctgtg a | 4531 |

<210> SEQ ID NO 2
<211> LENGTH: 1860
<212> TYPE: DNA
<213> ORGANISM: Parachlorella sp.
<220> FEATURE:
<221> NAME/KEY: misc_feature
<223> OTHER INFORMATION: SGI1 coding sequence

<400> SEQUENCE: 2

| | |
|---|---|
| atgtctggtt cagctggatc gggccaggct actctcagac atgacggtgg ctctgctggc | 60 |
| ggcagtgggc ctgtctcaga cggtttttca ccggccggcc tgaaggttct ggtcgtggac | 120 |
| gacgacctca tgtgccttaa ggtggtgtca gccatgttga agaggtgcag ctatcaagtg | 180 |
| gccacttgta gcagtggcag cgaggcactg acacttctac gtgaacgcaa cgaggacgga | 240 |
| tcctccgacc agttcgacct cgtactgtca gatgtttaca tgccggacat ggacggtttc | 300 |
| aagctgcttg aacacatcgg tctagagttg gagcttcccg ttatcatgat gtcatccaac | 360 |
| ggggacacga atgtcgtgct gcgggggtc acccacgggg ctgtggactt tctgatcaag | 420 |
| cccgttcgaa ttgaggagct gcggaacgtg tggcagcacg tggtgcgtcg tcgttccatg | 480 |
| gcgctggcca ggacgccaga cgaggggga cactcggacg aggactctca gcggcacagt | 540 |
| gtgaaacgca aggagtcgga gcagagcccg ctgcagctca gcacagagca gggcgggaac | 600 |
| aagaagccaa gagtggtgtg gtcggtggag atgaccaac agtttgtgaa cgcggtcaac | 660 |
| tccctgggca ttgacaaggc ggtgcccaag cggattctgg acctgatgaa cgtggagggg | 720 |
| ctgacgcgcg agaacgtggc cagccatctg cagaagtacc gcctgtacct gaagcgggtg | 780 |
| gagggagtgc aatcgggtgc ggcagcctcc aagcagcacc agcaccgca gtatcaccag | 840 |
| cagcagcagc agcagcaagc gcaacctcgt gcagctgtct cccctgcagc agcttccttt | 900 |
| ggtgcccttt ccttgggagc cccgcagcag gcgcagcagg gcatgccgca gctggggatg | 960 |
| cctgtgcagg gtctccctcc aaacttggca gccatgggat cccagccgcc gcacatcccc | 1020 |
| ttccagcagg ccctggccat gcaggcggcg gctgcggcgg ctgcagccag cggcgcgctc | 1080 |
| cccgggagtc tgccccccta catgccaccc cggggatga tgcccccgg catgccgggg | 1140 |
| ggggtccccg gtatgggagg ggtggtgggg catcctcaga tgcccgcccc agggatggac | 1200 |
| tttgcgggtt tcaacgggta tggcaacgct gcggggggc tgatgtttgg cgggcagcag | 1260 |
| caggcgcagc acgcgcagca gcacgcgtca gcgcaagcgg ctcgctggc gcagcagcag | 1320 |
| gcgcagcaag tatccatggg cttgggcctt atgcccccc cgttgggtt cccgcccacc | 1380 |
| tcgctcgccg cgccagcccc gcgctccgca gcaactgagc ccgccgcagc cccactcccc | 1440 |
| ctgacgtcct cgccgccagc tgcttcagca ggcggcagcg gcggcccagc agcagctgct | 1500 |

```
ccgcagcaca gcagcggcgc cgcagcagcc caagcccccc atcaccaccc acagtgctcg    1560
gagcagggag cgggggggct cccgcccccg ctgcccgcgt ccagcgcccc gcagtcctat    1620
cccctccctc cccctcctc gcaggccgct ttgcatgacc cggacgaaca ctaccccca     1680 ggctcggcag agatgcacca ccagcacctc ccagggctgt gtggctttaa cccggacgac    1740
ctgctggggg ggcagctggg ggacatgggg ttcctggggg agctgggggg ggcggtggga    1800
ggaaagcacg aacaggacga cttcctggac ctgctgctga aggggagga ggagctgtga    1860
```

```
<210> SEQ ID NO 3
<211> LENGTH: 619
<212> TYPE: PRT
<213> ORGANISM: Parachlorella sp.
<220> FEATURE:
<221> NAME/KEY: misc_feature
<223> OTHER INFORMATION: SGI1 polypeptide

<400> SEQUENCE: 3

Met Ser Gly Ser Ala Gly Ser Gly Gln Ala Thr Leu Arg His Asp Gly
1               5                   10                  15

Gly Ser Ala Gly Gly Ser Gly Pro Val Ser Asp Gly Phe Ser Pro Ala
            20                  25                  30

Gly Leu Lys Val Leu Val Asp Asp Leu Met Cys Leu Lys Val
        35                  40                  45

Val Ser Ala Met Leu Lys Arg Cys Ser Tyr Gln Val Ala Thr Cys Ser
50                  55                  60

Ser Gly Ser Glu Ala Leu Thr Leu Leu Arg Glu Arg Asn Glu Asp Gly
65                  70                  75                  80

Ser Ser Asp Gln Phe Asp Leu Val Leu Ser Asp Val Tyr Met Pro Asp
                85                  90                  95

Met Asp Gly Phe Lys Leu Leu Glu His Ile Gly Leu Glu Leu Glu Leu
            100                 105                 110

Pro Val Ile Met Met Ser Ser Asn Gly Asp Thr Asn Val Val Leu Arg
        115                 120                 125

Gly Val Thr His Gly Ala Val Asp Phe Leu Ile Lys Pro Val Arg Ile
130                 135                 140

Glu Glu Leu Arg Asn Val Trp Gln His Val Val Arg Arg Ser Met
145                 150                 155                 160

Ala Leu Ala Arg Thr Pro Asp Glu Gly Gly His Ser Asp Glu Asp Ser
                165                 170                 175

Gln Arg His Ser Val Lys Arg Lys Glu Ser Glu Gln Ser Pro Leu Gln
            180                 185                 190

Leu Ser Thr Glu Gln Gly Gly Asn Lys Lys Pro Arg Val Val Trp Ser
        195                 200                 205

Val Glu Met His Gln Gln Phe Val Asn Ala Val Asn Ser Leu Gly Ile
210                 215                 220

Asp Lys Ala Val Pro Lys Arg Ile Leu Asp Leu Met Asn Val Glu Gly
225                 230                 235                 240

Leu Thr Arg Glu Asn Val Ala Ser His Leu Gln Lys Tyr Arg Leu Tyr
                245                 250                 255

Leu Lys Arg Val Glu Gly Val Gln Ser Gly Ala Ala Ser Lys Gln
            260                 265                 270

His Gln His Pro Gln Tyr His Gln Gln Gln Gln Gln Ala Gln
        275                 280                 285

Pro Arg Ala Ala Val Ser Pro Ala Ala Ser Phe Gly Ala Leu Ser
290                 295                 300
```

```
Leu Gly Ala Pro Gln Ala Gln Gln Gly Met Pro Gln Leu Gly Met
305                 310                 315                 320

Pro Val Gln Gly Leu Pro Asn Leu Ala Ala Met Gly Ser Gln Pro
            325                 330                 335

Pro His Ile Pro Phe Gln Gln Ala Leu Ala Met Gln Ala Ala Ala
            340                 345                 350

Ala Ala Ala Ala Ser Gly Ala Leu Pro Gly Ser Leu Pro Pro Tyr Met
        355                 360                 365

Pro Pro Pro Gly Met Met Pro Pro Gly Met Pro Gly Val Pro Gly
        370                 375                 380

Met Gly Gly Val Val Gly His Pro Gln Met Pro Ala Pro Gly Met Asp
385                 390                 395                 400

Phe Ala Gly Phe Asn Gly Tyr Gly Asn Ala Ala Gly Gly Leu Met Phe
                405                 410                 415

Gly Gly Gln Gln Gln Ala Gln His Ala Gln Gln His Ala Ser Ala Gln
                420                 425                 430

Ala Gly Ser Leu Ala Gln Gln Gln Ala Gln Gln Val Ser Met Gly Leu
        435                 440                 445

Gly Leu Met Pro Pro Pro Leu Gly Phe Pro Pro Thr Ser Leu Ala Ala
450                 455                 460

Pro Ala Pro Arg Ser Ala Ala Thr Glu Pro Ala Ala Ala Pro Leu Pro
465                 470                 475                 480

Leu Thr Ser Ser Pro Pro Ala Ala Ser Ala Gly Gly Ser Gly Gly Pro
                485                 490                 495

Ala Ala Ala Ala Pro Gln His Ser Ser Gly Ala Ala Ala Gln Ala
                500                 505                 510

Pro His His His Pro Gln Cys Ser Glu Gln Gly Ala Gly Gly Leu Pro
                515                 520                 525

Pro Pro Leu Pro Ala Ser Ser Ala Pro Gln Ser Tyr Pro Leu Pro Pro
530                 535                 540

Pro Ser Ser Gln Ala Ala Leu His Asp Pro Asp Glu His Tyr Pro Pro
545                 550                 555                 560

Gly Ser Ala Glu Met His His Gln His Leu Pro Gly Leu Cys Gly Phe
                565                 570                 575

Asn Pro Asp Asp Leu Leu Gly Gly Gln Leu Gly Asp Met Gly Phe Leu
            580                 585                 590

Gly Glu Leu Gly Gly Ala Val Gly Gly Lys His Glu Gln Asp Asp Phe
            595                 600                 605

Leu Asp Leu Leu Leu Lys Gly Glu Glu Glu Leu
            610                 615

<210> SEQ ID NO 4
<211> LENGTH: 23
<212> TYPE: DNA
<213> ORGANISM: Parachlorella sp.
<220> FEATURE:
<221> NAME/KEY: misc_feature
<223> OTHER INFORMATION: Target sequence in SGI1 gene of Parachlorella
      strain WT-1185, including PAM

<400> SEQUENCE: 4
acaccacctt aaggcacatg agg                                            23

<210> SEQ ID NO 5
<211> LENGTH: 105
<212> TYPE: RNA
```

```
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Guide RNA for targeting Parachlorella SGI1 gene

<400> SEQUENCE: 5
ggacaccacc uuaaggcaca ugguuuuaga gcuagaaaua gcaaguuaaa auaaggcuag      60
uccguuauca acuugaaaaa guggcaccga gucggugcuu uuuuu                    105

<210> SEQ ID NO 6
<211> LENGTH: 2667
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: bleomycin resistance "BleR" gene, codon
      optimized for Parachlorella with Parachlorella introns

<400> SEQUENCE: 6
atggccaaac tgacatccgc tgttcctgtg ttgacagcaa gagatgttgc aggtgcagtg      60
gagttttgtg agttctgaga agctgattgt tgtttaactt ctttgaaagc tttatcgaag     120
attctgcaag cgatgaacat tgcttgtcaa gaccgagagc tgcatgccca cttgacatcc     180
agctttgaac ggctcttcat gtttgatttg tttctgattg tagggacaga tagactgggg     240
tttagcaggg actttgtgga ggacgatttt gcaggagtgg tgaggaatga tgtgacactg     300
tttatctcag cagtgcagga tcaagtgagt gcagcgtcag ctgtggcagt tgttggcttt     360
cgtctcagtc agtagtttgc tgggattgat tatggagggc acagttgcaa ttttgagttg     420
cacgttgcga caagcgtgtt gacaaagcgt ggtcaagccg ccagtcttg ccggtggcgg     480 gtggcttggt ctaacttccg ctctacagca atcgttttgt tcatggttac ggggctggcg     540
tgccagaaag tcctggtcag ccaccctcgc ttcaaagccg tagcccaaca actttgcgaa     600
tatgttcgat tgcaggtgg tgcccgataa tacactggca tgggtttggg tgagaggtac     660
agctctgcgt gcaacaggtt gcaagatgca gcgcaggtct tccctggtca aacgatgtat     720
gcagagttga gaggcacttg agctgggtga atggcgtggg ctcgtaggta gtgtgcaggg     780
caggaagggc agccaatttt ggagttgtgg tccggtgtcg ttgcttcgag ccttattagg     840
actcttgctc atcaaagcgt tagttgtgaa taagttgatc tgaaaggatg ttatgtacag     900
caagcagcag cagttaagag tctggggagt agctgcacag ggcgaggtgt caagatggga     960
agggtcctgc ctccttatgt gtttttccct gtaggggagg aagcctctta tgggcaatgg    1020
ttgggcatat tttccagcca gcccttcttt ctatagggc cagggtgggc ccagctcgtc    1080
ttggcttcca ccaccaggag agtgagggca ttgaagggcc ataaatagtc ctcccatcta    1140
cgtgcaccag agggtgtcgt ctaggctgtg catgccacga ggggaaggag ccaagaatga    1200
gtgtatgggt tgtttttcatg tttaggctgg gataaaactg ttttcaattg cgcctgccgg    1260
gtgaaaacca cagcagcatc agcaagcttg gagaaggcca gcccgcccag cacaggctca    1320
cgttcccact caggcggtca gtcgggcggg ggtgtgagtc aggcaggcga gggtgtctgt    1380
gcctgacatc agcacctctg cttagccact gcagcccctg gagcagggta gggcgtcatt    1440
tgcagcaatc acctgctgcc tcacacgtcg cagcttggaa tttcaacgac catcagcgct    1500
ggggttgttg aggatcata gcagattttg gtgcagcctg gttgtcatgc tctttgtgga    1560
```

```
atggcctcta tgttcgagca attcgttgga tgttgaggtg cttggggaca gagagtcgaa    1620
tgatgggcca gggtcaaaca tgcgagcgtt tggctgagtc agcggttttt gctggtcact    1680
ttttcttttg tttcttattt aggtttgatg gatgtgtttt gtgctgctgc cctgaagctg    1740
cagcagcgtg tctgccctgc gctactgcgg gcaccaaggc tatgtgctgg tgcactcggc    1800
tgcgctgcac ctgtgcacct cgcactccgt ccagcctcca tgcagcacac gtactcacgg    1860
tgtcctcctg acctgtcgta cgctattcca aacttgctct tttgctgccg ctgctctcgt    1920
acacaattgc tgttgattat cgatatctaa tcgagcgcct gctgactgaa ctccgcaggt    1980
ttggatgaac tgtatgcaga gtggtctgaa gtggtgagca ccaactttag gtgggtgggc    2040
tctgaaggag gaggagggag cgggtgatta acagggcct gcatgaagag gagcagggc     2100 tgcatggaca gcaggggaa ggtgcagaag ggagggtcaa gcgggttca ggtggctgtg      2160 ggtttctgca cgagcagtga agaagctgt atccttccac ctgctttcac tggcgaaagg    2220
ttgaaaacag gatgtcgcag ctggaaagat gttgcgctgt caagtgcaag ccatggttga    2280
gggtatgcct gtgtgcatgt gcttcttaaa gttactcctg ttctatggtt ctgggtgctt    2340
gttgtttgtg gtgcagggat gcaagcggac ctgcaatgac agagattgga gaacaacctt    2400
ggggaaggga gtttgcattg agagatcctg caggtgaggg ggcatgtaag caatggcagg    2460
caattcaaga acgaatcatt gctgcaaatg ctgggatggt atgcagctga ggtatctatt    2520
gccttgtatt ttgtctcgca ttgcatcggt ggtgcgttct gtggcctgag gcacagttct    2580
tgctgtttga taagggttcg actgagttgt cgtgtgtgct gtgctgcagg caattgcgtg    2640
cactttgttg cagaagaaca ggactga                                        2667

<210> SEQ ID NO 7
<211> LENGTH: 530
<212> TYPE: DNA
<213> ORGANISM: Parachlorella sp.
<220> FEATURE:
<221> NAME/KEY: misc_feature
<223> OTHER INFORMATION: RPS4 promoter

<400> SEQUENCE: 7
ccaccatggg ggaggtttga agtgtgcgcc tgatataatc atacacctaa aagcaccact      60
tgctgattgt gaagggacta tgtcgtttat gacgggacgt tacgctggcc gatggtttga    120
atttggacgc tgtggtagaa tgttatatgg acgtaaaggt tggcatattg aaaatcgtct    180
tcgcaggcaa acttctagac gtgtgaccca ccggtaaaac gacaagcgtg gcgcgtcgat    240
tgcgctttga acgtcgtttg ttggactcca gatgaacctc aaaatcaaag cggtgattga    300
cgaaaatcaa atgacagccc gcaaaatttc atcagccttc ggatcggatt ctcagaatct    360
gattgtccct gctggctaca tttatgaaat ttcgtacatt ttggcagaaa tgtcccaata    420
ccatagcact gccgcctgag ctcacccgag caatgcatac tgggtacctc gcccatctcg    480 ccctcttcc aagcccagtg ctgttgtaat agccaaaggg ctcagtaaca                530

<210> SEQ ID NO 8
<211> LENGTH: 546
<212> TYPE: DNA
<213> ORGANISM: Parachlorella sp.
<220> FEATURE:
<221> NAME/KEY: misc_feature
<223> OTHER INFORMATION: RPS4 terminator

<400> SEQUENCE: 8
gcatagcatc agcctgtggc agggttgtgg tagggctgag tggcagggtt aaaggggttg     60
```

-continued

```
cctaccccac ccctactctc atgacaccag caacagcagc agctcatgca gtactcaaat      120
cactgatgtc aatggtgtga cacatttggt taaggctgct ttttaaagtg ctgctttggg      180
ggcagtgact gtgcagagct tggagcgtat ccccatgtaa tcagaaccga cgagagttcg      240
gggcaacctt tcatcttcac attttttgtg atcagctaca gagtctgaaa tcaaatagag      300
gctgccatct aaacgcagga gtcacaacga aggcgaaaac tccaattgct gtactcaatg      360
cactaagtga ttgttcaatg gataaataca ctatgctcaa ttcatgccag cagagctgct      420
ccttccagcc agctacaatg gcttttcca cgccttttga agtatgaatg ttcagcttgc       480
tgtgcttgat gcatcaccat aaacacaatt ctacaacatt tcatgccaac aacagtacgg      540
gctttc                                                                546
```

<210> SEQ ID NO 9
<211> LENGTH: 302
<212> TYPE: PRT
<213> ORGANISM: Coccomyxa subellipsoidea
<220> FEATURE:
<221> NAME/KEY: misc_feature
<223> OTHER INFORMATION: SGI1 polypeptide, NCBI Accession XP_005652114

<400> SEQUENCE: 9

```
Met Gly Leu Lys Ala Arg Ala Ala Ser Val Ser Val His Ser Ser Ala
1               5                   10                  15

Asn Asn Thr Ala Ser Pro Leu Ser Ser Gly Arg Arg Gly Phe Pro His
            20                  25                  30

Ser Gly Glu Met Ser Gly Glu Asp Leu Ala Arg Ser Asp Ser Trp Glu
        35                  40                  45

Met Phe Pro Ala Gly Leu Lys Val Leu Val Val Asp Asp Asp Pro Leu
    50                  55                  60

Cys Leu Lys Val Val Glu His Met Leu Arg Arg Cys Asn Tyr Gln Val
65                  70                  75                  80

Thr Thr Cys Pro Asn Gly Lys Ala Ala Leu Glu Lys Leu Arg Asp Arg
                85                  90                  95

Ser Val His Phe Asp Leu Val Leu Ser Asp Val Tyr Met Pro Asp Met
            100                 105                 110

Asp Gly Phe Lys Leu Leu Glu His Ile Gly Leu Glu Leu Asp Leu Pro
        115                 120                 125

Val Ile Met Met Ser Ser Asn Gly Glu Thr Asn Val Val Leu Arg Gly
    130                 135                 140

Val Thr His Gly Ala Val Asp Phe Leu Ile Lys Pro Val Arg Val Glu
145                 150                 155                 160

Glu Leu Arg Asn Val Trp Gln His Val Val Arg Arg Lys Arg Asp Gln
                165                 170                 175

Ala Val Ser Gln Ala Arg Asp Ser Arg Asp Ile Ser Asp Glu Glu Gly
            180                 185                 190

Thr Asp Asp Gly Lys Pro Arg Asp Lys Lys Arg Lys Glu Val Ile Leu
        195                 200                 205

Val Leu Trp Trp Asp Met Gln Arg Arg Asp Ser Asp Asp Gly Val Ser
    210                 215                 220

Ala Lys Lys Ala Arg Val Val Trp Ser Val Glu Met His Gln Gln Phe
225                 230                 235                 240

Val Gln Ala Val Asn Gln Leu Gly Ile Asp Lys Ala Val Pro Lys Arg
                245                 250                 255

Ile Leu Asp Leu Met Asn Val Asp Gly Leu Thr Arg Glu Asn Val Ala
```

```
              260                 265                 270

Ser His Leu Gln Val Pro His Leu Ser Ile Phe Ser Pro Leu Phe Ala
        275                 280                 285

Glu Leu Met Ser Thr Leu Pro Arg Arg Cys Phe Tyr Asp Phe
    290                 295                 300
```

<210> SEQ ID NO 10
<211> LENGTH: 270
<212> TYPE: PRT
<213> ORGANISM: Ostreococcus lucimarinus
<220> FEATURE:
<221> NAME/KEY: misc_feature
<223> OTHER INFORMATION: SGI1 polypeptide, NCBI Accession XP_001415508

<400> SEQUENCE: 10

```
Phe Pro Ala Gly Leu Gly Val Leu Val Asp Asp Leu Leu Cys
1               5                   10                  15

Leu Lys Val Val Glu Lys Met Leu Lys Ala Cys Lys Tyr Lys Val Thr
            20                  25                  30

Ala Cys Ser Thr Ala Lys Thr Ala Leu Glu Ile Leu Arg Thr Arg Lys
        35                  40                  45

Glu Glu Phe Asp Ile Val Leu Ser Asp Val His Met Pro Asp Met Asp
    50                  55                  60

Gly Phe Lys Leu Leu Glu Ile Ile Gln Phe Glu Leu Ala Leu Pro Val
65                  70                  75                  80

Leu Met Met Ser Ala Asn Ser Asp Ser Ser Val Val Leu Arg Gly Ile
                85                  90                  95

Ile His Gly Ala Val Asp Tyr Leu Leu Lys Pro Val Arg Ile Glu Glu
            100                 105                 110

Leu Arg Asn Ile Trp Gln His Val Val Arg Arg Asp Tyr Ser Ser Ala
        115                 120                 125

Lys Ser Ser Gly Ser Glu Asp Val Glu Ala Ser Ser Pro Ser Lys Arg
    130                 135                 140

Ala Lys Thr Ser Gly Ser Asn Ser Lys Ser Glu Glu Val Asp Arg Thr
145                 150                 155                 160

Ala Ser Glu Met Ser Ser Gly Lys Ala Arg Lys Lys Pro Thr Gly Lys
                165                 170                 175

Lys Gly Gly Lys Ser Val Lys Glu Ala Glu Lys Lys Asp Val Val Asp
            180                 185                 190

Asn Ser Asn Ser Lys Lys Pro Arg Val Val Trp Ser Ala Glu Leu His
        195                 200                 205

Ala Gln Phe Val Thr Ala Val Asn Gln Leu Gly Ile Asp Lys Ala Val
    210                 215                 220

Pro Lys Arg Ile Leu Asp Leu Met Gly Val Gln Gly Leu Thr Arg Glu
225                 230                 235                 240

Asn Val Ala Ser His Leu Gln Lys Tyr Arg Leu Tyr Leu Lys Arg Leu
                245                 250                 255

Gln Gly Asn Asp Ala Arg Gly Gly Gly Asn Ala Ser Ser Thr
            260                 265                 270
```

<210> SEQ ID NO 11
<211> LENGTH: 941
<212> TYPE: PRT
<213> ORGANISM: Chlamydomonas reinhardtii
<220> FEATURE:
<221> NAME/KEY: misc_feature
<223> OTHER INFORMATION: SGI1 polypeptide

<400> SEQUENCE: 11

```
Met Asp Ser Gln Gly Val Lys Leu Glu Glu His Pro Gly His Thr Gly
1               5                   10                  15

Gly His Trp Gln Gly Phe Pro Ala Gly Leu Arg Leu Leu Val Val Asp
            20                  25                  30

Asp Pro Leu Cys Leu Lys Val Val Glu Gln Met Leu Arg Lys Cys
        35                  40                  45

Ser Tyr Glu Val Thr Val Cys Ser Asn Ala Thr Thr Ala Leu Asn Ile
    50                  55                  60

Leu Arg Asp Lys Asn Thr Glu Tyr Asp Leu Val Leu Ser Asp Val Tyr
65                  70                  75                  80

Met Pro Asp Met Asp Gly Phe Arg Leu Leu Glu Leu Val Gly Leu Glu
                85                  90                  95

Met Asp Leu Pro Val Ile Met Met Ser Ser Asn Gly Asp Thr Ser Asn
            100                 105                 110

Val Leu Arg Gly Val Thr His Gly Ala Cys Asp Tyr Leu Ile Lys Pro
        115                 120                 125

Val Arg Leu Glu Glu Leu Arg Asn Leu Trp Gln His Val Val Arg Arg
130                 135                 140

Arg Arg Gln His Ala Gln Glu Ile Asp Ser Asp Glu Gln Ser Gln Glu
145                 150                 155                 160

Arg Asp Glu Asp Gln Thr Arg Asn Lys Arg Lys Ala Asp Ala Ala Gly
                165                 170                 175

Val Thr Gly Asp Gln Cys Arg Leu Asn Gly Ser Gly Ser Gly Gly Ala
            180                 185                 190

Ala Gly Pro Gly Ser Gly Gly Ala Gly Gly Met Thr Asp Glu Met
        195                 200                 205

Leu Met Met Ser Gly Gly Glu Asn Gly Ser Asn Lys Lys Ala Arg Val
    210                 215                 220

Val Trp Ser Val Glu Met His Gln Gln Phe Val Asn Ala Val Asn Gln
225                 230                 235                 240

Leu Gly Ile Asp Lys Ala Val Pro Lys Lys Ile Leu Glu Ile Met Gly
                245                 250                 255

Val Asp Gly Ser Ala Gly Arg Leu Ala Asp Thr Ser Gly Arg Asp Val
            260                 265                 270

Cys Gly Thr Val Tyr Arg Leu Tyr Leu Lys Arg Val Ser Gly Val Thr
        275                 280                 285

Pro Ser Gly His His His Asn Ala Ala His Lys Ser Asn Lys Pro Ser
290                 295                 300

Pro His Thr Thr Pro Pro Pro Ala Leu Pro Gly Gln Ala Gly Thr
305                 310                 315                 320

His Pro Ala Asn Gln Ala Thr Ala Ile Pro Pro Pro Gln Pro Gly
                325                 330                 335

Ser Gly Thr Ala Ala Gly Ala Gly Ala Ala Ala Gly Thr Gly Gly
            340                 345                 350

Gly Ala Ala Ala Ala Asn Gly His Ala Ala Thr Thr Gly Ala Gly Thr
        355                 360                 365

Pro Gly Ala Ala Pro Gly Ala Gly Gly Val Gly Thr Gly Ala
        370                 375                 380

Gly Gly Leu Gly Ser Gly Pro Asp Ala Ala Ala Ala Gly Pro
385                 390                 395                 400

Gly Pro Gly Ala Ala Val Pro Gly Gly Leu Gly Gly Leu Pro Leu Pro
                405                 410                 415
```

Pro Gly Ala Gly Pro Gly Pro Gly Gly Phe Gly Gly Pro Ser
        420             425             430

Pro Pro Pro Pro His Pro Ala Ala Leu Leu Ala Asn Pro Met Ala
    435             440             445

Ala Ala Val Ala Gly Leu Asn Gln Ser Leu Leu Asn Ala Met Gly Ser
450             455             460

Leu Gly Val Gly Val Gly Gly Met Ser Pro Leu Gly Pro Val Gly Pro
465             470             475             480

Leu Gly Pro Leu Gly Gly Leu Pro Gly Leu Pro Gly Met Gln Pro Pro
            485             490             495

Pro Leu Gly Met Gly Gly Leu Gln Pro Gly Met Gly Pro Leu Gly Pro
        500             505             510

Leu Gly Leu Pro Gly Met Gly Gly Leu Pro Gly Leu Pro Gly Met Asn
        515             520             525

Pro Met Ala Asn Leu Met Gln Gly Met Ala Ala Gly Met Ala Ala Ala
    530             535             540

Asn Gln Met Asn Gly Met Gly Gly His Met Gly Gly His Met Gly Gly
545             550             555             560

Met Asn Gly Pro Met Gly Ala Leu Ala Gly Met Asn Gly Leu Asn Gly
            565             570             575

Ala Met Met Gly Gly Leu Pro Gly Met Gly Pro Gln Asn Met Phe
        580             585             590

Gln Ala Ala Ala Ala Ala Ala Gln Gln Gln Gln Gln Gln Gln Glu
        595             600             605

Gln Gln His Ala Met Met Gln Ala Ala Ala Gly Leu Leu Ala Ser
    610             615             620

Gln Gln Gln Gln Gln Gln Gln Gln Gln Gln Gln Gln Gln Gln Ala
625             630             635             640

Leu Gln Gln Gln Gln Gln Gly Met Ala Val Ser Pro Pro Gly Pro
            645             650             655

His Asn Ala Thr Pro Asn Gly Gln Leu His Thr His Pro Gln Ala His
            660             665             670

His Pro His Gln His Gly Leu His Ala His Ala His Pro His Gln His
        675             680             685

Leu Asn Thr Ala Pro Ala Gly Ala Leu Gly Leu Ser Pro Pro Gln Pro
    690             695             700

Pro Ala Gly Leu Leu Ser Ala Ser Gly Leu Ser Ser Gly Pro Asp Gly
705             710             715             720

Ser Gly Leu Gly Ser Gly Val Gly Gly Leu Leu Asp Gly Leu Gln Gln
            725             730             735

His Pro His His Pro Gln Leu Gln Leu Ala Gly Ser Leu Gly Thr Gly
        740             745             750

Gly Thr Gly Arg Ser Ser Gly Ala Ala Gly Arg Gly Ser Leu Asp Leu
        755             760             765

Pro Ala Asp Leu Met Gly Met Ala Leu Leu Asp Phe Pro Pro Val Pro
    770             775             780

Val Pro Gly Gly Ala Asp Val Gly Met Ala Gly Ala Gly Gly Ala
785             790             795             800

Ala Gly Ala His His His Gly His Gln Gly His Gln Gly Ile Gly Gly
            805             810             815

Gly Ala Gly Val Gly Ile Ala Gly Gly Val Gly Cys Gly Val Pro Ala
        820             825             830

```
Ala Ala His Gly Leu Glu Pro Ala Ile Leu Met Asp Pro Ala Asp
            835                 840                 845

Leu Gly Ala Val Phe Ser Asp Val Met Tyr Gly Thr Pro Gly Gly Gly
850                 855                 860

Gly Val Pro Gly Val Pro Gly Gly Val Gly Leu Gly Leu Gly
865                 870                 875                 880

Ala Gly Gln Val Pro Ser Gly Pro Ala Gly Ala Gly Leu His Ser
                885                 890                 895

His His His Gln His His His Gln His His Leu Gly His Val Val
            900                 905                 910

Pro Val Gly Gly Val Asp Pro Leu Ala Gly Asp Ala Ala Lys Met Ala
            915                 920                 925

Met Asn Asp Asp Asp Phe Phe Asn Phe Leu Leu Lys Asn
930                 935                 940

<210> SEQ ID NO 12
<211> LENGTH: 523
<212> TYPE: PRT
<213> ORGANISM: Chromochloris zofingiensis
<220> FEATURE:
<221> NAME/KEY: misc_feature
<223> OTHER INFORMATION: SGI1 polypeptide

<400> SEQUENCE: 12

Met Asp Gly Phe Lys Leu Leu Glu Thr Val Gly Leu Glu Leu Asp Leu
1               5                   10                  15

Pro Val Ile Met Met Ser Ser Asn Gly Glu His Thr Thr Val Met Arg
                20                  25                  30

Gly Val Thr His Gly Ala Cys Asp Phe Leu Ile Lys Pro Val Arg Ile
            35                  40                  45

Glu Glu Leu Arg Asn Ile Trp Gln His Val Ile Arg Arg Thr Arg His
    50                  55                  60

Pro Val Phe Arg Asp Leu Glu Pro Asp His Glu Gly Gly Asp Tyr
65                  70                  75                  80

Glu Ala Ser Lys Lys Arg Lys Asp Leu Tyr Arg Gly Glu Asn Ser Ser
                85                  90                  95

Gly Ser Gly Gly Ala Gly Gly Leu Glu Arg Asp Asp Asp Gly Ser Ala
            100                 105                 110

Ser Lys Lys Pro Arg Val Val Trp Ser Val Glu Met His Gln Gln Phe
    115                 120                 125

Val Gln Ala Val Asn Gln Leu Gly Ile Asp Lys Ala Val Pro Lys Lys
130                 135                 140

Ile Leu Glu Leu Met Asn Val Asp Gly Leu Thr Arg Glu Asn Val Ala
145                 150                 155                 160

Ser His Leu Gln Lys Tyr Arg Leu Tyr Leu Lys Arg Val Gln Gly Val
                165                 170                 175

Gln Ala Pro Phe Gly Leu Pro Asn Ile Gln Leu Pro Arg Gln Thr Ser
            180                 185                 190

Ser Lys Gly Ala Gly Ser Ser Ser Gln Gln Gln His His Gln Gln Gln
    195                 200                 205

Gln His Gln Gln Gln His Gln His Gln Thr Ala Leu Gly Thr
    210                 215                 220

Gly Gln Gln Gln Ser His Gln Leu Gln Pro Cys Pro Val Ser Thr Ala
225                 230                 235                 240

Thr Pro Val Met Pro Ser Pro Asp Ala Met Val Ala Ala Ser Met Met
                245                 250                 255
```

Ser Ser Gln Ala Met Ala Ala Met Ala Pro Gly Val Met Asn Pro Met
            260                 265                 270

Thr Ala Met Asn Ser Met Met Ala Gly Leu Asn Pro Asn Met Met Gly
        275                 280                 285

Met Ala Ala Gly Leu Gly Leu Ala Gly Leu Gly Ile Gly Gly Met Ala
290                 295                 300

Gly His Pro Val Pro Asn Pro Met Leu Ala Gly Met Gly Pro Met Gly
305                 310                 315                 320

Leu Gly Leu Pro Pro Pro Gly Met Pro Pro Pro Pro Gly Met
                325                 330                 335

Pro Pro Gly Met Pro Pro Gly Met Pro Gly Met Pro Ala Met Met
            340                 345                 350

Gln Gly Leu Ser Met Ala Gly Met Ser His Leu Ala Ala Ala Gly Met
            355                 360                 365

Arg Pro Pro Pro Gly Ala Leu Gly Gly His Leu Gly Gly Pro Gly Leu
370                 375                 380

Ser Pro Phe Gly Pro Pro Pro Pro Gly Ala Asp Pro Ala Asn Met
385                 390                 395                 400

Met Ala Asn Met Ser Ser Met Met Ala Asn Met Gln Ala Ala Leu Ala
            405                 410                 415

Phe Gln Ala Asp Ala Ala Ala Ala Gln His Gln Ala Ala Ser Thr
            420                 425                 430

Gly Ser Val Ala Pro Gly Arg Gln Gln Gln Val His Gln His Gln Gln
            435                 440                 445

Ala Val Gly Met Ala Val Asp Asp Ala Ala Ala Phe Pro Ser Pro Gly
            450                 455                 460

Cys Arg Pro Asn Gly Ser Ala Asp Ala Gly Ala Gln Ser Ala Ala Glu
465                 470                 475                 480

Pro Asn Asp Phe Ser Arg Val Phe Asp Pro Phe Ala Gln Pro Ala
            485                 490                 495

Ala Ser Pro Ser Gly Ala Ala Ala Gly Ser Asn Glu Ala Pro Gly
            500                 505                 510

Met Asp Asp Phe Leu Asp Phe Phe Leu Lys Ser
            515                 520

<210> SEQ ID NO 13
<211> LENGTH: 834
<212> TYPE: PRT
<213> ORGANISM: Volvox carteri
<220> FEATURE:
<221> NAME/KEY: misc_feature
<223> OTHER INFORMATION: SGI1 polypeptide

<400> SEQUENCE: 13

Met Asp Gly Arg Ala Glu Gly Thr Val Ala Ile Lys Gln Glu Asp His
1               5                   10                  15

Ala Ser Gly His Trp His Asn Phe Pro Ala Gly Leu Arg Leu Leu Val
            20                  25                  30

Val Asp Asp Asp Pro Leu Cys Leu Lys Val Val Glu Gln Met Leu Arg
        35                  40                  45

Lys Cys Ser Tyr Asp Val Thr Thr Cys Thr Asn Ala Thr Met Ala Leu
    50                  55                  60

Asn Leu Leu Arg Asp Lys Ser Thr Glu Tyr Asp Leu Val Leu Ser Asp
65                  70                  75                  80

Val Tyr Met Pro Asp Met Asp Gly Phe Lys Leu Leu Glu Val Val Gly

```
                    85                  90                  95
Leu Glu Met Asp Leu Pro Val Ile Met Met Ser Ser Asn Gly Asp Thr
                100                 105                 110

Ser Asn Val Leu Arg Gly Val Thr His Gly Ala Cys Asp Tyr Leu Ile
                115                 120                 125

Lys Pro Val Arg Leu Glu Glu Leu Arg Asn Leu Trp Gln His Val Val
                130                 135                 140

Arg Arg Arg Arg Gln Leu Asn Leu Asp Met Asp Ser Asp Glu His Ser
145                 150                 155                 160

Gln Glu Arg Asp Asp Gln Gly Arg Lys Arg Lys Ala Asp Thr Ala
                    165                 170                 175

Gly Cys Ile Gly Asp Gln Leu Arg Met Met Gly Ala Gly Cys Ser Gly
                180                 185                 190

Gly Ala Asn Gly Leu Gly Ser Thr Gly Asn Leu Gly Ala Val Ala Thr
                195                 200                 205

Gly Ser Ala Gly Leu Gly Leu Gly Leu Gly Thr Ala Ala Asp Glu Leu
210                 215                 220

Gly Leu Gly Leu Asp Asn Gly Ser Ser Lys Lys Ala Arg Val Val Trp
225                 230                 235                 240

Ser Val Glu Met His Gln Gln Phe Val Asn Ala Val Asn Gln Leu Gly
                    245                 250                 255

Ile Asp Lys Ala Val Pro Lys Lys Ile Leu Glu Ile Met Asn Val Asp
                260                 265                 270

Gly Leu Thr Arg Glu Asn Val Ala Ser His Leu Gln Lys Tyr Arg Leu
                275                 280                 285

Tyr Leu Lys Arg Val Ser Gly Ala Gln Gln Pro Gly Gln Asn Arg Val
290                 295                 300

Ser Arg Pro Ser Pro Gln Pro Gln Ser Pro Gln Val Pro Ser Gln
305                 310                 315                 320

Gln Gln Gln Ser Leu Pro Gly Gly Gly Ala Ala Ala Ala Gly Ala
                    325                 330                 335

Gly Gln Leu Gln Gly Gly Gly Ala Ala Ala Ala Ala Ser Leu
                340                 345                 350

Ala Ser Ile Leu Ala Gly Gly Pro Ala Gly Gly Ala Gly Ala
                355                 360                 365

Gly Pro Pro Gly Gly Gly Gln Leu Gly Ala Asp Gly Gly Pro
                370                 375                 380

Gly Pro Gly Leu Ser Ser Ala Val Ala Asn Ala Met Ser Ala Ala Ala
385                 390                 395                 400

Ala Ala Gly Gly Phe Pro Thr Pro Pro Pro Pro Pro His Pro
                    405                 410                 415

Ala Ala Leu Leu Ala Ala Asn Pro Met Met Ala Ala Ala Gly Leu
                420                 425                 430

Asn Pro Leu Leu Gly Ala Met Gly Gly Leu Gly Val Gly Pro Leu Gly
                435                 440                 445

Pro Leu Asn Pro Leu Asn Gly Met Pro Met Pro Gly Met Gln Pro Pro
                450                 455                 460

Leu Gly Leu Leu Pro Gly Leu Pro Gly Pro Gly Gln Leu Gly Leu
465                 470                 475                 480

Gly Pro Leu Gly Pro Ile Gly Leu Pro Gly Pro Gly Pro Leu Pro Ser
                485                 490                 495

Leu Pro Ala Gly Leu Pro Leu Asn Pro Met Ala Asn Gly Leu Gln Gln
                500                 505                 510
```

```
Met Ala Ala Ala Asn Leu Met Gln Gly Met Ala Gly Met Gly Gln Leu
            515                 520                 525

Pro Ala Leu Ser Met Asn Gly Met Asn Gly Ile Met Gly Pro Leu Pro
        530                 535                 540

Gly Val Gly Leu Pro Gly Pro Gln Gln His Leu Phe Pro Gln Gln Gln
545                 550                 555                 560

Gln Pro His Leu Gln Gln Gln Gln Gln Gln Gln Gln Lys Asp Leu
            565                 570                 575

Gln Met Ala Gln Lys Gln His Gln Ala Ala Ala Ala Ala Ala Val
            580                 585                 590

Ala Ala Ala Val Ala Ala Ala Gln His Gln Gln Gln Pro Gln Ala
            595                 600                 605

Gln Gln Gln Pro Gln Pro Gln Gln Gln Gln Pro Gly Lys Leu
            610                 615                 620

Pro Gln Ala Thr Val Gly Thr Pro Ala Leu Ala Ser Pro Ala Gly Ala
625                 630                 635                 640

Leu Pro Arg Gln Pro Ser Gly Gln His Pro His Thr Leu Ser Ser Ser
                645                 650                 655

Ser Leu His Thr Gln Gln Pro His Gln Gln Leu Leu His Ser Gln
            660                 665                 670

Pro Ser Ser Thr His Leu Ala Thr Asn Asn Thr Leu Ala Met Ala Pro
            675                 680                 685

Ala Leu Asn Gly Thr Leu Asp Val Gly Gly Lys Gly His Leu His Ala
            690                 695                 700

Ala Gly Gly Gln Gly Ala Gly Ala Gly Ala Val Leu Asp Ile
705                 710                 715                 720

Pro Pro Asp Leu Ile Gly Gly Leu Ile Glu Asp Gly Phe Gly Ala Pro
                725                 730                 735

Pro Gly Pro Thr Ile Gln Leu Ala His Gly Thr Ala Ala Val Leu Asp
            740                 745                 750

Pro Thr Met Leu Leu Asp Glu Gly Asp Asn Ser Asp Phe Ala Ala Val
            755                 760                 765

Phe Gln Glu Met Ser Ser Tyr Gly Gly Gly Val Ile Gly Gly Gly
            770                 775                 780

Gly Ser Gly Ala Gly Ala Met Gly Val Leu Gly His Gly Leu Leu Ala
785                 790                 795                 800

Ala Gly Gly Pro Val Met Val Asp Val Ala Ala Gly Leu Ala Gly Val
                805                 810                 815

Thr Glu Thr Ala Thr Arg Val Asp Asp Asp Phe Leu Asn Phe Leu Leu
            820                 825                 830

Lys Ser

<210> SEQ ID NO 14
<211> LENGTH: 446
<212> TYPE: PRT
<213> ORGANISM: Tetraselmis sp.
<220> FEATURE:
<221> NAME/KEY: misc_feature
<223> OTHER INFORMATION: SGI1 polypeptide 5172

<400> SEQUENCE: 14

Met Ser Cys Thr Val Ala Ser Phe Pro Pro Ala Ala Gly Gly Gln Gly
1               5                   10                  15

Ser Pro Ala Thr Pro Val Pro Tyr Gln Asp Leu Leu Val Lys Arg Gln
            20                  25                  30
```

```
Asp Gln Trp Ser Asn Phe Pro Ala Gly Leu Arg Val Leu Val Ala Asp
         35                  40                  45

Asn Asp Pro Ala Ser Leu Gln Gln Val Glu Lys Met Leu Lys Lys Cys
 50                  55                  60

Ser Tyr Gln Val Thr Leu Cys Ser Ser Gly Lys Asn Ser Leu Glu Ile
 65                  70                  75                  80

Leu Arg Lys Arg Arg Glu Glu Phe Asp Leu Val Leu Ala Asp Ala Asn
                 85                  90                  95

Leu Pro Asp Ile Asp Gly Phe Lys Leu Leu His Val Cys His Thr Glu
                100                 105                 110

Leu Ser Leu Pro Val Val Leu Met Ser Gly Thr Ser Asp Thr Gln Leu
            115                 120                 125

Val Met Arg Gly Val Met Asp Gly Ala Arg Asp Phe Leu Ile Lys Pro
        130                 135                 140

Leu Arg Val Glu Glu Leu Lys Val Leu Trp Gln His Leu Val Arg Phe
145                 150                 155                 160

Thr Ser Glu Ile Thr Lys Thr Asp Ala Gln Leu Asn Val Val Lys Val
                165                 170                 175

Glu Leu Asp Gly Gly Arg Pro Ala Gly Glu Val Ser Thr Ser Gln Asn
                180                 185                 190

Gly Ser Gln Cys Thr Glu Arg Glu Gly Glu Gly Asn Ser Ser Lys Lys
            195                 200                 205

Gln Arg Met Asn Trp Ser Asp Glu Met His Gln Gln Phe Val Asn Ala
        210                 215                 220

Val Asn Gln Leu Gly Ile Asp Lys Ala Val Pro Lys Arg Ile Leu Asp
225                 230                 235                 240

Leu Met Ser Val Glu Gly Leu Thr Arg Glu Asn Val Ala Ser His Leu
                245                 250                 255

Gln Lys Tyr Arg Ile Tyr Leu Lys Arg Met Ala Asn His Gln Glu Asn
                260                 265                 270

Gly Lys Gln Ala Val Met Ser Thr Asp Thr Ile Ala Arg Ala Glu Ala
            275                 280                 285

Ala Tyr Gln Gly Gly Met Pro Gln Gly Gln Met Met Gln Gln Glu
        290                 295                 300

His Ser Gly Gln Ala Val Gln Tyr Ser Gln Pro His Ala Pro Gly Gly
305                 310                 315                 320

Leu His Gln Gln Ala Met Pro Ala Gln Met His Met Gly Met Met Pro
                325                 330                 335

Ala Gly Pro Gln Pro Gly Ser Met Gln Met Ala Pro His His Val Met
            340                 345                 350

Gln Met Pro Asn Gly Gln Val Met Val Met Gln Met Gly Pro Arg
        355                 360                 365

Pro Gly Met Pro Pro Gly Met Pro Gln Met Met Ala Ser Ser Gln
370                 375                 380

Gln Met Gly Met Leu Gln Pro Gly Met Pro Ala Gly Gln Met Leu His
385                 390                 395                 400

Phe Gln His Pro Gln Gln Val His Gln His Pro Pro Ser Ser Gly Pro
                405                 410                 415

Met His Ala Val Gln His Met Glu Tyr Ala Tyr Ser Gln Pro Met Gln
            420                 425                 430

Met Ala Gly Trp Pro Val Gln Gly Gln Pro Gly Asn Gln Ala
        435                 440                 445
```

<210> SEQ ID NO 15
<211> LENGTH: 490
<212> TYPE: PRT
<213> ORGANISM: Tetraselmis sp.
<220> FEATURE:
<221> NAME/KEY: misc_feature
<223> OTHER INFORMATION: SGI1 polypeptide 5185

<400> SEQUENCE: 15

```
Met Thr Pro Thr Pro Pro Met Ser Cys Thr Val Ala Ser Phe Pro Pro
1               5                   10                  15

Ala Ala Gly Gly Gln Gly Ser Pro Ala Thr Pro Val Pro Tyr Gln Asp
            20                  25                  30

Leu Leu Val Lys Arg Gln Asp Gln Trp Ser Asn Phe Pro Ala Gly Leu
        35                  40                  45

Arg Val Leu Val Ala Asp Asn Asp Pro Ala Ser Leu Gln Gln Val Glu
    50                  55                  60

Lys Met Leu Lys Lys Cys Ser Tyr Gln Val Thr Leu Cys Ser Ser Gly
65                  70                  75                  80

Lys Asn Ser Leu Glu Ile Leu Arg Lys Arg Arg Glu Phe Asp Leu
                85                  90                  95

Val Leu Ala Asp Ala Asn Leu Pro Asp Ile Asp Gly Phe Lys Leu Leu
            100                 105                 110

His Val Cys His Thr Glu Leu Ser Leu Pro Val Val Leu Met Ser Gly
        115                 120                 125

Thr Ser Asp Thr Gln Leu Val Met Arg Gly Val Met Asp Gly Ala Arg
    130                 135                 140

Asp Phe Leu Ile Lys Pro Leu Arg Val Glu Glu Leu Lys Val Leu Trp
145                 150                 155                 160

Gln His Leu Val Arg Phe Thr Ser Glu Ile Thr Lys Thr Asp Ala Gln
                165                 170                 175

Leu Asn Val Val Lys Val Glu Leu Asp Gly Gly Arg Pro Ala Gly Glu
            180                 185                 190

Val Ser Thr Ser Gln Asn Gly Ser Gln Cys Thr Glu Arg Glu Gly Glu
        195                 200                 205

Gly Asn Ser Ser Lys Lys Gln Arg Met Asn Trp Ser Asp Glu Met His
    210                 215                 220

Gln Gln Phe Val Asn Ala Val Asn Gln Leu Gly Ile Asp Lys Ala Val
225                 230                 235                 240

Pro Lys Arg Ile Leu Asp Leu Met Ser Val Glu Gly Leu Thr Arg Glu
                245                 250                 255

Asn Val Ala Ser His Leu Gln Lys Tyr Arg Ile Tyr Leu Lys Arg Met
            260                 265                 270

Ala Asn His Gln Glu Asn Gly Lys Gln Ala Val Met Ser Thr Asp Thr
        275                 280                 285

Ile Ala Arg Ala Glu Ala Ala Tyr Gln Gly Gly Met Pro Gln Gly Gln
    290                 295                 300

Gln Met Met Gln Gln Glu His Ser Gly Gln Ala Val Gln Tyr Ser Gln
305                 310                 315                 320

Pro His Ala Pro Gly Gly Leu His Gln Gln Ala Met Pro Ala Gln Met
                325                 330                 335

His Met Gly Met Met Pro Ala Gly Pro Gln Pro Gly Ser Met Gln Met
            340                 345                 350

Ala Pro His His Val Met Gln Met Pro Asn Gly Gln Val Met Val Met
        355                 360                 365
```

```
Gln Gln Met Gly Pro Arg Pro Gly Met Pro Pro Gly Met Pro Gln Gln
        370                 375                 380

Met Met Ala Ser Ser Gln Gln Met Gly Met Leu Gln Pro Gly Met Pro
385                 390                 395                 400

Ala Gly Gln Met Leu His Phe Gln His Pro Gln Gln Val His Gln His
                405                 410                 415

Pro Pro Ser Ser Gly Pro Met His Ala Gly Gly Glu Met Ile Asp Pro
                420                 425                 430

Gly Ser Met Gln Arg Leu His Gln Gln Pro His Tyr Ile Gly Pro Asn
            435                 440                 445

Gly Gln His Met Pro Ala Pro Ala Met Gly Met Pro Ser Gly Thr Val
        450                 455                 460

Gln His Met Glu Tyr Ala Tyr Ser Gln Pro Met Gln Met Ala Gly Trp
465                 470                 475                 480

Pro Val Gln Gly Gln Pro Gly Asn Gln Ala
                485                 490

<210> SEQ ID NO 16
<211> LENGTH: 574
<212> TYPE: PRT
<213> ORGANISM: Tetraselmis sp.
<220> FEATURE:
<221> NAME/KEY: misc_feature
<223> OTHER INFORMATION: SGI1 polypeptide 5230

<400> SEQUENCE: 16

Met Thr Met Pro Leu Gly Gly Gly Leu Cys Met Lys Asp Arg Ile His
1               5                   10                  15

Gly Asp Glu Arg Tyr Arg Ser Lys Ala Lys Arg Gln Val Asn Thr Ile
            20                  25                  30

Phe Ala Phe Thr Gln Arg Asn Thr Trp Arg Gly Arg Phe Arg Leu Cys
        35                  40                  45

Ser Tyr Arg Thr Thr Glu Leu Leu Gly Gly Ser Lys Thr Thr Glu Pro
    50                  55                  60

Gly Arg Gly Thr Phe Val Leu Gln Ile Phe Met Cys Val Lys Asn Ala
65                  70                  75                  80

Ser Ile Asp Asp Gly Ser Arg His Ile Ser Thr Ser Arg Gly Leu Glu
                85                  90                  95

Ser Val Leu Lys Arg Arg Gly Gly Gln Gly Ala Pro Ala Ala Pro Val
            100                 105                 110

Pro Tyr His Asp Leu Leu Val Lys Arg Gln Asp Gln Trp Ser Asn Phe
        115                 120                 125

Pro Ala Gly Leu Arg Val Leu Val Ala Asp Asn Asp Pro Ala Ser Leu
    130                 135                 140

Gln Gln Val Glu Lys Met Leu Lys Lys Cys Ser Tyr Gln Val Thr Leu
145                 150                 155                 160

Cys Ser Ser Gly Lys Asn Ser Leu Glu Ile Leu Arg Lys Arg Arg Glu
                165                 170                 175

Glu Phe Asp Leu Val Leu Ala Asp Ala Asn Leu Pro Asp Ile Asp Gly
            180                 185                 190

Phe Lys Leu Leu His Val Cys His Thr Glu Leu Ser Leu Pro Val Val
        195                 200                 205

Leu Met Ser Gly Thr Ser Asp Thr Gln Leu Val Met Arg Gly Val Met
    210                 215                 220

Asp Gly Ala Arg Asp Phe Leu Ile Lys Pro Leu Arg Val Glu Glu Leu
```

```
                225                 230                 235                 240
Lys Val Leu Trp Gln His Leu Val Arg Phe Thr Ser Glu Ile Thr Lys
                245                 250                 255

Thr Asp Ala Gln Leu Asn Val Val Lys Val Glu Leu Asp Ser Gly Arg
                260                 265                 270

Pro Ala Gly Glu Val Ser Thr Ser Gln Asn Gly Ser Gln Cys Ala Glu
                275                 280                 285

Arg Glu Gly Gly Asn Ser Ser Lys Lys Gln Arg Met Asn Trp Ser
    290                 295                 300

Asp Glu Met His Gln Gln Phe Val Asn Ala Val Asn Gln Leu Gly Ile
305                 310                 315                 320

Asp Lys Ala Val Pro Lys Arg Ile Leu Asp Leu Met Ser Val Glu Gly
                325                 330                 335

Leu Thr Arg Glu Asn Val Ala Ser His Leu Gln Lys Tyr Arg Ile Tyr
                340                 345                 350

Leu Lys Arg Met Ala Asn His Gln Glu Asn Gly Lys Gln Ala Val Met
                355                 360                 365

Ser Thr Asp Thr Ile Ala Arg Ala Glu Ala Ala Tyr Gln Gly Gly Met
    370                 375                 380

Pro Gln Gly Gln Gln Met Met Gln Glu His Ser Gly Gln Ala Val
385                 390                 395                 400

Gln Tyr Ser Gln Pro His Ala Pro Ser Gly Leu His Gln Ala Met
                405                 410                 415

Pro Ala Gln Met His Met Gly Met Met Pro Ala Gly Pro Gln Pro Gly
                420                 425                 430

Ser Met Gln Met Ala Pro His His Val Met Gln Met Pro Asn Gly Gln
    435                 440                 445

Val Met Val Met Gln Gln Met Gly Pro Arg Pro Gly Met Pro Pro Gly
    450                 455                 460

Met Pro Gln Gln Met Met Ala Ser Ser Gln Gln Met Gly Met Leu Gln
465                 470                 475                 480

Pro Gly Met Pro Ala Gly Gln Met Leu His Phe Gln His Pro Gln Gln
                485                 490                 495

Val His Gln His Pro Pro Ser Ser Gly Pro Met His Ala Gly Gly Glu
                500                 505                 510

Met Ile Asp Pro Gly Ser Met Gln Arg Leu His Gln Gln Pro His Tyr
                515                 520                 525

Ile Val Pro Asn Ala Gln His Met Pro Ala Pro Ala Met Gly Met Pro
    530                 535                 540

Pro Gly Ala Val Gln His Met Glu Tyr Ala Tyr Ser Gln Pro Met Gln
545                 550                 555                 560

Met Ala Gly Trp Pro Val Gln Gly Gln Pro Gly Ser Gln Ala
                565                 570

<210> SEQ ID NO 17
<211> LENGTH: 674
<212> TYPE: PRT
<213> ORGANISM: Oocystis sp.
<220> FEATURE:
<221> NAME/KEY: misc_feature
<223> OTHER INFORMATION: SGI1 polypeptide 5549

<400> SEQUENCE: 17

Met Leu Ala Phe Thr His Gln Arg Met Thr Thr Ala Pro Ala Leu Ala
1               5                   10                  15
```

-continued

```
Val Ala Thr Ser His Phe Phe Ala His Val Arg Val Thr Thr Gly Ser
             20                  25                  30
Ser Ala Ile Ala Thr Val Phe Ala Ala Arg Ser Arg Gly Ser Gly Leu
         35                  40                  45
Leu Ala Gly Phe Asn Thr Met Glu Asn Val Lys Val Glu Val Pro Glu
     50                  55                  60
Val Val Pro Glu Asn Val Asn Phe Pro Ala Gly Leu Lys Val Leu Val
65                  70                  75                  80
Val Asp Asp Pro Leu Cys Leu Lys Val Ile Asp Gln Met Leu Arg
                 85                  90                  95
Arg Cys Asn Tyr Ala Ala Thr Thr Cys Gln Ser Ser Leu Glu Ala Leu
            100                 105                 110
Glu Leu Leu Arg Ser Ser Lys Glu Asn His Phe Asp Leu Val Leu Ser
        115                 120                 125
Asp Val Tyr Met Pro Asp Met Asp Gly Phe Lys Leu Leu Glu Ile Ile
    130                 135                 140
Gly Leu Glu Met Gly Leu Pro Val Ile Met Met Ser Ser Asn Gly Glu
145                 150                 155                 160
Thr Gly Val Val Phe Arg Gly Val Thr His Gly Ala Val Asp Phe Leu
                165                 170                 175
Ile Lys Pro Val Arg Ile Glu Glu Leu Arg Asn Leu Trp Gln His Val
            180                 185                 190
Val Arg Lys Thr Met Val Val Pro Ser Asn Asp Lys Ala Thr Ser Glu
        195                 200                 205
Glu Asp Gly Glu Glu Ser Lys His Arg Val Asp Arg Lys Arg Lys Glu
    210                 215                 220
Ser Phe His Ser Arg Ala Arg Glu Gln Val Glu Ile Ala Cys Ser Val
225                 230                 235                 240
Val Pro Ala Leu Leu Trp Pro Thr Val Pro Pro Ser Ser Val His Pro
                245                 250                 255
Thr Ser Ser Ser Phe Leu Arg Ser His Val Leu Leu Leu Gln Arg Ser
            260                 265                 270
Ser Gly Gly Lys Asp Val Leu Asp Glu Gly Gly Ser Asn Ala Lys Lys
        275                 280                 285
Pro Arg Val Val Trp Ser Val Glu Met His Gln Gln Phe Val Asn Ala
    290                 295                 300
Val Asn Gln Leu Gly Ile Asp Lys Ala Val Pro Lys Arg Ile Leu Asp
305                 310                 315                 320
Leu Met Asn Val Asp Gly Leu Thr Arg Glu Asn Val Ala Ser His Leu
                325                 330                 335
Gln Lys Tyr Arg Leu Tyr Leu Lys Arg Val Ala Gly Ile Asn Thr Ala
            340                 345                 350
Thr Gly Ser Arg Asn Gly Lys Gly Arg Ser Asp Val Ser Gly Leu Ser
        355                 360                 365
Gly Met Pro Asn Gly Ser Leu Pro Met Pro Gly Met Met Pro His
    370                 375                 380
Met Ala Ala Gly Met Leu Leu Ala Gly Met Ala Ala Asp Val Gly Pro
385                 390                 395                 400
Arg Pro His Pro Phe Pro Ile Met Pro Met Pro Ala Met Ala Leu Gln
                405                 410                 415
Gly Met His Gly Gly Met Ala Gln Met Met Gln Leu Pro Pro Gly Met
            420                 425                 430
Pro Pro Pro Met Met Met Pro Met Ala Pro Leu Leu Pro Ser Gln Leu
```

-continued

```
                435                 440                 445

Ala Ala Leu Gly Gln Gln Gln Gln Gln Gln Gln Gln Val Ala
        450                 455                 460

Arg Ser Glu Ser Met Pro Ser Glu Asn Gly Val Ala Gly Pro Ser Gly
465                 470                 475                 480

Ser Phe Thr Ala Met Leu Asn Gly Pro Ala Pro Met Glu Ser Ser Pro
                485                 490                 495

Phe Ala Ala Leu Gln Val Phe Gly Pro Pro Gln Gly Met Glu Gln Leu
                500                 505                 510

Thr Gln Gln Gln Gln Gln Gln Gln Ala Gly Ala Ala Ala Phe Val
                515                 520                 525

Ala Ala Phe Ala Ala Asn Gly Gly Asp Met Gln Gly Gly Gly
        530                 535                 540

Gly Pro Gly Pro Met Leu Gly Gly Ala Gly Gly Ala Gly Pro Leu Leu
545                 550                 555                 560

Gly Gly Val Gly Gly Gly Asp Pro Leu His Gly Gly Gly Ser Ser
                565                 570                 575

Ala Leu Gly Gly Arg Pro Met Met Ser Ala Glu Gln Pro Met Gly Gly
                580                 585                 590

Ser Gly Gly Leu Ala Ser Asn Ser Leu Thr Val Gln Asn Asp Leu
            595                 600                 605

Ala Gln Met Cys Ser Gln Leu Asp Val Asn Gly Leu Gln Ala Val Ala
        610                 615                 620

Ala Ala Ala Ala Gly Ala Met Gly Ala Pro Gly Gly Ala Gly Gly
625                 630                 635                 640

Ala Met Pro Pro Ser Ser Val Gly Val Gly Pro Asp Met Lys Leu
                645                 650                 655

Thr Glu Gln Asp Asp Phe Phe Ser Phe Leu Leu Lys Asp Ser Asn Leu
                660                 665                 670

Ile Asp

<210> SEQ ID NO 18
<211> LENGTH: 488
<212> TYPE: PRT
<213> ORGANISM: Micromonas sp. RCC299
<220> FEATURE:
<221> NAME/KEY: misc_feature
<223> OTHER INFORMATION: SGI1 polypeptide

<400> SEQUENCE: 18

Met Ser Thr Pro Ala Val Ser Lys Gly Phe Pro Ile Gly Leu Arg Val
1               5                   10                  15

Leu Val Val Asp Asp Asp Pro Leu Cys Leu Lys Ile Val Glu Lys Met
                20                  25                  30

Leu Lys Arg Cys Gln Tyr Glu Val Thr Thr Phe Ser Arg Gly Ala Glu
            35                  40                  45

Ala Leu Lys Thr Leu Arg Glu Arg Lys Asp Asp Phe Asp Ile Val Leu
        50                  55                  60

Ser Asp Val His Met Pro Asp Met Asp Gly Phe Lys Leu Leu Glu His
65                  70                  75                  80

Ile Ala Leu Glu Leu Asp Ile Pro Val Met Met Ser Ala Asn Cys
                85                  90                  95

Ala Thr Asp Val Val Leu Arg Gly Ile Ile His Gly Ala Val Asp Tyr
            100                 105                 110

Leu Leu Lys Pro Val Arg Ile Glu Glu Leu Arg Asn Ile Trp Gln His
```

```
            115                 120                 125
Val Val Arg Arg Lys Arg Glu Ser Ser Gln Gly Asn Leu Arg Ser Gly
130                 135                 140

Glu Gly Gly Ser Asn Gly Arg Thr Val Ser Gly Gly Ser Thr Gly Glu
145                 150                 155                 160

Gly Gly Gly Lys Asp Ser Lys Gly Ser Ser Glu Gln His Gly Asp Ala
                165                 170                 175

Lys Asp Lys Thr Gly Ser Ala Gly Gly Ser Gly Ser Ser Lys Arg
                180                 185                 190

Lys Lys Gly Ser Gly Lys Lys Gly Asp Glu Gly Thr Asp Glu Val Lys
            195                 200                 205

Asp Gly Ser Gly Gly Asp Glu Asn Glu Asp Ser Ser Ala Leu Lys Lys
210                 215                 220

Pro Arg Val Val Trp Ser Ala Glu Leu His Gln Gln Phe Val Thr Ala
225                 230                 235                 240

Val Asn Gln Leu Gly Ile Asp Lys Ala Val Pro Lys Arg Ile Leu Asp
                245                 250                 255

Leu Met Gly Val Gln Gly Leu Thr Arg Glu Asn Val Ala Ser His Leu
            260                 265                 270

Gln Lys Tyr Arg Leu Tyr Leu Lys Arg Leu Gln Gly Val Asn Ser Gly
            275                 280                 285

Gly Ala Pro Gly Gly Gly Pro Gly Phe Met Ser Pro Ile Ala Leu Asp
290                 295                 300

Gly Ser Met Val Gln Gly Gly Pro Gly Gly Arg Val Gly Ser Pro Ala
305                 310                 315                 320

Ile Gly Gly Pro Asn Gly Pro Ile Met Val Gly His Gly His Ile Asp
                325                 330                 335

Pro Ala Met Leu Ala Gly Gly Ala Pro Gln Thr Ile Gln Met Gly Met
                340                 345                 350

Val Tyr Gly Gly Pro Gly Met Gly Pro Pro Gln Met Met Ala Pro Asn
            355                 360                 365

Gly Lys Gly Gly Gly Gly Met Pro Gly Gly Tyr Val Met Gln Pro Gly
370                 375                 380

Gln Met Met Ala Pro Asn Gly Gln Met Met Pro Val Gly Gln Met Gly
385                 390                 395                 400

Pro Gly Gly Met Met Val Gln Gly Pro Gly Gly Met Met Gln Met
                405                 410                 415

His Asp Gly Gly Met Met Asn Gly Asn Gly Ser Tyr Gly Ser Leu Gln
            420                 425                 430

Asn Met Lys Gln Gly Asn Gly Val Val Met Met Pro Asn Gly Gly Met
            435                 440                 445

Gly Gly Val Asp Gly Ala Ile Pro Asn Met Ala Thr Gly Leu Ile Asn
            450                 455                 460

Gly Gln Gly Leu Pro Asp Asp Asp Val Leu Asp Met Phe Leu Lys Asp
465                 470                 475                 480

Gly Leu Pro Glu Gly Glu Gly Phe
                485

<210> SEQ ID NO 19
<211> LENGTH: 544
<212> TYPE: PRT
<213> ORGANISM: Micromonas pusilla
<220> FEATURE:
<221> NAME/KEY: misc_feature
<223> OTHER INFORMATION: SGI1 polypeptide
```

<400> SEQUENCE: 19

```
Met Thr Ala Glu Lys Lys Glu Leu Lys Val Phe Pro Ala Gly Leu Arg
1               5                   10                  15

Val Leu Val Val Asp Asp Pro Leu Cys Leu Arg Ile Val Glu Lys
            20                  25                  30

Met Leu Lys Arg Cys Gln Tyr Glu Val Thr Thr Phe Ser Arg Gly Ala
            35                  40                  45

Glu Ala Leu Glu Thr Leu Arg Ala Arg Asp Asp Phe Asp Ile Val
50                  55                  60

Leu Ser Asp Val His Met Pro Asp Met Asp Gly Phe Lys Leu Leu Glu
65                  70                  75                  80

His Ile Ala Leu Glu Leu Asp Val Pro Val Met Met Met Ser Ala Asn
                85                  90                  95

Cys Ala Thr Asp Val Val Leu Arg Gly Ile Ile His Gly Ala Val Asp
                100                 105                 110

Tyr Leu Leu Lys Pro Val Arg Leu Glu Glu Leu Arg Asn Ile Trp Gln
            115                 120                 125

His Val Val Arg Arg Gln Arg Glu Pro Ser Lys Asp Gly Ala Ala Gly
130                 135                 140

Lys Gly Gly Gly Ala Ser Gly Ala Pro Glu Val Ser Gly Asp Thr His
145                 150                 155                 160

Ala Asn Thr Asp Asp Lys Gln Asp Gly Asn Ala Thr Asp Ser Lys Gly
                165                 170                 175

Ser Gly Ser Gln Lys Arg Lys Ser Gly Lys Ser Gly Asp Asp Gly Gly
            180                 185                 190

Lys Asp Gly Gly Ser Gly Gly Lys Asp Gly Asp Ala Ser Asn Lys
            195                 200                 205

Gly Asn Asn Asn Lys Arg Lys Lys Gly Lys Ser Asn Asp Ala Thr Glu
210                 215                 220

Thr Ala Gly Gly Ala Gly Val Glu Asp Asn Asp Asp Thr Ser Gly Leu
225                 230                 235                 240

Lys Lys Pro Arg Val Val Trp Ser Pro Glu Leu His Gln Gln Phe Val
                245                 250                 255

Thr Ala Val Asn Gln Leu Gly Ile Asp Lys Ala Val Pro Lys Arg Ile
                260                 265                 270

Leu Asp Leu Met Gly Val Gln Gly Leu Thr Arg Glu Asn Val Ala Ser
            275                 280                 285

His Leu Gln Lys Tyr Arg Leu Tyr Leu Lys Arg Leu Gln Gly Val Asn
290                 295                 300

Asn Asn Gly Thr Val Pro Ser Gly Ala Ala Gly Phe Met Thr Gly Leu
305                 310                 315                 320

Ala Ile Asp Gly Val Gly Gly Val Met Gly Pro Thr Thr Gly Ser
                325                 330                 335

Pro Ala Met Asn Gly Pro Gly Gly Pro Gly Gly Leu Val Met Gly
            340                 345                 350

Pro Gly His Met Gly Gly Pro His Met Asp Gly Ser Gly Met Met His
            355                 360                 365

Met Gly Pro Gly Gly Pro Met Ala Gly Met Thr Val Val Tyr Gly Gly
            370                 375                 380

Gly Met Pro Gly Gly Met Pro Gly Gly Ala Asp Ser Lys Asn Gly Ala
385                 390                 395                 400

Ser Gly Gln Pro Pro Pro Gly Gly Tyr Val Val Met Gly Gly Pro His
```

-continued

```
                        405                 410                 415
Gly Gly Gly Pro Gly Ala Pro Met Met Met Gln His Gly Gly Met
                420                 425                 430
Val Pro Gly Pro Gly Pro Gly Leu Val Pro Gly Pro Gly Ser Leu
                435                 440                 445
Met Met Pro Ala Gly Met Met Pro Asp Gly Gly Gly Met Val Gly
                450                 455                 460
Val His Val Gly Pro Gly Val Val Met Gly Gln His Gln Leu Gly Gly
465                 470                 475                 480
Lys His Ser Ser Gly Gly Ala Gly Met Ala Gly Gly Ser Ala Ala Gly
                485                 490                 495
Lys Gly Ala Gln Arg Gly Gly Val Gly Gly Ala Phe Asp Val Pro Pro
                500                 505                 510
Thr Asn Gly Ser Leu Asp Ala Asp Glu Ile Gly Asp Asp Val Leu Thr
                515                 520                 525
Met Phe Leu Lys Asp Gly Leu Pro Glu Met Asn Asp Gly Asp Ala Leu
                530                 535                 540

<210> SEQ ID NO 20
<211> LENGTH: 776
<212> TYPE: PRT
<213> ORGANISM: Sphagnum fallax
<220> FEATURE:
<221> NAME/KEY: misc_feature
<223> OTHER INFORMATION: SGI1 polypeptide

<400> SEQUENCE: 20

Met Ser Gly Gly Asp Leu Ser Arg Val Arg Glu Gly Thr Ala Asp Leu
1               5                   10                  15
Asp Pro Val Met Ala Ser His Gln His Pro Pro Arg Gln Gln Ser
                20                  25                  30
His Gln Gln Pro Lys Asn His Gln Gln Glu Ala His Gln Gln His Cys
                35                  40                  45
Ser Ser Ala Glu Thr Thr Ser Pro Asn Asn Thr Ala Arg Gly Ala Gly
            50                  55                  60
Ala Thr Tyr Gly Lys Met Glu Pro Ala Asp Asp Phe Pro Ala Gly Leu
65              70                  75                  80
Arg Ile Leu Val Val Asp Asp Asp Pro Thr Cys Leu Ala Ile Leu Lys
                85                  90                  95
Lys Met Leu Gln Gln Cys Ser Tyr Gln Val Thr Thr Cys Gly Arg Ala
                100                 105                 110
Thr Arg Ala Leu Glu Leu Leu Arg Glu Asp Lys Asp Lys Phe Asp Leu
                115                 120                 125
Val Ile Ser Asp Val Tyr Met Pro Asp Met Asp Gly Phe Lys Leu Leu
                130                 135                 140
Glu Leu Val Gly Leu Glu Met Asp Leu Pro Val Ile Met Met Ser Gly
145                 150                 155                 160
Asn Gly Glu Thr Ser Val Val Met Lys Gly Ile Thr His Gly Ala Cys
                165                 170                 175
Asp Tyr Leu Leu Lys Pro Val Arg Ile Glu Glu Leu Ser Asn Ile Trp
                180                 185                 190
Gln His Val Val Arg Lys Leu Arg Ser Glu Pro Lys Glu His Ser Ala
                195                 200                 205
Ser Leu Glu Asp Gly Asp Arg Gln Arg Arg Gly Gly Ala Glu Asp Ala
                210                 215                 220
```

```
Asp Asn Thr Ser Ser Ala Ala Asp Thr Ala Asp Gly Ile Trp Arg Asn
225                 230                 235                 240

Lys Lys Lys Lys Glu Ala Lys Glu Asp Glu Glu Asp Phe Glu Gln Asp
            245                 250                 255

Asn Asp Asp Pro Ser Thr Leu Lys Lys Pro Arg Val Val Trp Ser Val
            260                 265                 270

Glu Leu His Gln Gln Phe Val Ser Ala Val Asn Gln Leu Gly Ile Asp
            275                 280                 285

Lys Ala Val Pro Lys Arg Ile Leu Glu Leu Met Ser Val Gln Gly Leu
            290                 295                 300

Thr Arg Glu Asn Val Ala Ser His Leu Gln Lys Tyr Arg Leu Tyr Leu
305                 310                 315                 320

Lys Arg Leu Ser Gly Val Thr Ser Gln Ser Asn Ser Leu Asn Val Ser
            325                 330                 335

Phe Gly Gly Pro Asp Ala Gly Tyr Gly Gly Leu Phe Gly Leu Asp Glu
            340                 345                 350

Met Ser Asp Tyr Arg Asn Leu Val Thr Asn Gly His Leu Pro Ala Gln
            355                 360                 365

Thr Ile Ala Ala Leu His His Ala Asn Met Ala Gly Arg Leu Gly Ala
370                 375                 380

Ser Ser Gly Met Val Gly Pro Ser Ser Pro Leu Asp Pro Ser Val Leu
385                 390                 395                 400

Ala Gln Ile Ala Ala Leu Gln Ser Gly Ser Leu Pro Arg Pro Gly Met
            405                 410                 415

Asp Gly Ser Leu Gln Gly Asn Gln Ala Gly Leu Leu Gln Ser Leu Ser
            420                 425                 430

Gly Ala Leu Asp Tyr Asn Ser Leu His Gln Ser His Leu Leu Pro Ala
            435                 440                 445

Ile Gly Gln Leu Gly Gln Leu Asp Glu Leu Pro Ser Leu Lys Ser Met
450                 455                 460

Gln His Gln Leu Gly Met Gly Ser Leu Gly Gly Ser Thr Arg Asn Leu
465                 470                 475                 480

Ala Gly Ser Pro Asn Glu Glu Leu Thr Met Gln Leu Leu Gln Gln Arg
            485                 490                 495

Ala Gln Gln Gln Ser Gly Gly Ser Pro Ile Asn Leu Pro Gln Ala Thr
            500                 505                 510

Gly Ile Leu Arg Pro Leu Ser Ser Asn Ile Asn Gln Gly Gly Ser Val
            515                 520                 525

Pro Asn Leu Val Gly Val Ile Pro Gly Thr Ala Ile Gly Leu Ser Asn
            530                 535                 540

Met Cys Ser Gly Gly Arg Glu Phe Gly Ser Ser Ser Gly Leu Leu Ser
545                 550                 555                 560

Ala Ser Gly Ser Leu Met Gln Ser Ser Thr Val Glu Ala Gln Asn Leu
            565                 570                 575

Asn Phe Gly Gly Ser Ser Gly Ser Ser Gly Cys Ser Phe Gln Ala Ser
            580                 585                 590

Val Leu Ser Ser Lys Thr Gly Gly Leu Glu Asp Leu Asn Pro Ala Lys
            595                 600                 605

Arg Val Arg Thr Thr Tyr Ser Ala Leu Ser His Ser Pro Asp Leu
            610                 615                 620

Gly Gln Ser Ser Arg Pro Ala Trp Leu Gly Ser Gln Glu Gly Leu Val
625                 630                 635                 640

His Gly Asp Pro Val Tyr Ser Pro His Gln Leu Ser Leu Pro Arg Gln
```

```
                        645                 650                 655
Asp Ile Val Gly Gly Ile Gly Ser Ser Gly Arg Pro Ala Tyr Met Gly
                660                 665                 670

Ser Gln Ser Met Gly Ser Leu Gly Met Asn Phe Pro Leu Ser Leu Ala
            675                 680                 685

Val Asp Ala Gly Ala Val Arg Pro Ser Leu Thr Arg Gly Gln Ser Leu
        690                 695                 700

Thr Glu Gln Val Ala Ala Asn Arg Glu Leu Lys Phe Pro Lys Glu Glu
705                 710                 715                 720

Arg Gly Arg Asp Asn Leu Met Cys Ala Arg Leu Gly Gly Gly Met Ile
                725                 730                 735

Thr Asn Glu Ser Ser Glu Glu Leu Leu Asn Tyr Leu Lys Gln Ser
            740                 745                 750

His Glu Gly Leu Gly Phe Met Glu Gly Asp Leu Val Ser Asp Gly Tyr
        755                 760                 765

Pro Val Asp Asn Leu Tyr Val Lys
    770                 775

<210> SEQ ID NO 21
<211> LENGTH: 715
<212> TYPE: PRT
<213> ORGANISM: Physcomitrella patens
<220> FEATURE:
<221> NAME/KEY: misc_feature
<223> OTHER INFORMATION: SGI1 polypeptide

<400> SEQUENCE: 21

Met Gly Gly Gly Tyr Leu Ser Ser Thr Val Asn Met Gly Glu Ser Arg
1               5                   10                  15

Asp Gly Gly Ser Pro Ala Met Ala Thr Leu Gln Gln Gln Gln Lys His
            20                  25                  30

Gln Pro Leu Asn Pro Asn His Gln Asn Pro Arg Asn Arg Ser Asn Ser
        35                  40                  45

Ser Pro Thr Asn Cys Tyr Ser Asn Thr Ala Trp Gly Ala Lys Pro Ala
    50                  55                  60

Lys Leu Asp Thr Pro Asp Glu Phe Pro Val Gly Met Arg Val Leu Val
65                  70                  75                  80

Val Asp Asp Asn Pro Thr Cys Leu Met Ile Leu Glu Gln Met Leu Val
                85                  90                  95

Arg Cys Ala Tyr Arg Val Thr Thr Cys Gly Lys Ala Thr Glu Ala Leu
            100                 105                 110

Ser Met Leu Arg Glu Asp Ile Gly Lys Phe Asp Val Ile Ser Asp
        115                 120                 125

Val Asp Met Pro Asp Met Asp Gly Phe Lys Leu Leu Glu Leu Val Gly
    130                 135                 140

Leu Glu Met Asp Leu Pro Val Ile Met Val Ser Gly Asn Gly Glu Thr
145                 150                 155                 160

Ser Ala Val Met Lys Gly Ile Thr His Gly Ala Cys Asp Tyr Leu Leu
                165                 170                 175

Lys Pro Val Arg Ile Glu Glu Leu Arg Asn Ile Trp Gln His Val Val
            180                 185                 190

Arg Lys Lys Arg Arg Glu Val Lys Ala Val Ala Thr Lys Ser Val Glu
        195                 200                 205

Glu Ala Gly Gly Cys Glu Arg Pro Lys Arg Gly Gly Ala Asp Asp
    210                 215                 220
```

```
Ala Asp Tyr Thr Ser Ser Ala Thr Asp Thr Thr Asp Ser Asn Trp Lys
225                 230                 235                 240

Leu Thr Lys Arg Arg Lys Gly Glu Phe Lys Asp Glu Asn Glu Glu Asp
            245                 250                 255

Asn Glu Gln Glu Asn Asp Asp Pro Ser Thr Leu Lys Arg Pro Arg Val
        260                 265                 270

Val Trp Ser Val Glu Leu His Gln Gln Phe Val Ser Ala Val Asn Gln
    275                 280                 285

Leu Gly Ile Asp Lys Ala Val Pro Lys Arg Ile Leu Glu Leu Met Gly
290                 295                 300

Val Gln Gly Leu Thr Arg Glu Asn Val Ala Ser His Leu Gln Lys Tyr
305                 310                 315                 320

Arg Leu Tyr Leu Lys Arg Leu Ser Gly Val Thr Ser Gln Gln Gly Asn
                325                 330                 335

Met Ser Ala His Phe Gly Gly Ser Asp Pro Phe Cys Met Met Pro Pro
            340                 345                 350

Asp Met Ser Leu Ala Asn Gly Gln Leu Thr Pro Gln Ala Leu Ala Lys
        355                 360                 365

Phe His Met Leu Gly Arg Met Asn Ala Thr Asn Gly Ile Gly Phe Ser
370                 375                 380

Gly Gly Gly Leu Asp Pro Gly Met Asn Gln Met Phe Leu Gln Asp Leu
385                 390                 395                 400

Pro Arg Pro Pro Gln Leu Asn Ser Met Leu Arg Asn Asn Thr Gly Leu
                405                 410                 415

Leu Ala Ser Val Pro Asn Gly Leu Gln His Leu Glu Gln Leu Ser Glu
            420                 425                 430

Pro His His Val His Val Val Asn Glu Leu Glu His Tyr Pro Ser Asn
        435                 440                 445

Thr Lys Val Tyr Pro Gln Leu Asn Gly Asn Leu Asp Val Ser Val Gly
    450                 455                 460

Pro Leu Gly Ala Ala Asn Gly Asn Leu Ala Ser Asn Pro Asn Ser Asp
465                 470                 475                 480

Thr Leu Leu Met His Ile Leu His Ser Arg Ala Ser Gln Gln Gly Val
                485                 490                 495

Gly Ser Pro Ser Thr Leu Pro Gln Pro Arg Cys Gly Leu Asn Pro Thr
            500                 505                 510

His Leu Leu Ser Asn Asp Ile Asn Phe Ala Pro Val Gly Ser Leu Pro
        515                 520                 525

Asn Leu Ala Gly Ser Leu Gly Pro Ala Val Gly Leu Ser Ala Ile Pro
    530                 535                 540

Gly Ser Ala Gly Gly Arg Asp Leu Ser Pro Ser Val Gly Gly Ser Gly
545                 550                 555                 560

Ala Ser Leu Ser Ser Pro Leu Gly Ser Leu Val Arg Arg Pro Leu Met
                565                 570                 575

Ala Glu Glu Gln Ser Asn Pro Val Asn Ser Thr Asn Gly Thr Tyr Ser
            580                 585                 590

Met Ala His Ser Gly Gln Ser Pro Lys Pro Ser Gly Asp Thr Leu Pro
        595                 600                 605

Thr Pro Leu Asn Glu Gly Leu Glu Gln Gln Pro Leu Trp Ala Leu
    610                 615                 620

Tyr Gln Asn Pro Met Asn Gln Leu Ser His Gly Pro Ser Gln Gly Phe
625                 630                 635                 640

Pro His Asp Ser Leu Gln Trp Ser Val Leu Thr Glu Asn Leu Ser Phe
```

645                 650                 655

Gly Asp Met Gly Gln Ser Leu Ser Ala Gly Leu Ile Ser Gln Phe Ser
            660                 665                 670

Ser Gln Gly Gln Asp Asn Gly Ile Gly Phe Ala Pro Pro Ser Gln Arg
            675                 680                 685

Gly Ser Tyr Thr Arg Gln Ser Val Ser Phe Pro Ala Ser Ser Ala Leu
            690                 695                 700

Asp Gly Arg Met Val Arg Ser Ser Tyr Glu Pro
705                 710                 715

<210> SEQ ID NO 22
<211> LENGTH: 664
<212> TYPE: PRT
<213> ORGANISM: Arabidopsis thaliana ARR2
<220> FEATURE:
<221> NAME/KEY: misc_feature
<223> OTHER INFORMATION: ARR2/SGI1 polypeptide

<400> SEQUENCE: 22

Met Val Asn Pro Gly His Gly Arg Gly Pro Asp Ser Gly Thr Ala Ala
1               5                   10                  15

Gly Gly Ser Asn Ser Asp Pro Phe Pro Ala Asn Leu Arg Val Leu Val
            20                  25                  30

Val Asp Asp Asp Pro Thr Cys Leu Met Ile Leu Glu Arg Met Leu Met
        35                  40                  45

Thr Cys Leu Tyr Arg Val Thr Lys Cys Asn Arg Ala Glu Ser Ala Leu
    50                  55                  60

Ser Leu Leu Arg Lys Asn Lys Asn Gly Phe Asp Ile Val Ile Ser Asp
65                  70                  75                  80

Val His Met Pro Asp Met Asp Gly Phe Lys Leu Leu Glu His Val Gly
                85                  90                  95

Leu Glu Met Asp Leu Pro Val Ile Met Met Ser Ala Asp Asp Ser Lys
            100                 105                 110

Ser Val Val Leu Lys Gly Val Thr His Gly Ala Val Asp Tyr Leu Ile
        115                 120                 125

Lys Pro Val Arg Ile Glu Ala Leu Lys Asn Ile Trp Gln His Val Val
    130                 135                 140

Arg Lys Lys Arg Asn Glu Trp Asn Val Ser Glu His Ser Gly Gly Ser
145                 150                 155                 160

Ile Glu Asp Thr Gly Gly Asp Arg Asp Arg Gln Gln Gln His Arg Glu
                165                 170                 175

Asp Ala Asp Asn Asn Ser Ser Ser Val Asn Glu Gly Asn Gly Arg Ser
            180                 185                 190

Ser Arg Lys Arg Lys Glu Glu Val Asp Asp Gln Gly Asp Asp Lys
        195                 200                 205

Glu Asp Ser Ser Ser Leu Lys Lys Pro Arg Val Val Trp Ser Val Glu
    210                 215                 220

Leu His Gln Gln Phe Val Ala Ala Val Asn Gln Leu Gly Val Asp Lys
225                 230                 235                 240

Ala Val Pro Lys Lys Ile Leu Glu Met Met Asn Val Pro Gly Leu Thr
                245                 250                 255

Arg Glu Asn Val Ala Ser His Leu Gln Lys Tyr Arg Ile Tyr Leu Arg
            260                 265                 270

Arg Leu Gly Gly Val Ser Gln His Gln Gly Asn Met Asn His Ser Phe
        275                 280                 285

```
Met Thr Gly Gln Asp Gln Ser Phe Gly Pro Leu Ser Ser Leu Asn Gly
            290                 295                 300

Phe Asp Leu Gln Ser Leu Ala Val Thr Gly Gln Leu Pro Pro Gln Ser
305                 310                 315                 320

Leu Ala Gln Leu Gln Ala Ala Gly Leu Gly Arg Pro Thr Leu Ala Lys
                325                 330                 335

Pro Gly Met Ser Val Ser Pro Leu Val Asp Gln Arg Ser Ile Phe Asn
            340                 345                 350

Phe Glu Asn Pro Lys Ile Arg Phe Gly Asp Gly His Gly Gln Thr Met
        355                 360                 365

Asn Asn Gly Asn Leu Leu His Gly Val Pro Thr Gly Ser His Met Arg
370                 375                 380

Leu Arg Pro Gly Gln Asn Val Gln Ser Ser Gly Met Met Leu Pro Val
385                 390                 395                 400

Ala Asp Gln Leu Pro Arg Gly Gly Pro Ser Met Leu Pro Ser Leu Gly
                405                 410                 415

Gln Gln Pro Ile Leu Ser Ser Ser Val Ser Arg Arg Ser Asp Leu Thr
            420                 425                 430

Gly Ala Leu Ala Val Arg Asn Ser Ile Pro Glu Thr Asn Ser Arg Val
        435                 440                 445

Leu Pro Thr Thr His Ser Val Phe Asn Asn Phe Pro Ala Asp Leu Pro
450                 455                 460

Arg Ser Ser Phe Pro Leu Ala Ser Ala Pro Gly Ile Ser Val Pro Val
465                 470                 475                 480

Ser Val Ser Tyr Gln Glu Glu Val Asn Ser Ser Asp Ala Lys Gly Gly
                485                 490                 495

Ser Ser Ala Ala Thr Ala Gly Phe Gly Asn Pro Ser Tyr Asp Ile Phe
            500                 505                 510

Asn Asp Phe Pro Gln His Gln His Asn Lys Asn Ile Ser Asn Lys
        515                 520                 525

Leu Asn Asp Trp Asp Leu Arg Asn Met Gly Leu Val Phe Ser Ser Asn
530                 535                 540

Gln Asp Ala Ala Thr Ala Thr Ala Thr Ala Ala Phe Ser Thr Ser Glu
545                 550                 555                 560

Ala Tyr Ser Ser Ser Thr Gln Arg Lys Arg Arg Glu Thr Asp Ala
                565                 570                 575

Thr Val Val Gly Glu His Gly Gln Asn Leu Gln Ser Pro Ser Arg Asn
            580                 585                 590

Leu Tyr His Leu Asn His Val Phe Met Asp Gly Gly Ser Val Arg Val
        595                 600                 605

Lys Ser Glu Arg Val Ala Glu Thr Val Thr Cys Pro Pro Ala Asn Thr
610                 615                 620

Leu Phe His Glu Gln Tyr Asn Gln Glu Asp Leu Met Ser Ala Phe Leu
625                 630                 635                 640

Lys Gln Glu Gly Ile Pro Ser Val Asp Asn Gly Phe Glu Phe Asp Gly
                645                 650                 655

Tyr Ser Ile Asp Asn Ile Gln Val
            660

<210> SEQ ID NO 23
<211> LENGTH: 1036
<212> TYPE: PRT
<213> ORGANISM: Arabidopsis halleri
<220> FEATURE:
<221> NAME/KEY: misc_feature
```

<223> OTHER INFORMATION: ARR18/SGI polypeptide

<400> SEQUENCE: 23

```
Leu Ser Lys Lys Gln Asn Glu Asp Ala Ser Gly Arg Lys Glu Glu Asp
1               5                   10                  15

Gly Lys Gly Asn Glu His Asn Gly Met Glu Ser Cys Thr Arg Met Lys
            20                  25                  30

Arg Thr Val Trp Thr Val Glu Leu His Gln Lys Phe Val Asn Ala Phe
        35                  40                  45

Gln Gln Leu Gly Leu Asp Lys Ala Ser Pro Glu Gln Ile His Ala Leu
    50                  55                  60

Met Asn Val Glu Gly Leu Pro Val Ile Asn Val Ala Ser His Leu Gln
65                  70                  75                  80

Lys Tyr Arg Leu Phe Leu Lys Lys Ile Tyr Glu Gly Gln Gln Leu Asp
                85                  90                  95

Met Ala Thr Ile Gln Leu Leu Leu Ser Ala Gly Ser His Phe Pro Gln
            100                 105                 110

Thr Pro Trp Thr Asn His Cys Ser Ser Phe Ile Gln Gln Gly His His
        115                 120                 125

Gln Asn Ser Ser Asn Ser Ser Glu Thr Tyr His Thr Thr Leu Ser Pro
    130                 135                 140

Arg Val Gln Lys Val Asn Thr Phe Gln Pro Ser Ser Pro Leu Lys
145                 150                 155                 160

Pro Leu Leu Phe Pro Lys Ser Asn Ile Ser Ala Phe Lys Glu Asp Phe
                165                 170                 175

Lys Ser Ile Lys Glu Pro Ala Ile Val Gly Asp Ser Ser Leu Asp Ser
            180                 185                 190

Ser Lys Pro Arg Asn Ser Phe Gln Thr Ala Ser Lys Phe Pro Lys Thr
        195                 200                 205

Asp Pro Cys Thr Gly Ser Tyr Ile Ile Glu Ile Met Thr Glu Pro Tyr
    210                 215                 220

Tyr Gly Lys Ser Ser Arg Arg His Ser Asn Phe Ser Ala Tyr Met Gly
225                 230                 235                 240

Asp Phe Lys Ser Ile Lys Asp Pro Glu Ile Val Gln Glu Ser Arg Thr
                245                 250                 255

Arg Lys Asn His Gly Arg Val Val Trp Ser His Glu Leu His Gln Lys
            260                 265                 270

Phe Leu Asn Ala Ile Asp Gln Leu Gly Gly Asn Glu Lys Ala Ile Pro
        275                 280                 285

Lys Lys Ile Leu Ala Val Met Asn Val Glu Gly Leu Thr Arg Leu Asn
    290                 295                 300

Val Ala Thr His Leu Gln Lys Tyr Arg Gln Cys Cys Ser Ala Glu Ala
305                 310                 315                 320

Gln Gln Leu Asn Met Ala Thr Arg Lys Leu Pro Ser Ser Glu His Leu
                325                 330                 335

Pro Gln Ser Pro Ser Thr Asn His His Ser Ser Leu Ser Pro Arg Val
            340                 345                 350

Gln Asp Val Asn Ile Arg Leu Trp Ser Ser Ser Pro Lys Arg Gln Asp
        355                 360                 365

Gln Ile Leu Val Tyr Val Leu Phe Ser Phe Glu Asn Asp Asn Gly Arg
    370                 375                 380

Glu Glu Thr Thr Cys Arg Arg Ile Ala Ser Thr Met Glu Leu Gly Ser
385                 390                 395                 400
```

```
Thr Glu Asp Gly Arg His Asp Lys Phe Pro Val Gly Met Arg Val Leu
                405                 410                 415
Ala Val Asp Asp Asn Pro Thr Cys Leu Arg Lys Leu Glu Glu Leu Leu
            420                 425                 430
Leu Arg Cys Lys Tyr His Val Thr Lys Thr Met Glu Ser Arg Lys Ala
        435                 440                 445
Leu Glu Leu Leu Arg Glu Asn Ser Asn Met Phe Asp Leu Val Ile Ser
    450                 455                 460
Asp Val Glu Met Pro Asp Thr Asp Gly Phe Lys Leu Leu Glu Ile Gly
465                 470                 475                 480
Leu Glu Met Asp Leu Pro Val Ile Met Leu Ser Ala His Ser Asp Tyr
                485                 490                 495
Asp Ser Val Met Lys Gly Ile Ile His Gly Ala Cys Asp Tyr Leu Val
            500                 505                 510
Lys Pro Val Gly Leu Lys Glu Leu Gln Asn Ile Trp His His Val Val
        515                 520                 525
Lys Lys Asn Ile Lys Ser Tyr Ala Lys Asn Ile Gly Pro Ser Arg Gln
    530                 535                 540
Leu Leu Pro Pro Ser Glu Ser Asn Leu Val Pro Ser Ala Ser Lys Lys
545                 550                 555                 560
Arg Lys Glu Lys Ala Ser Asp Ser Gly Asp Glu Asp Ser Asp Arg
                565                 570                 575
Glu Glu Asp Asp Gly Glu Gly Ser Glu Gln Asp Gly Glu Glu Ser Gly
            580                 585                 590
Thr Arg Lys Lys Pro Arg Val Val Trp Ser Gln Glu Leu His Gln Lys
        595                 600                 605
Phe Val Ser Ala Val Gln Gln Leu Gly Leu Asp Lys Ala Val Pro Lys
    610                 615                 620
Lys Ile Leu Asp Leu Met Ser Ile Glu Gly Leu Thr Arg Glu Asn Val
625                 630                 635                 640
Ala Ser His Leu Gln Lys Tyr Arg Leu Tyr Leu Lys Lys Ile Asp Glu
                645                 650                 655
Gly Gln Gln Gln Asn Met Thr Pro Asp Ala Phe Gly Thr Arg Asp Ser
            660                 665                 670
Ser Tyr Phe Gln Met Ala Gln Leu Asp Gly Leu Arg Asp Phe Thr Ala
        675                 680                 685
Thr Arg Gln Ile Pro Ser Ser Gly Leu Leu Ser Arg Ser His Leu Thr
    690                 695                 700
Lys Leu Gln Pro Pro Met Tyr Ser Ser Ile Asn Leu Gln Gly Met Asn
705                 710                 715                 720
Ser Ser Ser Phe Ile Gln Gln Gly His His Asn Ser Ser Asn Ser
                725                 730                 735
Ala Asn Pro Phe Gly Thr Tyr His Thr Thr Leu Ser Pro Arg Ile Gln
            740                 745                 750
Asn Val Asn Leu Leu Gln Arg Thr Ser Ser Pro Leu Glu Thr Leu Gln
        755                 760                 765
Phe Pro Arg Ser Lys Ser Tyr Ile Gly Asp Phe Lys Gly Ile Gly Asp
    770                 775                 780
Arg Ala Val Gly Gly Ser Phe Leu Asp Ser Cys Met Pro Phe Gly Ser
785                 790                 795                 800
Ser Ser Thr Ser Leu Pro Ser Ala Ser Thr Asn Thr Leu Met Leu Gln
                805                 810                 815
Ala Asn Tyr Thr Gln Pro Leu His Ile Ala Ser Asp Gly Asn Gln Pro
```

```
                820                 825                 830
Cys Ile Glu Gly Thr Pro Ser Asn Ser Ala Ser Pro Asn Ile Ser Phe
                835                 840                 845

Gln Gly Leu Ser Arg Phe Pro Ser His Ser Trp Gln Gly Asn Leu Asn
        850                 855                 860

Thr Thr Arg Phe Pro Pro Ser Ser Leu Pro Leu Asn Gln Ala Phe Leu
865                 870                 875                 880

Pro Asp Gln Val Thr Cys Ala Gly Asn Asn Leu Gly Asp Cys Thr Ser
                885                 890                 895

Leu Val Ser Ala Gly Asn Pro Gly Gly Glu Met Gln Cys Glu Pro Gln
        900                 905                 910

Leu Leu Gly Gly Phe Met Gln Asn Met Asn Pro Leu Asp Gly Gln Lys
        915                 920                 925

Trp Glu Gln Gln Asn Ser Met Leu Asn Asn Pro Phe Gly Asn Ile Glu
        930                 935                 940

Tyr Pro Leu Ser Ala Asp Asn Met Val Phe Arg Asp Asn Asn Ala Thr
945                 950                 955                 960

Arg Asn Lys Gly Leu Asp Glu Ser Leu Met Asn Pro Ile Asp Asn Ser
                965                 970                 975

Gln Glu Tyr Val Gly Lys Ala Thr Thr Met Leu Asp Pro Glu Met Lys
        980                 985                 990

Ser Gly Lys Pro Glu Asn Asp Asn Gln His Asp Val Phe Asp Asp Ile
        995                1000                1005

Met Asn Glu Met Met Lys Gln Glu Glu Asn Asn Gly Met Val Ser
        1010                1015                1020

Val Ala Thr Arg Phe Gly Phe Asp Ser Phe Pro Pro Pro
        1025                1030                1035

<210> SEQ ID NO 24
<211> LENGTH: 774
<212> TYPE: PRT
<213> ORGANISM: Arabidopsis lyrata
<220> FEATURE:
<221> NAME/KEY: misc_feature
<223> OTHER INFORMATION: SGI1 polypeptide

<400> SEQUENCE: 24

Met Gly Asp Phe Lys Ser Ile Lys Glu Pro Glu Ile Val Gln Glu Ser
1               5                   10                  15

Arg Thr Arg Lys Asn His Gly Arg Val Val Trp Ser His Glu Leu His
                20                  25                  30

Gln Lys Phe Leu His Ala Ile Asp Gln Leu Gly Gly Asn Asp Lys Ala
        35                  40                  45

Ile Pro Lys Lys Ile Leu Ala Val Met Asn Val Glu Gly Leu Thr Arg
    50                  55                  60

Leu Asn Val Ala Thr His Leu Gln Lys Tyr Arg Gln Cys Cys Ser Thr
65                  70                  75                  80

Glu Ala Gln Gln Leu Asn Met Ala Thr Arg Lys Leu Pro Ser Ser Glu
                85                  90                  95

His Leu Pro Gln Ser Pro Ser Thr Asn His His Ser Ser Leu Ser Pro
            100                 105                 110

Arg Val Gln Asp Asn Asp Asn Gly Arg Glu Glu Thr Thr Cys Arg Arg
        115                 120                 125

Ile Ala Ser Thr Met Glu Leu Gly Ser Thr Glu Asp Gly Arg His Asp
    130                 135                 140
```

-continued

```
Lys Phe Pro Val Gly Met Arg Val Leu Ala Val Asp Asp Asn Pro Thr
145                 150                 155                 160

Cys Leu Arg Lys Leu Glu Glu Leu Leu Arg Cys Lys Tyr His Val
                165                 170                 175

Thr Lys Thr Met Glu Ser Arg Lys Ala Leu Glu Leu Leu Arg Glu Asn
            180                 185                 190

Ser Asn Met Phe Asp Leu Val Ile Ser Asp Val Glu Met Pro Asp Thr
        195                 200                 205

Asp Gly Phe Lys Leu Leu Glu Ile Gly Leu Glu Met Asp Leu Pro Val
210                 215                 220

Ile Met Leu Ser Ala His Ser Asp Tyr Asp Ser Val Met Lys Gly Ile
225                 230                 235                 240

Ile His Gly Ala Cys Asp Tyr Leu Val Lys Pro Val Gly Leu Lys Glu
                245                 250                 255

Leu Gln Asn Ile Trp His His Val Val Lys Lys Asn Ile Lys Ser Tyr
                260                 265                 270

Ala Lys Asn Ile Gly Pro Ser Arg Gln Leu Leu Pro Pro Ser Glu Ser
            275                 280                 285

Asn Leu Val Pro Ser Ala Ser Lys Lys Arg Lys Glu Lys Ala Asn Asp
290                 295                 300

Ser Gly Asp Glu Asp Ser Asp Arg Glu Glu Asp Asp Gly Glu Gly
305                 310                 315                 320

Ser Glu Gln Asp Gly Asp Glu Ala Gly Thr Arg Lys Lys Pro Arg Val
                325                 330                 335

Val Trp Ser Gln Glu Leu His Gln Lys Phe Val Ser Ala Val Gln Gln
                340                 345                 350

Leu Gly Leu Asp Lys Ala Val Pro Lys Lys Ile Leu Asp Leu Met Ser
            355                 360                 365

Ile Glu Gly Leu Thr Arg Glu Asn Val Ala Ser His Leu Gln Lys Tyr
370                 375                 380

Arg Leu Tyr Leu Lys Lys Ile Asp Glu Gly Gln Gln Asn Met Thr
385                 390                 395                 400

Pro Asp Ala Phe Gly Thr Arg Asp Ser Ser Tyr Phe Gln Met Ala Gln
                405                 410                 415

Leu Asp Gly Leu Arg Asp Phe Thr Ala Thr Arg Gln Ile Pro Ser Ser
            420                 425                 430

Gly Leu Leu Ser Arg Ser His Leu Thr Lys Leu Gln Pro Pro Met Tyr
            435                 440                 445

Ser Ser Ile Asn Leu Gln Gly Met Asn Ser Ser Phe Ile Gln Gln
450                 455                 460

Gly His His Asn Ser Ser Asn Ser Ala Asn Pro Phe Gly Thr Tyr
465                 470                 475                 480

His Thr Thr Leu Ser Pro Arg Ile Gln Asn Val Asn Leu Phe Gln Arg
                485                 490                 495

Thr Ser Ser Pro Leu Glu Thr Leu Gln Phe Pro Arg Ser Lys Ser Tyr
            500                 505                 510

Ile Gly Asp Phe Lys Gly Ile Gly Asp Arg Ala Val Gly Gly Ser Phe
            515                 520                 525

Leu Asp Ser Cys Met Pro Phe Gly Ser Ser Ser Thr Ser Leu Pro Ser
530                 535                 540

Ala Ser Thr Asn Thr Leu Met Leu Gln Ala Asn Tyr Thr Gln Pro Leu
545                 550                 555                 560

His Ile Ser Ser Asp Gly Asn Gln Pro Cys Ile Glu Gly Thr Pro Ser
```

565                 570                 575

Asn Ser Ala Ser Pro Asn Ile Ser Phe Gln Gly Leu Ser Arg Phe Pro
                580                 585                 590

Ser His Ser Trp Gln Gly Asn Leu Asn Thr Thr Arg Phe Pro Pro Ser
                595                 600                 605

Ser Leu Pro Leu Asn Pro Ala Phe Leu Pro Asp Gln Val Thr Cys Ala
                610                 615                 620

Gly Asn Asn Leu Gly Asp Cys Thr Ser Leu Val Ser Ala Gly Asn Pro
625                 630                 635                 640

Gly Gly Glu Ile Gln Cys Glu Pro Gln Leu Leu Gly Gly Phe Met Gln
                645                 650                 655

Asn Met Asn Pro Leu Asp Gly Gln Lys Trp Glu Gln Gln Asn Cys Thr
                660                 665                 670

Met Leu Asn Asn Pro Phe Gly Asn Ile Glu Tyr Pro Leu Pro Ala Asp
                675                 680                 685

Asn Met Val Phe Arg Asp Asn Asn Ala Thr Arg Ser Lys Gly Leu Asp
                690                 695                 700

Glu Ser Leu Met Asn Pro Ile Asp Asn Ser Gln Glu Tyr Val Gly Lys
705                 710                 715                 720

Ala Thr Thr Met Leu Asp Pro Glu Met Lys Ser Gly Lys Pro Glu Asn
                725                 730                 735

Asp Asn Gln His Asp Val Phe Asp Leu Met Asn Glu Met Met Lys
                740                 745                 750

Gln Glu Glu Asn Asn Gly Met Val Ser Val Ala Thr Arg Phe Gly Phe
                755                 760                 765

Asp Ser Phe Pro Pro Pro
                770

<210> SEQ ID NO 25
<211> LENGTH: 578
<212> TYPE: PRT
<213> ORGANISM: Helianthus annus
<220> FEATURE:
<221> NAME/KEY: misc_feature
<223> OTHER INFORMATION: SGI1 polypeptide

<400> SEQUENCE: 25

Met Thr Thr Gly Ser Ser Phe Gly Ser Gly Ser Leu Gly Cys Lys Gln
1               5                   10                  15

Glu Thr Gly Val Pro Asp Gln Phe Pro Ala Gly Leu Arg Val Leu Val
                20                  25                  30

Val Asp Asp Asp Val Ile Cys Leu Lys Ile Leu Glu Gln Met Leu Arg
                35                  40                  45

Arg Cys Ser Tyr His Val Thr Thr Cys Ser Gln Ala Thr Ala Ala Leu
                50                  55                  60

Asn Leu Leu Arg Glu Arg Lys Gly Cys Phe Asp Val Val Leu Ser Asp
65                  70                  75                  80

Val His Met Pro Asp Met Asp Gly Phe Lys Leu Leu Glu Leu Val Gly
                85                  90                  95

Leu Glu Met Asp Leu Pro Val Ile Met Met Ser Ala Asp Gly Arg Thr
                100                 105                 110

Asn Leu Val Leu Arg Gly Ile Arg His Gly Ala Cys Asp Tyr Leu Ile
                115                 120                 125

Lys Pro Ile Arg Glu Glu Gln Leu Lys Asn Ile Trp Gln His Val Ile
                130                 135                 140

```
Arg Lys Lys Trp Asn Glu Asn Lys Glu His Glu His Ser Gly Ser Val
145                 150                 155                 160

Asp Asp Lys Asp Arg His Lys Arg Gly Gly Asp Asp Asn Asp Tyr Ala
            165                 170                 175

Ser Ser Val Asn Glu Gly Gly Asp Gly Ile Leu Thr Ser His Lys Lys
            180                 185                 190

Lys Arg His Asn Asn Lys Glu Glu Asp Asp Gly Glu Leu Glu Thr Asp
        195                 200                 205

Glu Pro Gly Gly Ser Lys Lys Ala Arg Val Val Trp Ser Val Glu Leu
        210                 215                 220

His Gln Gln Phe Val Thr Ala Val Asn Gln Leu Gly Ile Asp Lys Ala
225                 230                 235                 240

Val Pro Lys Arg Ile Leu Glu Leu Met Asn Val Pro Gly Leu Thr Arg
            245                 250                 255

Glu Asn Val Ala Ser His Leu Gln Lys Phe Arg Leu Tyr Leu Lys Arg
            260                 265                 270

Leu Ser Gly Val Ala Gln Gln Gly Gly Pro Asn Ser Phe Cys Gly
        275                 280                 285

Ser Ile Asp Gln Asn Pro Lys Leu Ala Ser Tyr Ala Arg Phe Glu Ile
290                 295                 300

Gln Ala Leu Ala Ala Ser Gly Gln Ile Pro Pro Gln Thr Leu Val Ala
305                 310                 315                 320

Leu His Ala Glu Leu Leu Gly Gln Pro Thr Ala Asn Val Gly Met Pro
                325                 330                 335

Val Leu Asp His Gln Pro Leu Met Gln Pro Ser Lys Cys Gly Pro Val
            340                 345                 350

Asp His Val Met Ser Tyr Gly Gln Thr Leu Pro Ser Asn Val Thr Lys
            355                 360                 365

Gln Val Pro Gln Pro Ala Ile Glu Asp Val His Ser Gly Leu Gly Ala
        370                 375                 380

Trp His Ser Asn Asn Met Val Gly Gly Tyr Gly Gln Leu Gly Gly Gln
385                 390                 395                 400

Asn Trp His Asn Met Leu Leu Gly Met Leu Gln Ser Gln Ser His Gln
                405                 410                 415

Leu Gln Lys Gln Ser Ile Thr Val Gln Pro Ser Arg Leu Val Val Pro
            420                 425                 430

Ser Gln Ser Ser Asn Phe Gln Ala Val Asn Asn Gly Val Pro Val Asn
        435                 440                 445

Gln Thr Thr Gly Phe Asn Asn Ser Thr Val Ile Asn Tyr Ala Val Gly
        450                 455                 460

Gln Arg Thr Glu Arg Asp Val Glu Asn Gln Ile Gly Gly Gln Ser Ser
465                 470                 475                 480

Val Ser Asn Ile Ser Val Lys Glu Met Gly Glu Lys Gln Ile Ser Phe
                485                 490                 495

Gly Glu Ser Val His Val Leu Asp Gln Gly Ser Leu Arg Asn Leu Gly
            500                 505                 510

Phe Val Gly Lys Lys Ser Ser Ile Pro Ser Arg Phe Ala Val Tyr Glu
        515                 520                 525

Ala Ala Glu Ser Leu Thr His Asn Leu Asn Tyr Gly Asp Asn Asn Gly
        530                 535                 540

Glu Arg Arg Val Lys Gln Glu Pro Asn Ile Glu Phe Leu Glu Asn Ser
545                 550                 555                 560

Lys Ala Gly Ala His Arg Val Ser Gln Asn Asp Leu Met Ser Lys Gln
```

Val Arg

<210> SEQ ID NO 26
<211> LENGTH: 428
<212> TYPE: PRT
<213> ORGANISM: Vitis vinifera
<220> FEATURE:
<221> NAME/KEY: misc_feature
<223> OTHER INFORMATION: GSVIVT01011650001

<400> SEQUENCE: 26

```
Met Ala Ala Leu Leu Lys Val Pro Pro Gln Ser Ser Gly Gly Thr Asn
1               5                   10                  15

Gly Ser Cys Lys Ala Asp Val Val Ser Asp Gln Phe Pro Ala Gly
            20                  25                  30

Leu Arg Val Leu Val Val Asp Asp Asp Val Thr Cys Leu Lys Ile Leu
        35                  40                  45

Glu Gln Met Leu Arg Arg Cys Leu Tyr His Val Thr Thr Cys Ser Gln
    50                  55                  60

Ala Thr Ile Ala Leu Asn Ile Leu Arg Glu Lys Lys Gly Cys Phe Asp
65                  70                  75                  80

Ile Val Leu Ser Asp Val His Met Pro Asp Met Asp Gly Tyr Lys Leu
                85                  90                  95

Leu Glu His Val Gly Leu Glu Met Asp Leu Pro Val Ile Met Met Ser
            100                 105                 110

Ala Asp Gly Arg Thr Ser Ala Val Met Arg Gly Ile Arg His Gly Ala
        115                 120                 125

Cys Asp Tyr Leu Ile Lys Pro Ile Arg Glu Glu Glu Leu Lys Asn Ile
    130                 135                 140

Trp Gln His Val Val Arg Lys Lys Trp Asn Glu Asn Lys Glu His Glu
145                 150                 155                 160

His Ser Gly Ser Leu Glu Asp Asn Asp Arg His Lys Arg Gly Gly Glu
                165                 170                 175

Asp Ala Glu Tyr Ala Ser Ser Val Asn Glu Gly Ala Glu Gly Ile Leu
            180                 185                 190

Lys Gly Gln Lys Lys Arg Arg Asp Ser Lys Asp Glu Asp Asp Gly Glu
        195                 200                 205

Leu Glu Asn Glu Asp Pro Ser Thr Ser Lys Lys Pro Arg Val Val Trp
    210                 215                 220

Ser Val Glu Leu His Gln Gln Phe Val Ser Ala Val Asn Gln Leu Gly
225                 230                 235                 240

Ile Asp Lys Ala Val Pro Lys Arg Ile Leu Glu Leu Met Asn Val Pro
                245                 250                 255

Gly Leu Thr Arg Glu Asn Val Ala Ser His Leu Gln Lys Phe Arg Leu
            260                 265                 270

Tyr Leu Lys Arg Leu Ser Gly Val Ala Gln Gln Gly Gly Ile Pro
        275                 280                 285

Asn Ser Phe Cys Gly Pro Val Glu Pro Asn Val Lys Leu Gly Ser Leu
    290                 295                 300

Gly Arg Phe Asp Ile Gln Ala Leu Ala Ala Ser Gly Gln Ile Pro Pro
305                 310                 315                 320

Gln Thr Leu Ala Ala Leu Gln Ala Glu Leu Leu Gly Arg Pro Thr Ser
                325                 330                 335

Asn Leu Val Leu Pro Ala Met Asp Gln Pro Ala Leu Leu Gln Ala Ser
```

```
            340                 345                 350
Leu Gln Gly Pro Lys Cys Ile Pro Val Glu His Gly Val Ala Phe Gly
            355                 360                 365

Gln Pro Leu Val Lys Cys Gln Thr Asn Ile Ser Lys His Phe Pro Pro
            370                 375                 380

Thr Val Val Ser Thr Glu Asp Val Pro Ser Gly Phe Gly Ala Trp Pro
385                 390                 395                 400

Ser Asn Ser Leu Gly Thr Val Gly Thr Ser Gly Ser Leu Gly Gly Leu
            405                 410                 415

Ser Ala Gln Asn Asn Asn Ile Leu Met Asp Met Lys
            420                 425

<210> SEQ ID NO 27
<211> LENGTH: 659
<212> TYPE: PRT
<213> ORGANISM: Amborella trichopoda
<220> FEATURE:
<221> NAME/KEY: misc_feature
<223> OTHER INFORMATION: SGI1 polypeptide

<400> SEQUENCE: 27

Met Ala Asn Val Gln Lys Leu Pro His Ser Ser Ile Ser Thr Ala Ser
1               5                   10                  15

Ser Tyr Gly Ser Cys Arg Gly Glu Gly Val Pro Asp Gln Phe Pro Ala
            20                  25                  30

Gly Leu Arg Val Leu Val Val Asp Asp Asp Thr Thr Cys Leu Arg Ile
            35                  40                  45

Leu Glu Gln Met Leu Arg Lys Cys Met Tyr Lys Val Thr Thr Cys Cys
            50                  55                  60

Arg Ala Thr Asp Ala Leu Asp Thr Leu Arg Gly Ser Lys Gly Cys Phe
65                  70                  75                  80

Asp Val Val Ile Ser Asp Val Tyr Met Pro Asp Met Asp Gly Phe Lys
                85                  90                  95

Leu Leu Glu His Val Gly Leu Glu Met Asp Leu Pro Val Ile Met Met
            100                 105                 110

Ser Ala Asp Ala Arg Phe Ser Ala Val Met Lys Gly Ile Lys His Gly
            115                 120                 125

Ala Cys Asp Tyr Leu Ile Lys Pro Val Arg Ile Glu Glu Leu Lys Asn
            130                 135                 140

Ile Trp Gln His Val Val Arg Lys Lys Trp Asn Glu Thr Lys Glu His
145                 150                 155                 160

Asp Gln Ser Gly Ser Ile Glu Asp Asn Glu Arg His Lys Arg Gly Ser
                165                 170                 175

Asp Asp Ala Glu Tyr Ala Ser Ser Val Asn Glu Gly Thr Asp Gly Asn
            180                 185                 190

Trp Lys Val Gln Lys Lys Arg Lys Asp Ser Lys Glu Glu Glu Asp Asp
            195                 200                 205

Gly Glu Gln Glu Asn Glu Asp Pro Ser Ala Ala Lys Lys Pro Arg Val
            210                 215                 220

Val Trp Ser Val Glu Leu His Gln Gln Phe Val Asn Ala Val Asn Gln
225                 230                 235                 240

Leu Gly Ile Asp Lys Ala Val Pro Lys Arg Ile Leu Glu Leu Met Asn
                245                 250                 255

Val Gln Gly Leu Thr Arg Glu Asn Val Ala Ser His Leu Gln Lys Phe
            260                 265                 270
```

```
Arg Leu Tyr Leu Lys Arg Leu Ser Gly His Gln Ala Gly Val Ser Ser
            275                 280                 285

Ser Phe Cys Gly Ser Val Asp Pro Asn Ser Lys Leu Gly Pro Leu Ser
290                 295                 300

Gln Leu Asp Ile Arg Ala Leu Thr Ala Ser Gly Gln Ile Pro Ser Gln
305                 310                 315                 320

Thr Leu Ala Ala Leu Gln Ala Glu Leu Leu Gly Arg Pro Ser Asn Asn
            325                 330                 335

Val Ala Met Pro Val Tyr Gly Gln Thr Leu Val Lys Cys Gln Pro Asn
            340                 345                 350

Leu Pro Lys Gln Phe Pro Gln Pro Asn Leu Pro Val Asp Asp Val Gln
            355                 360                 365

Ser Ser Leu Ser Ile Trp Gln His His Leu Ser Ser Gly Met Pro Leu
            370                 375                 380

Gly Gly Leu Asn Pro Gln Asn Asn Gly Leu Leu Met Gln Gln Gln Gln
385                 390                 395                 400

Gln Leu Thr Ile Glu Ser Asn Arg Pro Cys Asn Val Gln Pro Ser Cys
            405                 410                 415

His Val Ala Pro Ser Asn Gly Gly Phe Thr Met Arg Asn Asn Pro Thr
            420                 425                 430

Ser Ser Asn Ala Ser Ser Val Glu Tyr Asn Ser Leu Leu Ser Ser Gln
            435                 440                 445

Gly Asp Val Gly Gln Ile Ser Gln Ala Ser Gly Ser Asp Leu Ala Thr
            450                 455                 460

Thr Val Gln Ser Asn Gly Gly Phe Lys Ser Leu Asp Tyr Arg Asn Met
465                 470                 475                 480

Gly Gln Val Ser Leu Glu Ser Thr Ser Asp Leu Val Ser Thr Gln Asn
            485                 490                 495

Asn Gly Phe Lys Gly Met Glu Leu Arg Asn Val Gly Ser Leu Gly Gly
            500                 505                 510

Tyr Pro Leu Ser Ser Ser Val Ser Ala Gly Ser Thr Lys Thr Glu Asn
            515                 520                 525

Gly Gln Ser Phe Ser Gln Val Arg Thr Gly Pro Arg Met Ser Met Gly
            530                 535                 540

Pro Thr Gly Gln Phe Val Gly Pro Pro Thr Ile Arg Arg Leu Pro Met
545                 550                 555                 560

Val Asp Gly Gly Thr His Arg Asn Ser Leu Gly Phe Val Gly Lys Gly
                565                 570                 575

Val Ser Ile Pro Ser Arg Phe Met Pro Asp Ser Gly Ser Pro Thr Gly
            580                 585                 590

Val Gly Glu Glu Cys Thr Leu Pro Lys Gln Glu Val Asp Pro Asp Phe
            595                 600                 605

Phe Asp Ser Leu Lys Val Gly Pro Val Gly Val Gln His Tyr Ala Ser
610                 615                 620

Gly Asp Leu Met Ser Val Leu Ser Lys Gln Gln Ala Ser Thr Gly
625                 630                 635                 640

Asn Leu Asp Cys Glu Phe Gly Ile Asp Gly Tyr Gln Leu Gly Asn Ile
            645                 650                 655

His Val Lys

<210> SEQ ID NO 28
<211> LENGTH: 669
<212> TYPE: PRT
<213> ORGANISM: Ricinus communis
```

```
<220> FEATURE:
<221> NAME/KEY: misc_feature
<223> OTHER INFORMATION: SGI1 polypeptide

<400> SEQUENCE: 28
```

| | | | | | | | | | | | | | | |
|---|---|---|---|---|---|---|---|---|---|---|---|---|---|---|
| Met | Ala | Ala | Leu | Gln | Arg | Val | Ala | Ser | Ser | Val | Ser | Ala | Thr | Ala | Ser |
| 1 | | | | 5 | | | | | 10 | | | | | 15 | |
| Asn | Tyr | Ser | Ser | Cys | Lys | Gly | Asn | Gly | Val | Val | Thr | Ala | Thr | Ala | Asp |
| | | | 20 | | | | | 25 | | | | | 30 | | |
| Val | Ala | Val | Ser | Asp | Gln | Phe | Pro | Ala | Gly | Leu | Arg | Val | Leu | Val | Val |
| | | 35 | | | | | 40 | | | | | 45 | | | |
| Asp | Asp | Asp | Thr | Thr | Cys | Leu | Arg | Ile | Leu | Glu | Gln | Met | Leu | Arg | Arg |
| 50 | | | | | 55 | | | | | 60 | | | | | |
| Cys | Leu | Tyr | His | Val | Thr | Thr | Cys | Ser | Gln | Ala | Lys | Val | Ala | Leu | Asn |
| 65 | | | | 70 | | | | | 75 | | | | | 80 | |
| Leu | Leu | Arg | Glu | Arg | Lys | Gly | Cys | Phe | Asp | Val | Val | Leu | Ser | Asp | Val |
| | | | | 85 | | | | | 90 | | | | | 95 | |
| His | Met | Pro | Asp | Met | Asp | Gly | Phe | Lys | Leu | Leu | Glu | His | Val | Gly | Leu |
| | | | 100 | | | | | 105 | | | | | 110 | | |
| Glu | Met | Asp | Leu | Pro | Val | Ile | Met | Met | Ser | Ala | Asp | Gly | Arg | Thr | Ser |
| | | | 115 | | | | | 120 | | | | | 125 | | |
| Ala | Val | Met | Arg | Gly | Ile | Arg | His | Gly | Ala | Cys | Asp | Tyr | Leu | Ile | Lys |
| | | 130 | | | | | 135 | | | | | 140 | | | |
| Pro | Ile | Arg | Glu | Glu | Glu | Leu | Lys | Asn | Ile | Trp | Gln | His | Val | Val | Arg |
| 145 | | | | | 150 | | | | | 155 | | | | | 160 |
| Lys | Lys | Trp | His | Glu | Asn | Lys | Glu | Ile | Glu | His | Ser | Gly | Ser | Leu | Glu |
| | | | | 165 | | | | | 170 | | | | | 175 | |
| Asp | Asn | Asp | Arg | His | Lys | Arg | Gly | Asn | Glu | Asp | Ala | Glu | Tyr | Thr | Ser |
| | | | 180 | | | | | 185 | | | | | 190 | | |
| Ser | Val | Asn | Glu | Gly | Thr | Glu | Gly | Val | Leu | Lys | Gly | Gln | Lys | Arg | Arg |
| | | | 195 | | | | | 200 | | | | | 205 | | |
| Ser | Asn | Ser | Lys | Asp | Glu | Asp | Gly | Glu | Pro | Asp | Ser | Asp | Pro | | |
| | 210 | | | | | 215 | | | | | 220 | | | | |
| Ser | Thr | Ser | Lys | Lys | Pro | Arg | Val | Val | Trp | Ser | Val | Glu | Leu | His | Gln |
| 225 | | | | | 230 | | | | | 235 | | | | | 240 |
| Gln | Phe | Val | Ser | Ala | Val | Asn | Gln | Leu | Gly | Ile | Asp | Lys | Ala | Val | Pro |
| | | | | 245 | | | | | 250 | | | | | 255 | |
| Lys | Arg | Ile | Leu | Glu | Leu | Met | Asn | Val | Pro | Gly | Leu | Thr | Arg | Glu | Asn |
| | | | 260 | | | | | 265 | | | | | 270 | | |
| Val | Ala | Ser | His | Leu | Gln | Lys | Phe | Arg | Leu | Tyr | Leu | Lys | Arg | Leu | Ser |
| | | 275 | | | | | 280 | | | | | 285 | | | |
| Gly | Val | Ala | Gln | Gln | Gly | Gly | Ile | Ser | Ser | Thr | Phe | Cys | Gly | Pro | Met |
| | 290 | | | | | 295 | | | | | 300 | | | | |
| Asp | Ser | Asn | Val | Lys | Leu | Asn | Ser | Leu | Gly | Arg | Phe | Asp | Ile | Gln | Ala |
| 305 | | | | | 310 | | | | | 315 | | | | | 320 |
| Leu | Ala | Ala | Ser | Gly | Gln | Ile | Pro | Pro | Gln | Thr | Leu | Ala | Ala | Leu | His |
| | | | | 325 | | | | | 330 | | | | | 335 | |
| Ala | Glu | Leu | Phe | Gly | Arg | Pro | Thr | Gly | Ser | Leu | Val | Thr | Thr | Met | Asp |
| | | | 340 | | | | | 345 | | | | | 350 | | |
| Gln | Pro | Thr | Leu | Leu | Gln | Ala | Ser | Arg | Gln | Ser | Pro | Lys | Cys | Ile | Pro |
| | | | 355 | | | | | 360 | | | | | 365 | | |
| Val | Glu | His | Gly | Val | Thr | Phe | Gly | Gln | Pro | Ile | Val | Lys | Cys | Ser | Ser |
| | | 370 | | | | | 375 | | | | | 380 | | | |
| Gly | Ile | Ser | Lys | His | Phe | Pro | Gln | Asn | Met | Val | Ser | Val | Glu | Glu | Val |

```
            385                 390                 395                 400
Ser Ser Gly Tyr Gly Ala Trp Pro Ser Asn Ser Leu Gly Thr Val Gly
                405                 410                 415

Pro Ser Thr Asn Leu Gly Gly Met Thr Thr Gln Asn Gly Asn Met Leu
            420                 425                 430

Met Asp Ile Phe His Gln Gln Lys Gln Gln Pro Gln Gln Gln
            435                 440                 445

Gln Ser Leu Ala Asp Pro Ser Arg Ser Ile Asn Val Gln Pro Ser Cys
    450                 455                 460

Leu Val Pro Ser Gln Ser Ser Ala Cys Phe Gln Ala Gly Asn Ser
465                 470                 475                 480

Pro Ala Ser Val Asn Gln Ser Asn Phe Asn Arg Asn Val Val Ile Asp
                485                 490                 495

Tyr Ser Leu Leu Ser Ser Gln Ser Asn Asn Ser Ala Leu Asn Ile Gly
            500                 505                 510

His Ile Pro Glu Gly Asp Leu Lys Thr Thr Gly Ala Val Asn Gly Tyr
            515                 520                 525

Ser Ala Pro Gly Ser Leu Ser Pro Ala Ser Ser Cys Ser Val Asn
    530                 535                 540

Ala Asp Ser Gly Val Pro Arg Gln Val Gln Asn Pro Thr Leu Ala Phe
545                 550                 555                 560

Gly Ala Val Arg Gln Leu Pro Ala Leu Ser Pro Asn Ile Phe Asn Ile
                565                 570                 575

Gln Gly Ser Tyr Gly Val Arg Ser Asp Asp Ile Leu Asp Gln Gly Pro
            580                 585                 590

Phe Phe Lys Asn Leu Gly Phe Val Gly Lys Gly Thr Cys Ile Pro Ser
        595                 600                 605

Arg Phe Ala Val Asp Glu Phe Glu Thr Pro Ser Ser Asn Leu Ser His
        610                 615                 620

Gly Lys Leu Tyr Val Glu Asn Asn Asp Asn Lys Val Lys Gln Glu Pro
625                 630                 635                 640

Asn Ile Asp Phe Thr Asp Thr Ser Arg Val Gly Ile Pro Val Leu Gln
                645                 650                 655

Gln Tyr Pro Pro Asn Asp Leu Met Ser Val Phe Thr Glu
            660                 665

<210> SEQ ID NO 29
<211> LENGTH: 654
<212> TYPE: PRT
<213> ORGANISM: Solanum lycopersicum
<220> FEATURE:
<221> NAME/KEY: misc_feature
<223> OTHER INFORMATION: Solyc04g008050.2.1

<400> SEQUENCE: 29

Met Val Ser Met Ser Gly Glu Val Ala Thr Cys Lys Ser Glu Ala Thr
1               5                   10                  15

Val Val Thr Asp His Phe Pro Val Gly Leu Arg Val Leu Val Val Asp
                20                  25                  30

Asp Asp Val Val Cys Leu Arg Ile Ile Glu Gln Met Leu Arg Arg Cys
            35                  40                  45

Lys Tyr Ser Val Thr Thr Cys Thr Gln Ala Met Val Ala Leu Asn Leu
    50                  55                  60

Leu Arg Glu Lys Arg Gly Thr Phe Asp Ile Val Leu Ser Asp Val His
65                  70                  75                  80
```

```
Met Pro Asp Met Asp Gly Phe Lys Leu Leu Glu Leu Val Gly Leu Glu
                85                  90                  95
Met Asp Leu Pro Val Ile Met Met Ser Gly Asp Gly Arg Thr Asn Leu
            100                 105                 110
Val Met Arg Gly Val Gln His Gly Ala Cys Asp Tyr Leu Ile Lys Pro
        115                 120                 125
Ile Arg Asp Glu Glu Leu Lys Asn Ile Trp Gln His Val Val Arg Lys
    130                 135                 140
Arg Tyr Asn Ser Ser Lys Glu Pro Glu Cys Ser Gly Ser Leu Asp Asp
145                 150                 155                 160
Asn Asp Arg Tyr Arg Arg Ser Asp Asp Ala Glu Cys Ala Ser Ser
                165                 170                 175
Val Ile Glu Gly Ala Asp Gly Val Leu Lys Pro Gln Lys Lys Lys Arg
            180                 185                 190
Glu Ala Lys Glu Asp Asp Thr Glu Met Glu Asn Asp Pro Ser Thr
        195                 200                 205
Thr Lys Lys Pro Arg Val Val Trp Ser Val Glu Leu His Gln Gln Phe
    210                 215                 220
Val Ser Ala Val Asn Gln Leu Gly Ile Asp Lys Ala Val Pro Lys Arg
225                 230                 235                 240
Ile Leu Glu Leu Met Asn Val Pro Gly Leu Thr Arg Glu Asn Val Ala
                245                 250                 255
Ser His Leu Gln Lys Phe Arg Leu Tyr Leu Lys Arg Leu Ser Gly Val
            260                 265                 270
Val Gln Gln Gln Gly Gly Leu Pro Ser Thr Phe Cys Gly Pro Ile Glu
        275                 280                 285
Gln Asn Ser Glu Leu Gly Ser Leu Gly Arg Phe Asp Ile Gln Ala Leu
    290                 295                 300
Ala Ala Ser Gly Gln Ile Pro Pro Glu Thr Leu Thr Ala Leu His Ala
305                 310                 315                 320
Glu Leu Leu Gly Arg Ser Thr Ser Asn Leu Val Leu Pro Ala Val Glu
                325                 330                 335
Gln Gln Asn Leu Val Gln Val Ser Leu Gln Gln Ala Lys Cys Ile Pro
            340                 345                 350
Val Asp Gln Val Met Ala Tyr Gly Gln Pro Leu Leu Lys Cys Pro Ala
        355                 360                 365
Ser Ile Ser Asn Ser Lys His Leu Ser Gln Ala Ile Leu Ser Ala Glu
    370                 375                 380
Asp Val His Ser Gly Phe Gly Ser Gln Arg Ala Lys Asn Ile Cys Met
385                 390                 395                 400
Val Pro Ser Ser Asn Pro Ile Ala Pro Asn Ser Asn Met Leu Thr Ala
                405                 410                 415
Met Met Gln Gln Gln Trp Gln Lys Gln Gln Ile Glu Leu Gln
            420                 425                 430
His Arg Gln Ser Gly Pro Pro Glu Val Asn Arg Ser Ile Asn Val Gln
        435                 440                 445
Pro Ser Cys Leu Val Leu Pro Ser Gln Leu Pro Gly His Phe Gln Val
    450                 455                 460
Gly Asp Ser Pro Ala Ser Ile Ser Arg Ala Gly Ser Leu Ser Lys Ser
465                 470                 475                 480
Ser Val Ile Asp Tyr Gly Val Leu Ser Pro Gln Ser Asn Asn Ser Ser
                485                 490                 495
Gly Val Val Gln Val Leu Asp Arg Glu Leu Lys Pro Glu Cys Gly Leu
```

```
                500                 505                 510
Asn Arg Leu Pro Ser Gly Gly Ser Leu Ser Arg Ser Cys Ser Ile Asn
            515                 520                 525

Ala Asp Asn Ser Val Asp Leu Gln Leu His Asn Ser Ser Ala Phe
    530                 535                 540

Gly Ser Ser Lys Gln Leu Pro Gly Leu Ile Pro Ser His Leu Gly Ser
545                 550                 555                 560

Pro Val Pro Tyr Cys Ile Asn Ser Ser Leu Val Leu Asp Gln Gly Arg
                565                 570                 575

Met Lys Gly Ala Ser Ile Pro Ser Arg Phe Ala Val Asp Glu Ser Asp
            580                 585                 590

Ser Pro Met Cys Asn Phe Asn Thr Ala Lys Ile Tyr Leu Glu Glu Thr
        595                 600                 605

Lys Val Lys Gln Glu Pro Asn Met Asn Val Met Glu Asn Ala Lys Val
    610                 615                 620

Gly Pro Ala Ile Phe Gln Lys Phe Gln Pro Gly Asp Leu Met Ser Val
625                 630                 635                 640

Phe Arg Leu Ser Phe Ala Arg Val Lys Val Ser Ser Pro
                645                 650

<210> SEQ ID NO 30
<211> LENGTH: 653
<212> TYPE: PRT
<213> ORGANISM: Solanum tuberosum
<220> FEATURE:
<221> NAME/KEY: misc_feature
<223> OTHER INFORMATION: SGI1 polypeptide

<400> SEQUENCE: 30

Met Ser Gly Asp Val Ala Thr Cys Lys Ser Glu Ala Thr Val Val Thr
1               5                   10                  15

Asp His Phe Pro Leu Gly Leu Arg Val Leu Val Asp Asp Asp Val
                20                  25                  30

Val Cys Leu Arg Ile Ile Glu Gln Met Leu Arg Arg Cys Lys Tyr Ser
            35                  40                  45

Val Thr Thr Cys Thr Gln Ala Met Val Ala Leu Asn Leu Leu Arg Glu
    50                  55                  60

Lys Arg Gly Thr Phe Asp Ile Val Leu Ser Asp Val His Met Pro Asp
65                  70                  75                  80

Met Asp Gly Phe Lys Leu Leu Glu Leu Val Gly Leu Glu Met Asp Leu
                85                  90                  95

Pro Val Ile Met Met Ser Gly Asp Gly Arg Thr Asn Leu Val Met Arg
            100                 105                 110

Gly Val Gln His Gly Ala Cys Asp Tyr Leu Ile Lys Pro Ile Arg Asp
        115                 120                 125

Glu Glu Leu Lys Asn Ile Trp Gln His Val Val Arg Lys Arg Tyr Asn
    130                 135                 140

Ser Ser Lys Glu Leu Glu Cys Ser Gly Ser Leu Asp Asp Asn Asp Arg
145                 150                 155                 160

Tyr Lys Arg Gly Ser Asp Asp Ala Glu Cys Ala Ser Ser Val Ile Glu
                165                 170                 175

Gly Ala Asp Gly Val Leu Lys Pro Gln Lys Lys Arg Glu Ala Lys
            180                 185                 190

Glu Glu Asp Asp Thr Glu Met Glu Asn Asp Asp Pro Ser Thr Ser Lys
        195                 200                 205
```

```
Lys Pro Arg Val Val Trp Ser Val Glu Leu His Gln Gln Phe Val Ser
210                 215                 220

Ala Val Asn Gln Leu Gly Ile Asp Lys Ala Val Pro Lys Arg Ile Leu
225                 230                 235                 240

Glu Leu Met Asn Val Pro Gly Leu Thr Arg Glu Asn Val Ala Ser His
            245                 250                 255

Leu Gln Glu Asn Gln Lys Phe Arg Leu Tyr Leu Lys Arg Leu Ser Gly
        260                 265                 270

Val Val Gln Gln Gly Gly Leu Pro Ser Thr Phe Cys Gly Pro Ile
    275                 280                 285

Glu Gln Asn Ser Glu Leu Gly Ser Leu Gly Arg Phe Asp Ile Gln Ala
290                 295                 300

Leu Ala Ala Ser Gly Gln Ile Pro Pro Glu Thr Leu Thr Ala Leu His
305                 310                 315                 320

Ala Glu Leu Leu Gly Arg Ser Thr Ser Asn Leu Val Leu Pro Ala Val
            325                 330                 335

Glu Ile Gln Asn Leu Leu Gln Ala Ser Leu Gln Ala Lys Cys Ile
        340                 345                 350

Pro Ala Asp Gln Val Met Ala Tyr Gly Gln Pro Leu Leu Lys Cys His
            355                 360                 365

Pro Ser Ile Ser Asn Ser Lys His Leu Ser Gln Ser Ile Leu Ser Ala
370                 375                 380

Glu Asp Val His Ser Gly Phe Gly Ser Gln Arg Ala Lys Asn Ile Cys
385                 390                 395                 400

Leu Val Pro Ser Ser Asn Pro Ile Gly Leu Ala Ala Pro Asn Ser Asn
            405                 410                 415

Met Leu Met Ala Met Gln Gln Gln Trp Gln Lys Gln Gln Gln
        420                 425                 430

Met Glu Leu Gln His Arg Arg Ser Gly Pro Pro Glu Val Asn His Ser
    435                 440                 445

Ile Asn Val Gln Pro Ser Cys Leu Val Leu Pro Ser Gln Leu Pro Gly
450                 455                 460

Asn Phe Gln Val Gly Asp Ser Pro Ala Ser Ile Ser Arg Ala Gly Ser
465                 470                 475                 480

Leu Ser Lys Ser Ser Val Ile Asp Tyr Gly Val Leu Ser Pro Gln Ser
            485                 490                 495

Asn Asn Ser Ser Gly Val Val Gln Val Leu Asp Arg Glu Leu Lys Pro
        500                 505                 510

Glu Cys Gly Leu Asn Arg Leu Pro Ser Gly Gly Ser Leu Ser Arg Ser
    515                 520                 525

Cys Ser Ile Asn Ala Asp Asn Ser Val Gly Leu Gln Leu His Asn Ser
530                 535                 540

Ser Ser Ala Phe Gly Ser Ser Lys Gln Leu Pro Ala Leu Ile Pro Asn
545                 550                 555                 560

His Leu Gly Ser Pro Val Pro Tyr Tyr Ile Asn Ser Ser Gln Val Leu
            565                 570                 575

Asp Gln Gly His Thr Arg Asn Pro Gly Val Gly Lys Cys Ala Ser Ile
        580                 585                 590

Pro Ser Arg Phe Ala Val Asp Glu Ser Asp Ser Pro Met Cys Asn Phe
    595                 600                 605

Asn Thr Ala Lys Asn Tyr Leu Glu Glu Thr Lys Val Lys Gln Glu Pro
610                 615                 620

Asn Met Asn Val Met Glu Asn Ala Lys Val Gly Pro Ala Ile Phe Gln
```

```
                625                 630                 635                 640

Lys Phe Gln Pro Gly Asp Leu Met Ser Val Phe Ser Asp
                645                 650

<210> SEQ ID NO 31
<211> LENGTH: 669
<212> TYPE: PRT
<213> ORGANISM: Gossypium hirsutum
<220> FEATURE:
<221> NAME/KEY: misc_feature
<223> OTHER INFORMATION: SGI1 polypeptide

<400> SEQUENCE: 31

Met Ala Thr Met His Arg Val Val Gln Ser Ser Val Ser Thr Ser Asp
1               5                   10                  15

Ala Thr Thr Thr Ser Tyr Asp Gly Leu Thr Ser Cys Lys Ala Ala Asp
                20                  25                  30

Ile Val Ile Ser Asp Gln Phe Pro Ala Gly Leu Arg Val Leu Val Val
            35                  40                  45

Asp Asp Asp Ile Thr Cys Leu Lys Ile Leu Glu Lys Met Leu His Arg
    50                  55                  60

Cys Arg Tyr His Val Thr Thr Cys Pro Gln Ala Lys Val Ala Leu Asn
65                  70                  75                  80

Leu Leu Arg Glu Arg Lys Gly Cys Phe Asp Val Ile Leu Ser Asp Val
                85                  90                  95

Tyr Met Pro Asp Met Asp Gly Tyr Lys Leu Leu Glu His Val Gly Leu
                100                 105                 110

Glu Met Asp Leu Pro Val Ile Met Met Ser Ala Asp Gly Ser Thr Arg
            115                 120                 125

Ala Val Met Lys Gly Ile Arg His Gly Ala Cys Asp Tyr Leu Ile Lys
    130                 135                 140

Pro Ile Arg Glu Glu Leu Lys Asn Ile Trp Gln His Val Val Arg
145                 150                 155                 160

Lys Lys Trp Asn Glu Asn Lys Glu Leu Glu His Ser Gly Ser Leu Asp
                165                 170                 175

Asp Thr Asp Gln His Lys Gln Arg His Asp Asp Ala Glu Tyr Ala Ser
            180                 185                 190

Ser Val Asn Asp Ala Thr Glu Thr Ser Leu Lys Pro Leu Lys Lys Arg
    195                 200                 205

Ser Asn Ser Lys Glu Glu Asp Asp Gly Glu Ile Asp Asn Asp Asp Pro
210                 215                 220

Ser Thr Ser Lys Lys Pro Arg Val Val Trp Ser Val Glu Leu His Gln
225                 230                 235                 240

Gln Phe Val Ser Ala Val Asn Gln Leu Gly Ile Asp Lys Ala Val Pro
                245                 250                 255

Lys Arg Ile Leu Glu Leu Met Asn Val Pro Gly Leu Thr Arg Glu Asn
            260                 265                 270

Val Ala Ser His Leu Gln Lys Phe Arg Leu Tyr Leu Lys Arg Ile Ser
    275                 280                 285

Gly Val Ala Gln Gln Gly Gly Ile Ala Asn Pro Leu Cys Gly Pro Val
290                 295                 300

Glu Ala Asn Val Lys Ile Gly Ser Leu Gly Ser Phe Asn Ile Gln Ala
305                 310                 315                 320

Leu Ala Ala Ser Gly Gln Ile Pro Pro Gln Thr Leu Ala Ala Val His
                325                 330                 335
```

```
Ala Glu Leu Leu Gly Arg Ser Ala Gly Asn Leu Val Val Ala Thr Asp
            340                 345                 350

Gln Pro Ala Leu Leu Gln Ala Thr Pro Gln Gly Ala Lys Cys Ile Gln
        355                 360                 365

Val Asp Gln Gly Val Ala Phe Val Gln His Ser Val Lys Ser Glu Ser
    370                 375                 380

Ser Ser Ser Lys His Phe Ser Gln Ser Phe Ala Pro Val Glu Asp Val
385                 390                 395                 400

Ala Ser Gly Phe Arg Ser Trp Pro Ser Asn Asn Ile Gly Thr Ala Gly
                405                 410                 415

Pro Ser Asn Ser Gly Gly Leu Ser Ser Gln Asn Gly Asn Met Leu Ile
            420                 425                 430

Asp Leu Leu Gln Gln Gln Gln Leu Gln Lys Pro Gln Gln Arg Ser
        435                 440                 445

Thr Val Ser Glu Leu Arg Arg Ser Ile Asn Val Gln Pro Ser Cys His
    450                 455                 460

Val Val Pro Ser Gln Ser Ser Ala Ser Phe Arg Ala Gly Asn Ser Pro
465                 470                 475                 480

Val Ser Val Thr Gln Asn Gly Ser Tyr Ser Arg Thr Ala Val Ile Asp
                485                 490                 495

Tyr Ser Leu Leu Ser Ser Gln Ser Asn Cys Pro Ser Leu Asn Ile Gly
            500                 505                 510

Gln Val Ser Asp Val Asn Leu Gln Thr Thr Gly Val Leu Ser Gly Tyr
        515                 520                 525

Ile Pro Pro Ala Ser Val Ser Pro Ser Val Ser Cys Ser Val Asn
    530                 535                 540

Ala Asp Asn Cys Ala Ser Gln Gln Val Gln Thr Ser Ser Met Thr Phe
545                 550                 555                 560

Lys Ala Ser Arg His Leu Pro Gly Phe Val His Ser Thr Ser Asn Ile
                565                 570                 575

Pro Asp Pro Tyr Gly Ser Thr Lys Ser Gly Asp Leu Leu Asn Gln Glu
            580                 585                 590

Pro Phe Asn Asn Leu Gly Tyr Ile Asn Lys Gly Thr Cys Leu Pro Ala
        595                 600                 605

Lys Phe Ala Val Asp Glu Phe Gln Ser His Leu Ser Ser Ser His
    610                 615                 620

Gly Lys Val Phe Ser Glu Asn Ile Gly Thr Arg Val Lys Gln Glu Pro
625                 630                 635                 640

Ser Met Glu Phe Gly Asp Asn Ala Lys Val Gly Ile Pro Met Leu Gln
                645                 650                 655

Gln Phe Arg Pro Asn Asp Leu Met Ser Val Phe Thr Glu
            660                 665

<210> SEQ ID NO 32
<211> LENGTH: 681
<212> TYPE: PRT
<213> ORGANISM: Theobroma cacao
<220> FEATURE:
<221> NAME/KEY: misc_feature
<223> OTHER INFORMATION: SGI1 polypeptide

<400> SEQUENCE: 32

Met Asn Ser Ser Gly Lys Gly Ser Met Ser Ala Ala Ser Ser
1               5                   10                  15

Ala Ala Trp Lys Ala Gly Asp Val Val Pro Asp Gln Phe Pro Ala Gly
            20                  25                  30
```

```
Leu Arg Val Leu Val Asp Asp Pro Thr Cys Leu Met Ile Leu
        35              40              45

Glu Lys Met Leu Arg Thr Cys Leu Tyr Glu Val Thr Lys Cys Asn Arg
 50              55              60

Ala Glu Thr Ala Leu Ser Leu Leu Arg Glu Asn Lys Asn Gly Phe Asp
 65              70              75              80

Ile Val Ile Ser Asp Val His Met Pro Asp Met Asp Gly Phe Lys Leu
            85              90              95

Leu Glu His Ile Gly Leu Glu Met Asp Leu Pro Val Ile Met Met Ser
            100             105             110

Ala Asp Asp Gly Lys His Val Val Met Lys Gly Val Thr His Gly Ala
        115             120             125

Cys Asp Tyr Leu Ile Lys Pro Val Arg Ile Glu Ala Leu Lys Asn Ile
        130             135             140

Trp Gln His Val Val Arg Lys Arg Lys Asn Glu Trp Lys Asp Phe Glu
145             150             155             160

Gln Ser Gly Ser Val Glu Glu Gly Asp Arg Gln Pro Lys Gln Ser Glu
                165             170             175

Glu Ala Asp Tyr Ser Ser Ser Ala Asn Glu Gly Asn Trp Lys Ser Ser
            180             185             190

Lys Lys Arg Lys Asp Asp Asp Glu Ala Glu Glu Arg Asp Asp Thr
        195             200             205

Ser Thr Leu Lys Lys Pro Arg Val Val Trp Ser Val Glu Leu His Gln
        210             215             220

Gln Phe Val Ala Ala Val Asn Gln Leu Gly Ile Asp Lys Ala Val Pro
225             230             235             240

Lys Lys Ile Leu Glu Leu Met Asn Val Pro Gly Leu Thr Arg Glu Asn
            245             250             255

Val Ala Ser His Leu Gln Lys Tyr Arg Leu Tyr Leu Arg Arg Leu Ser
            260             265             270

Gly Val Ser Gln His Gln Ser Asn Leu Asn Asn Ser Phe Met Ser Pro
        275             280             285

Gln Glu Ala Thr Phe Gly Pro Leu Ser Pro Leu Asn Gly Leu Asp Leu
        290             295             300

Gln Thr Leu Ala Ala Thr Gly Gln Leu Pro Ala Gln Ser Leu Ala Thr
305             310             315             320

Phe Gln Ala Ala Gly Leu Gly Arg Ser Thr Ala Lys Ser Gly Ile Ala
            325             330             335

Met Pro Leu Val Asp Gln Arg Asn Ile Phe Ser Phe Glu Asn Pro Lys
            340             345             350

Leu Arg Phe Gly Glu Gly Gln Gln Gln His Met Asn Asn Asn Lys Gln
        355             360             365

Leu Asn Leu Leu His Gly Ile Pro Thr Thr Met Glu Pro Lys Gln Leu
        370             375             380

Ala Ser Leu His His Ser Ala Gln Ser Ile Gly Asn Ile Asn Met Gln
385             390             395             400

Val Thr Ser His Gly Val Gln Gly Ser Gln Asn Asn Ser Leu Leu Ile
            405             410             415

Gln Met Ala Gln Pro Gln Pro Arg Gly Gln Ile Leu Asn Asp Ser Thr
            420             425             430

Gly Ser His Ala Pro Arg Leu Pro Ser Thr Leu Gly Gln Pro Ile Leu
        435             440             445
```

```
Ser Asn Gly Ile Ala Ala Asn Val Ser Thr Arg Asn Gly Ile Pro Glu
    450                 455                 460

Asn Ile Arg Gly Pro Gly Tyr Asn Pro Val Ser Gln Thr Ser Ser Leu
465                 470                 475                 480

Leu Asn Phe Pro Met Asn His Thr Ser Glu Leu Pro Gly Asn Ser Phe
                485                 490                 495

Pro Leu Gly Thr Thr Pro Gly Ile Ser Ser Leu Thr Ser Lys Gly Ala
            500                 505                 510

Phe Gln Glu Asp Ile Asn Ser Asp Val Lys Gly Ser Gly Phe Met
        515                 520                 525

Pro Ser Tyr Asp Ile Phe Asn Asp Leu Asn Gln His Lys Pro Gln Asn
    530                 535                 540

Trp Glu Leu Gln Asn Val Gly Met Thr Phe Asp Ala Ser Gln His Ser
545                 550                 555                 560

Asn Ser Leu Gln Gly Asn Leu Asp Leu Ala Gln Ser Ile Leu Val Gln
                565                 570                 575

Gln Gly Phe Ser Ser Gly Gln Met Asn Gly Asn Arg Ser Ala Ala
            580                 585                 590

Val Val Ser Lys Ala Met Phe Ser Ala Gly Asp Cys Thr Glu Gln Gly
    595                 600                 605

Asn Ala Gln Asn Val Asn His His Leu Asn Asn Leu Leu Val Asp Asn
610                 615                 620

Thr Ile Arg Ile Lys Ser Glu Arg Val Ala Asp Ala Gly Pro Ala Asn
625                 630                 635                 640

Leu Phe Pro Asp His Phe Gly Gln Glu Asp Leu Met Ser Ala Leu Leu
                645                 650                 655

Lys Gln Gln Asp Gly Ile Ala Pro Ala Glu Asn Glu Phe Asp Phe Asp
            660                 665                 670

Gly Tyr Ser Met Asp Asn Ile Pro Val
            675                 680

<210> SEQ ID NO 33
<211> LENGTH: 579
<212> TYPE: PRT
<213> ORGANISM: Phaseolus vulgaris
<220> FEATURE:
<221> NAME/KEY: misc_feature
<223> OTHER INFORMATION: SGI1 polypeptide

<400> SEQUENCE: 33

Met Asn Leu Ser Asn Gly Lys Gly Ser Met Ser Thr Val Thr Thr Thr
1               5                   10                  15

Ala Val Met Lys Ser Gly Asp Ala Val Ser Asp Gln Phe Pro Ala Gly
            20                  25                  30

Leu Arg Val Leu Val Asp Asp Pro Thr Cys Leu Met Ile Leu
        35                  40                  45

Glu Lys Met Leu Arg Thr Cys Leu Tyr Glu Val Thr Lys Cys Asn Arg
    50                  55                  60

Ala Glu Thr Ala Leu Ser Leu Leu Arg Glu Asn Lys Asn Gly Phe Asp
65                  70                  75                  80

Ile Val Ser Ala Asn Glu Gly Ser Trp Arg Asn Ser Lys Lys Arg Arg
                85                  90                  95

Asp Glu Glu Glu Glu Ala Glu Asp Arg Asp Asp Thr Ser Thr Leu Lys
            100                 105                 110

Lys Pro Arg Val Val Trp Ser Val Glu Leu His Gln Gln Phe Val Ala
        115                 120                 125
```

```
Ala Val Asp Gln Leu Gly Ile Asp Lys Ala Val Pro Lys Lys Ile Leu
            130                 135                 140

Glu Leu Met Asn Val Pro Gly Leu Thr Arg Glu Asn Val Ala Ser His
145                 150                 155                 160

Leu Gln Lys Tyr Arg Leu Tyr Leu Arg Arg Leu Ser Gly Val Ser Gln
                165                 170                 175

His Gln Asn Asn Leu Asn Asn Ser Phe Leu Gly Ser Gln Glu Ala Thr
            180                 185                 190

Phe Gly Thr Ile Ser Ser Ile Asn Gly Ile Asp Leu Gln Thr Leu Ala
                195                 200                 205

Val Thr Gly Gln Leu Pro Ala Gln Ser Leu Ala Thr Leu Gln Ala Ala
210                 215                 220

Gly Leu Gly Arg Ser Thr Ala Lys Thr Gly Val Pro Met Pro Leu Met
225                 230                 235                 240

Asp Gln Arg Asn Leu Phe Ser Phe Glu Asn Pro Arg Val Arg Phe Gly
                245                 250                 255

Glu Gly Gln Gln Gln His Leu Ser Ser Ser Lys Pro Met Asn Leu Leu
            260                 265                 270

Leu Gly Ile Pro Thr Asn Met Glu Pro Lys Gln Leu Ala Asn Leu His
                275                 280                 285

Gln Ser Thr Gln Ser Ile Ala Ser Leu Asn Met Arg Val Asn Ala Ser
290                 295                 300

Ala Thr Gln Gly Asn Pro Leu Met Met Gln Met Pro Gln Ser Gln Pro
305                 310                 315                 320

Arg Gly Gln Met Leu Ser Glu Asn Thr Gly Pro Arg Val Pro Arg Leu
                325                 330                 335

Pro Ser Ser Leu Gly Gln Pro Thr Val Ser Asn Gly Ile Ser Asn Gly
            340                 345                 350

Phe Leu Gly Arg Asn Gly Ile Ala Gly Asn Asn Arg Gly Pro Ala Tyr
                355                 360                 365

Asn Pro Val Pro Pro Asn Ser Ser Leu Leu Ser Phe Pro Met Asn Gln
370                 375                 380

Ser Ser Glu Val Ser Val Asn Asn Ser Leu Pro Leu Gly Ser Ser Pro
385                 390                 395                 400

Gly Ile Ser Ser Ile Thr Thr Lys Gly Ser Phe Gln Glu Glu Val Thr
                405                 410                 415

Ser Gly Ile Lys Ala Thr Gly Gly Phe Pro Ser Tyr Asp Ile Phe Asn
            420                 425                 430

Glu Leu His His Gln Lys Ser His Asp Trp Glu Ile Thr Asn Pro Ser
            435                 440                 445

Leu Thr Tyr Ser Ala Ser His His Ala Asn Pro Leu Gln Gly Asn Ile
450                 455                 460

Asp Val Ser Pro Ser Val Leu Val His Gln Gly Phe Ser Ser Thr Gln
465                 470                 475                 480

Gln Asn Gly Gln Ser Arg Asp Ala Thr Leu Ile Gly Lys Ala Met Phe
                485                 490                 495

Ser Leu Gly Glu Gly Ser Glu Gln Asp Asn Leu Gln Asn Ala Val Gln
            500                 505                 510

His Leu His Pro Leu Leu Val Asp Asn Ser Ile Arg Val Lys Ala Glu
            515                 520                 525

Arg Ile Pro Asp Ala Ser Ser Gln Thr Asn Leu Phe Pro Asp His Tyr
530                 535                 540
```

-continued

Val Gln Glu Asp Leu Met Ser Ala Leu Leu Lys Gln Gln Glu Gly Met
545                 550                 555                 560

Gly Pro Ala Glu Ser Glu Phe Glu Phe Asp Ala Tyr Ser Leu Asp Asn
                565                 570                 575

Ile Pro Val

<210> SEQ ID NO 34
<211> LENGTH: 679
<212> TYPE: PRT
<213> ORGANISM: Glycine max
<220> FEATURE:
<221> NAME/KEY: misc_feature
<223> OTHER INFORMATION: SGI1 polypeptide

<400> SEQUENCE: 34

Met Asn Leu Ser Asn Gly Lys Gly Ser Met Ser Thr Leu Thr Ala Ser
1               5                   10                  15

Val Val Met Lys Ser Gly Asp Ala Val Ser Asp Gln Phe Pro Ala Gly
                20                  25                  30

Leu Arg Val Leu Val Asp Asp Pro Thr Cys Leu Met Ile Leu
            35                  40                  45

Glu Lys Met Leu Arg Thr Cys Leu Tyr Glu Val Thr Lys Cys Asn Arg
50                  55                  60

Ala Glu Thr Ala Leu Ser Leu Leu Arg Glu Asn Lys Asn Gly Phe Asp
65                  70                  75                  80

Ile Val Ile Ser Asp Val His Met Pro Asp Met Asp Gly Phe Lys Leu
                85                  90                  95

Leu Glu His Ile Gly Leu Glu Met Asp Leu Pro Val Ile Met Met Ser
                100                 105                 110

Ala Asp Asp Gly Lys Ser Val Val Met Lys Gly Val Thr His Gly Ala
            115                 120                 125

Cys Asp Tyr Leu Ile Lys Pro Val Arg Ile Glu Ala Leu Lys Asn Ile
130                 135                 140

Trp Gln His Val Val Arg Lys Arg Lys Asn Glu Trp Lys Asp Ala Glu
145                 150                 155                 160

Gln Ser Gly Ser Ala Glu Glu Gly Asp Arg Gln Pro Lys Ala Ser Asp
                165                 170                 175

Glu Ala Asp Tyr Ser Ser Ser Ala Asn Glu Gly Ser Trp Arg Asn Ser
            180                 185                 190

Lys Lys Arg Arg Asp Glu Glu Glu Ala Glu Asp Arg Asp Thr
                195                 200                 205

Ser Thr Leu Lys Lys Pro Arg Val Val Trp Ser Val Glu Leu His Gln
210                 215                 220

Gln Phe Val Ala Ala Val Asp Gln Leu Gly Ile Asp Lys Ala Val Pro
225                 230                 235                 240

Lys Lys Ile Leu Glu Leu Met Asn Val Pro Gly Leu Thr Arg Glu Asn
                245                 250                 255

Val Ala Ser His Leu Gln Lys Tyr Arg Leu Tyr Leu Arg Arg Leu Ser
            260                 265                 270

Gly Val Ser Gln His Gln Asn Asn Met Asn Asn Ser Phe Leu Ser Pro
                275                 280                 285

Gln Glu Ala Thr Phe Gly Thr Ile Ser Ser Ile Asn Gly Ile Asp Leu
        290                 295                 300

Gln Thr Leu Ala Val Ala Gly Gln Leu Pro Ala Gln Ser Leu Ala Thr
305                 310                 315                 320

Leu Gln Ala Ala Gly Leu Gly Arg Pro Thr Gly Lys Ala Gly Val Pro
              325                 330                 335

Met Pro Leu Met Asp Gln Arg Asn Leu Phe Ser Phe Glu Asn Pro Arg
          340                 345                 350

Leu Arg Phe Gly Glu Gly Gln Gln Gln His Leu Ser Thr Ser Lys Pro
      355                 360                 365

Met Asn Leu Leu His Gly Ile Pro Thr Asn Met Glu Pro Lys Gln Leu
  370                 375                 380

Ala Asn Leu His Gln Ser Thr Gln Ser Ile Gly Ser Leu Asn Met Arg
385                 390                 395                 400

Val Asn Ala Ser Ala Thr Gln Gly Ser Pro Leu Leu Met Gln Met Ala
              405                 410                 415

Gln Ser Gln Pro Arg Gly Gln Met Leu Ser Glu Asn Ile Gly Pro Arg
          420                 425                 430

Val Pro Arg Leu Pro Ser Ser Leu Gly Gln Pro Thr Val Ser Asn Gly
      435                 440                 445

Ile Ser Asn Gly Leu Leu Gly Arg Asn Gly Ile Ala Gly Asn Asn Arg
  450                 455                 460

Gly Pro Ala Tyr Asn Pro Val Pro Pro Ser Ser Ser Leu Leu Ser Phe
465                 470                 475                 480

Pro Met Asn Gln Thr Ser Glu Met Ser Val Asn Asn Ser Phe Pro Leu
              485                 490                 495

Gly Ser Thr Pro Gly Ile Ser Ser Ile Thr Thr Lys Gly Ser Phe Gln
          500                 505                 510

Glu Glu Val Thr Ser Gly Ile Lys Gly Ser Gly Gly Phe Pro Ser Tyr
      515                 520                 525

Asp Ile Phe Asn Glu Leu His His Gln Lys Pro His Asp Trp Glu Ile
  530                 535                 540

Thr Asn Pro Asn Leu Thr Tyr Asn Ala Ser Gln His Ala Asn Pro Leu
545                 550                 555                 560

Gln Gly Asn Ile Asp Val Thr Pro Ser Val Leu Val His Gln Gly Phe
              565                 570                 575

Ser Ser Thr Gln Gln Thr Gly Gln Ser Arg Asp Ala Ala Leu Ile Gly
          580                 585                 590

Lys Ala Met Phe Ser Met Gly Glu Gly Leu Glu Gln Asn Asn Phe Gln
      595                 600                 605

Asn Ala Ser Gln Asn Leu Asn Ser Leu Leu Leu Asp Asn Ser Ile Arg
  610                 615                 620

Val Lys Ala Glu Arg Ile Pro Asp Ala Ser Ser Gln Thr Asn Leu Phe
625                 630                 635                 640

Pro Glu His Tyr Gly Gln Glu Asp Leu Met Ser Ala Leu Leu Lys Gln
              645                 650                 655

Gln Glu Gly Met Gly Pro Ser Glu Asn Glu Phe Asp Phe Asp Gly Tyr
          660                 665                 670

Ser Leu Asp Asn Ile Pro Val
      675

<210> SEQ ID NO 35
<211> LENGTH: 668
<212> TYPE: PRT
<213> ORGANISM: Chenopodium quinoa
<220> FEATURE:
<221> NAME/KEY: misc_feature
<223> OTHER INFORMATION: SGI1 polypeptide

<400> SEQUENCE: 35

-continued

```
Met Asn Leu Gly Gly Gly Leu Met Gly Ser Met Ala Met Pro Ser Ser
1               5                   10                  15

Thr Val Ser Arg Lys Ser Ser Glu Val Val Thr Ala Asp Gln Phe Pro
                20                  25                  30

Val Gly Leu Arg Val Leu Val Val Asp Asp Asp Pro Thr Cys Leu Thr
                35                  40                  45

Ile Leu Glu Lys Met Leu Arg Thr Cys Arg Tyr Glu Val Thr Lys Thr
        50                  55                  60

Asn Arg Ala Glu His Ala Leu Asn Met Leu Arg Glu Asn Lys Asn Gly
65                  70                  75                  80

Phe Asp Val Val Ile Ser Asp Val His Met Pro Asp Met Asp Gly Phe
                85                  90                  95

Lys Leu Leu Glu Gln Val Gly Leu Glu Met Asp Leu Pro Val Ile Met
                100                 105                 110

Met Ser Ala Asp Asp Ser Lys Gln Val Val Met Lys Gly Val Thr His
        115                 120                 125

Gly Ala Cys Asp Tyr Leu Ile Lys Pro Val Arg Ile Glu Ala Leu Lys
130                 135                 140

Asn Ile Trp Gln His Val Val Arg Lys Lys Tyr Gly Tyr Asn Lys
145                 150                 155                 160

Asp Val Glu Gln Ser Gly Ser Trp Asp Glu Gly Asp Arg Gln Leu Lys
                165                 170                 175

His Asp Asp Ala Val Ser Ser Pro Ala Asn Asp Gly Ser Trp Lys Asn
                180                 185                 190

Ser Lys Arg Lys Ser Gly Glu Asp Asp Glu Ala Asp Lys Asp Asp
                195                 200                 205

Thr Thr Thr Leu Lys Lys Pro Arg Val Val Trp Ser Val Glu Leu His
        210                 215                 220

Gln Gln Phe Val Ala Ala Val Asn Gln Leu Gly Ile Asp Lys Ala Val
225                 230                 235                 240

Pro Lys Lys Ile Leu Glu Leu Met Asn Val Pro Gly Leu Thr Arg Glu
                245                 250                 255

Asn Val Ala Ser His Leu Gln Lys Tyr Arg Leu Tyr Leu Arg Arg Leu
                260                 265                 270

Ser Gly Val Ser Gln His Gln Gly Gly Leu Asn Ser Ser Phe Met Pro
                275                 280                 285

Gln Asp Pro Ser Phe Ser Thr Met Ser Ser Leu Gly Gly Ile Asp Leu
        290                 295                 300

Gln Thr Leu Ala Ala Thr Gly Gln Leu Ser Ala Gln Thr Leu Ala Ala
305                 310                 315                 320

Tyr Thr Arg Leu Pro Pro Thr Ile Lys Pro Gly Ile Ser Met Pro Phe
                325                 330                 335

Val Asp Gln Arg Asn Leu Phe Ser Phe Glu Asn Ser Lys Leu Arg Tyr
                340                 345                 350

Gly Asp Gly Gln Gln Ser Gln Ile Ser Asn Val Ser Lys Gln Met Asn
                355                 360                 365

Leu Leu His Gly Phe Pro Thr Thr Met Glu Pro Lys Gln Leu Ala Val
        370                 375                 380

Leu Asn Gln Ser Ala Gln Thr Leu Gly Ser Met Asn Met Gln Ala Asn
385                 390                 395                 400

Ala Ser Ser Ser His Gln Ser Ser Leu Leu Met Gln Gln Met Val
                405                 410                 415
```

```
Pro Gln Gln Arg Gly His Ile Ser Asn Glu Ser Ile Ser Ser Gln Val
            420                 425                 430

Pro Arg Ile Gln Pro Ser Val Gly Gln Pro Leu Gln Ser Asn Gly Asn
        435                 440                 445

Ala Asn Ala Val Leu Ser Arg Asn Gly Ile Pro Tyr Asp Pro Val Asn
    450                 455                 460

Gln Ser Ala Ser Val Val Asp Phe Ser Val Asn His Ile Pro Glu Leu
465                 470                 475                 480

Pro Gly Asn Ser Phe Pro Leu Gly Ser Thr Pro Gly Ile Thr Ser Ile
                485                 490                 495

Thr Ser Lys Gly Phe Asn Gln Glu Ile Gly Ser Asp Ile Lys Val
            500                 505                 510

Ser Arg Gly Phe Val Gly Ser Tyr Asp Met Phe Ser Glu Leu Gln His
        515                 520                 525

Lys Pro Gln Glu Trp Gln Met Gln Asn Pro Asn Met Gly Phe Ala Gly
    530                 535                 540

Ser Ser Gln His Val Pro Ser Val Gln Ser Gly Val Asn Val Ala Pro
545                 550                 555                 560

Ser Ile Met Val Asn Gln Ser Tyr Val Ser Gly Gln Lys Asn Glu Gln
                565                 570                 575

Asn Gly His Ser Met Ala Gly Lys Pro Met Tyr Ser Ala Gly Leu Glu
            580                 585                 590

Asn Gln His Met Gly Met Gln Asn Val Asn Gln Asn Tyr Asn Ser Ile
        595                 600                 605

His Val Asn Asn Ser Ser Arg Val Lys Ala Glu Ser Val Ser Asp Val
    610                 615                 620

Val Asn Leu Gly Ala Asn Leu Phe Asp Tyr Ser Pro Glu Asp Met Leu
625                 630                 635                 640

Ser Thr Ile Met Leu Lys Gln Gln Glu Gly Ile Gly Ser Gly Asp Phe
                645                 650                 655

Asp Phe Asp Gly Tyr Thr Leu Asp Asn Ile Pro Val
            660                 665

<210> SEQ ID NO 36
<211> LENGTH: 670
<212> TYPE: PRT
<213> ORGANISM: Malus domestica
<220> FEATURE:
<221> NAME/KEY: misc_feature
<223> OTHER INFORMATION: SGI1 polypeptide
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (530)..(530)
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid

<400> SEQUENCE: 36
```

-continued

```
Met Ala Ala Leu Gln Arg Val Ala Gln Ser Val Ser Thr Thr Ala
1               5                   10                  15

Ser Ser Tyr Gly Ser Cys Lys Val Gly Gly Val Leu Ser Pro Ser
            20                  25                  30

Ala Gly Ile Glu Met Ala Val Pro Asn Gln Phe Pro Ala Gly Leu Arg
            35                  40                  45

Val Leu Val Val Asp Asp Thr Thr Cys Leu Arg Ile Leu Glu Leu
    50              55                  60

Met Leu Leu Arg Cys Leu Tyr Gln Val Thr Thr Cys Ser Glu Ala Thr
65              70                  75                  80

Val Ala Leu Asn Leu Leu Arg Glu Arg Lys Asp Cys Phe Asp Val Val
                85                  90                  95

Leu Ser Asp Val His Met Pro Asp Met Asp Gly Phe Lys Leu Leu Glu
            100                 105                 110

His Val Gly Leu Glu Met Asp Leu Pro Val Ile Met Met Ser Ala Asp
            115                 120                 125

Gly Arg Thr Ser Val Val Met Arg Gly Ile Arg His Gly Ala Cys Asp
    130                 135                 140

Phe Leu Ile Lys Pro Ile Ser Glu Ala Glu Leu Lys Asn Ile Trp Gln
145                 150                 155                 160

His Val Val Arg Lys Lys Trp Asn Gly Ser Lys Glu Leu Glu His Ser
                165                 170                 175

Gly Ser Leu Glu Asp Asn Asp Pro His Lys Arg Gly Asn Asn Asp Phe
            180                 185                 190

Glu Tyr Xaa Ser Ser Val Asn Glu Gly Thr Glu Val Ser Leu Lys Gly
            195                 200                 205

His Lys Lys Arg Ile Asn Xaa Lys Glu Asp Asp Gly Asp Thr Glu
    210                 215                 220

Asn Asp Asp Leu Ser Thr Ser Lys Lys Pro Arg Val Val Trp Ser Val
225                 230                 235                 240

Glu Leu His Gln Gln Phe Val Thr Ala Val Asn Gln Leu Gly Leu Asp
            245                 250                 255

Lys Ala Val Pro Lys Arg Ile Leu Glu Leu Met Asn Val Pro Gly Leu
            260                 265                 270

Thr Arg Glu Asn Val Ala Ser His Leu Gln Lys Phe Arg Leu Tyr Leu
    275                 280                 285

Lys Arg Leu Ser Gly Val Ala Gln Gln Gln Ser Gly Ile Ala Asn Pro
    290                 295                 300

Leu Cys Gly Pro Val Asp Ser Asn Gly Lys Leu Gly Ser Leu Ser Arg
305                 310                 315                 320

Phe Asp Phe Gln Ala Leu Ala Ala Ser Gly Gln Ile Pro Pro Gln Thr
            325                 330                 335

Leu Ala Ala Leu Gln Ala Glu Leu Leu Gly Gln Pro Ala Gly Asn Leu
            340                 345                 350

Val Pro Ala Met Asp Gln Pro Leu Leu His Ala Ser Leu Gln Ala
    355                 360                 365

Pro Lys Arg Pro Pro Val Glu His Gly Val Pro Phe Met Gln Pro Phe
    370                 375                 380

Val Lys Ser Gln Ser Asn Val Ser Lys His Phe Pro Gln Ser Val Ile
385                 390                 395                 400

Ser Ala Glu Asp Ala Ser Leu Gly Phe Gly Gln Trp Arg Ser Asn Ser
            405                 410                 415

Arg Ser Thr Val Ala Pro Ser Asn Asp His Gly Gly Leu Ser Thr Gln
```

```
                    420                 425                 430
Asn Ser Asn Leu Leu Met Gly Ile Val Pro Gln Glu Gln Arg Gln His
            435                 440                 445

Lys Arg Thr Gln Gln Gln Ser Val Leu Thr Glu Pro Ser Arg Ser Phe
        450                 455                 460

Asn Val Gln Pro Ser Cys Leu Val Val Pro Ser Gln Ser Ser Thr Gly
465                 470                 475                 480

Phe Gln Ala Gly Asn Ser Pro Ala Ser Val Asn Gln Ser Ser Ser Phe
                485                 490                 495

Asn Arg Ser Thr Val Val Asp Tyr Ser Leu Pro Ser Asp Gln Ser Asn
            500                 505                 510

Asn Ser Leu Asn Val Gly His Ile Pro Thr Gly Asn Pro Lys Thr Ser
        515                 520                 525

Gly Xaa Leu Gly Gly Tyr Ser Gly Pro Gly Ser Xaa Cys Ala Thr Ser
    530                 535                 540

Cys Leu Val Asn Ala Asp Asn Ser Thr Ser Tyr Gln Asn Ser Thr Ala
545                 550                 555                 560

Thr Phe Ser Asp Ser Arg Glu Leu Pro Gly Phe Leu His Asn Thr Ala
                565                 570                 575

Asn Ser Xaa Gly Phe Tyr Val Asp Lys Ser Gly Glu Met Leu Asp Gln
            580                 585                 590

Gly Pro Leu Arg Asn Leu Gly Phe Val Gly Lys Glu Thr Cys Ile Pro
        595                 600                 605

Ser Arg Phe Ala Val Asp Asp Phe Glu Ser Gln Met Ser Asn Leu Asn
610                 615                 620

Pro Gly Arg Ile His Val Glu Ser Ser Gly Thr Leu Val Lys Gln Glu
625                 630                 635                 640

Pro Ser Glu Asp Tyr Val Asp Asn Ala Lys Leu Gly Ile Pro Ile Leu
                645                 650                 655

His Gln Tyr Ser Ser Ser Asp Phe Met Ser Pro Phe Ala Asp
            660                 665                 670

<210> SEQ ID NO 37
<211> LENGTH: 802
<212> TYPE: PRT
<213> ORGANISM: Zea mays
<220> FEATURE:
<221> NAME/KEY: misc_feature
<223> OTHER INFORMATION: SGI1 polypeptide

<400> SEQUENCE: 37

Pro Tyr Pro Thr His Thr Leu Leu Pro Gln Pro His Leu Ser Leu Ser
1               5                   10                  15

Ala Cys Val Leu Leu Val Leu Leu Ser Leu Ser Ser Pro Ala Leu Thr
            20                  25                  30

Ser Pro Pro Phe Pro Ala Val Ser Trp Ile Ser Arg Ile Gln Thr Thr
        35                  40                  45

Ala Leu Val Ser Leu Pro Ser Cys Leu Leu Pro Ala Tyr Val Gln Glu
    50                  55                  60

Gly Pro Cys Leu Gly Asp Pro Gly Ala Trp Phe Leu Gly Ser Ala Ala
65                  70                  75                  80

Ser Ala Ala Val Gly Phe Ala Glu Pro Glu Pro Pro Glu Met Thr Val
                85                  90                  95

Asp Glu Leu Lys Leu Gln Ala Arg Ala Ser Gly Gly His Gly Ala Lys
            100                 105                 110
```

-continued

Asp Gln Phe Pro Val Gly Met Arg Val Leu Ala Val Asp Asp Pro
         115                 120                 125
Thr Cys Leu Lys Ile Leu Glu Asn Leu Leu Leu Arg Cys Gln Tyr His
    130                 135                 140
Val Thr Thr Thr Gly Gln Ala Ala Thr Ala Leu Lys Leu Leu Arg Glu
145                 150                 155                 160
Lys Lys Asp Gln Phe Asp Leu Val Ile Ser Asp Val His Met Pro Asp
                165                 170                 175
Met Asp Gly Phe Lys Leu Leu Glu Leu Val Gly Leu Glu Met Asp Leu
            180                 185                 190
Pro Val Ile Met Leu Ser Ala Asn Gly Glu Thr Gln Thr Val Met Lys
        195                 200                 205
Gly Ile Thr His Gly Ala Cys Asp Tyr Leu Leu Lys Pro Val Arg Ile
    210                 215                 220
Glu Gln Leu Arg Thr Ile Trp Gln His Val Val Arg Arg Ser Cys
225                 230                 235                 240
Asp Ala Lys Asn Ser Gly Asn Asp Asn Asp Ser Gly Lys Lys Leu
                245                 250                 255
Gln Val Val Ser Ala Glu Gly Asp Asn Gly Val Asn Arg Asn Lys
            260                 265                 270
Arg Ile Ser Arg Lys Gly Arg Asp Asp Asn Gly Asp Asp Gly Asp Asp
    275                 280                 285
Ser Asp Asp Asn Ser Asn Glu Asn Gly Asp Ser Ser Ser Gln Lys Lys
    290                 295                 300
Pro Arg Val Val Trp Ser Val Glu Leu His Arg Lys Phe Val Ala Ala
305                 310                 315                 320
Val Asn Gln Leu Gly Ile Asp Lys Ala Val Pro Lys Lys Ile Leu Asp
                325                 330                 335
Leu Met Asn Val Glu Asn Ile Thr Arg Glu Asn Val Ala Ser His Leu
            340                 345                 350
Gln Lys Tyr Arg Leu Tyr Leu Lys Arg Leu Ser Ala Asp Ala Ser Arg
        355                 360                 365
Gln Ala Asn Leu Thr Ala Ala Phe Gly Gly Arg Asn Pro Ala Tyr Val
    370                 375                 380
Asn Met Gly Leu Asp Ala Phe Arg Gln Tyr Asn Ala Tyr Gly Arg Tyr
385                 390                 395                 400
Arg Pro Val Pro Thr Thr Asn His Ser Gln Pro Asn Asn Leu Leu Ala
                405                 410                 415
Arg Met Asn Ser Pro Ala Phe Gly Met His Gly Leu Leu Pro Ser Gln
            420                 425                 430
Pro Leu Gln Ile Gly His Asn Gln Asn Asn Leu Ser Thr Ser Leu Gly
        435                 440                 445
Asn Val Gly Gly Met Asn Asn Gly Asn Leu Ile Arg Gly Ala His Met
    450                 455                 460
Pro Leu Gln Asp Thr Ser Lys Cys Phe Pro Thr Gly Pro Ser Gly Asn
465                 470                 475                 480
Ser Phe Ala Asn Ile Ser Asn Ser Thr Gln Leu Val Thr Thr Asn Asn
                485                 490                 495
Leu Pro Leu Gln Ser Leu Glu Pro Ser Asn Gln His Leu Gly Arg
            500                 505                 510
Leu His Ser Ser Ala Asp Pro Phe Asn Ser Phe Val Gly Glu Pro Pro
        515                 520                 525
Gln Phe Ala Asp Leu Gly Arg Cys Asn Thr Thr Trp Pro Thr Ala Val

```
                 530                 535                 540
Ser Ser Ser Asn Val Gln Glu Ile Gly Gln Lys Asp Arg Ile Val Asn
545                 550                 555                 560

Arg Pro Lys Leu Glu Pro Leu Ser Ser Phe Thr Glu Ala Ser Ser Gln
                565                 570                 575

Ile Pro Leu Leu Gly Asn Glu Met Gln Ser His Gln Val Ala Ser Leu
                580                 585                 590

Ala Ser Asn Gly Leu Pro Met Pro Phe Thr Gln Glu Ala Val Pro Phe
                595                 600                 605

Ala Tyr Gly Ser Ser Thr Asn Ser Arg Glu Met Leu Asn Asn Asn Leu
                610                 615                 620

Ala Leu Ser Asn Ser Gly Val Asn Ser Thr Leu Pro Asn Leu Arg Ile
625                 630                 635                 640

Asp Gly Ser Val Val Pro Gly Gln Thr Leu Gly Gly Ser Asn Ser Gly
                645                 650                 655

Gly Cys Val Val Pro Pro Leu Gln Asp Gly Arg Ile Asp His Gln Ala
                660                 665                 670

Val Ser Ser His Leu Asn Tyr Asn Asn Glu Leu Met Gly Thr Gly Arg
                675                 680                 685

Leu Gln Arg Gly Leu Ser Gly Gly Leu Asp Asp Ile Val Val Asp Met
                690                 695                 700

Phe Arg Pro Asp Arg Ala Asp Asp Gly Val Ser Phe Ile Asp Gly Asp
705                 710                 715                 720

Trp Glu Leu Arg Pro Gly Ser Ser Val Thr Ser Glu Tyr Gln Leu Cys
                725                 730                 735

Gly Ile Cys Tyr Leu Asn Ser Tyr Asp Tyr Val Phe Lys Ser Gly Val
                740                 745                 750

Asn Cys Gly Tyr Arg Asp Ile Gln His Val Tyr Glu Pro Arg Asn Asp
                755                 760                 765

Val Leu Phe Pro Leu Gly Asn Arg Phe Ala Val Pro Phe Val Asp Cys
                770                 775                 780

His Cys Ile Val Ala Ser Leu Ala Glu Thr Glu Val Lys Gly Lys Asp
785                 790                 795                 800

Gln Ala

<210> SEQ ID NO 38
<211> LENGTH: 591
<212> TYPE: PRT
<213> ORGANISM: Brassica rapa
<220> FEATURE:
<221> NAME/KEY: misc_feature
<223> OTHER INFORMATION: SGI1 polypeptide

<400> SEQUENCE: 38

Met Leu Asn Pro Gly Val Val Gly Gly Ser Ser Asn Ser Asp Pro Phe
1               5                   10                  15

Pro Ser Gly Leu Arg Val Leu Val Val Asp Asp Asp Pro Thr Cys Leu
                20                  25                  30

Met Ile Leu Glu Arg Met Leu Lys Thr Cys Leu Tyr Arg Val Thr Lys
            35                  40                  45

Cys Asn Arg Ala Glu Ile Ala Leu Ser Leu Leu Arg Lys Asn Lys Asn
        50                  55                  60

Gly Phe Asp Ile Val Ile Ser Asp Val His Met Pro Asp Met Asn Gly
65                  70                  75                  80

Phe Lys Leu Leu Glu His Val Gly Leu Glu Met Asp Leu Pro Val Ile
```

-continued

```
                85                  90                  95
Met Met Ser Ala Asp Asp Ser Lys Ser Val Val Leu Lys Gly Val Thr
                100                 105                 110

His Gly Ala Val Asp Tyr Leu Ile Lys Pro Val Arg Ile Glu Ala Leu
                115                 120                 125

Lys Asn Ile Trp Gln His Val Val Arg Lys Lys Gln Asn Val Ser Glu
            130                 135                 140

His Ser Gly Ser Val Glu Glu Thr Gly Gly Asp Arg Gln Gln Gln Gln
145                 150                 155                 160

Arg Gly Asp Asp Asp Asp Gly Asn Asn Ser Ser Ser Gly Asn Asn
                165                 170                 175

Glu Gly Asn Leu Arg Lys Arg Lys Glu Glu Glu Gln Gly Asp Asp Lys
                180                 185                 190

Glu Asp Thr Ser Ser Leu Lys Lys Pro Arg Val Val Trp Ser Val Glu
                195                 200                 205

Leu His Gln Gln Phe Val Ala Ala Val Asn His Leu Gly Val Asp Lys
                210                 215                 220

Ala Val Pro Lys Lys Ile Leu Glu Met Met Asn Val Gln Gly Leu Thr
225                 230                 235                 240

Arg Glu Asn Val Ala Ser His Leu Gln Lys Tyr Arg Ile Tyr Leu Lys
                245                 250                 255

Arg Leu Gly Gly Val Ser Gln Gly Asn Met Asn His Ser Phe Leu Thr
                260                 265                 270

Gly Gln Asp Pro Ser Tyr Gly Pro Leu Asn Gly Phe Asp Leu Gln Gly
                275                 280                 285

Leu Ala Thr Ala Gly Gln Leu Gln Ala Gln Ser Leu Ala Gln Leu Gln
                290                 295                 300

Ala Val Gly Leu Gly Gln Ser Ser Pro Leu Ile Lys Pro Gly Ile
305                 310                 315                 320

Thr Ser Val Asp Gln Arg Ser Phe Phe Thr Phe Gln Asn Ser Lys Ser
                325                 330                 335

Arg Phe Gly Asp Gly His Gly Pro Met Met Met Asn Gly Gly Gly Gly
                340                 345                 350

Asn Lys Gln Thr Ser Leu Leu His Gly Val Pro Thr Gly His Met Arg
                355                 360                 365

Leu Gln Gln Gln Met Ala Gly Met Arg Val Ala Gly Pro Ser Met
                370                 375                 380

Gln Gln Gln Gln Gln Ser Met Leu Ser Arg Arg Ser Val Pro Glu
385                 390                 395                 400

Thr Arg Ser Ser Arg Val Leu Pro Ala Ala Thr His Ser Ala Leu Asn
                405                 410                 415

Asn Ser Phe Pro Leu Ala Ser Ala Pro Gly Met Met Ser Val Ser Asp
                420                 425                 430

Thr Lys Gly Val Asn Glu Phe Cys Asn Pro Ser Tyr Asp Ile Leu Asn
                435                 440                 445

Asn Phe Pro Gln Gln Gln His His Asn Asn Asn Asn Arg Val Asn
                450                 455                 460

Glu Trp Asp Leu Arg Asn Val Gly Met Val Phe Asn Ser His Gln Asp
465                 470                 475                 480

Asn Thr Thr Ser Ala Ala Phe Ser Thr Ser Glu Ala Tyr Ser Ser Ser
                485                 490                 495

Ser Thr His Lys Arg Lys Arg Glu Ala Glu Leu Val Val Glu His Gly
                500                 505                 510
```

```
Gln Asn Gln Gln Gln Pro Gln Ser Arg Ser Val Lys Pro Met Asn Gln
            515                 520                 525

Thr Tyr Met Asp Gly Gly Ser Val Arg Met Lys Thr Glu Thr Val
        530                 535                 540

Thr Cys Pro Pro Gln Ala Thr Thr Met Phe His Glu Gln Tyr Ser Asn
545                 550                 555                 560

Gln Asp Asp Leu Leu Ser Asp Leu Leu Lys Gln Glu Gly Leu Leu Asp
                565                 570                 575

Thr Glu Phe Asp Phe Glu Gly Tyr Ser Phe Asp Ser Ile Leu Val
            580                 585                 590

<210> SEQ ID NO 39
<211> LENGTH: 691
<212> TYPE: PRT
<213> ORGANISM: Oryza sativa
<220> FEATURE:
<221> NAME/KEY: misc_feature
<223> OTHER INFORMATION: SGI1 polypeptide

<400> SEQUENCE: 39

Met Ala Pro Val Glu Asp Gly Gly Val Glu Phe Pro Val Gly Met
1               5                   10                  15

Lys Val Leu Val Val Asp Asp Pro Thr Cys Leu Ala Val Leu Lys
                20                  25                  30

Arg Met Leu Leu Glu Cys Arg Tyr Asp Ala Thr Thr Cys Ser Gln Ala
            35                  40                  45

Thr Arg Ala Leu Thr Met Leu Arg Glu Asn Arg Arg Gly Phe Asp Val
    50                  55                  60

Ile Ile Ser Asp Val His Met Pro Asp Met Asp Gly Phe Arg Leu Leu
65                  70                  75                  80

Glu Leu Val Gly Leu Glu Met Asp Leu Pro Val Ile Met Met Ser Ala
                85                  90                  95

Asp Ser Arg Thr Asp Ile Val Met Lys Gly Ile Lys His Gly Ala Cys
            100                 105                 110

Asp Tyr Leu Ile Lys Pro Val Arg Met Glu Glu Leu Lys Asn Ile Trp
        115                 120                 125

Gln His Val Ile Arg Lys Lys Phe Asn Glu Asn Lys Glu His Glu His
    130                 135                 140

Ser Gly Ser Leu Asp Asp Thr Asp Arg Thr Arg Pro Thr Asn Asn Asp
145                 150                 155                 160

Asn Glu Tyr Ala Ser Ser Ala Asn Asp Gly Ala Glu Gly Ser Trp Lys
                165                 170                 175

Ser Gln Lys Lys Lys Arg Asp Lys Asp Asp Asp Gly Glu Leu Glu
            180                 185                 190

Ser Gly Asp Pro Ser Ser Thr Ser Lys Lys Pro Arg Val Val Trp Ser
        195                 200                 205

Val Glu Leu His Gln Gln Phe Val Asn Ala Val Asn His Leu Gly Ile
    210                 215                 220

Asp Lys Ala Val Pro Lys Lys Ile Leu Glu Leu Met Asn Val Pro Gly
225                 230                 235                 240

Leu Thr Arg Glu Asn Val Ala Ser His Leu Gln Lys Phe Arg Leu Tyr
                245                 250                 255

Leu Lys Arg Ile Ala Gln His His Ala Gly Ile Ala Asn Pro Phe Cys
            260                 265                 270

Pro Pro Ala Ser Ser Gly Lys Val Gly Ser Leu Gly Gly Leu Asp Phe
```

```
            275                 280                 285
Gln Ala Leu Ala Ala Ser Gly Gln Ile Pro Gln Ala Leu Ala Ala
            290                 295                 300
Leu Gln Asp Glu Leu Leu Gly Arg Pro Thr Asn Ser Leu Val Leu Pro
305                 310                 315                 320
Gly Arg Asp Gln Ser Ser Leu Arg Leu Ala Val Lys Gly Asn Lys
            325                 330                 335
Pro His Gly Glu Arg Glu Ile Ala Phe Gly Gln Pro Ile Tyr Lys Cys
            340                 345                 350
Gln Asn Asn Ala Tyr Gly Ala Phe Pro Gln Ser Ser Pro Ala Val Gly
            355                 360                 365
Gly Met Pro Ser Phe Ser Ala Trp Pro Asn Asn Lys Leu Gly Met Ala
            370                 375                 380
Asp Ser Thr Gly Thr Leu Gly Gly Met Ser Asn Ser Gln Asn Ser Asn
385                 390                 395                 400
Ile Val Leu His Glu Leu Gln Gln Gln Pro Asp Ala Met Leu Ser Gly
                    405                 410                 415
Thr Leu His Ser Leu Asp Val Lys Pro Ser Gly Ile Val Met Pro Ser
            420                 425                 430
Gln Ser Leu Asn Thr Phe Ser Ala Ser Glu Gly Leu Ser Pro Asn Gln
            435                 440                 445
Asn Thr Leu Met Ile Pro Ala Gln Ser Ser Gly Phe Leu Ala Ala Met
            450                 455                 460
Pro Pro Ser Met Lys His Glu Pro Val Leu Ala Thr Ser Gln Pro Ser
465                 470                 475                 480
Ser Ser Leu Leu Gly Gly Ile Asp Leu Val Asn Gln Ala Ser Thr Ser
                    485                 490                 495
Gln Pro Leu Ile Ser Ala His Gly Gly Gly Asn Leu Ser Gly Leu Val
            500                 505                 510
Asn Arg Asn Pro Asn Val Val Pro Ser Gln Gly Ile Ser Thr Phe His
            515                 520                 525
Thr Pro Asn Asn Pro Tyr Leu Val Ser Pro Asn Ser Met Gly Met Gly
            530                 535                 540
Ser Lys Gln Pro Pro Gly Val Leu Lys Thr Glu Asn Ser Asp Ala Leu
545                 550                 555                 560
Asn His Ser Tyr Gly Tyr Leu Gly Gly Ser Asn Pro Pro Met Asp Ser
                    565                 570                 575
Gly Leu Leu Ser Ser Gln Ser Lys Asn Thr Gln Phe Gly Leu Leu Gly
                    580                 585                 590
Gln Asp Asp Ile Thr Gly Ser Trp Ser Pro Leu Pro Asn Val Asp Ser
            595                 600                 605
Tyr Gly Asn Thr Val Gly Leu Ser His Pro Gly Ser Ser Ser Ser Ser
            610                 615                 620
Phe Gln Ser Ser Asn Val Ala Leu Gly Lys Leu Pro Asp Gln Gly Arg
625                 630                 635                 640
Gly Lys Asn His Gly Phe Val Gly Lys Gly Thr Cys Ile Pro Ser Arg
                    645                 650                 655
Phe Ala Val Asp Glu Ile Glu Pro Thr Asn Asn Leu Ser His Ser
            660                 665                 670
Ile Gly Ser Ser Gly Asp Ile Met Ser Pro Asp Ile Phe Gly Phe Ser
            675                 680                 685
Gly Gln Met
    690
```

<210> SEQ ID NO 40
<211> LENGTH: 126
<212> TYPE: PRT
<213> ORGANISM: Parachlorella sp.
<220> FEATURE:
<221> NAME/KEY: misc_feature
<223> OTHER INFORMATION: Response Regulator receiver domain of SGI1
      polypeptide of SEQ ID NO:3

<400> SEQUENCE: 40

Pro Ala Gly Leu Lys Val Leu Val Val Asp Asp Leu Met Cys Leu
1               5                   10                  15

Lys Val Val Ser Ala Met Leu Lys Arg Cys Ser Tyr Gln Val Ala Thr
                20                  25                  30

Cys Ser Ser Gly Ser Glu Ala Leu Thr Leu Leu Arg Glu Arg Asn Glu
            35                  40                  45

Asp Gly Ser Ser Asp Gln Phe Asp Leu Val Leu Ser Asp Val Tyr Met
        50                  55                  60

Pro Asp Met Asp Gly Phe Lys Leu Leu Glu His Ile Gly Leu Glu Leu
65                  70                  75                  80

Glu Leu Pro Val Ile Met Met Ser Ser Asn Gly Asp Thr Asn Val Val
                85                  90                  95

Leu Arg Gly Val Thr His Gly Ala Val Asp Phe Leu Ile Lys Pro Val
            100                 105                 110

Arg Ile Glu Glu Leu Arg Asn Val Trp Gln His Val Val Arg
        115                 120                 125

<210> SEQ ID NO 41
<211> LENGTH: 123
<212> TYPE: PRT
<213> ORGANISM: Coccomyxa subellipsoidea
<220> FEATURE:
<221> NAME/KEY: misc_feature
<223> OTHER INFORMATION: Response Regulator receiver domain of SGI1
      polypeptide of SEQ ID NO:9

<400> SEQUENCE: 41

Pro Ala Gly Leu Lys Val Leu Val Val Asp Asp Pro Leu Cys Leu
1               5                   10                  15

Lys Val Val Glu His Met Leu Arg Arg Cys Asn Tyr Gln Val Thr Thr
                20                  25                  30

Cys Pro Asn Gly Lys Ala Ala Leu Glu Lys Leu Arg Asp Arg Ser Val
            35                  40                  45

His Phe Asp Leu Val Leu Ser Asp Val Tyr Met Pro Asp Met Asp Gly
        50                  55                  60

Phe Lys Leu Leu Glu His Ile Gly Leu Glu Leu Asp Leu Pro Val Ile
65                  70                  75                  80

Met Met Ser Ser Asn Gly Glu Thr Asn Val Val Leu Arg Gly Val Thr
                85                  90                  95

His Gly Ala Val Asp Phe Leu Ile Lys Pro Val Arg Val Glu Glu Leu
            100                 105                 110

Arg Asn Val Trp Gln His Val Val Arg Arg Lys
        115                 120

<210> SEQ ID NO 42
<211> LENGTH: 122
<212> TYPE: PRT
<213> ORGANISM: Ostreococcus lucimarinus
<220> FEATURE:

```
<221> NAME/KEY: misc_feature
<223> OTHER INFORMATION: Response Regulator receiver domain of SGI1
      polypeptide of SEQ ID NO:10

<400> SEQUENCE: 42

Pro Ala Gly Leu Gly Val Leu Val Asp Asp Leu Leu Cys Leu
1               5                   10                  15

Lys Val Val Glu Lys Met Leu Lys Ala Cys Lys Tyr Lys Val Thr Ala
                20                  25                  30

Cys Ser Thr Ala Lys Thr Ala Leu Glu Ile Leu Arg Thr Arg Lys Glu
            35                  40                  45

Glu Phe Asp Ile Val Leu Ser Asp Val His Met Pro Asp Met Asp Gly
        50                  55                  60

Phe Lys Leu Leu Glu Ile Ile Gln Phe Glu Leu Ala Leu Pro Val Leu
65                  70                  75                  80

Met Met Ser Ala Asn Ser Asp Ser Ser Val Val Leu Arg Gly Ile Ile
                85                  90                  95

His Gly Ala Val Asp Tyr Leu Leu Lys Pro Val Arg Ile Glu Glu Leu
            100                 105                 110

Arg Asn Ile Trp Gln His Val Val Arg Arg
        115                 120

<210> SEQ ID NO 43
<211> LENGTH: 123
<212> TYPE: PRT
<213> ORGANISM: Chlamydomonas reinhardtii
<220> FEATURE:
<221> NAME/KEY: misc_feature
<223> OTHER INFORMATION: Response Regulator receiver domain of SGI1
      polypeptide of SEQ ID NO:11

<400> SEQUENCE: 43

Pro Ala Gly Leu Arg Leu Leu Val Val Asp Asp Asp Pro Leu Cys Leu
1               5                   10                  15

Lys Val Val Glu Gln Met Leu Arg Lys Cys Ser Tyr Glu Val Thr Val
                20                  25                  30

Cys Ser Asn Ala Thr Thr Ala Leu Asn Ile Leu Arg Asp Lys Asn Thr
            35                  40                  45

Glu Tyr Asp Leu Val Leu Ser Asp Val Tyr Met Pro Asp Met Asp Gly
        50                  55                  60

Phe Arg Leu Leu Glu Leu Val Gly Leu Glu Met Asp Leu Pro Val Ile
65                  70                  75                  80

Met Met Ser Ser Asn Gly Asp Thr Ser Asn Val Leu Arg Gly Val Thr
                85                  90                  95

His Gly Ala Cys Asp Tyr Leu Ile Lys Pro Val Arg Leu Glu Glu Leu
            100                 105                 110

Arg Asn Leu Trp Gln His Val Val Arg Arg Arg
        115                 120

<210> SEQ ID NO 44
<211> LENGTH: 61
<212> TYPE: PRT
<213> ORGANISM: Chromochloris zofingiensis
<220> FEATURE:
<221> NAME/KEY: misc_feature
<223> OTHER INFORMATION: Response Regulator receiver domain of SGI1
      polypeptide of SEQ ID NO:12

<400> SEQUENCE: 44

Met Asp Gly Phe Lys Leu Leu Glu Thr Val Gly Leu Glu Leu Asp Leu
```

```
                1               5                   10                  15
Pro Val Ile Met Met Ser Ser Asn Gly Glu His Thr Thr Val Met Arg
                20                  25                  30

Gly Val Thr His Gly Ala Cys Asp Phe Leu Ile Lys Pro Val Arg Ile
        35                  40                  45

Glu Glu Leu Arg Asn Ile Trp Gln His Val Ile Arg Arg
50                  55                  60
```

<210> SEQ ID NO 45
<211> LENGTH: 123
<212> TYPE: PRT
<213> ORGANISM: Volvox carteri
<220> FEATURE:
<221> NAME/KEY: misc_feature
<223> OTHER INFORMATION: Response Regulator receiver domain of SGI1
      polypeptide of SEQ ID NO:13

<400> SEQUENCE: 45

```
Pro Ala Gly Leu Arg Leu Leu Val Val Asp Asp Pro Leu Cys Leu
1               5                   10                  15

Lys Val Val Glu Gln Met Leu Arg Lys Cys Ser Tyr Asp Val Thr Thr
                20                  25                  30

Cys Thr Asn Ala Thr Met Ala Leu Asn Leu Leu Arg Asp Lys Ser Thr
        35                  40                  45

Glu Tyr Asp Leu Val Leu Ser Asp Val Tyr Met Pro Asp Met Asp Gly
50                  55                  60

Phe Lys Leu Leu Glu Val Val Gly Leu Glu Met Asp Leu Pro Val Ile
65                  70                  75                  80

Met Met Ser Ser Asn Gly Asp Thr Ser Asn Val Leu Arg Gly Val Thr
                85                  90                  95

His Gly Ala Cys Asp Tyr Leu Ile Lys Pro Val Arg Leu Glu Glu Leu
            100                 105                 110

Arg Asn Leu Trp Gln His Val Val Arg Arg Arg
        115                 120
```

<210> SEQ ID NO 46
<211> LENGTH: 121
<212> TYPE: PRT
<213> ORGANISM: Tetraselmis sp.
<220> FEATURE:
<221> NAME/KEY: misc_feature
<223> OTHER INFORMATION: Response Regulator receiver domain of SGI1
      polypeptides of SEQ ID NO:14, SEQ ID NO:15, and SEQ ID NO:16

<400> SEQUENCE: 46

```
Pro Ala Gly Leu Arg Val Leu Val Ala Asp Asn Asp Pro Ala Ser Leu
1               5                   10                  15

Gln Gln Val Glu Lys Met Leu Lys Lys Cys Ser Tyr Gln Val Thr Leu
                20                  25                  30

Cys Ser Ser Gly Lys Asn Ser Leu Glu Ile Leu Arg Lys Arg Arg Glu
        35                  40                  45

Glu Phe Asp Leu Val Leu Ala Asp Ala Asn Leu Pro Asp Ile Asp Gly
50                  55                  60

Phe Lys Leu Leu His Val Cys His Thr Glu Leu Ser Leu Pro Val Val
65                  70                  75                  80

Leu Met Ser Gly Thr Ser Asp Thr Gln Leu Val Met Arg Gly Val Met
                85                  90                  95

Asp Gly Ala Arg Asp Phe Leu Ile Lys Pro Leu Arg Val Glu Glu Leu
            100                 105                 110
```

```
Lys Val Leu Trp Gln His Leu Val Arg
        115                 120

<210> SEQ ID NO 47
<211> LENGTH: 123
<212> TYPE: PRT
<213> ORGANISM: Oocystis sp.
<220> FEATURE:
<221> NAME/KEY: misc_feature
<223> OTHER INFORMATION: Response Regulator receiver domain of SGI1
      polypeptide of SEQ ID NO:17

<400> SEQUENCE: 47

Pro Ala Gly Leu Lys Val Leu Val Asp Asp Pro Leu Cys Leu
1               5                   10                  15

Lys Val Ile Asp Gln Met Leu Arg Arg Cys Asn Tyr Ala Ala Thr Thr
            20                  25                  30

Cys Gln Ser Ser Leu Glu Ala Leu Glu Leu Arg Ser Ser Lys Glu
            35                  40                  45

Asn His Phe Asp Leu Val Leu Ser Asp Val Tyr Met Pro Asp Met Asp
            50                  55                  60

Gly Phe Lys Leu Leu Glu Ile Ile Gly Leu Glu Met Gly Leu Pro Val
65                  70                  75                  80

Ile Met Met Ser Ser Asn Gly Glu Thr Gly Val Val Phe Arg Gly Val
                85                  90                  95

Thr His Gly Ala Val Asp Phe Leu Ile Lys Pro Val Arg Ile Glu Glu
                100                 105                 110

Leu Arg Asn Leu Trp Gln His Val Val Arg Lys
            115                 120

<210> SEQ ID NO 48
<211> LENGTH: 123
<212> TYPE: PRT
<213> ORGANISM: Micromonas sp. RCC299
<220> FEATURE:
<221> NAME/KEY: misc_feature
<223> OTHER INFORMATION: Response Regulator receiver domain of SGI1
      polypeptide of SEQ ID NO:18

<400> SEQUENCE: 48

Pro Ile Gly Leu Arg Val Leu Val Asp Asp Pro Leu Cys Leu
1               5                   10                  15

Lys Ile Val Glu Lys Met Leu Lys Arg Cys Gln Tyr Glu Val Thr Thr
            20                  25                  30

Phe Ser Arg Gly Ala Glu Ala Leu Lys Thr Leu Arg Glu Arg Lys Asp
            35                  40                  45

Asp Phe Asp Ile Val Leu Ser Asp Val His Met Pro Asp Met Asp Gly
            50                  55                  60

Phe Lys Leu Leu Glu His Ile Ala Leu Glu Leu Asp Ile Pro Val Met
65                  70                  75                  80

Met Met Ser Ala Asn Cys Ala Thr Asp Val Val Leu Arg Gly Ile Ile
                85                  90                  95

His Gly Ala Val Asp Tyr Leu Leu Lys Pro Val Arg Ile Glu Glu Leu
                100                 105                 110

Arg Asn Ile Trp Gln His Val Val Arg Arg Lys
            115                 120

<210> SEQ ID NO 49
<211> LENGTH: 123
```

```
<212> TYPE: PRT
<213> ORGANISM: Micromonas pusilla
<220> FEATURE:
<221> NAME/KEY: misc_feature
<223> OTHER INFORMATION: Response Regulator receiver domain of SGI1
      polypeptide of SEQ ID NO:19

<400> SEQUENCE: 49

Pro Ala Gly Leu Arg Val Leu Val Val Asp Asp Pro Leu Cys Leu
1               5                   10                  15

Arg Ile Val Glu Lys Met Leu Lys Arg Cys Gln Tyr Glu Val Thr Thr
            20                  25                  30

Phe Ser Arg Gly Ala Glu Ala Leu Glu Thr Leu Arg Ala Arg Arg Asp
        35                  40                  45

Asp Phe Asp Ile Val Leu Ser Asp Val His Met Pro Asp Met Asp Gly
    50                  55                  60

Phe Lys Leu Leu Glu His Ile Ala Leu Glu Leu Asp Val Pro Val Met
65                  70                  75                  80

Met Met Ser Ala Asn Cys Ala Thr Asp Val Val Leu Arg Gly Ile Ile
                85                  90                  95

His Gly Ala Val Asp Tyr Leu Leu Lys Pro Val Arg Leu Glu Glu Leu
            100                 105                 110

Arg Asn Ile Trp Gln His Val Val Arg Arg Gln
        115                 120

<210> SEQ ID NO 50
<211> LENGTH: 123
<212> TYPE: PRT
<213> ORGANISM: Sphagnum fallax
<220> FEATURE:
<221> NAME/KEY: misc_feature
<223> OTHER INFORMATION: Response Regulator receiver domain of SGI1
      polypeptide of SEQ ID NO:20

<400> SEQUENCE: 50

Pro Ala Gly Leu Arg Val Leu Val Val Asp Asp Pro Ile Cys Leu
1               5                   10                  15

Met Ile Leu Asp Arg Met Leu Arg Gln Cys Ser Tyr Gln Val Thr Thr
            20                  25                  30

Cys Gly Arg Ala Thr Lys Ala Leu Glu Leu Leu Arg Glu Val Lys Asp
        35                  40                  45

Lys Phe Asp Leu Val Ile Ser Asp Val Tyr Met Pro Asp Met Asp Gly
    50                  55                  60

Phe Lys Leu Leu Glu Leu Val Gly Leu Glu Met Asp Leu Pro Val Ile
65                  70                  75                  80

Met Met Ser Ser Asp Gly Glu Thr Ser Ala Val Met Lys Gly Ile Thr
                85                  90                  95

His Gly Ala Cys Asp Tyr Leu Leu Lys Pro Val Arg Leu Glu Glu Leu
            100                 105                 110

Arg Asn Ile Trp Gln His Val Val Arg Lys Lys
        115                 120

<210> SEQ ID NO 51
<211> LENGTH: 123
<212> TYPE: PRT
<213> ORGANISM: Physcomitrella patens
<220> FEATURE:
<221> NAME/KEY: misc_feature
<223> OTHER INFORMATION: Response Regulator receiver domain of SGI1
      polypeptide of SEQ ID NO:20
```

-continued

<400> SEQUENCE: 51

Pro Val Gly Met Arg Val Leu Val Val Asp Asp Asn Pro Thr Cys Leu
1               5                   10                  15

Met Ile Leu Glu Gln Met Leu Val Arg Cys Ala Tyr Arg Val Thr Thr
            20                  25                  30

Cys Gly Lys Ala Thr Glu Ala Leu Ser Met Leu Arg Glu Asp Ile Gly
        35                  40                  45

Lys Phe Asp Val Val Ile Ser Asp Val Asp Met Pro Asp Met Asp Gly
    50                  55                  60

Phe Lys Leu Leu Glu Leu Val Gly Leu Glu Met Asp Leu Pro Val Ile
65                  70                  75                  80

Met Val Ser Gly Asn Gly Glu Thr Ser Ala Val Met Lys Gly Ile Thr
                85                  90                  95

His Gly Ala Cys Asp Tyr Leu Leu Lys Pro Val Arg Ile Glu Glu Leu
            100                 105                 110

Arg Asn Ile Trp Gln His Val Val Arg Lys Lys
        115                 120

<210> SEQ ID NO 52
<211> LENGTH: 123
<212> TYPE: PRT
<213> ORGANISM: Arabidopsis thaliana
<220> FEATURE:
<221> NAME/KEY: misc_feature
<223> OTHER INFORMATION: Response Regulator receiver domain of SGI1
      polypeptide of SEQ ID NO:22

<400> SEQUENCE: 52

Pro Ala Asn Leu Arg Val Leu Val Val Asp Asp Pro Thr Cys Leu
1               5                   10                  15

Met Ile Leu Glu Arg Met Leu Met Thr Cys Leu Tyr Arg Val Thr Lys
            20                  25                  30

Cys Asn Arg Ala Glu Ser Ala Leu Ser Leu Leu Arg Lys Asn Lys Asn
        35                  40                  45

Gly Phe Asp Ile Val Ile Ser Asp Val His Met Pro Asp Met Asp Gly
    50                  55                  60

Phe Lys Leu Leu Glu His Val Gly Leu Glu Met Asp Leu Pro Val Ile
65                  70                  75                  80

Met Met Ser Ala Asp Asp Ser Lys Ser Val Val Leu Lys Gly Val Thr
                85                  90                  95

His Gly Ala Val Asp Tyr Leu Ile Lys Pro Val Arg Ile Glu Ala Leu
            100                 105                 110

Lys Asn Ile Trp Gln His Val Val Arg Lys Lys
        115                 120

<210> SEQ ID NO 53
<211> LENGTH: 121
<212> TYPE: PRT
<213> ORGANISM: Arabidopsis halleri
<220> FEATURE:
<221> NAME/KEY: misc_feature
<223> OTHER INFORMATION: Response Regulator receiver domain of SGI1
      polypeptide of SEQ ID NO:24

<400> SEQUENCE: 53

Pro Val Gly Met Arg Val Leu Ala Val Asp Asp Asn Pro Thr Cys Leu
1               5                   10                  15

Arg Lys Leu Glu Glu Leu Leu Leu Arg Cys Lys Tyr His Val Thr Lys
            20                  25                  30

```
Thr Met Glu Ser Arg Lys Ala Leu Glu Leu Leu Arg Glu Asn Ser Asn
        35                  40                  45

Met Phe Asp Leu Val Ile Ser Asp Val Glu Met Pro Asp Thr Asp Gly
    50                  55                  60

Phe Lys Leu Leu Glu Ile Gly Leu Glu Met Asp Leu Pro Val Ile Met
65                  70                  75                  80

Leu Ser Ala His Ser Asp Tyr Asp Ser Val Met Lys Gly Ile Ile His
                85                  90                  95

Gly Ala Cys Asp Tyr Leu Val Lys Pro Val Gly Leu Lys Glu Leu Gln
                100                 105                 110

Asn Ile Trp His His Val Val Lys Lys
            115                 120
```

<210> SEQ ID NO 54
<211> LENGTH: 123
<212> TYPE: PRT
<213> ORGANISM: Vitis vinifera
<220> FEATURE:
<221> NAME/KEY: misc_feature
<223> OTHER INFORMATION: Response Regulator receiver domain of SGI1
      polypeptide of SEQ ID NO:26

<400> SEQUENCE: 54

```
Pro Ala Gly Leu Arg Val Leu Val Asp Asp Val Thr Cys Leu
1               5                   10                  15

Lys Ile Leu Glu Gln Met Leu Arg Arg Cys Leu Tyr His Val Thr Thr
            20                  25                  30

Cys Ser Gln Ala Thr Ile Ala Leu Asn Ile Leu Arg Lys Lys Gly
            35                  40                  45

Cys Phe Asp Ile Val Leu Ser Asp Val His Met Pro Asp Met Asp Gly
    50                  55                  60

Tyr Lys Leu Leu Glu His Val Gly Leu Glu Met Asp Leu Pro Val Ile
65                  70                  75                  80

Met Met Ser Ala Asp Gly Arg Thr Ser Ala Val Met Arg Gly Ile Arg
                85                  90                  95

His Gly Ala Cys Asp Tyr Leu Ile Lys Pro Ile Arg Glu Glu Glu Leu
                100                 105                 110

Lys Asn Ile Trp Gln His Val Val Arg Lys Lys
            115                 120
```

<210> SEQ ID NO 55
<211> LENGTH: 123
<212> TYPE: PRT
<213> ORGANISM: Glycine max
<220> FEATURE:
<221> NAME/KEY: misc_feature
<223> OTHER INFORMATION: Response Regulator receiver domain of SGI1
      polypeptide of SEQ ID NO:34

<400> SEQUENCE: 55

```
Pro Ala Gly Leu Arg Val Leu Val Asp Asp Pro Thr Cys Leu
1               5                   10                  15

Met Ile Leu Glu Lys Met Leu Arg Thr Cys Leu Tyr Glu Val Thr Lys
            20                  25                  30

Cys Asn Arg Ala Glu Thr Ala Leu Ser Leu Leu Arg Glu Asn Lys Asn
            35                  40                  45

Gly Phe Asp Ile Val Ile Ser Asp Val His Met Pro Asp Met Asp Gly
    50                  55                  60
```

```
Phe Lys Leu Leu Glu His Ile Gly Leu Glu Met Asp Leu Pro Val Ile
 65                  70                  75                  80

Met Met Ser Ala Asp Asp Gly Lys Ser Val Val Met Lys Gly Val Thr
                 85                  90                  95

His Gly Ala Cys Asp Tyr Leu Ile Lys Pro Val Arg Ile Glu Ala Leu
            100                 105                 110

Lys Asn Ile Trp Gln His Val Val Arg Lys Arg
        115                 120
```

<210> SEQ ID NO 56
<211> LENGTH: 123
<212> TYPE: PRT
<213> ORGANISM: Zea mays
<220> FEATURE:
<221> NAME/KEY: misc_feature
<223> OTHER INFORMATION: Response Regulator receiver domain of SGI1
    polypeptide of SEQ ID NO:37

<400> SEQUENCE: 56

```
Pro Val Gly Met Lys Val Leu Val Val Asp Asp Pro Thr Cys Leu
 1               5                  10                  15

Val Val Leu Lys Arg Met Leu Leu Glu Cys Arg Tyr Asp Val Thr Thr
                 20                  25                  30

Cys Pro Gln Ala Thr Arg Ala Leu Thr Met Leu Arg Glu Asn Arg Arg
             35                  40                  45

Gly Phe Asp Val Ile Ile Ser Asp Val His Met Pro Asp Met Asp Gly
         50                  55                  60

Phe Arg Leu Leu Glu Leu Val Gly Leu Glu Met Asp Leu Pro Val Ile
 65                  70                  75                  80

Met Met Ser Ala Asp Ser Arg Thr Asp Ile Val Met Lys Gly Ile Lys
                 85                  90                  95

His Gly Ala Cys Asp Tyr Leu Ile Lys Pro Val Arg Met Glu Glu Leu
            100                 105                 110

Lys Asn Ile Trp Gln His Val Val Arg Lys Lys
        115                 120
```

<210> SEQ ID NO 57
<211> LENGTH: 123
<212> TYPE: PRT
<213> ORGANISM: Oryza sativa
<220> FEATURE:
<221> NAME/KEY: misc_feature
<223> OTHER INFORMATION: Response Regulator receiver domain of SGI1
    polypeptide of SEQ ID NO:39

<400> SEQUENCE: 57

```
Pro Val Gly Met Lys Val Leu Val Val Asp Asp Pro Thr Cys Leu
 1               5                  10                  15

Ala Val Leu Lys Arg Met Leu Leu Glu Cys Arg Tyr Asp Ala Thr Thr
                 20                  25                  30

Cys Ser Gln Ala Thr Arg Ala Leu Thr Met Leu Arg Glu Asn Arg Arg
             35                  40                  45

Gly Phe Asp Val Ile Ile Ser Asp Val His Met Pro Asp Met Asp Gly
         50                  55                  60

Phe Arg Leu Leu Glu Leu Val Gly Leu Glu Met Asp Leu Pro Val Ile
 65                  70                  75                  80

Met Met Ser Ala Asp Ser Arg Thr Asp Ile Val Met Lys Gly Ile Lys
                 85                  90                  95

His Gly Ala Cys Asp Tyr Leu Ile Lys Pro Val Arg Met Glu Glu Leu
```

```
                100               105               110
Lys Asn Ile Trp Gln His Val Ile Arg Lys Lys
            115               120
```

<210> SEQ ID NO 58
<211> LENGTH: 60
<212> TYPE: PRT
<213> ORGANISM: Parachlorella sp.
<220> FEATURE:
<221> NAME/KEY: misc_feature
<223> OTHER INFORMATION: Myb domain of SGI1 polypeptide of SEQ ID NO:3

<400> SEQUENCE: 58

```
Lys Lys Pro Arg Val Val Trp Ser Val Glu Met His Gln Gln Phe Val
1               5                   10                  15

Asn Ala Val Asn Ser Leu Gly Ile Asp Lys Ala Val Pro Lys Arg Ile
            20                  25                  30

Leu Asp Leu Met Asn Val Glu Gly Leu Thr Arg Glu Asn Val Ala Ser
        35                  40                  45

His Leu Gln Lys Tyr Arg Leu Tyr Leu Lys Arg Val
    50                  55                  60
```

<210> SEQ ID NO 59
<211> LENGTH: 51
<212> TYPE: PRT
<213> ORGANISM: Coccomyxa subellipsoidea
<220> FEATURE:
<221> NAME/KEY: misc_feature
<223> OTHER INFORMATION: Myb domain of SGI1 polypeptide of SEQ ID NO:9

<400> SEQUENCE: 59

```
Lys Lys Ala Arg Val Val Trp Ser Val Glu Met His Gln Gln Phe Val
1               5                   10                  15

Gln Ala Val Asn Gln Leu Gly Ile Asp Lys Ala Val Pro Lys Arg Ile
            20                  25                  30

Leu Asp Leu Met Asn Val Asp Gly Leu Thr Arg Glu Asn Val Ala Ser
        35                  40                  45

His Leu Gln
    50
```

<210> SEQ ID NO 60
<211> LENGTH: 61
<212> TYPE: PRT
<213> ORGANISM: Ostreococcus lucimarinus
<220> FEATURE:
<221> NAME/KEY: misc_feature
<223> OTHER INFORMATION: Myb domain of SGI1 polypeptide of SEQ ID NO:10

<400> SEQUENCE: 60

```
Lys Lys Pro Arg Val Val Trp Ser Ala Glu Leu His Ala Gln Phe Val
1               5                   10                  15

Thr Ala Val Asn Gln Leu Gly Ile Asp Lys Ala Val Pro Lys Arg Ile
            20                  25                  30

Leu Asp Leu Met Gly Val Gln Gly Leu Thr Arg Glu Asn Val Ala Ser
        35                  40                  45

His Leu Gln Lys Tyr Arg Leu Tyr Leu Lys Arg Leu Gln
    50                  55                  60
```

<210> SEQ ID NO 61
<211> LENGTH: 65
<212> TYPE: PRT
<213> ORGANISM: Chlamydomonas reinhardtii -continued

```
<220> FEATURE:
<221> NAME/KEY: misc_feature
<223> OTHER INFORMATION: Myb domain of SGI1 polypeptide of SEQ ID NO:11

<400> SEQUENCE: 61

Lys Lys Ala Arg Val Val Trp Ser Val Glu Met His Gln Gln Phe Val
 1               5                  10                  15

Asn Ala Val Asn Gln Leu Gly Ile Asp Lys Ala Val Pro Lys Lys Ile
            20                  25                  30

Leu Glu Ile Met Gly Val Asp Gly Ser Ala Gly Arg Leu Ala Asp Thr
        35                  40                  45

Ser Gly Arg Asp Val Cys Gly Thr Val Tyr Arg Leu Tyr Leu Lys Arg
    50                  55                  60

Val
65

<210> SEQ ID NO 62
<211> LENGTH: 61
<212> TYPE: PRT
<213> ORGANISM: Chromochloris zofingiensis
<220> FEATURE:
<221> NAME/KEY: misc_feature
<223> OTHER INFORMATION: Myb domain of SGI1 polypeptide of SEQ ID NO:12

<400> SEQUENCE: 62

Lys Lys Pro Arg Val Val Trp Ser Val Glu Met His Gln Gln Phe Val
 1               5                  10                  15

Gln Ala Val Asn Gln Leu Gly Ile Asp Lys Ala Val Pro Lys Lys Ile
            20                  25                  30

Leu Glu Leu Met Asn Val Asp Gly Leu Thr Arg Glu Asn Val Ala Ser
        35                  40                  45

His Leu Gln Lys Tyr Arg Leu Tyr Leu Lys Arg Val Gln
    50                  55                  60

<210> SEQ ID NO 63
<211> LENGTH: 60
<212> TYPE: PRT
<213> ORGANISM: Volvox carteri
<220> FEATURE:
<221> NAME/KEY: misc_feature
<223> OTHER INFORMATION: Myb domain of SGI1 polypeptide of SEQ ID NO:13

<400> SEQUENCE: 63

Lys Lys Ala Arg Val Val Trp Ser Val Glu Met His Gln Gln Phe Val
 1               5                  10                  15

Asn Ala Val Asn Gln Leu Gly Ile Asp Lys Ala Val Pro Lys Lys Ile
            20                  25                  30

Leu Glu Ile Met Asn Val Asp Gly Leu Thr Arg Glu Asn Val Ala Ser
        35                  40                  45

His Leu Gln Lys Tyr Arg Leu Tyr Leu Lys Arg Val
    50                  55                  60

<210> SEQ ID NO 64
<211> LENGTH: 60
<212> TYPE: PRT
<213> ORGANISM: Tetraselmis sp.
<220> FEATURE:
<221> NAME/KEY: misc_feature
<223> OTHER INFORMATION: Myb domain of SGI1 polypeptides of SEQ ID
      NO:14, SEQ ID NO:15, and SEQ ID NO:16

<400> SEQUENCE: 64
```

```
Lys Lys Gln Arg Met Asn Trp Ser Asp Glu Met His Gln Gln Phe Val
 1               5                  10                  15

Asn Ala Val Asn Gln Leu Gly Ile Asp Lys Ala Val Pro Lys Arg Ile
                20                  25                  30

Leu Asp Leu Met Ser Val Glu Gly Leu Thr Arg Glu Asn Val Ala Ser
             35                  40                  45

His Leu Gln Lys Tyr Arg Ile Tyr Leu Lys Arg Met
     50                  55                  60

<210> SEQ ID NO 65
<211> LENGTH: 60
<212> TYPE: PRT
<213> ORGANISM: Oocystis sp.
<220> FEATURE:
<221> NAME/KEY: misc_feature
<223> OTHER INFORMATION: Myb domain of SGI1 polypeptide of SEQ ID NO:17

<400> SEQUENCE: 65

Lys Lys Pro Arg Val Val Trp Ser Val Glu Met His Gln Gln Phe Val
 1               5                  10                  15

Asn Ala Val Asn Gln Leu Gly Ile Asp Lys Ala Val Pro Lys Arg Ile
                20                  25                  30

Leu Asp Leu Met Asn Val Asp Gly Leu Thr Arg Glu Asn Val Ala Ser
             35                  40                  45

His Leu Gln Lys Tyr Arg Leu Tyr Leu Lys Arg Val
     50                  55                  60

<210> SEQ ID NO 66
<211> LENGTH: 61
<212> TYPE: PRT
<213> ORGANISM: Micromonas sp. RCC299
<220> FEATURE:
<221> NAME/KEY: misc_feature
<223> OTHER INFORMATION: Myb domain of SGI1 polypeptide of SEQ ID NO:18

<400> SEQUENCE: 66

Lys Lys Pro Arg Val Val Trp Ser Ala Glu Leu His Gln Gln Phe Val
 1               5                  10                  15

Thr Ala Val Asn Gln Leu Gly Ile Asp Lys Ala Val Pro Lys Arg Ile
                20                  25                  30

Leu Asp Leu Met Gly Val Gln Gly Leu Thr Arg Glu Asn Val Ala Ser
             35                  40                  45

His Leu Gln Lys Tyr Arg Leu Tyr Leu Lys Arg Leu Gln
     50                  55                  60

<210> SEQ ID NO 67
<211> LENGTH: 61
<212> TYPE: PRT
<213> ORGANISM: Micromonas pusillada
<220> FEATURE:
<221> NAME/KEY: misc_feature
<223> OTHER INFORMATION: Myb domain of SGI1 polypeptide of SEQ ID NO:19

<400> SEQUENCE: 67

Lys Lys Pro Arg Val Val Trp Ser Pro Glu Leu His Gln Gln Phe Val
 1               5                  10                  15

Thr Ala Val Asn Gln Leu Gly Ile Asp Lys Ala Val Pro Lys Arg Ile
                20                  25                  30

Leu Asp Leu Met Gly Val Gln Gly Leu Thr Arg Glu Asn Val Ala Ser
             35                  40                  45

His Leu Gln Lys Tyr Arg Leu Tyr Leu Lys Arg Leu Gln
```

<210> SEQ ID NO 68
<211> LENGTH: 60
<212> TYPE: PRT
<213> ORGANISM: Sphagnum fallax
<220> FEATURE:
<221> NAME/KEY: misc_feature
<223> OTHER INFORMATION: Myb domain of SGI1 polypeptide of SEQ ID NO:20

<400> SEQUENCE: 68

```
Lys Lys Pro Arg Val Val Trp Ser Val Glu Leu His Gln Gln Phe Val
1               5                   10                  15
Ser Ala Val Asn Gln Leu Gly Ile Asp Lys Ala Val Pro Lys Lys Ile
            20                  25                  30
Leu Glu Leu Met Ser Val His Gly Leu Thr Arg Glu Asn Val Ala Ser
        35                  40                  45
His Leu Gln Lys Tyr Arg Leu Tyr Leu Arg Arg Leu
    50                  55                  60
```

<210> SEQ ID NO 69
<211> LENGTH: 60
<212> TYPE: PRT
<213> ORGANISM: Physcomitrella patens
<220> FEATURE:
<221> NAME/KEY: misc_feature
<223> OTHER INFORMATION: Myb domain of SGI1 polypeptide of SEQ ID NO:21

<400> SEQUENCE: 69

```
Lys Arg Pro Arg Val Val Trp Ser Val Glu Leu His Gln Gln Phe Val
1               5                   10                  15
Ser Ala Val Asn Gln Leu Gly Ile Asp Lys Ala Val Pro Lys Arg Ile
            20                  25                  30
Leu Glu Leu Met Gly Val Gln Gly Leu Thr Arg Glu Asn Val Ala Ser
        35                  40                  45
His Leu Gln Lys Tyr Arg Leu Tyr Leu Lys Arg Leu
    50                  55                  60
```

<210> SEQ ID NO 70
<211> LENGTH: 61
<212> TYPE: PRT
<213> ORGANISM: Arabidopsis thaliana
<220> FEATURE:
<221> NAME/KEY: misc_feature
<223> OTHER INFORMATION: Myb domain of SGI1 polypeptide of SEQ ID NO:22

<400> SEQUENCE: 70

```
Lys Lys Pro Arg Val Val Trp Ser Val Glu Leu His Gln Gln Phe Val
1               5                   10                  15
Ala Ala Val Asn Gln Leu Gly Val Asp Lys Ala Val Pro Lys Lys Ile
            20                  25                  30
Leu Glu Met Met Asn Val Pro Gly Leu Thr Arg Glu Asn Val Ala Ser
        35                  40                  45
His Leu Gln Lys Tyr Arg Ile Tyr Leu Arg Arg Leu Gly
    50                  55                  60
```

<210> SEQ ID NO 71
<211> LENGTH: 61
<212> TYPE: PRT
<213> ORGANISM: Arabidopsis halleri
<220> FEATURE:
<221> NAME/KEY: misc_feature
<223> OTHER INFORMATION: Myb domain of SGI1 polypeptides of SEQ ID NO:23 and SEQ ID NO:24

<400> SEQUENCE: 71

Lys Lys Pro Arg Val Val Trp Ser Gln Glu Leu His Gln Lys Phe Val
1               5                   10                  15

Ser Ala Val Gln Gln Leu Gly Leu Asp Lys Ala Val Pro Lys Lys Ile
            20                  25                  30

Leu Asp Leu Met Ser Ile Glu Gly Leu Thr Arg Glu Asn Val Ala Ser
        35                  40                  45

His Leu Gln Lys Tyr Arg Leu Tyr Leu Lys Lys Ile Asp
    50                  55                  60

<210> SEQ ID NO 72
<211> LENGTH: 60
<212> TYPE: PRT
<213> ORGANISM: Vitis vinifera
<220> FEATURE:
<221> NAME/KEY: misc_feature
<223> OTHER INFORMATION: Myb domain of SGI1 polypeptide of SEQ ID NO:26

<400> SEQUENCE: 72

Lys Lys Pro Arg Val Val Trp Ser Val Glu Leu His Gln Gln Phe Val
1               5                   10                  15

Ser Ala Val Asn Gln Leu Gly Ile Asp Lys Ala Val Pro Lys Arg Ile
            20                  25                  30

Leu Glu Leu Met Asn Val Pro Gly Leu Thr Arg Glu Asn Val Ala Ser
        35                  40                  45

His Leu Gln Lys Phe Arg Leu Tyr Leu Lys Arg Leu
    50                  55                  60

<210> SEQ ID NO 73
<211> LENGTH: 60
<212> TYPE: PRT
<213> ORGANISM: Glycine max
<220> FEATURE:
<221> NAME/KEY: misc_feature
<223> OTHER INFORMATION: Myb domain of SGI1 polypeptide of SEQ ID NO:34

<400> SEQUENCE: 73

Lys Lys Pro Arg Val Val Trp Ser Val Glu Leu His Gln Gln Phe Val
1               5                   10                  15

Ala Ala Val Asp Gln Leu Gly Ile Asp Lys Ala Val Pro Lys Lys Ile
            20                  25                  30

Leu Glu Leu Met Asn Val Pro Gly Leu Thr Arg Glu Asn Val Ala Ser
        35                  40                  45

His Leu Gln Lys Tyr Arg Leu Tyr Leu Arg Arg Leu
    50                  55                  60

<210> SEQ ID NO 74
<211> LENGTH: 60
<212> TYPE: PRT
<213> ORGANISM: Zea mays
<220> FEATURE:
<221> NAME/KEY: misc_feature
<223> OTHER INFORMATION: Myb domain of SGI1 polypeptide of SEQ ID NO:37

<400> SEQUENCE: 74

Lys Lys Pro Arg Val Val Trp Ser Val Glu Leu His Gln Gln Phe Val
1               5                   10                  15

Asn Ala Val Asn His Leu Gly Ile Asp Lys Ala Val Pro Lys Lys Ile
            20                  25                  30

Leu Glu Leu Met Asn Val Pro Gly Leu Thr Arg Glu Asn Val Ala Ser
            35                  40                  45

His Leu Gln Lys Phe Arg Leu Tyr Leu Lys Arg Ile
    50                  55                  60

<210> SEQ ID NO 75
<211> LENGTH: 60
<212> TYPE: PRT
<213> ORGANISM: Oryza sativa
<220> FEATURE:
<221> NAME/KEY: misc_feature
<223> OTHER INFORMATION: Myb domain of SGI1 polypeptide of SEQ ID NO:39

<400> SEQUENCE: 75

Lys Lys Pro Arg Val Val Trp Ser Val Glu Leu His Gln Gln Phe Val
1               5                   10                  15

Asn Ala Val Asn His Leu Gly Ile Asp Lys Ala Val Pro Lys Lys Ile
            20                  25                  30

Leu Glu Leu Met Asn Val Pro Gly Leu Thr Arg Glu Asn Val Ala Ser
            35                  40                  45

His Leu Gln Lys Phe Arg Leu Tyr Leu Lys Arg Ile
    50                  55                  60

<210> SEQ ID NO 76
<211> LENGTH: 5607
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cas9 gene codon optimized for Parachlorella
      that includes sequences encoding an N-terminal FLAG tag, nuclear
      localization signal, and peptide linker and contains introns from
      Parachlorella

<400> SEQUENCE: 76
atgcccaaga agaagcggaa agtcggggac tacaaggacg acgatgacaa actggagcct      60
ggggagaagc cctataagtg tcctgagtgc gggaagagct tcagccaatc tggagcactg     120
acaaggcacc agaggacaca tacacgcgac aagaagtaca gcatcgggct ggatatcggg     180
accaattctg tgggatgggc cgtgattacc gacgagtata aggtgcccag caagaagttc     240
aaggtgctgg gaacacagac cgccacagca ttaagaaga acctgatcgg ggcgctgctg      300
tttgattctg gagagacagc agaggcaacc gtgagtgaga acagttttca gatcgaatag     360
cacccccccg cctctgcagc agtcgcatac cggctgcagt aatagcttgg ttcaacggcg     420
acctgaacaa gtactgtagt ttctatgcat acgaacttta tcgaatagaa tcacgcttgg     480
gtatcgatca taccttagcg ctcaatttca ttggctgcta cagaccatat tttcctcttc     540
acttgttgca gcgcctgaaa agaacagcaa gaaggcgcta cacccgccgc aagaatagga     600
tttgctacct gcaagagatc ttcagcaacg agatggccaa ggtggacgac agcttcttcc     660
atagactgga ggagtcgttc ctggtggagg aggataagaa gcacgagagg caccccatct     720
tcggtgagaa gagtttggct accaaatcta tcttttcata tcacatatac cgcctgatat     780
tctgaggtgg tggcttttgt ctttttcttt cagtattttt cttcgttggg aacctaccgc     840
gagggcattc attgtggcgg atctgtaagt gcgaccaggc tgtatccaat attttttcct     900
atcgcaggga acattgtgga tgaggtggcc taccacgaga agtacccccac aatctaccac     960 ctgcgcaaga agctggtgag aatctctgct tgtcgaatgt gtccagttgt gtcttgaatc    1020

```
ctggcaagat gttcttttca ccatccgtcc tgcaaaagtg tcagaagtag catctctcga    1080
tcgcgttgtc acttcaacgc ctccgcaact cccccgttg tgaatcctgt ggtcatggct     1140
cagcttttca gatctctacc tgcatgttgt ttgcctgtct cagtcctgcc tgcacaaatc    1200
atcgcccttg tttactcctt gcaatcacgg attgtgtgca ggtggacagc acagataagg    1260
ccgatctgag gctgatctac ctggcattgg cccacatgat caagtttagg gggcacttcc    1320
tcatcgaggg ggatttgaac cccgacaaca gcgatgtgga caagctgttc atccagctgg    1380
tgagtggagg gctggggttt ggggtgggg ggtggggagg gaggcacgga tggtgttttc     1440
tcatgtccaa ccgtggttca tgcaaccgaa cagcagtttc acaagatggt tccaacaggg    1500
tgctccattt ctccctgaca aaacctcgtg cggtccatct ggtatagctg ggttagtagg    1560
gggttgtggg ctgtccacag tcagtgcgaa gcaggctcta ttgagcgtgt gctagtgtgt    1620
gctgtgctga ttggcatttt gttgggccga gtgttaggat tagggtaaat caccctaatt    1680
aaccttacat aataggactg tatgcaaatt tgttttccaa aaactctacc cagcgtggtc    1740
agactgcatg cactgtggag catgcatggg gctgaccctg ttgatcctgc tcattctgct    1800
tcctccaggt gcagacctac aaccagctgt ttgaggagaa ccccatcaac gcatctgggg    1860
ttgacgcaaa ggccattctg tctgcaaggt aggtgcagga agaagtgaat gatgcacaca    1920
tggtggaatc gtgatacaag cagcagcaag tgttggacca agacatgtgc gtgctttgct    1980
gctgccaagc tggcactgca ccaggtcgtg cattgatctg cacatttgat atactgtgag    2040
agtcagacga cgtcctttca gagcctgtgt gtgattctcc aggggttaac acgagtttcc    2100
tttctgccag tgagtcaccc tctcgctgct cgctcctggt gcaggctgag caagtcaagg    2160
agactggaga acctgatcgc ccaattgcct ggagagaaga agaacgggct gttcgggaac    2220
ctgatcgcat tgtctctggg gttgaccccc aacttcaaga gcaacttcga cctggcagag    2280
gacgcaaaac tgcagctgag caaggacacc tacgacgatg atctggacaa cctgctggcc    2340
cagattggga tcagtacgc agacctgttc ctggcagcca agaatctgag cgacgcaatt     2400
ctgctgagcg acattctgcg cgtgaacacc gagatcacca aggcacctct gagcgcaagc    2460
atgatcaaga ggtacgacga gcaccaccaa gacctgacac tgctgaaagc actggtgaga    2520
cagcagctgc ctgagaagta caaggagatc ttcttcgacc agagcaagaa cgggtacgct    2580
gggtacattg atgaggagc aagccaagag gagttctaca agttcatcaa gcccatcctg    2640
gagaagatgg acgggacaga agagttgctg gtgaagctga atcgcgagga tctgctgagg    2700
aagcaggaga cattcgacaa tgggagcatc ccacaccaga tccatctggg agagctgcac    2760
gcaattctga ggagacaaga ggacttctac ccgttcctga aggacaatcg cgagaagatc    2820
gagaagatcc tcacgttccg catcccgtac tatgtgggac ctctggcaag ggggaactct    2880
agatttgcct ggatgacccg caagagcgag gagacaatta cacctggaa cttcgaggag     2940 gtggtggata aggggcatc tgcacagagc ttcatcgaga ggatgaccaa cttcgacaag     3000
aacctgccca cgagaaggt actgcctaag cattcactgc tgtacgagta cttcaccgtg    3060
tacaacgagc tgaccaaggt gaagtacgtg acagagggga tgaggaagcc agcatttctg    3120
agcggagagc aaaagaaggc catcgtggat ctgctgttca gaccaaccg caaggtgacc    3180 gtgaagcagc tgaaggagga ctacttcaag aagatcgagt gcttcgacag cgtggagatt    3240
tctggagtgg aggaccgctt caacgcatct ttggggacat accacgacct gctgaagatc    3300
atcaaggaca aggacttcct ggacaacgag gagaacgagg acatcctgga ggacattgtg    3360
ctgacactga ccctgttcga ggatagggag atgatcgagg agcgcctgaa gacatacgca    3420
```

```
cacctgtttg acgacaaggt gatgaagcag ctgaagagga ggcgctatac tggatgggga   3480
aggctgtcaa ggaagctgat taacgggatc cgcgacaagc agagcgggaa gacaattctg   3540
gacttcctga agagcgacgg gttcgcaaac cgcaacttca tgcagctgat ccacgacgat   3600
agcctgacct tcaaggagga catccagaag gcccaagtgt ctggacaagg ggatagcctg   3660
catgagcaca tcgcaaatct ggctgggtca cccgcaatca agaagggaat tctgcagacc   3720
gtgaaggtgg tggatgagct ggtgaaggtg atgggaaggc acaaacccga gaacatcgtg   3780
atcgagatgg caaggagaa ccagacaacc cagaagggac agaagaactc tagggagcgc   3840
atgaagcgca tcgaggaggg aattaaggag ctgggaagcc agatcctgaa ggagcatcct   3900
gtggagaaca cccaactgca gaacgagaag ctgtacctgt actacctgca gaacggagg    3960
gacatgtacg tggatcaaga gctggacatc aaccgcctga cgactatga cgtggaccac   4020
attgtgcctc agtcgttcct gaaggacgac agcatcgaca caaggtgct gacaaggagc    4080
gacaagaatc gcggaaagag cgacaacgtg ccttcagaag aggtggtgaa gaagatgaag   4140
aactactggc gccagctgct gaacgcaaag ctgattacac agcgcaagtt cgacaacctg   4200
accaaggcag agaggggagg actgtcagaa ctggataagg ccgggttcat caagaggcaa   4260
ctggtggaga cacgccagat cacaaagcat gtggcccaga ttctggacag ccgcatgaac   4320
accaagtacg acgagaacga caagctgatc cgcgaggtga aggtgattac cctgaagagc   4380
aagctggtga gcgactttcg caaggacttc cagttctaca aggtgcgcga gatcaacaac   4440
taccaccacg cacacgacgc ctacctgaat gcagttgtgg gaacagccct gatcaagaag   4500
tacccaagc tggagagcga gttcgtgtat ggggactaca aggtgtacga cgtgcgcaag   4560
atgatcgcca gtctgagca agagatcggg aaggcaaccg ccaagtactt cttctacagc   4620
aacatcatga acttcttcaa gaccgagatc accctggcca tggggagat taggaagaga   4680
cccctgatcg agaccaacgg agagactgga gagatcgtgt gggataaggg gagggacttt   4740
gcaacagtgc gcaaagtgct gagcatgcct caagtgaaca tcgtgaagaa gaccgaggtg   4800
cagactgggg gattctcaaa ggagagcatt ctgcccaagc gcaacagcga taagctgatt   4860
gcacgcaaga aggactggga ccccaagaag tatgggggt tgatagccc caccgtggca    4920
tattctgtgt tggttgtggc caaggtggag aaggggaaga gcaagaagct gaagagcgtg   4980
aaggagctgc tgggatcac cattatggag aggagcagct cgagaagaa ccccatcgac     5040
ttcctggagg caagggggta aggaggtg aagaaggacc tgatcatcaa gctgcccaag     5100
tacagcctgt tcgagctgga gaatggggag aagaggatgc tggcatctgc tggagaactg   5160
cagaagggga atgagttggc actgcctagc aagtacgtga acttcctgta cctggccagc   5220
cactacgaga agctgaaggg atcacccgag gacaatgagc agaagcagct gtttgtggag   5280
cagcacaagc actacctgga cgagatcatc gagcagatca gcgagttcag caagcgcgtg   5340
attctggcag acgcaaacct ggataaggtg ctgagcgcct acaacaagca ccgcgataag   5400
cccattcgcg agcaagcaga gaacatcatc cacctgttca ccctgaccaa cctgggagca   5460
cctgcagcat tcaagtactt cgacaccacc atcgaccgca gaggtacac aagcaccaag    5520
gaagtgctga cgcaaccct gattcaccag agcattactg ggctgtacga gacacgcatc    5580
gacctgtcac aactgggagg ggactga                                       5607
```

<210> SEQ ID NO 77
<211> LENGTH: 588
<212> TYPE: DNA

<213> ORGANISM: Parachlorella sp.
<220> FEATURE:
<221> NAME/KEY: misc_feature
<223> OTHER INFORMATION: RPS17 promoter

<400> SEQUENCE: 77

```
caacacctag ttggtaaata ccgttgctga tattgctctg taccagtaaa agagggctgc    60
gatgagcgtt tttagtgcac ttcttcaaca cggaatattt ttcacaaatt ggtatgagaa   120
ccaattttgc aaaatgttcg ccctgtaaag tatcgctctg gacgatcag cttgacgtaa    180
ttgtaggcga aaaggggcgtt caaagtgcag ctttatgtat gaacgtcata aaatataaag   240
catagcacaa tcactgatag aaaatatttg tgcgcattaa aactctcact tctgttgcgg    300
atacaacgac ggaaatgaga agcttgtgta agaagcaatt caagttttca ttttgtcatc    360
taaggtgtga tcctccgata ttcattaccg aatgctgatc tgagttggaa agatggcaat    420
atttagctgt gcacactttg acctccaggc cttggcggga atttagtatt ctagctttcc    480
tattggaacg ataggccagc caagtctcca gcttgtatac gctacaccag cagacatgct    540
ctcaatttag ctgacagtgt cttcatattt gtattatctg ttgtgtct                 588
```

<210> SEQ ID NO 78
<211> LENGTH: 455
<212> TYPE: DNA
<213> ORGANISM: Parachlorella sp.
<220> FEATURE:
<221> NAME/KEY: misc_feature
<223> OTHER INFORMATION: RPS17 terminator

<400> SEQUENCE: 78

```
ggtgcgaata gtgcttcagt aaaaaagtag caacttggtg caatatcgtc agggtcgtgt    60
ggtctgctcg ccagcaagtt ttttggcaca ggagagcgct ttttccgagt accgccaaag   120
ttcaagcatg tgctgtgatt cgctgttgcc tcttatgata attgctcaaa gtttccaagc   180
attctatgtc caccctgcac cactaagttg tatggtgctt attctgcagg ggatgattca   240
tggtgcctaa aaattttgtg ctgctgtcgc gtctgttttc tgtcgcagtt tagtgaatgt   300
aactccaaat accaaacttt tcatcacaat catattgatg cctttgtaag tgaattacag   360
cgttttttgc cataaaaaga agtaccgtga cattggggtc gtcataacaa gaagctttat   420
gaacaagcag cttgatctac gagacttata cataa                              455
```

<210> SEQ ID NO 79
<211> LENGTH: 2691
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Basticidin resistance gene codon optimized for
    Parachlorella, containing Parachlorella introns

<400> SEQUENCE: 79

```
atggcaaaac ctctctccca ggaagagtct accctgattg aaagggcaac agcaaccatc    60
aacagcattc ccattagcga ggactactct gttgtgagtt ctgagaagct gattgttgtt   120
taacttcttt gaaagcttta tcgaagattc tgcaagcgat gaacattgct tgtcaagacc   180
gagagctgca tgcccacttg acatccagct ttgaacggct cttcatgttt gatttgtttc   240
tgattgtagg catctgcagc attgagctct gatggaagga tctttacagg agtgagtgca   300
gcgtcagctg tggcagttgt tggctttcgt ctcagtcagt agtttgctgg gattgattat   360
```

```
ggagggcaca gttgcaattt tgagttgcac gttgcgacaa gcgtgttgac aaagcgtggt    420
caagccggcc agtcttgccg gtggcgggtg gcttggtcta acttccgctc tacggcaatc    480
gttttgttca tggttacggg gctggcgtgc cagaaagtcc tggtcagcca ccctcgcttc    540
aaagccgtag cccaacaact tgcgaatat gttcgatttg caggtgaacg tgtaccactt    600
tacaggagga ccttgtgcag aattggtggt gttaggtaca gctctgcgtg caacaggttg    660
caagatgcag cgcaggtctt ccctggtcaa acgatgtatg cagagttgag aggcacttga    720
gctgggtgaa tggcgtgggc tcgtaggtag tgtgcagggc aggaagggca gccaattttg    780
gagttgtggt ccggtgtcgt tgcttcgagc cttattagga ctcttgctca tcaaagcgtt    840
agttgtgaat aagttgatct gaaaggatgt tatgtacagc aagcagcagc agttaagagt    900
ctggggagta gctgcacagg gcgaggtgtc aagatgggaa gggtcctgcc tcctatgtg     960 ttttccctg taggggagga agcctcttat gggcaatggt tgggcatatt ttccagccag    1020
cccttctttc tataggggcc agggtgggcc cagctcgtct tggcttccac caccaggaga   1080
gtgagggcat tgaagggcca taaatagtcc tcccatctac gtgcaccaga gggtgtcgtc   1140
taggctgtgc atgccacgag gggaaggagc caagaatgag tgtatgggtt gttttcatgt   1200
ttaggctggg ataaaactgt tttcaattgc gcctgccggg tgaaaaccac agcagcatca   1260
gcaagcttgg agaaggccag cccgcccagc acaggctcac gttcccactc aggcggtcag   1320 tcggcgggg gtgtgagtca ggcaggcgag ggtgtctgtg cctgacatca gcacctctgc    1380
ttagccactg cagcccctgg agcagggtag ggcgtcattt gcagcaatca cctgctgcct   1440
cacacgtcgc agcttggaat tcaacgacc atcagcgctg gggttgttga gggatcatag    1500
cagattttgg tgcagcctgg ttgtcatgct ctttgtggaa tggcctctat gttcgagcaa   1560
ttcgttggat gttgaggtgc ttggggacag agagtcgaat gatgggccag ggtcaaacat   1620
gcgagcgttt ggctgagtca gcggttttttg ctggtcactt tttctttgt ttcttattta   1680 ggtttgatgg atgtgttttg tgctgctgcc ctgaagctgc agcagcgtgt ctgccctgcg   1740
ctactgcggg caccaaggct atgtgctggt gcactcggct gcgctgcacc tgtgcacctc   1800
gcactccgtc cagcctccat gcagcacacg tactcacggt gtcctcctga cctgtcgtac   1860
gctattccaa acttgctctt ttgctgccgc tgctctcgta cacaattgct gttgattatc   1920
gatatctaat cgagcgcctg ctgactgaac tccgcaggta cagcagctgc agcagcagca   1980
ggaaatttga catgcattgt ggcaataggt gggtgggctc tgaaggagga ggagggagcg   2040
ggtgattaaa cagggcctgc atgaagagga gcaggggctg cgtggacagc aggggaaggg   2100
tgcagaaggg agggtcaagc ggggttcagg tggctgtggg tttctgcacg agcagtgaaa   2160
gaagctgtat ccttccacct gcttccactg gcgaaaggtt gaaaacagga tgtcgcagct   2220
ggaaagatgt tgcgctgtca agtgcaagcc atggttgagg gtatgcctgt gtgcatgtgc   2280
ttcttaaagt tactcctgtt ctatggttct gggtgcttgt tgtttgtggt gcagggaacg   2340
agaatagggg gattttgtca ccttgcggaa gatgtagaca ggtgttgttg gatctgcatc   2400
ccgggattaa ggtgaggggg catgtaagca atggcaggca attcaagaac gaatcattgc   2460
tgcaaatgct gggatggtat gcagctgagg tatctattgc cttgtatttt gtctcgcatt   2520
gcatcggtgg tgcgttctgt ggcctgaggc acagttcttg ctgtttgata agggttcgac   2580
tgagttgtcg tgtgtgctgt gctgcaggca atcgtgaagg attcagatgg gcagcctaca   2640
gcagtgggaa ttagagaact gctgccttct gggtatgtgt gggaaggata a            2691
```

<210> SEQ ID NO 80
<211> LENGTH: 530
<212> TYPE: DNA
<213> ORGANISM: Parachlorella sp.
<220> FEATURE:
<221> NAME/KEY: misc_feature
<223> OTHER INFORMATION: RPS4 promoter

<400> SEQUENCE: 80

| | | | | | |
|---|---|---|---|---|---|
| ccaccatggg | ggaggtttga | agtgtgcgcc | tgatataatc | atacacctaa | aagcaccact | 60 |
| tgctgattgt | gaagggacta | tgtcgtttat | gacgggacgt | tacgctggcc | gatggtttga | 120 |
| atttggacgc | tgtggtagaa | tgttatatgg | acgtaaaggt | tggcatattg | aaaatcgtct | 180 |
| tcgcaggcaa | acttctagac | gtgtgaccca | ccggtaaaac | gacaagcgtg | gcgcgtcgat | 240 |
| tgcgctttga | acgtcgtttg | ttggactcca | gatgaacctc | aaaatcaaag | cggtgattga | 300 |
| cgaaaatcaa | atgacagccc | gcaaaatttc | atcagccttc | ggatcggatt | ctcagaatct | 360 |
| gattgtccct | gctggctaca | tttatgaaat | ttcgtacatt | ttggcagaaa | tgtcccaata | 420 |
| ccatagcact | gccgcctgag | ctcacccgag | caatgcatac | tgggtacctc | gcccatctcg | 480 |
| ccctctttcc | aagcccagtg | ctgttgtaat | agccaaaggg | ctcagtaaca | | 530 |

<210> SEQ ID NO 81
<211> LENGTH: 546
<212> TYPE: DNA
<213> ORGANISM: Parachlorella sp.
<220> FEATURE:
<221> NAME/KEY: misc_feature
<223> OTHER INFORMATION: RPS4 terminator

<400> SEQUENCE: 81

| | | | | | |
|---|---|---|---|---|---|
| gcatagcatc | agcctgtggc | agggttgtgg | tagggctgag | tggcagggtt | aaaggggttg | 60 |
| cctaccccac | ccctactctc | atgacaccag | caacagcagc | agctcatgca | gtactcaaat | 120 |
| cactgatgtc | aatggtgtga | cacatttggt | taaggctgct | ttttaaagtg | ctgctttggg | 180 |
| ggcagtgact | gtgcagagct | tggagcgtat | ccccatgtaa | tcagaaccga | cgagagttcg | 240 |
| gggcaacctt | tcatcttcac | atttttttgtg | atcagctaca | gagtctgaaa | tcaaatagag | 300 |
| gctgccatct | aaacgcagga | gtcacaacga | aggcgaaaac | tccaattgct | gtactcaatg | 360 |
| cactaagtga | ttgttcaatg | gataaataca | ctatgctcaa | ttcatgccag | cagagctgct | 420 |
| ccttccagcc | agctacaatg | gcttttttcca | cgccttttga | agtatgaatg | ttcagcttgc | 480 |
| tgtgcttgat | gcatcaccat | aaacacaatt | ctacaacatt | tcatgccaac | aacagtacgg | 540 |
| gctttc | | | | | | 546 |

<210> SEQ ID NO 82
<211> LENGTH: 702
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Encodes TurboGFP

<400> SEQUENCE: 82

| | | | | | |
|---|---|---|---|---|---|
| atgttggaga | gcgacgagag | cggcctgccc | gccatggaga | tcgagtgccg | catcaccggc | 60 |
| accctgaacg | gcgtggagtt | cgagctggtg | ggcggcggag | agggcacccc | cgagcagggc | 120 |
| cgcatgacca | acaagatgaa | gagcaccaaa | ggcgccctga | ccttcagccc | ctacctgctg | 180 |

```
agccacgtga tgggctacgg cttctaccac ttcggcacct accccagcgg ctacgagaac      240
cccttcctgc acgccatcaa caacggcggc tacaccaaca cccgcatcga gaagtacgag      300
gacggcggcg tgctgcacgt gagcttcagc taccgctacg aggccggccg cgtgatcggc      360
gacttcaagg tgatgggcac cggcttcccc gaggacagcg tgatcttcac cgacaagatc      420
atccgcagca acgccaccgt ggagcacctg caccccatgg gcgataacga tctggatggc      480
agcttcaccc gcaccttcag cctgcgcgac ggcggctact acagctccgt ggtggacagc      540
cacatgcact tcaagagcgc catccacccc agcatcctgc agaacggggg ccccatgttc      600
gccttccgcc gcgtggagga ggatcacagc aacaccgagc tgggcatcgt ggagtaccag      660
cacgccttca agaccccgga tgcagatgcc ggtgaagaat aa                        702
```

<210> SEQ ID NO 83
<211> LENGTH: 572
<212> TYPE: DNA
<213> ORGANISM: Parachlorella sp.
<220> FEATURE:
<221> NAME/KEY: misc_feature
<223> OTHER INFORMATION: ACP1 promoter

<400> SEQUENCE: 83

```
agtttgcata gttaagtatg ctggctattg cagtacctta tatgcaaaca agtgctcaat      60
ctgtttcatc attgtctgtg gcaaattgc ctgccaatat tctccagtta ttgcctgttg      120
tttcaaatga ttgaaattgg aagttgtatt gctctacatt tttgacttgt gattttttca     180
tttgttgata tctgacaact gtgaactgca ctgaacttgc tgtgcttata atgcatttt      240 tttgttttgg gccacgttga ttccttgtga tactttcctg ctatcaaacc aaaaatatac     300
tctcatgact gacgtgcaac aaatgcatgg aagctttcaa cgttacgaca gctgcttgcc    360
ccccatcagc tattctacat gtgtaaccta ccttgcatgg ccaccacaac gctactgcat    420
gcaagatctg cgcaactgg atgtcccaat agtagaagta tccggattat ctccgagagt    480
tttacatatg taatcgacgc catttctgtc atcaactata aatccattgc tcctgcattt    540
ctggcactga cattctacca caagcaatac ca                                  572
```

<210> SEQ ID NO 84
<211> LENGTH: 869
<212> TYPE: DNA
<213> ORGANISM: Parachlorella sp.
<220> FEATURE:
<221> NAME/KEY: misc_feature
<223> OTHER INFORMATION: ACP1 terminator

<400> SEQUENCE: 84

```
gcagcagctt gttatgcctt ccccatgggc atcagcatgc tgcaagctgt ctagatatcc      60
agctttcagt ggaggttgag cgagggtcag cagcggttcc ctggcgatgg cggtcagctt     120
ttctggaagc cttcactagg actgcgccca gcgcatgtga cgccaatcga acttgtgtgc    180
aaggccaaat tttgtgaccc tgtgctgcac ttcatgtatt caagaattga gaagaaattt    240
cattgctgcc cttcttcac tttaatttcc atccctggat ccacctccca ccattgtggt    300
tgatgggtag gggttttggg taggtgcagt tcgttgtgca cgttgacatg tgtaacggtg    360
agcaaaggaa ttgctgggca agtagctatt gcagcttaag ggcatggtga aacacttgtg   420
ctgtatttac agaggaagcc agacaggtaa ggagtgtgtg gcagcttgga acaggagggc    480
tggtcgcaac aagtatgcat atcccatgat tgttgacata agagcagcag gtgcatattg    540
ccagcctttg tgaaagtgga ttgaaaatcg attagttggt gtgatagctg aggctaggca    600
```

```
ctgccaacct gcagtgaaat gaggctccaa gaccgggtaa taatacaggc aatcgaatcc    660
agttgaaatt acggcgatta atccaagcg agcgttgtaa gaacatctgc acctgtctga    720
agtagtgagc ggataatgag cattgcttgc cttctatcac tatacctgac agttacgtgt   780
cacacactct caagcacaac acacagcggc aaagttactt gctaaacctc acagtcaagc   840
tgaaaataaa ggctaaatta cgtgagacc                                     869
```

<210> SEQ ID NO 85
<211> LENGTH: 2879
<212> TYPE: DNA
<213> ORGANISM: Tetraselmis sp.
<220> FEATURE:
<221> NAME/KEY: misc_feature
<223> OTHER INFORMATION: SGI1 gene, T-5172

<400> SEQUENCE: 85

```
atgagctgca cagtggcgtc ctttccgccc gcggcggggg ggcagggctc gcctgccacg    60
cccgtcccat accaggacct gctcgtgaag cggcaagacc agtggagcaa cttcccggcc   120
gggctgcgcg tgctggtggc agacaacgac cccgcctcgc tgcagcaagt ggagaagatg   180
ctaaagaagt gtagctacca aggtgaggct gcgctgcccc tcgaaaggcg gccggccccc   240
caccccagct ggccacttgc gcagtgcgcg tgttatcttg ataatccgaa aacgcgtttt   300
tttgcctcgt tttatcccgc tagtcgtaca atccggtcgg ggcccaggca ggcaccggcg   360
gccacgcgca gacccacaca ccagctcacc ggttgctgct acactgatgc atgctttacg   420
cccggtccca acagtaacac tgtgcagctc ggggaagaac tccctggaga tcctccgcaa   480
gcggcgagag gaattcgacc tcgtgctggc ggacgcaaat ctaccaggtt ttcccctca    540 ccctgtctgc tcgaggggt acaccggtac tactaaccgc gacaattccg cccgctcacc    600
gccgccttcc cacgccacaa gcgacggaac tgattgtatt cctgctcccg gtctttcgcc   660
tgcagacata tgatggcttca agcttcttca cgtctgccac accgagctgt cgctccccgt   720
cgtccgtaag agcctgctgc ccgctcgaca tccacctcgc acttcaattt gctattcagt   780
catcgtaccg tgccctgccc tgcacttccc tgccctgagg tatcccagtc gcatcccggc   840 cttcccccc cccccccccc cccttccccc aaacgtagtg atgtccggca ccagcgacac   900
acagctggta atgcgcggcg tgatggatgg cgcgcgggac tttctgatca gcccctgcg   960 cgtggaggag ctcaaggtgc tctggcagca ccttgtgcgc ttcacttcgg agatcaccaa  1020
gacagacgcg cagctaaatg ttgtcaaggt ggagctggac ggcggaaggc ctgcgggcga  1080
agtctctacg agtcagaacg gctcggtatg ccacagcagc ccatttgaag cagcccgttt  1140
cttgtagggc gcgaattatg cctcggcgcg ttttcctccc tcctcgcgct gactccttgt  1200
gtgccccaca cagcaatgca ccgagcgcga gggcgaaggc aattcatcaa gaagcagcg   1260 catgaattgg agcgatgaaa tgcatcagca gtttgtcaat gccgttaacc agcttggcat  1320
cgacagtgcg atccccccc ccccccccc ccccctctt cctgcgactg ctctccgctc    1380
tccataagag taattgcgct cgcccacatg agctcgtgcc gaccctgctg tcctgcgctg  1440 ctcccgggt ccgcagaggc cgtacccaag cggattctag acctcatgag cgtggagggc  1500
ctcacacgag aaaacgtagc cagccacttg caggtccccc cccaccccc tttctcggca   1560 tgttgggcga gtgactggtc aaccctgcca atgatggctg aaccacagag cacttctgag  1620
atgcatgttc ttctgcagct gctgacctgt gcacccctc cgccacatcg gattccccc    1680 tccctgtcat cctcctccca tgccccgcac gcgtgcagaa ataccgcatc tacttgaagc  1740
```

```
gcatggccaa ccaccaggaa aatgggaagc aagcggtgat gagcacggac acgatcgccc      1800
gcgctgaagc ggcgtaccag ggaggcatgc cccaggggca gcagatgatg cagcaggagc      1860
acagcggcca ggcggtgcag tacagccagc cgcatgcccc cggcggcctg caccagcaag      1920
ccatgcccgc ccagatgcac atgggcatga tgccggccgg cccgcagccc ggcagcatgc      1980
agatggcgcc gcaccacgtc atgcaaatgc caatgggca ggtgatggtg atgcagcaga       2040
tggggccgcg cccggggatg ccacccggga tgccgcagca gatgatgcc agctcgcagc       2100 agatgggcat gcttcagccc ggcatgccgg cgggtcagat gttgcacttt cagcacccgc      2160
agcaagtgca ccagcatccg ccaagctcag ggcctatgca cgcaggtgcg ctacgcccct      2220
caatgagtcc atcccccccc cccccccccc ccaacccgcc aagaaaaac atgcagtaaa       2280 tacgctctgt tttcgcatca acatttgatt ttagggacaa agagaatgac ctgtgcatgc      2340
agggttggaa aacttaacat tcacgcacca tacaagtaca tcatagcctt tgtatgttgc      2400
aatattagag gccactttca gagtttcagt ggctacctct attggcaatt ctgccgcgtc      2460
tacgtgccca tgtgttgttc catttaattg gccttgcggc tcgtcgcgcg cgtgaagcc       2520 taccatggtg catttgtttt cctctttgat gcttattgac ctggtttctc ccctgtgtcc      2580
atgtagaatg tgttttagt gtgtgcatat cagtcgatgg ggtgttgtct tttgattgct       2640
gctgcactct ctttgtggct gatgtagatc tgtctgacgc aggggagag atgatagacc       2700 caggcagcat gcagcggttg catcagcagc cacactacat cggccccaac gggcagcaca      2760
tgccagcgcc tgcgatgggg atgccgtctg gcacagtcca gcacatggag tacgcctaca      2820
gccagcccat gcagatggct ggctggccgg tccaaggcca cccggcaac caagcctag       2879
```

<210> SEQ ID NO 86
<211> LENGTH: 1341
<212> TYPE: DNA
<213> ORGANISM: Tetraselmis sp.
<220> FEATURE:
<221> NAME/KEY: misc_feature
<223> OTHER INFORMATION: SGI1 T-5172 coding sequence

<400> SEQUENCE: 86

```
atgagctgca cagtggcgtc ctttccgccc gcggcggggg ggcagggctc gcctgccacg       60
cccgtcccat accaggacct gctcgtgaag cggcaagacc agtggagcaa cttcccggcc      120
gggctgcgcg tgctggtggc agacaacgac cccgcctcgc tgcagcaagt ggagaagatg      180
ctaaagaagt gtagctacca agtaacactg tgcagctcgg ggaagaactc cctggagatc      240
ctccgcaagc ggcgagagga attcgacctc gtgctggcgg acgcaaatct accagacata      300
gatggcttca agcttcttca cgtctgccac accgagctgt cgctccccgt cgtcctgatg      360
tccggcacca gcgacacaca gctggtaatg cgcggcgtga tggatggcgc gcgggacttt      420
ctgatcaagc cctgcgcgt ggaggagctc aaggtgctct ggcagcacct tgtgcgcttc       480
acttcggaga tcaccaagac agacgcgcag ctaaatgttg tcaaggtgga gctggacggc      540
ggaaggcctg cgggcgaagt ctctacgagt cagaacggct cgcaatgcac cgagcgcgag      600
ggcgaaggca attcatcaaa gaagcagcgc atgaattgga gcgatgaaat gcatcagcag      660
tttgtcaatg ccgttaacca gcttggcatc gacaaggccg tacccaagcg gattctagac      720
ctcatgagcg tggagggcct cacacgagaa aacgtagcca gccacttgca gaaataccgc      780
atctacttga agcgcatggc caaccaccag gaaaatggga agcaagcggt gatgagcacg      840
gacacgatcg cccgcgctga agcggcgtac cagggaggca tgcccagggg gcagcagatg      900
```

| | |
|---|---|
| atgcagcagg agcacagcgg ccaggcggtg cagtacagcc agccgcatgc ccccggcggc | 960 |
| ctgcaccagc aagccatgcc cgcccagatg cacatgggca tgatgccggc cggcccgcag | 1020 |
| cccggcagca tgcagatggc gccgcaccac gtcatgcaaa tgcccaatgg gcaggtgatg | 1080 |
| gtgatgcagc agatggggcc gcgccgcggg atgccacccg gatgccgca gcagatgatg | 1140 |
| gccagctcgc agcagatggg catgcttcag cccggcatgc cggcgggtca gatgttgcac | 1200 |
| tttcagcacc cgcagcaagt gcaccagcat ccgccaagct cagggcctat gcacgcagtc | 1260 |
| cagcacatgg agtacgccta cagccagccc atgcagatgg ctggctggcc ggtccaaggc | 1320 |
| caacccggca accaagccta g | 1341 |

<210> SEQ ID NO 87
<211> LENGTH: 2909
<212> TYPE: DNA
<213> ORGANISM: Tetraselmis sp.
<220> FEATURE:
<221> NAME/KEY: misc_feature
<223> OTHER INFORMATION: SGI1 T-5185 gene

<400> SEQUENCE: 87

| | |
|---|---|
| atgactccta ccccacccat gagctgcaca gtggcgtcct ttccgcccgc ggcggggggg | 60 |
| cagggctcgc ctgccacgcc cgtcccatac caggacctgc tcgtgaagcg gcaagaccag | 120 |
| tggagcaact tcccggccgg gctgcgcgtg ctggtggcag acaacgaccc cgcctcgctg | 180 |
| cagcaagtgg agaagatgct aaagaagtgt agctaccaag gtgaggctgc gctgcccctc | 240 |
| gaaaggcggc cggccccca ccccagctgg ccacgtgcgc agtgcgcgtg ttatcttgat | 300 |
| aatccgaaaa cgcgttttttt tgcctcgttt tatcccgcaa gtcgtacaat ccggtcgggg | 360 |
| cccaggcagg caccggcggc cacgcgcaga cccacacacc agctcaccgg ttgctgctac | 420 |
| actgatgcat gctttacgcc cggtccccaa cagtaacact gtgcagctcg gggaagaact | 480 |
| ccctggagat cctccgcaag cggcgagagg aattcgacct cgtgctggcg gacgcaaatc | 540 |
| taccaggttt tccccctcac cctgtctgct cgaggggta caccggtact actaaccgcg | 600 |
| acaattccgc ccgctcaccg ccgccttccc acgccacaag cgacggaact gattgtattc | 660 |
| ctgctcccgg tctttcgcct gcagacatag atggcttcaa gcttcttcac gtctgccaca | 720 |
| ccgagctgtc gctccccgtc gtccgtaaga gcctgctgcc cgctcgacat ccacctcgca | 780 |
| cttcaatttg ctattcagtc atcgtaccgt gccctgccct gcacttccct gccctgaggt | 840 |
| atcccagtcg catcccggcc accccccccc ccccccccc cccccttcc cccaaacgta | 900 |
| gtgatgtccg gcaccagcga cacacagctg gtaatgcgcg gcgtgatgga tggcgcgcgg | 960 |
| gactttctga tcaagcccct gcgcgtggag gagctcaagg tgctctggca gcaccttgtg | 1020 |
| cgcttcactt cggagatcac caagacagac gcgcagctaa atgttgtcaa ggtggagctg | 1080 |
| gacgcggaa ggcctgcggg cgaagtctct acgagtcaga acggctcggt atgccacagc | 1140 |
| agcccatttg aagcagccca tttcttgtag ggcgcgaatt atgcctcggc gcgttttcct | 1200 |
| cccgcctcgc gcgctgactc cttgtgtgcc ccacacagca atgcaccgag cgcgagggcg | 1260 |
| aaggcaattc atcaaagaag cagcgcatga attggagcga tgaaatgcat cagcagtttg | 1320 |
| tcaatgccgt taaccagctt ggcatcgaca gtgcgatccc tcccctcccc cccgccccc | 1380 |
| ccacccaccc ccctcttcct gcgactcgcg tccactttcc ttaagagtaa ttgagctcgc | 1440 |
| ccacatgagc tcgtgccgac cctgctgtcc tgcgctgctc ccggggtccg cagaggccgt | 1500 |
| acccaagcgg attctagacc tcatgagcgt ggagggcctc acacgagaaa acgtagccag | 1560 |

```
ccacttgcag gtcccccccc cccccccccc tttctcggca tgttgggcga gtgactggtc    1620
aacccctgca atgatggctg aaccacagag cacttctgag atgcatgttc tttctgcagc    1680
tgctgaccta tgcacccct ccgtcacatc ggattctccc ctccctgtca tcctcctccc    1740
atgccccgca cgcgtgcaga aataccgcat ctacttgaag cgcatggcca accaccagga    1800
aaatgggaag caagcggtga tgagcacgga cacgatcgcc cgcgctgaag cggcgtacca    1860
gggaggcatg cccagggc agcagatgat gcagcaggag cacagcggcc aggcggtgca    1920
gtacagccag ccgcatgccc ccggcggcct gcaccagcaa gccatgcccg cccagatgca    1980
catgggcatg atgccggccg gcccgcagcc cggcagcatg cagatggcgc cgcaccacgt    2040
catgcaaatg cccaatgggc aggtgatggt gatgcagcag atggggccgc cccggggat    2100 gccgcccggg atgccgcagc agatgatggc cagctcgcag cagatgggca tgcttcagcc    2160
cggcatgccg gcgggtcaga tgttgcactt tcagcacccg cagcaagtgc accagcatcc    2220
gccaagctca gggcctatgc acgcaggtgc gctacgcccc tcaatgagtc catgcccccc    2280
ccaacccgcc caagaaaaac atgcagtaaa tacacactgt tttcgcatca acatttgatt    2340
ttagggacaa agagaatgac ctgtgcatgc agggttggaa aacttaacat tcacgcacca    2400
tacaagtaca tcatagcctt tgtatgttgc aatattagag gccactttca gagtttcagt    2460
ggctacctct attggcaatt ctgccgcgtc tacgtgccca cgtgttgttg catttaattg    2520
gccttgcggc tcgtcgcgcg gcgtgaagcc taccatggtg catttgcttt cctctttgat    2580
gcttattgac ctggtttctc ccctgcgtcc atgtagaatg tgttttagt gtgtgcacat    2640 cagtcgatgg ggtgttgtct tttgattgct gctgcactct ctttgtggct gatgtagatc    2700
tgtctgacgc aggggagag atgatagacc caggcagcat gcagcggttg catcagcagc    2760
cgcactacat cggccccaac gggcagcaca tgccagcgcc tgcgatgggg atgccgtctg    2820
gcacagtcca gcacatggag tacgcctaca gccagcccat gcagatggct ggctggccgg    2880
tccaaggcca acctggcaac caagcctag                                      2909
```

<210> SEQ ID NO 88
<211> LENGTH: 1473
<212> TYPE: DNA
<213> ORGANISM: Tetraselmis sp.
<220> FEATURE:
<221> NAME/KEY: misc_feature
<223> OTHER INFORMATION: SGI1 T-5185 coding sequence

<400> SEQUENCE: 88

```
atgactccta ccccacccat gagctgcaca gtggcgtcct ttccgcccgc ggcggggggg     60
cagggctcgc ctgccacgcc cgtcccatac caggacctgc tcgtgaagcg gcaagaccag    120
tggagcaact ccccggccgg gctgcgcgtg ctggtggcag acaacgaccc cgcctcgctg    180
cagcaagtgg agaagatgct aaagaagtgt agctaccaag taacactgtg cagctcgggg    240
aagaactccc tggagatcct ccgcaagcgg cgagaggaat tcgacctcgt gctggcggac    300
gcaaatctac cagacataga tggcttcaag cttcttcacg tctgccacac cgagctgtcg    360
ctccccgtcg tcctgatgtc cggcaccagc gacacacagc tggtaatgcg cggcgtgatg    420
gatggcgcgc gggactttct gatcaagccc ctgcgcgtgg aggagctcaa ggtgctctgg    480
cagcaccttg tgcgcttcac ttcggagatc accaagacag acgcgcagct aaatgttgtc    540
aaggtggagc tggacggcgg aaggcctgcg ggcgaagtct ctacgagtca gaacggctcg    600
caatgcaccg agcgcgaggg cgaaggcaat tcatcaaaga agcagcgcat gaattggagc    660
```

-continued

```
gatgaaatgc atcagcagtt tgtcaatgcc gttaaccagc ttggcatcga caaggccgta      720
cccaagcgga ttctagacct catgagcgtg gagggcctca cacgagaaaa cgtagccagc      780
cacttgcaga ataccgcat ctacttgaag cgcatggcca accaccagga aaatgggaag       840
caagcggtga tgagcacgga cacgatcgcc cgcgctgaag cggcgtacca gggaggcatg      900
ccccaggggc agcagatgat gcagcaggag cacagcggcc aggcggtgca gtacagccag      960
ccgcatgccc ccggcggcct gcaccagcaa gccatgcccg cccagatgca catgggcatg     1020
atgccggccg gcccgcagcc cggcagcatg cagatggcgc cgcaccacgt catgcaaatg     1080
cccaatgggc aggtgatggt gatgcagcag atggggccgc gcccggggat gccgcccggg     1140
atgccgcagc agatgatggc cagctcgcag cagatgggca tgcttcagcc cggcatgccg     1200
gcgggtcaga tgttgcactt tcagcacccg cagcaagtgc accagcatcc gccaagctca     1260
gggcctatgc acgcaggggg agagatgata gacccaggca gcatgcagcg gttgcatcag     1320
cagccgcact acatcggccc caacgggcag cacatgccag cgcctgcgat ggggatgccg     1380
tctggcacag tccagcacat ggagtacgcc tacagccagc ccatgcagat ggctggctgg     1440
ccggtccaag gccaacctgg caaccaagcc tag                                  1473
```

<210> SEQ ID NO 89
<211> LENGTH: 3005
<212> TYPE: DNA
<213> ORGANISM: Tetraselmis sp.
<220> FEATURE:
<221> NAME/KEY: misc_feature
<223> OTHER INFORMATION: SGI1 T-5230 gene

<400> SEQUENCE: 89

```
atgagctgca cagtggcgtc gtttccgcca gcggcggggg gggcagggcg cgcctgccgc       60
gcccgtgcca taccacgacc tgctcgtgaa gcggcaagac cagtggagca acttcccggc      120
cgggctgcgc gtgctggtgg cagacaacga ccccgcctcg ctacagcaag tggagaagat     180
gctaaagaag tgtagctacc aaggtgaggc tgctctgccc ctcgaagggc ggccggcacc     240
ccaccccagc tagacacgtt cgcagtgcgc gtgttatctt gataacccga aaacgcgttt     300
ttttgcctcg ttttatcccg ctagtcgtac ataccggtcg gggcccaggc aggcaccggc     360
ggccacgcgc agacccacac accagctcac ccgttgctgc tacactgatg catgctttac     420
gcccggtccc caacagtaac actgtgcagc tcgggcaaga attccctgga gatcctccgc     480
aagcggcgag aggaattcga cctcgtgctg gcggacgcaa atctaccagg ttttcccct     540 caccctgtgt gctcgagggg gtacaccgat actacaaacc gcgacaattc cgcccgctca     600
ccgccgcctt cccacgccac aagcgacgaa actgattgta tttctgctcc cggtcttttg     660
cctgcagaca tagatggctt caagcttctg cacgtctgcc acaccgagct gtccctcccc     720
gtcgtccgtg agagcctgct gccacccgct cgacatccag ctcgcacttc aatctgccat     780
tcacttatac cgtgccctgc cctgcacttc cctgccctga ggtatcccat tcgtatcccg     840
gcatgggttc tgaaagcgct caccgcgccc gccccccccc cccccccccc ccccaacgt     900 agtgatgtcc ggcaccagcg acacgcagct ggtaatgcgc ggcgtgatgg atggcgcgcg     960
tgactttctg atcaagcccc tgcgcgtgga ggagctcaag gtgctctggc agcaccttgt    1020
gcgcttcact tcggagatca ccaagacaga cgcgcagcta aatgttgtca aggtggagct    1080
ggacagcgga aggcctgcgg gagaagtctc tacgagtcag aacggctcgg tatgccacag    1140
catctcattt gaagccgcgt cttccttgta gggcgcgaat catgcctcgg cgcgtctcca    1200
```

```
tctcgcctcg cgctgacttt ctgtgtgccc caaacagcaa tgcgccgagc gtgagggcga    1260
aggcaattca tcaaagaagc agcgcatgaa ttggagcgat gaaatgcatc agcagtttgt    1320
caatgccgtt aaccagcttg gcatcgacag tgcgaccccc cccctcttc ctgcgactgc    1380 gctccactct ccttaagagt aattgcactc ccccacataa gctcgttccg accctgctgt    1440
cctgcgctgc tccgggggtc cgcagaggcc gtacccaagc ggattctaga cctcatgagc    1500
gtggagggcc tcacacgaga aaacgtagcc agccacttgc aggtcccccc ccccccccc    1560 ccccttctc ggcatgttgg gcgagtgact ggtcaaccct gcaataatgg ctgaaccaca    1620
gagcacttct tagatgcatg tttttcctgc agctgctgac ctatgctccc cccccccc    1680 cccccccccc cgtcacatgc gattccctcc cccccctcc ctgcgctccg tcacatcgga    1740 ttccccctt cctgtcatcc tcctgcaatg ccccgcgcgc gtgcagaaat accgcatcta    1800
cttgaagcgc atggccaacc accaggaaaa tgggaagcaa gcggtgatga gcacggacac    1860
gatcgcccgc gctgaagcgg cgtaccaggg aggcatgccc caggggcagc agatgatgca    1920
gcaggaacac agcggccagg cggtgcagta cagccagccg catgccccca gcggcctgca    1980
ccagcaagcc atgcccgccc agatgcacat gggcatgatg ccggccggcc cgcagcccgg    2040
cagcatgcag atggcgccgc accacgtcat gcaaatgccc aacgggcagg tgatggtgat    2100
gcagcagatg gggccgcgcc cggggatgcc gcccgggatg ccgcagcaga tgatggccag    2160
ctcgcagcag atgggcatgc ttcagcccgg catgccggcg ggtcagatgt tgcactttca    2220
gcacccgcag caagtgcacc agcatccgcc aagctcaggg cctatgcacg caggtgcgct    2280
acgcccctca atgagtccat gcccccccc cccccccc cacccccccc ccccagaat    2340 gcagtaaaca cactctgttt ccgcttcgtt atttggtttt agagaataac cagtgcatgc    2400
aggattggaa tacttatcat ttacgcacca tgcaactaca ccacaccctt tgcatgtcgc    2460
aatattagag gccactttta gagtttcagg gactatctct attggcaatt ctgccgcgtc    2520
tacgtgccca tgtgctgttc cagtaattgg cctcgccgct cgtcacatgg catgaagccc    2580
accatggtgc atttgctgta ctctgaagct tcttgacctg gtttctccca tgtgtgtgtg    2640
tgtgtgtgtg tgtgtgtgtt gttgtggggg gggggggggg gcagaacatt tttcaggcac    2700
gaacccatgt agagtgtggt tttagtttgt acatatcagt gaatgaggtg ttgtcttttg    2760
attgttgctg cactctcttt gtggctgatg tagatctgtc tgacgcaggg ggagagatga    2820
tagacccagg cagcatgcag cggttgcatc agcagccgca ctacatcgtc cccaacgcgc    2880
agcacatgcc agcgcctgca atggggatgc cgcctggcgc agtccagcac atggagtacg    2940
cctacagcca gcccatgcag atggctggct ggccggtcca aggccaacct ggcagtcagg    3000
cctag                                                                3005
```

<210> SEQ ID NO 90
<211> LENGTH: 1725
<212> TYPE: DNA
<213> ORGANISM: Tetraselmis sp.
<220> FEATURE:
<221> NAME/KEY: misc_feature
<223> OTHER INFORMATION: SGI1 T-5230 coding sequence

<400> SEQUENCE: 90

```
atgaccatgc cactcggcgg tggtctgtgc atgaaggatc gcatccatgg ggatgagagg      60
taccgttcca aggccaaacg ccaagtaaat acgatatttg cgttcaccca gcgcaacaca     120
tggcgcggac gcttccggct atgctcttat aggacaactg aattactggg cggaagcaaa     180
```

```
acgacggagc cgggaagggg aaccttcgtg ctgcagattt tcatgtgtgt taagaacgcc    240
tccatcgacg acggctcacg ccatatttcc acgagccggg ggctggagtc cgtcctgaag    300 cggcggggg ggcagggcgc gcctgccgcg cccgtgccat accacgacct gctcgtgaag     360
cggcaagacc agtggagcaa cttcccggcc gggctgcgcg tgctggtggc agacaacgac    420
cccgcctcgc tacagcaagt ggagaagatg ctaaagaagt gtagctacca agtaacactg    480
tgcagctcgg gcaagaattc cctggagatc ctccgcaagc ggcgagagga attcgacctc    540
gtgctggcgg acgcaaatct accagacata gatggcttca agcttctgca cgtctgccac    600
accgagctgt ccctccccgt cgtcctgatg tccggcacca cgacacgca gctggtaatg     660 cgcggcgtga tggatggcgc gcgtgacttt ctgatcaagc ccctgcgcgt ggaggagctc    720
aaggtgctct ggcagcacct tgtgcgcttc acttcggaga tcaccaagac agacgcgcag    780
ctaaatgttg tcaaggtgga gctggacagc ggaaggcctg cgggagaagt ctctacgagt    840
cagaacggct cgcaatgcgc cgagcgtgag ggcgaaggca attcatcaaa gaagcagcgc    900
atgaattgga gcgatgaaat gcatcagcag tttgtcaatg ccgttaacca gcttggcatc    960
gacaaggccg tacccaagcg gattctagac ctcatgagcg tggagggcct cacacgagaa   1020
aacgtagcca gccacttgca gaaataccgc atctacttga agcgcatggc caaccaccag   1080
gaaaatggga agcaagcggt gatgagcacg gacacgatcg cccgcgctga gcggcgtac    1140 cagggaggca tgccccaggg gcagcagatg atgcagcagg aacacagcgg ccaggcggtg   1200
cagtacagcc agccgcatgc ccccagcggc ctgcaccagc aagccatgcc cgcccagatg   1260
cacatgggca tgatgccggc cggcccgcag cccggcagca tgcagatggc gccgcaccac   1320
gtcatgcaaa tgcccaacgg gcaggtgatg gtgatgcagc agatgggcc gcgcccgggg    1380 atgccgcccg ggatgccgca gcagatgatg gccagctcgc agcagatggg catgcttcag   1440
cccggcatgc cggcgggtca gatgttgcac tttcagcacc cgcagcaagt gcaccagcat   1500
ccgccaagct cagggcctat gcacgcaggg ggagagatga tagacccagg cagcatgcag   1560
cggttgcatc agcagccgca ctacatcgtc cccaacgcgc agcacatgcc agcgcctgca   1620
atggggatgc cgcctggcgc agtccagcac atggagtacg cctacagcca gcccatgcag   1680
atggctggct ggccggtcca aggccaacct ggcagtcagg cctag                   1725
```

<210> SEQ ID NO 91
<211> LENGTH: 20
<212> TYPE: DNA
<213> ORGANISM: Tetraselmis sp.
<220> FEATURE:
<221> NAME/KEY: misc_feature
<223> OTHER INFORMATION: SGI1 MA1 target sequence for Cas9

<400> SEQUENCE: 91

```
gcaccttgtg cgcttcactt                                                 20
```

<210> SEQ ID NO 92
<211> LENGTH: 19
<212> TYPE: DNA
<213> ORGANISM: Tetraselmis sp.
<220> FEATURE:
<221> NAME/KEY: misc_feature
<223> OTHER INFORMATION: SGI1 JC2 target sequence for Cas9

<400> SEQUENCE: 92

```
cagctaaatg ttgtcaagg                                                  19
```

<210> SEQ ID NO 93
<211> LENGTH: 1941
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nourseothricin expression cassette

<400> SEQUENCE: 93

```
ggcggcatgt ctgcgcaagc cctgctgcta actggctccc gcgactgaat tcggaatgta      60
tgcgtggtta ttgcgtttcg tgtgcatata cttccgtgat actttcgcca actccatcag     120
cagtagttta tggacaggcg gcggccgccg cccgccgatg acatcgtagt cgctcgtcgt     180
cagggaagtg ccgtcaggag cgtggtggcg gcggcgcggc ggctcgcgca ccggcggccg     240
gtgcggaaag gtgagcggag gcgcccgtga cgtccccctt tcgcccacca ccctctacgc     300
tcaacccaca ggtgattcag cacgcccctcc gcccccgccc tccaggcaac cagtcacgct     360
agtccgcccc agcgtatcgc cggcccttcc cgcgctggct ttagcggcag gctcgccgcc     420
tgatccggcg cgccctcgcc gccgccaccg agaatcttcg cagcagccgc accgccggga     480
agtgtactgg gcgaggggca gcaccgtgtc gcagcaaatg tgcgaggcgc gcaggaaacg     540
caggcatgcc gctggaatcc acgcggacaa tggaggggaa aggggggat tcgtttttggt      600
ggcccccagc gtagatgggg cagggtgacc aggtctcctt ttttccttca actgcccaga     660
ttcgtccgag gttgggcatt ccttgcatta cgggaaatac cgcgcggctc tgtaatgccg     720
gttgcgattt acgccttgta cttcaaatta ttgttttcg gggaaaccca ccaggctggg      780
ttcgctagcg aagcgtccaa gcctgactga gtagctgcct gcctggtcac cacttgaggt     840
ccaccacacc gcagtcactt gccctgccgc catggcggtt ctgagtgctg ccatctctgc     900
ctctgcagct gccaggcagg ctcgccatct gcctgctgta cgccagcaca tctgacctcc     960
ccccgccccc ctgtcttcct ctctcatagg aacatcctct aggacgaaaa gactttgaga    1020
cagctctacc tgtcgaggaa aaatgaccac actcgacgac accgcataca gataccgcac    1080
aagcgttcct ggcgacgcag aggcaattga ggcattagat ggcagcttca ccaccgacac    1140
cgtgtttaga gtgacagcaa ccggcgacgg ctttacactt agagaggttc cagtggaccc    1200
gccattgaca aaggtgtttc cagacgacga gagcgacgat gagagcgatg ctggtgaaga    1260
tggcgaccca gatagccgca catttgtggc atacggcgat gatggcgacc ttgctgggtt    1320
tgtggtggtg agctactctg gctggaatag acgcttgacc gtggaggata tcgaggttgc    1380
accagagcat agaggccatg gagtgggtag agcactgatg ggtctggcaa ccgagtttgc    1440
aagggagaga ggtgctggtc atctgtggtt ggaggtgaca aacgtgaacg caccagcgat    1500
ccacgcatac agaagaatgg gcttcacgct gtgcggcctg gatacagcac tgtatgatgg    1560
cacagcgagc gatggtgagc aagcactgta catgagcatg ccatgcccgt aagcgctgtg    1620
cgcctagctt tgcctttgca ccaacgatga cggcgatgct ctgcatgtac cccgtgcggg    1680
tgtatgtaaa tccatgtgcc ggagagcact tcgctccttc atcacacttt ttcgccatcc    1740
gccattcccc gccccagcct gaccaacctc tatgccccac cacccgggac tggcatgcct    1800
gacccttttca catgcgcggt cggccttggg tcttctctct acacaagcgg cgacttgctc    1860
gccaaagagg ataggtcaaa ggtcagtgaa catgttctct atatcacgct gtcggcgggt    1920
gttccactcg gtctgtcgaa a                                              1941
```

<210> SEQ ID NO 94
<211> LENGTH: 1042
<212> TYPE: DNA
<213> ORGANISM: Tetraselmis sp.
<220> FEATURE:
<221> NAME/KEY: misc_feature
<223> OTHER INFORMATION: RB40 promoter

<400> SEQUENCE: 94

| | | | | | |
|---|---|---|---|---|---|
| ggcggcatgt | ctgcgcaagc | cctgctgcta | actggttccc | ggggctgaat | tcggaatgta | 60 |
| tgcgtggtta | ttgcgtttcc | tgtgcatata | cttccgtgat | actttcgcca | actccatcag | 120 |
| cagtagttta | tggacaggcg | gcggccgccg | cccgccgacg | acatcgtagt | cgctcgtcgt | 180 |
| cagggaagtg | ccgtcaggag | cgtggtggcg | gcggcgcggc | ggctcgcgcc | ccggcggccg | 240 |
| gtgcggaaag | gtgagcggag | gcgcccgtga | cgtccccctt | tcgcccacca | ccctctacgc | 300 |
| tcaacccaca | ggtgattcag | caagccctcc | ggccccgccc | tccaggcaac | cagtcacgct | 360 |
| agtccacccc | agcgtatcgc | cggccccttcc | cgcgctggct | ttagcggcag | gctcgccgcc | 420 |
| tgatccggcg | cgccctcgcc | gccgccaccg | agaatcttcg | cagcagccgc | accgccggga | 480 |
| agtgtactgg | gcgaggggca | gcaccgtgtc | gcagcaaatg | tgcgaggcgc | gcaggaaacg | 540 |
| caggcatgcc | gctggaatcc | acgcggacaa | tggagggaa | aggggggat | tcgttttggt | 600 |
| ggcccccagc | gtagatgggg | cagggtgacc | aggtctcctt | tttctccttca | actgcccaga | 660 |
| ttcgtccgag | gttgggcatt | ccttgcatta | cgggaaatac | cgcgcggctc | tgtaatgccg | 720 |
| gttgcgattt | acgccttgta | cttcaaatta | ttgttttttcg | gggaaaccca | ccaggctggg | 780 |
| ttcgctagcg | aagcgtccaa | gcctgactga | gtagctgcct | gcctggtcac | cacttgaggt | 840 |
| ccaccacacc | gcagtcactt | gccctgccgc | catggcggtt | ctgagtgctg | ccatctctgc | 900 |
| ctctgcagct | gccaggcagg | ctcgccatct | gcctgctgta | cgccagcaca | tctgacctcc | 960 |
| ccccgccccc | ctgtcttcct | ctctcatagg | aacatcctct | aggacgaaaa | gactttgaga | 1020 |
| cagctctacc | tgtcgaggaa | aa | | | | 1042 |

<210> SEQ ID NO 95
<211> LENGTH: 329
<212> TYPE: DNA
<213> ORGANISM: Tetraselmis sp.
<220> FEATURE:
<221> NAME/KEY: misc_feature
<223> OTHER INFORMATION: RB40 terminator

<400> SEQUENCE: 95

| | | | | | |
|---|---|---|---|---|---|
| gcgctgtgcg | cctagctttg | cctttgcacc | aacgatgacg | gcgatgctct | gcatgtaccc | 60 |
| cgcgcgggtg | tatgtaaatc | catgtgccgg | agagcacttc | gctccttcat | cacactttt | 120 |
| cgccatccgc | cattccccgc | cccagcctga | ccaacctcta | tgccccacca | cccgggactg | 180 |
| gcatgcctga | ccctttcaca | tgcgcggtcg | gccttgggtc | ttctctctac | acaagcggcg | 240 |
| acttgctcgc | caaagaggat | aggtcaaagg | tcagtgaaca | tgttctctat | atcacgctgt | 300 |
| cggcgggtgt | tccactcggt | ctgtcgaaa | | | | 329 |

<210> SEQ ID NO 96
<211> LENGTH: 570
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<223> OTHER INFORMATION: nourseothricin resistance gene codon optimized
      for Tetraselmis

<400> SEQUENCE: 96
atgaccacac tcgacgacac cgcatacaga taccgcacaa gcgttcctgg cgacgcagag      60
gcaattgagg cattagatgg cagcttcacc accgacaccg tgtttagagt gacagcaacc     120
ggcgacggct ttacacttag agaggttcca gtggacccgc cattgacaaa ggtgtttcca     180
gacgacgaga gcgacgatga gagcgatgct ggtgaagatg gcgacccaga tagccgcaca     240
tttgtggcat acggcgatga tggcgacctt gctgggtttg tggtggtgag ctactctggc     300
tggaatagac gcttgaccgt ggaggatatc gaggttgcac cagagcatag aggccatgga     360
gtgggtagag cactgatggg tctggcaacc gagtttgcaa gggagagagg tgctggtcat     420
ctgtggttgg aggtgacaaa cgtgaacgca ccagcgatcc acgcatacag aagaatgggc     480
ttcacgctgt gcggcctgga tacagcactg tatgatggca cagcgagcga tggtgagcaa     540
gcactgtaca tgagcatgcc atgcccgtaa                                      570

<210> SEQ ID NO 97
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer MCA1818

<400> SEQUENCE: 97
ggcggcatgt ctgcgcaagc                                                  20

<210> SEQ ID NO 98
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Primer MCA1819

<400> SEQUENCE: 98
tttcgacaga ccgagtggaa cacc                                             24
```